United States Patent
Schostarez et al.

(10) Patent No.: US 6,960,664 B2
(45) Date of Patent: Nov. 1, 2005

(54) AZA HYDROXYLATED ETHYL AMINE COMPOUNDS

(75) Inventors: Heinrich Schostarez, Portage, MI (US); Robert Alan Chrusciel, Portage, MI (US); Rebecca S. Centko, Portage, MI (US)

(73) Assignee: Pharmacia & UpJohn Company, Kalamazoo, MI (US)

( * ) Notice: Subject to any disclaimer, the term of this patent is extended or adjusted under 35 U.S.C. 154(b) by 238 days.

(21) Appl. No.: 10/152,601

(22) Filed: May 22, 2002

(65) Prior Publication Data
US 2003/0229138 A1 Dec. 11, 2003

Related U.S. Application Data

(60) Provisional application No. 60/360,601, filed on Mar. 1, 2002, provisional application No. 60/301,355, filed on Jun. 27, 2001, and provisional application No. 60/292,856, filed on May 22, 2001.

(51) Int. Cl.$^7$ ............................................. C07D 277/20
(52) U.S. Cl. ...................... 548/195; 548/190; 548/193; 548/194; 548/196; 548/200
(58) Field of Search ................................ 548/193, 194, 548/195, 196, 190, 200; 514/365, 603, 614; 564/147, 200

(56) References Cited

U.S. PATENT DOCUMENTS

| 6,225,345 B1 | 5/2001 | Fassler et al. |
| 6,258,806 B1 * | 7/2001 | Grobelny .................... 514/218 |

FOREIGN PATENT DOCUMENTS

| WO | WO 99 36404 | 7/1999 |
| WO | WO 02 002506 | 1/2002 |

OTHER PUBLICATIONS

U.S. Appl. No. 09/895,871, Fang et al., filed Jun. 29, 2001.
U.S. Appl. No. 09/895,843, Beck et al., filed Jun. 29, 2001.
U.S. Appl. No. 09/896,139, Fang et al., filed Jun. 29, 2001.
U.S. Appl. No. 10/152,601, Schostarez et al., filed May 22, 2002.
U.S. Appl. No. 10/291,318, Varghese et al., filed Nov. 8, 2002.

* cited by examiner

*Primary Examiner*—Shailendra Kumar
(74) *Attorney, Agent, or Firm*—McDonnell Boehnen Hulbert & Berghoff LLP

(57) ABSTRACT

Disclosed are compounds of formula:

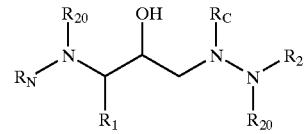

and pharmaceutically acceptable salts and esters thereof, useful in treating and/or preventing Alzheimer's disease and other similar diseases, wherein $R_N$, $R_C$, $R_1$, $R_2$ and $R_{20}$ are defined herein. These compounds include inhibitors of the beta-secretase enzyme that are useful in the treatment of Alzheimer's disease and other diseases characterized by deposition of A beta peptide in a mammal. The compounds of the invention are useful in pharmaceutical compositions and methods of treatment to reduce A beta peptide formation.

15 Claims, No Drawings

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 2
```

```
Ser Glu Val Lys Met Asp Ala Glu Phe Arg Cys Lys Lys
1               5                  10
```

<210> SEQ ID NO 3
<211> LENGTH: 22
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

```
Gly Leu Asn Ile Lys Thr Glu Glu Ile Ser Glu Ile Ser Tyr Glu Val
1               5                  10                  15

Glu Phe Arg Cys Lys Lys
            20
```

<210> SEQ ID NO 4
<211> LENGTH: 34
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

```
Ala Asp Arg Gly Leu Thr Thr Arg Pro Gly Ser Gly Leu Thr Asn Ile
1               5                  10                  15

Lys Thr Glu Glu Ile Ser Glu Val Asn Leu Asp Ala Glu Phe Arg Cys
            20                  25                  30

Lys Lys
```

<210> SEQ ID NO 5
<211> LENGTH: 33
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green

<400> SEQUENCE: 5

```
Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Ala Cys Lys
            20                  25                  30
```

Lys

<210> SEQ ID NO 6
<211> LENGTH: 33
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial Sequence

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial Sequence

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30

AZA HYDROXYLATED ETHYL AMINE COMPOUNDS

BACKGROUND OF THE INVENTION

1. Field of the Invention

This invention relates to aza hydroxylated ethyl amine derivatives and more specifically to such compounds that are useful in the treatment and/or prevention of Alzheimer's disease and similar diseases. More specifically the invention relates to substituted aza hydroxy ethyl amines that are capable of inhibiting beta-secretase, an enzyme that cleaves amyloid precursor protein to produce amyloid beta peptide (A beta), a major component of the amyloid plaques found in the brains of Alzheimer's sufferers.

2. Description of Related Art

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sindha et al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

BACE1 knockout mice fail to produce A beta, and present a normal phenotype. When crossed with transgenic mice that over express APP, the progeny show reduced amounts of A beta in brain extracts as compared with control animals (Luo et al., 2001 *Nature Neuroscience* 4:231–232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

Various pharmaceutical agents have been proposed for the treatment of Alzheimer's disease but without any real success.

At present there are no effective treatments for halting, preventing, or reversing the progression of Alzheimer's disease. There is an urgent need for compounds capable of slowing A-beta peptide production and/or deposition in the brain, which presents a therapeutic approach to treatment of Alzheimer's disease.

SUMMARY OF THE INVENTION

The invention provides compounds of the formula below, pharmaceutical compositions containing the compounds, and methods useful in the treatment of Alzheimer's disease. More specifically, it provides compounds that are capable of inhibiting beta-secretase, an enzyme that cleaves amyloid precursor protein to produce A beta peptide, a major component of the amyloid plaques found in the brains of Alzheimer's sufferers.

Accordingly, in a broad aspect, the invention is provides towards compounds of formula I:

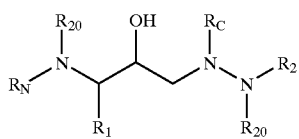

and pharmaceutically acceptable salts or esters thereof, where Rc is (I) —$C_1$–$C_{10}$ alkyl optionally substituted with one, two or three groups independently selected from the group consisting of $C_1$–$C_3$ alkyl, halogen, —OH, —SH, —C≡N, —$CF_3$, $C_1$–$C_6$ alkoxy, —O-phenyl, —$NR_{1-a}R_{1-b}$, —OC=O $NR_{1-a}R_{1-b}$, —S(=O)$_{0-2}$ $R_{1-a}$, —$NR_{1-a}$C=O $NR_{1-a}R_{1-b}$, —C=O $NR_{1-a}R_{1-b}$, and —S(=O)$_2$ $NR_{1-a}R_{1-b}$ wherein $R_{1-a}$ and $R_{1-b}$ at each occurrence are independently H or $C_1$–$C_6$ alkyl, (II) —$(CH_2)_{0-3}$—($C_3$–$C_8$) cycloalkyl where cycloalkyl can be optionally substituted with one, two or three substituents independently selected from the group consisting of $C_1$–$C_3$ alkyl, halogen, —OH, —SH, —C≡N, —$CF_3$, $C_1$–$C_6$ alkoxy, —O-phenyl, —$CO_2H$, —$CO_2$—($C_1$–$C_4$ alkyl), and —$NR_{1-a}R_{1-b}$ (III) —$(CR_{C-x}R_{C-y})_{0-4}$—$R_{C-aryl}$ where $R_{C-x}$ and $R_{C-y}$ are independently selected from the group consisting of
—H,
$C_1$–$C_4$ alkyl optionally substituted with 1 or 2 —OH,
$C_1$–$C_4$ alkoxy optionally substituted with 1, 2, or 3 halogen,
—$(CH_2)_{0-4}$—$C_3$–$C_8$ cycloalkyl,
$C_2$–$C_6$ alkenyl containing one or two double bonds,
$C_2$–$C_6$ alkynyl containing one or two triple bonds, and phenyl, or $R_{C-x}$ and $R_{C-y}$ are taken together with the carbon to which they are attached to form a carbocycle of three, four, five, six or seven carbon atoms, where one carbon atom is optionally replaced by a group selected from —O—, —S—, —$SO_2$—, —$NR_{N-2}$— and $R_{C-aryl}$, wherein $R_{C-aryl}$ at each occurrence is independently phenyl; naphthyl; tetralinyl; indanyl; dihydronaphthyl; or 6,7,8,9-tetrahydro-5H-benzo[a]cycloheptenyl, each of which is optionally substituted with 1, 2, or 3 groups that are independently:

(1) $C_1$–$C_6$ alkyl, optionally substituted with one, two or three substituents selected from the group consisting of $C_1$–$C_3$ alkyl, halogen, —OH, —SH, —C≡N, —$CF_3$, $C_1$–$C_3$ alkoxy, and —$NR_{1-a}R_{1-b}$,
(2) —OH,
(3) —$NO_2$,
(4) halogen,
(5) —$CO_2H$,
(6) —C≡N,
(7) —$(CH_2)_{0-4}$—CO—$NR_{N-2}R_{N-3}$ where $R_{N-2}$ and $R_{N-3}$ are independently selected from the group consisting of:
(a) —H,
(b) —$C_1$–$C_6$ alkyl optionally substituted with one substituent selected from the group consisting of:
(i) —OH, and
(ii) —$NH_2$,
(c) —$C_1$–$C_6$ alkyl optionally substituted with 1, 2, or 3 groups that are independently —F, —Cl, —Br, —I, or OH, (d) —$C_3$–$C_7$ cycloalkyl,
(e) —($C_1$–$C_2$ alkyl)-($C_3$–$C_7$ cycloalkyl),
(f) —($C_1$–$C_6$ alkyl)-O-($C_1$–$C_3$ alkyl),
(g) —$C_2$–$C_6$ alkenyl
(h) —$C_2$–$C_6$ alkynyl
(i) —$C_1$–$C_6$ alkyl chain with one double bond and one triple bond,
(j) —$R_{1-aryl}$ wherein $R_{1-aryl}$ at each occurrence is independently phenyl, naphthyl, indanyl, indenyl, dihydronaphthyl, or tetralinyl each of which is optionally substituted with 1, 2, 3, or 4 groups that are independently:
   (i) $C_1$–$C_6$ alkyl optionally substituted with one, two or three substituents independently selected from the group consisting of $C_1$–$C_3$ alkyl, —F, —Cl, —Br, —I, —OH, —SH, —$NR_{1-a}R_{1-b}$, —C≡N, —$CF_3$, and $C_1$–$C_3$ alkoxy,
   (ii) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$,
   (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$,
   (iv) —F, Cl, —Br and —I,
   (v) —$C_1$–$C_6$ alkoxy optionally substituted with 1, 2, or 3 —F,
   (vi) —$NR_{N-2}R_{N-3}$,
   (vii) —OH,
   (viii) —C≡N,
   (ix) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1-a}R_{1-b}$,
   (x) —CO—($C_1$–$C_4$ alkyl),
   (xi) —$SO_2$—$NR_{1-a}R_{1-b}$,
   (xii) —CO—$NR_{1-a}R_{1-b}$, or
   (xiii) —$SO_2$-($C_1$–$C_4$ alkyl),
(k) —$R_{1-heteroaryl}$ wherein $R_{1-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1\text{-}heteroaryl}$ group is optionally substituted with 1, 2, 3, or 4 groups that are independently:

(i) $C_1$–$C_6$ alkyl optionally substituted with 1, 2, or 3 groups independently selected from the group consisting of $C_1$–$C_3$ alkyl, —F, —Cl, —Br, —I, —OH, —SH, —$NR_{1\text{-}a}R_{1\text{-}b}$ —C≡N, —$CF_3$, and $C_1$–$C_3$ alkoxy, (ii) $C_2$–$C_6$ alkenyl optionally substituted with 1, 2, or 3 groups that are independently —F, Cl, —OH, —SH, —C≡N, —$CF_3$, $C_1$–$C_3$ alkoxy, and —$NR_{1\text{-}a}R_{1\text{-}b}$, (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$, (iv) —F, —Cl, —Br and —I, (v) —$C_1$–$C_6$ alkoxy optionally substituted with one, two, or three —F, (vi) —$(CH_2)_{0\text{-}4}$—$NR_{N\text{-}2}R_{N\text{-}3}$, (vii) —OH, (viii) —C≡N, (ix) $(CH_2)_{0\text{-}4}$—$C_3$–$C_7$ cycloalkyl, optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$, (x) $(CH_2)_{0\text{-}4}$—CO—($C_1$–$C_6$ alkyl), (xi) $(CH_2)_{0\text{-}4}$—$SO_2$—$NR_{N\text{-}2}R_{N\text{-}3}$, (xii) $(CH_2)_{0\text{-}4}$—CO—$NR_{N\text{-}2}R_{N\text{-}3}$, (xiii) $(CH_2)_{0\text{-}4}$—$SO_2$-($C_1$–$C_6$ alkyl), (xiv) $(CH_2)_{0\text{-}4}$—$N(R_{N\text{-}2})$—$SO_2$—, and (xv) $(CH_2)_{0\text{-}4}$—$N(R_{N\text{-}2})$—C(O)—, (8) —$(CH_2)_{0\text{-}4}$—CO—($C_1$–$C_{12}$ alkyl), (9) —$(CH_2)_{0\text{-}4}$—CO—($C_2$–$C_{12}$ alkenyl),

(10) —$(CH_2)_{0\text{-}4}$—CO—($C_2$–$C_{12}$ alkynyl),

(11) —$(CH_2)_{0\text{-}4}$—CO—$(CH_2)_{0\text{-}4}$ ($C_3$–$C_7$ cycloalkyl)

(12) —$(CH_2)_{0\text{-}4}$—CO—$R_{1\text{-}aryl}$,

(13) —$(CH_2)_{0\text{-}4}$—CO—$R_{1\text{-}heteroaryl}$,

(14) —$(CH_2)_{0\text{-}4}$—CO—$R_{1\text{-}heterocycle}$ wherein $R_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyriazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with 1, 2, 3, or 4 groups that are independently:

(a) $C_1$–$C_6$ alkyl optionally substituted with one, two or three substituents independently selected from the group consisting of $C_1$–$C_3$ alkyl, halogen, —OH, —SH, —$NR_{1\text{-}a}R_{1\text{-}b}$ —C≡N, —$CF_3$, and $C_1$–$C_3$ alkoxy, (b) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1\text{-}a}R_{1\text{-}b}$ (c) $C_2$–$C_6$ alkynyl with one or two triple bonds, optionally substituted with one, two or three substituents independently selected from the group consisting of —F, —Cl, —OH, —SH, —C≡N, —$CF_3$, $C_1$–$C_3$ alkoxy, and —$NR_{1\text{-}a}R_{1\text{-}b}$ (d) halogen, (e) $C_1$–$C_6$ alkoxy, (f) —$C_1$–$C_6$ alkoxy optionally substituted with one, two, or three —F, (g) —$NR_{N\text{-}2}R_{N\text{-}3}$, (h) —OH, (i) —C≡N, (j) $(CH_2)_{0\text{-}4}$—($C_3$–$C_7$ cycloalkyl), optionally substituted with 1, 2, or 3 groups independently selected from the group consisting of —F, —Cl, —OH, —SH, —C≡N, —$CF_3$, $C_1$–$C_3$ alkoxy, and —$NR_{1\text{-}a}R_{1\text{-}b}$, (k) —$(CH_2)_{0\text{-}4}$—CO—($C_1$–$C_4$ alkyl), (l) —$(CH_2)_{0\text{-}4}$—$SO_2$—$NR_{1\text{-}a}R_{1\text{-}b}$, (m) —$(CH_2)_{0\text{-}4}$—CO—$NR_{1\text{-}a}R_{1\text{-}b}$, (n) —$(CH_2)_{0\text{-}4}$—$SO_2$-($C_1$–$C_6$ alkyl), and (o) =O, (p) —$(CH_2)_{0\text{-}4}$—$N(R_{N\text{-}2})$—$SO_2$—

(q) —$(CH_2)_{0\text{-}4}$—$N(R_{N\text{-}2})$—C(O)—

(15) —$(CH_2)_{0\text{-}4}$—CO—$R_{N\text{-}4}$ wherein $R_{N\text{-}4}$ at each occurrence is independently selected from the group consisting of morpholinyl, thiomorpholinyl, pyrrolidinonyl, pyrrolyl, pyrazolyl, thienyl, pyridyl N-oxide, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with 1, 2, 3, or 4 groups that are independently $C_1$–$C_6$ alkyl,

(16) —$(CH_2)_{0\text{-}4}$—$CO_2$—$R_{N\text{-}5}$ where $R_{N\text{-}5}$ at each occurrence is independently selected from the group consisting of:

(a) $C_1$–$C_6$ alkyl, (b) —$(CH_2)_{0\text{-}2}$—($R_{1\text{-}aryl}$)

(c) $C_2$–$C_6$ alkenyl, (d) $C_1$–$C_6$ alkynyl, (e) $C_3$–$C_7$ cycloalkyl, and
(f) —$(CH_2)_{0-4}$—$(R_{1\text{-}heteroaryl})$
(17) —$(CH_2)_{0-4}$—$SO_2$—$NR_{N-2}R_{N-3}$,
(18) —$(CH_2)_{0-4}$—SO—($C_1$–$C_8$ alkyl),
(19) —$(CH_2)_{0-4}$—$SO_2$-($C_1$–$C_{12}$ alkyl),
(20) —$(CH_2)_{0-4}$—$SO_2$-($C_3$–$C_7$ cycloalkyl),
(21) —$(CH_2)_{0-4}$—N(H or $R_{N-5}$)—$CO_2$—$R_{N-5}$,
(22) —$(CH_2)_{0-4}$—N(H or $R_{N-5}$)—CO—N($R_{N-5}$)$_2$,
(23) —$(CH_2)_{0-4}$—N—CS—N($R_{N-5}$)$_2$,
(24) —$(CH_2)_{0-4}$—N(—H or $R_{N-5}$)—CO—$R_{N-2}$,
(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO-($C_1$–$C_6$ alkyl),
(28) —$(CH_2)_{0-4}$—O—P(O)—$(OR_{100})_2$ where $R_{100}$ is independently H or $C_1$–$C_4$ alkyl,
(29) —$(CH_2)_{0-4}$—O—CO—N($R_{N-5}$)$_2$,
(30) —$(CH_2)_{0-4}$—O—CS—N($R_{N-5}$)$_2$,
(31) —$(CH_2)_{0-4}$—O—($R_{N-5}$),
(32) —$(CH_2)_{0-4}$—O—($R_{N-5}$)—COOH,
(33) —$(CH_2)_{0-4}$—S—($R_{N-5}$),
(34) —$(CH_2)_{0-4}$—O—($C_1$–$C_6$ alkyl) wherein the alkyl group is optionally substituted with one, two, three, four, or five substituents independently selected from the group consisting of F, Cl, Br, and I,
(35) —$(CH_2)_{0-4}$-($C_3$–$C_8$ cycloalkyl),
(36) $C_2$–$C_6$ alkenyl optionally substituted with $C_1$–$C_3$ alkyl, halogen, —OH, —SH, —C≡N, —$CF_3$, $C_1$–$C_3$ alkoxy, or —$NR_{1-a}R_{1-b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$, and
(38) —$(CH_2)_{0-4}$—N(—H or $R_{N-5}$)—$SO_2$—$R_{N-2}$;

(IV) —$(CR_{C-x}R_{C-y})_{0-4}$—$R_{C\text{-}heteroaryl}$ wherein $R_{C\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzoisothiazolyl, benzimidazolyl, benzofuranyl, furanyl, thienyl, pyrrolyl, oxadiazolyl, thiadiazolyl, triazolyl, tetrazolyl, oxazolopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, imidazopyrazolyl, quinazolinonyl, pyrazopyridyl, benzooxadiazolyl, dihydropyrimidinonyl, dihydrobenzofuranonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{C\text{-}heteroaryl}$ group is bonded by any atom of the parent $R_{C\text{-}heteroaryl}$ group substituted by hydrogen such that the new bond to the $R_{C\text{-}heteroaryl}$ group replaces the hydrogen atom and its bond, where heteroaryl is optionally substituted 1, 2, 3, or 4 groups that are independently:
(1) $C_1$–$C_6$ alkyl, optionally substituted with 1, 2, or 3 groups independently selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
(2) —OH,
(3) —$NO_2$,
(4) —F, —Cl, —Br, —I,
(5) —CO—OH,
(6) —C≡N,
(7) —$(CH_2)_{0-4}$—CO—$NR_{N-2}R_{N-3}$,
(8) —$(CH_2)_{0-4}$—CO—($C_1$–$C_{12}$ alkyl)
(9) —$(CH_2)_{0-4}$—CO—($C_2$–$C_{12}$ alkenyl with one, two or three double bonds),
(10) —$(CH_2)_{0-4}$—CO—($C_2$–$C_{12}$ alkynyl with one, two or three triple bonds),
(11) —$(CH_2)_{0-4}$—CO—($C_3$–$C_7$ cycloalkyl),
(12) —$(CH_2)_{0-4}$—CO—$R_{1\text{-}aryl}$ where $R_{1\text{-}aryl}$ is as defined above,
(13) —$(CH_2)_{0-4}$—CO—$R_{1\text{-}heteroaryl}$,
(14) —$(CH_2)_{0-4}$—CO—$R_{1\text{-}heterocycle}$,
(15) —$(CH_2)_{0-4}$—CO—$R_{N-4}$,
(16) —$(CH_2)_{0-4}$—CO—O—$R_{N-5}$,
(17) —$(CH_2)_{0-4}$—$SO_2$—$NR_{N-2}R_{N-3}$,
(18) —$(CH_2)_{0-4}$—SO—($C_1$–$C_8$ alkyl),
(19) —$(CH_2)_{0-4}$—$SO_2$-($C_1$–$C_{12}$ alkyl),
(20) —$(CH_2)_{0-4}$—$SO_2$-($C_3$–$C_7$ cycloalkyl),
(21) —$(CH_2)_{0-4}$—N(H or $R_{N-5}$)—CO—O—$R_{N-5}$,
(22) —$(CH_2)_{0-4}$—N(H or $R_{N-5}$)—CO—N($R_{N-5}$)$_2$,
(23) —$(CH_2)_{0-4}$—N—CS—N($R_{N-5}$)$_2$,
(24) —$(CH_2)_{0-4}$—N(—H or $R_{N-5}$)—CO—$R_{N-2}$,
(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO—($C_1$–$C_6$ alkyl)
(28) —$(CH_2)_{0-4}$—O—P(O)—$(OR_{100})_2$ where $R_{100}$ is —H or $C_1$–$C_4$ alkyl,
(29) —$(CH_2)_{0-4}$—O—CO—N($R_{N-5}$)$_2$,
(30) —$(CH_2)_{0-4}$—O—CS—N($R_{N-5}$)$_2$,
(31) —$(CH_2)_{0-4}$—O—($R_{N-5}$),
(32) —$(CH_2)_{0-4}$—O—($R_{N-5}$)—COOH,
(33) —$(CH_2)_{0-4}$—S—($R_{N-5}$),
(34) —$(CH_2)_{0-4}$—O—($C_1$–$C_6$ alkyl optionally substituted with one, two, three, four, or five of —F),
(35) $C_3$–$C_7$ cycloalkyl,
(36) $C_2$–$C_6$ alkenyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(38) —$(CH_2)_{0-4}$—N(—H or $R_{N-5}$)—$SO_2$—$R_{N-2}$,
(39) —$(CH_2)_{0-4}$-($C_3$–$C_7$ cycloalkyl)
(V) —$(CR_{C-x}R_{C-y})_{0-4}$—$R_{C\text{-}aryl}$—$R_{101}$—$R_{C\text{-}aryl}$,
(VI) —$(CR_{C-x}R_{C-y})_{0-4}$—$R_{C\text{-}aryl}$—$R_{101}$—$R_{C\text{-}heteroaryl}$,
(VII) —$(CR_{C-x}R_{C-y})_{0-4}$—$R_{C\text{-}heteroaryl}$—$R_{101}$—$R_{C\text{-}aryl}$, (VIII) —$(CR_{C-x}R_{C-y})_{0-4}$—$R_{C-heteroaryl}$—$R_{101}$—$R_{C-heteroaryl}$, (IX) —$(CR_{C-x}R_{C-y})_{0-4}$—$R_{C-aryl}$—$R_{101}$—$R_{1-heterocycle}$, (X) —$(CR_{C-x}R_{C-y})_{0-4}$—$R_{C-heteroaryl}$—$R_{101}$—$R_{1-heterocycle}$, (XI) —$(CR_{C-x}R_{C-y})_{0-4}$—$R_{1-heterocycle}$—$R_{101}$—$R_{C-aryl}$, (XII) —$(CR_{C-x}R_{C-y})_{0-4}$—$R_{1-heterocycle}$—$R_{101}$—$R_{C-heteroaryl}$, (XIII) —$(CR_{C-x}R_{C-y})_{0-4}$—$R_{1-heterocycle}$—$R_{101}$—$R_{1-heterocycle}$, wherein $R_{101}$ is a bond, $(CH_2)_{0-4}$, —O—, —NH—, or —$N(C_1$-$C_6$ alkyl)

(XIV) —$(CR_{C-x}R_{C-y})_{0-4}$—$R_{1-heterocycle}$, (XV) —[C $(R_{C-1})(R_{C-2})]_{1-3}$—CO—$N(R_{C-3})_2$ where $R_{C-1}$ and $R_{C-2}$ are the same or different and are selected from the group consisting of:
- (A) —H,
- (B) —$C_1$-$C_6$ alkyl, optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (C) $C_2$-$C_6$ alkenyl with one or two double bonds, optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (D) $C_2$-$C_6$ alkynyl optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (E) —$(CH_2)_{1-2}$—$S(O)_{0-2}$-$(C_1$-$C_6$ alkyl),
- (F) —$(CH_2)_{0-4}$—$C_3$-$C_7$ cycloalkyl, optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (G) —$(C_1$-$C_4$ alkyl)—$R_{1-aryl}$,
- (H) —$(C_1$-$C_4$ alkyl)—$R_{C-heteroaryl}$,
- (I) —$(C_1$-$C_4$ alkyl)—$R_{1-heterocycle}$,
- (J) —$R_{C-heteroaryl}$,
- (K) —$R_{1-heterocycle}$,
- (M) —$(CH_2)_{1-4}$—$R_{C-4}$—$(CH_2)_{0-4}R_{1-aryl}$ where $R_{C-4}$ is —O—, —S— or —$NR(C_1$-$C_6$ alkyl)—,
- (N) —$(CH_2)_{1-4}$—$R_{C-4}$—$(CH_2)_{0-4}$—$R_{C-heteroaryl}$,
- (O) —$R_{1-aryl}$, and where $R_{C-3}$ at each occurrence is independently:
- (A) —H,
- (B) —$C_1$-$C_6$ alkyl optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (C) $C_2$-$C_6$ alkenyl with one or two double bonds, optionally substituted with one, two or three substituents independently selected from the group consisting of $C_1$-$C_3$ alkyl, halogen, —OH, —SH, —C≡N, —$CF_3$, $C_1$-$C_6$ alkoxy, —O-phenyl, and —$NR_{1-a}R_{1-b}$,
- (D) $C_2$-$C_6$ alkynyl with one or two triple bonds, optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (E) —$(CH_2)_{0-4}$—$C_3$-$C_7$ cycloalkyl, optionally substituted with 1, 2, or 3 groups that are independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (F) —$R_{1-aryl}$,
- (G) —$R_{C-heteroaryl}$,
- (H) —$R_{1-heterocycle}$,
- (I) —$(C_1$-$C_4$ alkyl)—$R_{1-aryl}$,
- (J) —$(C_1$-$C_4$ alkyl)—$R_{C-heteroaryl}$,
- (K) —$(C_1$-$C_4$ alkyl)—$R_{1-heterocycle}$,
- (XVI) —$CH(R_{C-aryl})_2$,
- (XVII) —$CH(R_{C-heteroaryl})_2$,
- (XVIII) —$CH(R_{C-aryl}) (R_{C-heteroaryl})$,
- (XIX) -cyclopentyl, -cyclohexyl, or -cycloheptyl ring fused to $R_{C-aryl}$ or $R_{C-heteroaryl}$ or $R_{1-heterocycle}$ where $R_{C-aryl}$ or $R_{C-heteroaryl}$ or $R_{1-heterocycle}$ are as defined above where one carbon of cyclopentyl, cyclohexyl, or -cycloheptyl is optionally replaced with NH, $NR_{N-5}$, O, $S(=O)_{0-2}$, and where cyclopentyl, cyclohexyl, or cycloheptyl can be optionally substituted with one or two —$C_1$-$C_3$ alkyl, —F, —OH, —SH, —C≡N, —$CF_3$, $C_1$-$C_6$ alkoxy, =O, or —$NR_{1-a}R_{1-b}$,
- (XX) $C_2$-$C_{10}$ alkenyl optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (XXI) $C_2$-$C_{10}$ alkynyl optionally substituted with one, two or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$,
- (XXI) —$(CH_2)_{0-2}$—$CHR_{C-6}$—$(CH_2)_{0-1}$—$R_{C-aryl}$ wherein $R_{C-6}$ is —$(CH_2)_{0-6}$—OH,
- (XXII) —$(CH_2)_{0-1}$—$CHR_{C-6}$—$(CH_2)_{0-1}$—$R_{C-heteroaryl}$,
- (XXIII) —CH(—$R_{C-aryl}$ or $R_{C-heteroaryl}$)—CO—O ($C_1$-$C_4$ alkyl),
- (XXIV) —CH(—$CH_2$—OH)—CH(—OH)-alkyl—$NO_2$,
- (XXV) —$(C_1$-$C_6$ alkyl)—O—$(C_1$-$C_6$ alkyl)—OH,
- (XXVII) —$CH_2$—NH—$CH_2$—CH(—O—$CH_2$—$CH_3)_2$,
- (XXVIII) —H, and
- (XXIX) —$(CH_2)_{0-6}$—C (=$NR_{1-a}$) ($NR_{1-a}$—$R_{1-b}$) where $R_N$ is (I) $R_{N-1}$—$X_N$— where $X_N$ is selected from the group consisting of:
- (A) —CO—,
- (B) —$SO_2$—,
- (C) —$(CR'''R''')_{1-6}$ wherein R''' and R''' at each occurrence are the same or different and are —H or $C_1$-$C_4$ alkyl,
- (D) —CO—$(CR'''R''')_{1-6}$—$X_{N-1}$ wherein $X_{N-1}$ is selected from the group consisting of —O—, —S— and —NR''—,
- (E) a single bond, and
- (F) —CO—$(CR''R'')_{1-6}$—, where $R_{N-1}$ is selected from the group consisting of:
(A) $R_{N-aryl}$ wherein $R_{N-aryl}$ at each occurrence is independently phenyl; naphthyl; tetralinyl; indanyl; indenyl; dihydronaphthyl; or 6,7,8,9-tetrahydro-5H-benzo[a]cycloheptenyl; each of which is optionally substituted with one, two or three of the following substituents which can be the same or different and are:

(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$, wherein R$_{1-a}$ and R$_{1-b}$ at each occurrence are independently H or $C_1$–$C_6$ alkyl,
(2) —OH,
(3) —NO$_2$,
(4) —F, —Cl, —Br, —I,
(5) —CO$_2$H,
(6) —C≡N,
(7) —(CH$_2$)$_{0-4}$—CO—NR$_{N-2}$R$_{N-3}$ where R$_{N-2}$ and R$_{N-3}$ are the same or different and are selected from the group consisting of:
  (a) —H,
  (b) —$C_1$–$C_8$ alkyl optionally substituted with one substituent selected from the group consisting of:
    (i) —OH,
    (ii) —NH$_2$,
    (iii) phenyl,
  (c) —$C_1$–$C_8$ alkyl optionally substituted with 1, 2, or 3 groups that are independently —F, —Cl, —Br, or —I,
  (d) —$C_3$–$C_8$ cycloalkyl,
  (e) —($C_1$–$C_2$ alkyl)-($C_3$–$C_8$ cycloalkyl),
  (f) —($C_1$–$C_6$ alkyl)-O-($C_1$–$C_3$ alkyl),
  (g) —$C_2$–$C_6$ alkenyl,
  (h) —$C_2$–$C_6$ alkynyl,
  (i) —$C_1$–$C_6$ alkyl chain with one double bond and one triple bond,
  (j) —R$_{1-aryl}$, wherein R$_{1-aryl}$ at each occurrence is independently phenyl, naphthyl, indanyl, indenyl, dihydronaphthyl, or tetralinyl each of which is optionally substituted with 1, 2, 3, or 4 groups that are independently:
    (i) $C_1$–$C_6$ alkyl optionally substituted with one, two or three substituents independently selected from the group consisting of $C_1$–$C_3$ alkyl, —F, —Cl, —Br, —I, —OH, —SH, —NR$_{1-a}$R$_{1-b}$, —C≡N, —CF$_3$, and $C_1$–$C_3$ alkoxy,
    (ii) $C_2$–$C_6$ alkenyl with one or two double bonds, optionally substituted with one, two or three substituents independently selected from the group consisting of —F, —Cl, —OH, —SH, —C≡N, —CF$_3$, $C_1$–$C_3$ alkoxy, and —NR$_{1-a}$R$_{1-b}$,
    (iii) $C_2$–$C_6$ alkynyl optionally substituted with 1, 2, or 3 groups that are independently selected from the group consisting of —F, —Cl, —OH, —SH, —C≡N, —CF$_3$, $C_1$–$C_3$ alkoxy, and —NR$_{1-a}$R$_{1-b}$,
    (iv) —F, Cl, —Br and —I,
    (v) —$C_1$–$C_6$ alkoxy optionally substituted with 1, 2, or 3 —F,
    (vi) —NR$_{N-2}$R$_{N-3}$,
    (vii) —OH,
    (viii) —C≡N,
    (ix) $C_3$–$C_7$ cycloalkyl, optionally substituted with 1, 2, or 3 groups that are selected from the group consisting of —F, —Cl, —OH, —SH, —C≡N, —CF$_3$, $C_1$–$C_3$ alkoxy, and —NR$_{1-a}$R$_{1-b}$,
    (x) —CO-($C_1$–$C_4$ alkyl),
    (xi) —SO$_2$—NR$_{1-a}$R$_{1-b}$,
    (xii) —CO—NR$_{1-a}$R$_{1-b}$, or
    (xiii) —SO$_2$-($C_1$–$C_4$ alkyl),
  (k) —R$_{1-heteroaryl}$, wherein R$_{1-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide,
where the R$_{1-heteroaryl}$ group is optionally substituted with 1, 2, 3, or 4 groups that are independently:
  (i) $C_1$–$C_6$ alkyl optionally substituted with 1, 2, or 3 groups independently selected from the group consisting of $C_1$–$C_3$ alkyl, —F, —Cl, —Br, —I, —OH, —SH, —NR$_{1-a}$R$_{1-b}$, —C≡N, —CF$_3$, and $C_1$–$C_3$ alkoxy,
  (ii) $C_2$–$C_6$ alkenyl optionally substituted with 1, 2, or 3 groups that are independently —F, —Cl, —OH, —SH, —C≡N, —CF$_3$, $C_1$–$C_3$ alkoxy, or —NR$_{1-a}$R$_{1-b}$,
  (iii) $C_2$–$C_6$ alkynyl optionally substituted with 1, 2, or 3 groups that are independently —F, Cl, —OH, —SH, —C≡N, —CF$_3$, $C_1$–$C_3$ alkoxy, or —NR$_{1-a}$R$_{1-b}$,
  (iv) —F, —Cl, —Br and —I,
  (v) —$C_1$–$C_6$ alkoxy optionally substituted with one, two, or three —F,
  (vi) —(CH$_2$)$_{0-4}$—NR$_{N-2}$R$_{N-3}$,
  (vii) —OH,
  (viii) —C≡N,
  (ix) (CH$_2$)$_{0-4}$—$C_3$–$C_7$ cycloalkyl, optionally substituted with 1, 2, or 3 groups that are independently selected from the group consisting of —F, —Cl, —OH, —SH, —C≡N, —CF$_3$, $C_1$–$C_3$ alkoxy, and —NR$_{1-a}$R$_{1-b}$, (x) $(CH_2)_{0-4}$—CO-($C_1$-$C_6$ alkyl),
(xi) $(CH_2)_{0-4}$—$SO_2$—$NR_{N-2}R_{N-3}$,
(xii) $(CH_2)_{0-4}$—CO—$NR_{N-2}R_{N-3}$,
(xiii) $(CH_2)_{0-4}$—$SO_2$-($C_1$-$C_6$ alkyl),
(xiv) $(CH_2)_{0-4}$—N($R_{N-2}$)—$SO_2$—, and
(xv) $(CH_2)_{0-4}$—N($R_{N2}$)—C(O)—, (l) —$R_{1-heterocycle}$, wherein $R_{1-heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the $R_{1-heterocycle}$ group is bonded by any atom of the parent $R_{1-heterocycle}$ group substituted by hydrogen such that the new bond to the $R_{1-heterocycle}$ group replaces the hydrogen atom and its bond, where heterocycle is optionally substituted with 1, 2, 3, or 4 groups that are independently:

(a) $C_1$-$C_6$ alkyl optionally substituted with one, two or three substituents independently selected from the group consisting of $C_1$-$C_3$ alkyl, halogen, —OH, —SH, —$NR_{1-a}R_{1-b}$ —C≡N, —$CF_3$, and $C_1$-$C_3$ alkoxy, (b) $C_2$-$C_6$ alkenyl with one or two double bonds, optionally substituted with one, two or three substituents independently selected from the group consisting of —F, —Cl, —OH, —SH, —C_N, —$CF_3$, $C_1$-$C_3$ alkoxy, and —$NR_{1-a}R_{1-b}$ (c) $C_2$-$C_6$ alkynyl with one or two triple bonds, optionally substituted with one, two or three substituents independently selected from the group consisting of —F, —Cl, —OH, —SH, —C≡N, —$CF_3$, $C_1$-$C_3$ alkoxy, and —$NR_{1-a}R_{1-b}$ (d) halogen,
(e) $C_1$-$C_6$ alkoxy,
(f) —$C_1$-$C_6$ alkoxy optionally substituted with one, two, or three —F,
(g) —$NR_{N-2}R_{N-3}$,
(h) —OH,
(i) —C≡N,
(j) $(CH_2)_{0-4}$-($C_3$-$C_8$ cycloalkyl), optionally substituted with 1, 2, or 3 groups independently selected from the group consisting of —F, —Cl, —OH, —SH, —C≡N, —$CF_3$, $C_1$-$C_3$ alkoxy, and —$NR_{1-a}R_{1-b}$,
(k) —$(CH_2)_{0-4}$—CO—($C_1$-$C_4$ alkyl),
(l) —$(CH_2)_{0-4}$—$SO_2$—$NR_{1-a}R_{1-b}$,
(m) —$(CH_2)_{0-4}$—C—$NR_{1-a}R_{1-b}$,
(n) —$(CH_2)_{0-4}$—$SO_2$-($C_1$-$C_6$ alkyl), and
(o) =O,
(p) —$(CH_2)_{0-4}$—N($R_{N-2}$)—$SO_2$—
(q) —$(CH_2)_{0-4}$—N($R_{N-2}$)—C(O)—
(8) —$(CH_2)_{0-4}$—CO—($C_1$-$C_{12}$ alkyl),
(9) —$(CH_2)_{0-4}$—CO—($C_2$-$C_{12}$ alkenyl)
(10) —$(CH_2)_{0-4}$—CO—($C_2$-$C_{12}$ alkynyl)
(11) —$(CH_2)_{0-4}$—CO—($C_3$-$C_8$ cycloalkyl),
(12) —$(CH_2)_{0-4}$—CO—$R_{1-aryl}$,
(13) —$(CH_2)_{0-4}$—CO—$R_{1-heteroaryl}$,
(14) —$(CH_2)_{0-4}$—CO—$R_{1-heterocycle}$,
(15) —$(CH_2)_{0-4}$—CO—$R_{N-4}$ wherein $R_{N-4}$ is selected from the group consisting of phenyl, morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl, thienyl, pyrazolyl, pyridyl N-oxide, oxazolyl, thiazolyl, imidazolyl, and pyrrolidinyl where each group is optionally substituted with one, two, three, or four groups that are independently $C_1$-$C_6$ alkyl,
(16) —$(CH_2)_{0-4}$—CO—O—$R_{N-5}$ where $R_{N-5}$ is selected from the group consisting of;
  (a) $C_1$-$C_6$ alkyl,
  (b) —$(CH_2)_{0-2}$—($R_{1-aryl}$)
  (c) $C_2$-$C_6$ alkenyl,
  (d) $C_2$-$C_6$ alkynyl,
  (e) —$(CH_2)_{0-2}$—$C_3$-$C_8$ cycloalkyl,
  (f) —$(CH_2)_{0-2}$—($R_{1-heteroaryl}$), and
  (g) —$(CH_2)_{0-2}$—($R_{1-heterocycle}$)
(17) —$(CH_2)_{0-4}$—$SO_2$—$NR_{N-2}R_{N-3}$,
(18) —$(CH_2)_{0-4}$—SO—($C_1$-$C_8$ alkyl),
(19) —$(CH_2)_{0-4}$—$SO_2$-($C_1$-$C_{12}$ alkyl),
(20) —$(CH_2)_{0-4}$—$SO_2$-($C_3$-$C_8$ cycloalkyl),
(21) —$(CH_2)_{0-4}$—N(H or $R_{N-5}$)—CO—O—$R_{N-5}$,
(22) —$(CH_2)_{0-4}$—N(H or $R_{N-5}$)—CO—N($R_{N-5}$)$_2$,
(23) —$(CH_2)_{0-4}$—N—CS—N($R_{N-5}$)$_2$,
(24) —$(CH_2)_{0-4}$—N(H or $R_{N-5}$)—CO—$R_{N-2}$,
(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO—($C_1$-$C_6$ alkyl),
(28) —$(CH_2)_{0-4}$—O—P(O)—$(OR_{100})_2$ wherein $R_{100}$ at each occurrence is independently —H or $C_1$-$C_4$ alkyl,
(29) —$(CH_2)_{0-4}$—O—CO—N($R_{N-5}$)$_2$,
(30) —$(CH_2)_{0-4}$—O—CS—N($R_{N-5}$)$_2$,
(31) —$(CH_2)_{0-4}$—O—($R_{N-5}$),
(32) —$(CH_2)_{0-4}$—O—($R_{N-5}$)—COOH,
(33) —$(CH_2)_{0-4}$—S—($R_{N-5}$),
(34) —$(CH_2)_{0-4}$—O—($C_1$-$C_6$ alkyl optionally substituted with one, two, three, four, or five of —F),
(35) $C_3$-$C_8$ cycloalkyl,
(36) $C_2$-$C_6$ alkenyl optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$,
(37) $C_2$-$C_6$ alkynyl optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$,
(38) —$(CH_2)_{0-4}$—N(H or $R_{N-5}$)—$SO_2$—$R_{N-2}$,
(39) —$(CH_2)_{1-4}$-($C_3$-$C_8$ cycloalkyl), (B) —$R_{N-heteroaryl}$ where $R_{N-heteroaryl}$ is selected from the group consisting of: pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzisothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, imidazopyrazolyl, quinazolinonyl, pyrazopyridyl, benzooxadiazolyl, dihydropyrimidinonyl, and dihydrobenzfuranonyl, where the $R_{N\text{-}heteroaryl}$ group is bonded by any atom of the parent $R_{N\text{-}heteroaryl}$ group substituted by hydrogen such that the new bond to the $R_{N\text{-}heteroaryl}$ group replaces the hydrogen atom and its bond, where heteroaryl is optionally substituted with one, two, three, or four of:

(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$,
(2) —OH,
(3) —NO$_2$,
(4) —F, —Cl, —Br, —I,
(5) —CO$_2$H,
(6) —C≡N,
(7) —(CH$_2$)$_{0\text{-}4}$—CO—NR$_{N\text{-}2}$R$_{N\text{-}3}$,
(8) —(CH$_2$)$_{0\text{-}4}$—CO-(C$_1$–C$_{12}$ alkyl),
(9) —(CH$_2$)$_{0\text{-}4}$—CO—(C$_2$–C$_{12}$ alkenyl)
(10) —(CH$_2$)$_{0\text{-}4}$—CO—(C$_2$–C$_{12}$ alkynyl),
(11) —(CH$_2$)$_{0\text{-}4}$—CO—(C$_3$–C$_8$ cycloalkyl),
(12) —(CH$_2$)$_{0\text{-}4}$—CO—R$_{1\text{-}aryl}$,
(13) —(CH$_2$)$_{0\text{-}4}$—CO—R$_{1\text{-}heteroaryl}$,
(14) —(CH$_2$)$_{0\text{-}4}$—CO—R$_{1\text{-}heterocycle}$,
(15) —(CH$_2$)$_{0\text{-}4}$—CO—R$_{N\text{-}4}$,
(16) —(CH$_2$)$_{0\text{-}4}$—CO—O—R$_{N\text{-}5}$,
(17) —(CH$_2$)$_{0\text{-}4}$—SO$_2$—NR$_{N\text{-}2}$R$_{N\text{-}3}$,
(18) —(CH$_2$)$_{0\text{-}4}$—SO—(C$_1$–C$_8$ alkyl),
(19) —(CH$_2$)$_{0\text{-}4}$—SO$_2$-(C$_1$–C$_{12}$ alkyl),
(20) —(CH$_2$)$_{0\text{-}4}$—$_{SO2}$—(C$_3$–C$_8$ cycloalkyl),
(21) —(CH$_2$)$_{0\text{-}4}$—N(H or R$_{N\text{-}5}$)—CO—O—R$_{N\text{-}5}$,
(22) —(CH$_2$)$_{0\text{-}4}$—N(H or R$_{N\text{-}5}$)—CO—N(R$_{N\text{-}5}$)$_2$,
(23) —(CH$_2$)$_{0\text{-}4}$—N—CS—N(R$_{N\text{-}5}$)$_2$,
(24) —(CH$_2$)$_{0\text{-}4}$—N(—H or R$_{N\text{-}5}$)—CO—R$_{N\text{-}2}$,
(25) —(CH$_2$)$_{0\text{-}4}$—NR$_{N\text{-}2}$R$_{N\text{-}3}$,
(26) —(CH$_2$)$_{0\text{-}4}$R$_{N\text{-}4}$,
(27) —(CH$_2$)$_{0\text{-}4}$—O—CO—(C$_1$–C$_6$ alkyl),
(28) —(CH$_2$)$_{0\text{-}4}$—P(O)—(OR$_{100}$)$_2$,
(29) —(CH$_2$)$_{0\text{-}4}$—O—CO—N(R$_{N\text{-}5}$)$_2$,
(30) —(CH$_2$)$_{0\text{-}4}$—O—CS—N(R$_{N\text{-}5}$)$_2$,
(31) —(CH$_2$)$_{0\text{-}4}$—O—(R$_{N\text{-}5}$)
(32) —(CH$_2$)$_{0\text{-}4}$—O—(R$_{N\text{-}5}$)—COOH,
(33) —(CH$_2$)$_{0\text{-}4}$—S—(R$_{N\text{-}5}$),
(34) —(CH$_2$)$_{0\text{-}4}$—O—(C$_1$–C$_6$ alkyl optionally substituted with one, two, three, four, or five of —F),
(35) $C_3$–$C_8$ cycloalkyl,
(36) $C_2$–$C_6$ alkenyl optionally substituted with $C_1$–$C_3$ alkyl, —F, —Cl, —Br, —I, —OH, —SH, —C≡N, —CF$_3$, $C_1$–$C_3$ alkoxy, or —NR$_{1\text{-}a}$R$_{1\text{-}b}$,
(37) $C_2$–$C_6$ alkynyl optionally substituted with $C_1$–$C_3$ alkyl, —F, —Cl, —Br, —I, —OH, —SH, —C≡N, —CF$_3$, $C_1$–$C_3$ alkoxy, or —NR$_{1\text{-}a}$R$_{1\text{-}b}$,
(38) —(CH$_2$)$_{0\text{-}4}$—N(—H or R$_{N\text{-}5}$)—SO$_2$—R$_{N\text{-}2}$,
(39) —(CH$_2$)$_{1\text{-}4}$—C$_3$–C$_8$ cycloalkyl, (C) R$_{N\text{-}aryl}$—W—R$_{N\text{-}aryl}$,
(D) R$_{N\text{-}aryl}$—W—R$_{N\text{-}heteroaryl}$,
(E) R$_{N\text{-}aryl}$—W—R$_{1\text{-}heterocycle}$,
(F) R$_{N\text{-}heteroaryl}$—W—R$_{N\text{-}aryl}$,
(G) R$_{N\text{-}heteroaryl}$—W—R$_{N\text{-}heteroaryl}$,
(H) R$_{N\text{-}heteroaryl}$—W—R$_{N\text{-}1\text{-}heterocycle}$,
(I) R$_{N\text{-}heterocycle}$—W—R$_{N\text{-}aryl}$,
(J) R$_{N\text{-}heterocycle}$—W—R$_{N\text{-}heteroaryl}$,
(K) R$_{N\text{-}heterocycle}$—W—R$_{N\text{-}1\text{-}heterocycle}$,
where W is
(1) —(CH$_2$)$_{1\text{-}4}$—,
(2) —O—,
(3) —S(O)$_{0\text{-}2}$—,
(4) —N(R$_{N\text{-}5}$)—,
(5) —CO—; or
(6) a bond;

(II) —CO—(C$_1$–C$_{10}$ alkyl) wherein the alkyl is optionally substituted with one two or three substituents independently selected from the group consisting of:
(A) —OH,
(B) —C$_1$–C$_6$ alkoxy,
(C) —C$_1$–C$_6$ thioalkoxy,
(D) —CO—O—R$_{N\text{-}8}$ where
R$_{N\text{-}8}$ at each occurrence is independently —H, C$_1$–C$_6$ alkyl or -phenyl,
(E) —CO—NR$_{N\text{-}2}$R$_{N\text{-}3}$,
(F) —CO—R$_{N\text{-}4}$,
(G) —SO$_2$-(C$_1$–C$_8$ alkyl),
(H) —SO$_2$—NR$_{N\text{-}2}$R$_{N\text{-}3}$,
(I) —NH—CO—(C$_1$–C$_6$ alkyl),
(J) —NH—CO—O—R$_{N\text{-}8}$,
(K) —NR$_{N\text{-}2}$R$_{N\text{-}3}$,
(L) —R$_{N\text{-}4}$,
(M) —O—CO—(C$_1$–C$_6$ alkyl),
(N) —O—CO—NR$_{N\text{-}8}$R$_{N\text{-}8}$,
(O) —O—(C$_1$–C$_5$ alkyl)-COOH,
(P) —O—(C$_1$–C$_6$ alkyl optionally substituted with one, two, or three of —F, —Cl, —Br, —I),
(O) —NH—SO$_2$-(C$_1$–C$_6$ alkyl),
(R) halogen,
(S) —N(H or R$_{N\text{-}5}$)—SO$_2$—R$_{N\text{-}2}$,
(T) —N(H or R$_{N\text{-}5}$)—CO—(R$_{N\text{-}2}$), and
(U) —SO$_2$—R$_{N\text{-}2}$, (III) —CO—(C$_1$–C$_6$ alkyl)-O-(C$_1$–C$_6$ alkyl) wherein each alkyl is unsubstituted or independently substituted with one, two, or three substituents selected from the group consisting of
(A) —OH,
(B) —C$_1$–C$_6$ alkoxy,
(C) —C$_1$–C$_6$ thioalkoxy,
(D) —CO—O—R$_{N\text{-}8}$,
(E) —CO—NR$_{N\text{-}2}$R$_{N\text{-}3}$,
(F) —CO—R$_{N\text{-}4}$,
(G) —SO$_2$(C$_1$–C$_8$ alkyl), (H) —$SO_2$—$NR_{N-2}R_{N-3}$,
(I) —NH—CO—($C_1$-$C_6$ alkyl),
(J) —NH—CO—O—$R_{N-8}$,
(K) —$NR_{N-2}R_{N-3}$,
(L) —$R_{N-4}$,
(M) —O—CO—($C_1$-$C_6$ alkyl),
(N) —O—CO—$NR_{N-8}R_{N-8}$,
(O) —O—($C_1$-$C_5$ alkyl)-$CO_2H$,
(P) —O—($C_1$-$C_6$ alkyl optionally substituted with one, two, or three groups that are independently —F, —Cl, —Br, or —I)
(Q) —NH—$SO_2$-($C_1$-$C_6$ alkyl),
(R) halogen,
(S) —N(H or $R_{N-5}$)—$SO_2$—$R_{N-2}$,
(T) —N(H or $R_{N-5}$)—CO-($R_{N-2}$), and
(U) —$SO_2$—$R_{N-2}$, (IV) —CO—($C_1$-$C_6$ alkyl)-S-($C_1$-$C_6$ alkyl) wherein each alkyl is unsubstituted or substituted with one, two, or three of substituents independently selected from the group consisting of:
(A) —OH,
(B) —$C_1$-$C_6$ alkoxy,
(C) —$C_1$-$C_6$ thioalkoxy,
(D) —CO—O—$R_{N-8}$,
(E) —CO—$NR_{N-2}R_{N-3}$,
(F) —CO—$R_{N-4}$,
(G) —$SO_2$($C_1$-$C_8$ alkyl),
(H) —$SO_2$—$NR_{N-2}R_{N-3}$,
(I) —NH—CO—($C_1$-$C_6$ alkyl),
(J) —NH—CO—O—$R_{N-8}$,
(K) —$NR_{N-2}R_{N-3}$,
(L) —$R_{N-4}$,
(M) —O—CO—($C_1$-$C_6$ alkyl),
(N) —O—CO—$NR_{N-8}R_{N-8}$,
(O) —O—($C_1$-$C_5$ alkyl)-COOH,
(P) —O—($C_1$-$C_6$ alkyl optionally substituted with one, two, or three groups that are independently —F, —Cl, —Br, or —I),
(Q) —NH—$SO_2$-($C_1$-$C_6$ alkyl),
(R) halogen,
(S) —N(H or $R_{N-5}$)—$SO_2$—$R_{N-2}$,
(T) —N(H or $R_{N-5}$)—CO—($R_{N-2}$), and
(U) —$SO_2$—$R_{N-2}$, (V) —CO—CH (—($CH_2$)$_{0-2}$—O—$R_{N-10}$)—($CH_2$)$_{0-2}$—$R_{N-aryl}$/$R_{N-heteroaryl}$), wherein $R_{N-10}$ is selected from the group consisting of:
(A) —H,
(B) $C_1$-$C_6$ alkyl,
(C) $C_3$-$C_8$ cycloalkyl,
(D) $C_2$-$C_6$ alkenyl with one double bond,
(E) $C_2$-$C_6$ alkynyl with one triple bond,
(F) $R_{1-aryl}$,
(G) $R_{N-heteroaryl}$,
(H) $R_{N-heterocycle}$, (VI) —CO—($C_3$-$C_8$ cycloalkyl) where the cycloalkyl group is optionally substituted with one or two substituents independently selected from the group consisting of:
(A) —($CH_2$)$_{0-4}$—OH,
(B) —($CH_2$)$_{0-4}$—$C_1$-$C_6$ alkoxy,
(C) —($CH_2$)$_{0-4}$—$C_1$-$C_6$ thioalkoxy,
(D) —($CH_2$)$_{0-4}$—CO—O—$R_{N-8}$,
(E) —($CH_2$)$_{0-4}$—CO—$NR_{N-2}R_{N-3}$,
(F) —($CH_2$)$_{0-4}$—CO—$R_{N-4}$,
(G) —($CH_2$)$_{0-4}$—$SO_2$-($C_1$-$C_8$ alkyl),
(H) —($CH_2$)$_{0-4}$—$SO_2$—$NR_{N-2}R_{N-3}$,
(I) —($CH_2$)$_{0-4}$—NH—CO—($C_1$-$C_6$ alkyl),
(J) —NH—CO—O—$R_{N-8}$,
(K) —($CH_2$)$_{0-4}$—$NR_{N-2}R_{N-3}$,
(L) —($CH_2$)$_{0-4}$—$R_{N-4}$,
(M) —O—CO—($C_1$-$C_6$ alkyl),
(N) —O—CO—$NR_{N-8}R_{N-8}$,
(O) —O—($C_1$-$C_6$ alkyl)-$CO_2H$,
(P) —O—($C_1$-$C_6$ alkyl optionally substituted with one, two, or three groups that are independently selected from —F, —Cl, —Br, and —I),
(Q) —NH—$SO_2$—($C_1$-$C_6$ alkyl),
(R) halogen,
(S) —N(H or $R_{N-5}$)—$SO_2$—$R_{N-2}$, and
(T) —N(H or $R_{N-5}$)—CO—($R_{N-2}$), and
(U) —$SO_2$—$R_{N-2}$;

where $R_1$ and $R_2$ are independently H, aryl, heteroaryl, or
(I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —$CF_3$, $C_1$-$C_3$ alkoxy, —$NR_{1-a}R_{1-b}$ where $R_{1-a}$ and $R_{1-b}$ are independently —H or $C_1$-$C_6$ alkyl, and —OC=O $NR_{1-a}R_{1-b}$,
(II) —$CH_2$—S(O)$_{0-2}$-($C_1$-$C_6$ alkyl),
(III) —$CH_2$—$CH_2$—S(O)$_{0-2}$-($C_1$-$C_6$ alkyl),
(IV) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(V) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(VI) —($CH_2$)$_{n1}$—($R_{1-aryl}$) where $n_1$ is zero or one and where $R_{1-aryl}$ is phenyl, 1-naphthyl, 2-naphthyl and indanyl, indenyl, dihydronaphthalyl, or tetralinyl optionally substituted with one, two, three or four of the following substituents on the aryl ring:
(A) $C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$,
(B) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(C) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(D) —F, Cl, —Br or —I,
(F) —$C_1$-$C_6$ alkoxy optionally substituted with one, two or three of —F,
(G) —$NR_{N-2}R_{N-3}$ where $R_{N-2}$ and $R_{N-3}$ are as defined below,
(H) —OH,
(I) —C≡N,
(J) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$,
(K) —CO—($C_1$-$C_4$ alkyl),
(L) —$SO_2$—$NR_{1-a}R_{1-b}$, (M) —CO—NR$_{1-a}$R$_{1-b}$,
(N) —SO$_2$-(C$_1$–C$_4$ alkyl),
(VII) —(CH$_2$)—(R$_{1-heteroaryl}$) where n$_1$ is as defined above and where R$_{1-heteroaryl}$ is selected from the group consisting of:
pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl., benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, where the R$_{1-heteroaryl}$ group is bonded to —(CH$_2$)$_{n1}$— by any ring atom of the parent R$_{N-heteroaryl}$ group substituted by hydrogen such that the new bond to the R$_{1-heteroaryl}$ group replaces the hydrogen atom and its bond, where heteroaryl is optionally substituted with one, two, three or four:
(1) C$_1$–C$_6$ alkyl optionally substituted with one, two or three substituents selected from the group consisting of C$_1$–C$_3$ alkyl, —F, —Cl, —Br, —I, —OH, —SH, —C≡N, —CF$_3$, C$_1$–C$_3$ alkoxy, and —NR$_{1-a}$R$_{1-b}$,
(2) C$_2$–C$_6$ alkenyl with one or two double bonds, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(3) C$_2$–C$_6$ alkynyl with one or two triple bonds, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(4) —F, Cl, —Br or —I,
(6) —C$_1$–C$_6$ alkoxy optionally substituted with one, two, or three of —F,
(7) —NR$_{N-2}$R$_{N-3}$ where R$_{N-2}$ and R$_{N-3}$ are as defined below,
(8) —OH,
(9) —C≡N,
(10) C$_3$–C$_7$ cycloalkyl, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(11) —CO—(C$_1$–C$_4$ alkyl),
(12) —SO$_2$—NR$_{1-a}$R$_{1-b}$,
(13) —CO—NR$_{1-a}$R$_{1-b}$, or
(14) —SO$_2$-(C$_1$–C$_4$ alkyl), with the proviso that when n$_1$ is zero R$_{1-heteroaryl}$ is not bonded to the carbon chain by nitrogen, or
(VIII) —(CH$_2$)$_{n1}$—(R$_{1-heterocycle}$) where n$_1$ is as defined above and R$_{1-heterocycle}$ is selected from the group consisting of:
morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homomorpholinyl S-oxide, homothiomorpholinyl S,S-dioxide, oxazolidinonyl, dihydropyrazolyl, dihydropyrrolyl dihydropyrazinyl dihydropyridinyl dihydropyrimidinyl, dihydrofuryl, dihydropyranyl, tetrahydrothienyl S-oxide, tetrahydrothienyl S,S-dioxide, homothiomorpholinyl S-oxide,
where the R$_{1-heterocycle}$ group is bonded by any atom of the parent R$_{1-heterocycle}$ group substituted by hydrogen such that the new bond to the R$_{1-heterocycle}$ group replaces the hydrogen atom and its bond, where heterocycle is optionally substituted with one, two, three or four:
(1) C$_1$–C$_6$ alkyl optionally substituted with one, two or three substituents selected from the group consisting of C$_1$–C$_3$ alkyl, —F, —Cl, —Br, —I, —OH, —SH, —C≡N, —CF$_3$, C$_1$–C$_3$ alkoxy, and —NR$_{1-a}$R$_{1-b}$,
(2) C$_2$–C$_6$ alkenyl with one or two double bonds, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(3) C$_2$–C$_6$ alkynyl with one or two triple bonds, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(4) —F, Cl, —Br, or —I,
(5) C$_1$–C$_6$ alkoxy,
(6) —C$_1$–C$_6$ alkoxy optionally substituted with one, two, or three —F,
(7) —NR$_{N-2}$R$_{N-3}$ where R$_{N-2}$ and R$_{N-3}$ are as defined below,
(8) —OH,
(9) —C≡N,
(10) C$_3$–C$_7$ cycloalkyl, optionally substituted with one, two or three substituents selected from the group consisting of —F, —Cl, —OH, —SH, —C≡N, —CF$_3$, C$_1$–C$_3$ alkoxy, and —NR$_{1-a}$R$_{1-b}$,
(11) —CO—(C$_1$–C$_4$ alkyl),
(12) —SO$_2$—NR$_{1-a}$R$_{1-b}$,
(13) —CO—NR$_{1-a}$R$_{1-b}$,
(14) —SO$_2$-(C$_1$–C$_4$ alkyl),
(15) =O, with the proviso that when n$_1$ is zero R$_{1-heterocycle}$ is not bonded to the carbon chain by nitrogen; and
where R$_{20}$ is H or C$_{1-6}$ alkyl or alkenyl.
In alternative broad aspect, the invention provides compounds of formula I, wherein each of the R$_2$ groups (I)–

(VIII) is attached to the nitrogen carrying $R_{20}$ by —Z—, wherein Z is —C(O)—, —CO$_2$ or —SO$_2$—.

The invention also provides compounds, compositions, kits, and methods for inhibiting beta-secretase-mediated cleavage of amyloid precursor protein (APP). More particularly, the compounds, compositions, and methods of the invention are effective to inhibit the production of A-beta peptide and to treat and/or prevent any human or veterinary disease or condition associated with a pathological form of A-beta peptide.

The invention also include methods of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, frontotemporal dementias with parkinsonism (FTDP), dementia associated with progressive supranuclear palsy, dementia associated with cortical basal degeneration, or diffuse Lewy body type of Alzheimer's disease and who is in need of such treatment, which includes administration of a therapeutically effective amount of a compound of formula (I), or a pharmaceutically acceptable salt or ester thereof.

The compounds of the invention possess beta-secretase inhibitory activity. The inhibitory activities of the compounds of the invention is readily demonstrated, for example, using one or more of the assays described herein or known in the art.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The invention also includes a pharmaceutical composition which includes a compound of formula (I), or a pharmaceutically acceptable salt or ester thereof.

The invention also includes the use of a compound of formula (I), or a pharmaceutically acceptable salt or ester thereof, for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of the formula hereinabove can be employed where the disease is Alzheimer's disease.

In an embodiment, this use of a compound of the formula hereinabove can help prevent or delay the onset of Alzheimer's disease.

In an embodiment, this use of a compound of the formula hereinabove can be employed where the disease is mild cognitive impairment.

In an embodiment, this use of a compound of the formula hereinabove can be employed where the disease is Down's syndrome.

In an embodiment, this use of a compound of the formula hereinabove can be employed where the disease is Hereditary Cerebral Hemorrhage with Amyloidosis of the Dutch-Type.

In an embodiment, this use of a compound of the formula hereinabove can be employed where the disease is cerebral amyloid angiopathy.

In an embodiment, this use of a compound of the formula hereinabove can be employed where the disease is degenerative dementias.

In an embodiment, this use of a compound of the formula hereinabove can be employed where the disease is diffuse Lewy body type of Alzheimer's disease.

In an embodiment, this use of a substituted amine employs a pharmaceutically acceptable salt selected from the group consisting of salts of the following acids hydrochloric, hydrobromic, hydroiodic, nitric, sulfuric, phosphoric, citric, methanesulfonic, $CH_3$—$(CH_2)_1$—COOH where n is 0 through 4, HOOC—$(CH_2)_n$—COOH where n is as defined above, HOOC—CH=CH—COOH, and phenyl-COOH.

The invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of a compound of formula (I), or a pharmaceutically acceptable salt or ester thereof.

The invention also includes a method for inhibiting beta-secretase activity, including exposing said beta-secretase to an effective inhibitory amount of a compound of formula, or a pharmaceutically acceptable salt or ester thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The invention also includes a method for inhibiting cleavage of amyloid precursor protein (APP), in a reaction mixture, at a site between Met596 and AspS97, numbered for the APP-695 amino acid isotype; or at a corresponding site of an isotype or mutant thereof, including exposing said reaction mixture to an effective inhibitory amount of a compound of formula (I), or a pharmaceutically acceptable salt or ester thereof.

In an embodiment, this method employs a cleavage site: between Met652 and Asp653, numbered for the APP-751 isotype; between Met671 and Asp672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in Vitro.

In an embodiment, this method exposes said reaction mixture in a cell.

In an embodiment, this method exposes said reaction mixture in an animal cell.

In an embodiment, this method exposes said reaction mixture in a human cell.

The invention also includes a method for inhibiting production of amyloid beta peptide (A beta) in a cell, including administering to said cell an effective inhibitory amount of a compound of formula (I), or a pharmaceutically acceptable salt or ester thereof.

In an embodiment, this method includes administering to an animal.

In an embodiment, this method includes administering to a human.

The invention also includes a method for inhibiting the production of beta-amyloid plaque in an animal, including administering to said animal an effective inhibitory amount of a compound of formula (I), or a pharmaceutically acceptable salt or ester thereof.

In an embodiment, this method includes administering to a human.

The invention also includes a method for treating or preventing a disease characterized by beta-amyloid deposits in the brain including administering to a patient an effective therapeutic amount of a hydroxyethylene compound of formula (I), or a pharmaceutically acceptable salt or ester thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The invention also includes a composition including beta-secretase complexed with a compound of formula (I), or a pharmaceutically acceptable salt or ester thereof.

The invention also includes a method for producing a beta-secretase complex including exposing beta-secretase to a compound of formula (I), or a pharmaceutically acceptable salt or ester thereof, in a reaction mixture under conditions suitable for the production of said complex.

In an embodiment, this method employs exposing in vitro.

In an embodiment, this method employs a reaction mixture that is a cell.

The invention also includes a component kit including component parts capable of being assembled, in which at least one component part includes a compound of formula I enclosed in a container.

In an embodiment, this component kit includes lyophilized compound, and at least one further component part includes a diluent.

The invention also includes a container kit including a plurality of containers, each container including one or more unit dose of a compound of formula (I), or a pharmaceutically acceptable salt or ester thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The invention also includes an agent kit including a compound of formula (I), or a pharmaceutically acceptable salt or ester thereof; and one or more therapeutic agent selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The invention also includes a composition including: a compound of formula (I), or a pharmaceutically acceptable salt or ester thereof; and an inert diluent or edible carrier.

In an embodiment, this composition includes a carrier that is an oil.

The invention also includes a composition including: a compound of formula (I), or a pharmaceutically acceptable salt or ester thereof; and a binder, excipient, disintegrating agent, lubricant, or gildant.

The invention also includes a composition including: a compound of formula (I), or a pharmaceutically acceptable salt or ester thereof; disposed in a cream, ointment, or patch.

DETAILED DESCRIPTION OF THE INVENTION

As noted above, the invention provides compounds of formula

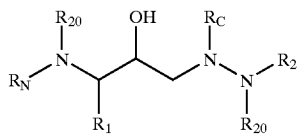

(I)

where $R_N$, $R_C$, $R_1$, $R_2$ and $R_{20}$ are as defined above, and pharmaceutically acceptable salts and esters thereof.

In a preferred embodiment, the invention provides for compounds of formula II:

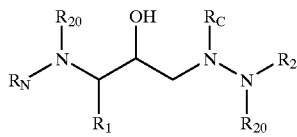

(II)

or a pharmaceutically acceptable salt thereof,
where Rc is
(I) —$C_1$–$C_{10}$ alkyl optionally substituted with one, two or three groups independently selected from the group consisting of $C_1$–$C_3$ alkyl, halogen, —OH, —SH, —C≡N, —$CF_3$, $C_1$–$C_6$ alkoxy, —O-phenyl, —$NR_{1-a}R_{1-b}$, —OC=O $NR_{1-a}R_{1-b}$, —S(=O)$_{0-2}$ $R_{1-a}$, —$NR_{1-a}$C=O $NR_{1-a}R_{1-b}$, —C=O $NR_{1-a}R_{1-b}$, and —S (=O)$_2$ $NR_{1-a}$ $R_{1-b}$ wherein
$R_{1-a}$ and $R_{1-b}$ at each occurrence are independently H or $C_1$–$C_6$ alkyl,
(II) —$(CH_2)_{0-3}$-($C_3$–$C_8$) cycloalkyl where cycloalkyl can be optionally substituted with one, two or three substituents independently selected from the group consisting of $C_1$–$C_3$ alkyl, halogen, —OH, —SH, —C≡N, —$CF_3$, $C_1$–$C_6$ alkoxy, —O-phenyl, —$CO_2H$, —$CO_2$-($C_1$–$C_4$ alkyl), and —$NR_{1-a}R_{1-b}$,
(III) —$(CR_{C-x}R_{C-y})_{0-4}$—$R_{C-aryl}$ where $R_{C-x}$ and $R_{C-y}$ are independently selected from the group consisting of
—H, $C_1$–$C_4$ alkyl optionally substituted with 1 or 2 —OH,
$C_1$–$C_4$ alkoxy optionally substituted with 1, 2, or 3 halogen,
—$(CH_2)_{0-4}$—$C_3$–$C_8$ cycloalkyl,
$C_2$–$C_6$ alkenyl containing one or two double bonds,
$C_2$–$C_6$ alkynyl containing one or two triple bonds, and phenyl, or
$R_{C-x}$ and $R_{C-y}$ are taken together with the carbon to which they are attached to form a carbocycle of three, four, five, six or seven carbon atoms, where one carbon atom is optionally replaced by a group selected from —O—, —S—, —$SO_2$—, —$NR_{N-2}$— and $R_{C-aryl}$, wherein
$R_{C-aryl}$ is phenyl, which is optionally substituted with 1, 2, or 3 groups that are independently:
(1) $C_1$–$C_6$ alkyl, optionally substituted with one, two or three substituents selected from the group consisting of $C_1$–$C_3$ alkyl, halogen, —OH, —SH, —C≡N, —$CF_3$, $C_1$–$C_3$ alkoxy, and —$NR_{1-a}R_{1-b}$,
(2) —OH,
(3) —$NO_2$,
(4) halogen,
(5) —$CO_2H$,
(6) —C≡N,
(7) —$(CH_2)_{0-4}$—CO—$NR_{N-2}R_{N-3}$ where $R_{N-2}$ and $R_{N-3}$ are independently selected from the group consisting of:
(a) —H,
(b) —$C_1$–$C_6$ alkyl optionally substituted with one substituent selected from the group consisting of:
(i) —OH, and
(ii) —$NH_2$,
(c) —$C_1$–$C_6$ alkyl optionally substituted with 1, 2, or 3 groups that are independently —F, —Cl, —Br, —I, or OH,
(d) —$C_3$–$C_7$ cycloalkyl,
(e) —($C_1$–$C_2$ alkyl)-($C_3$–$C_7$ cycloalkyl),
(f) —($C_1$–$C_6$ alkyl)-O-($C_1$–$C_3$ alkyl),
(g) —$C_2$–$C_6$ alkenyl
(h) —$C_2$–$C_6$ alkynyl
(i) —$C_1$–$C_6$ alkyl chain with one double bond and one triple bond,
(j) —$R_{1-aryl}$ wherein $R_{1-aryl}$ at each occurrence is independently phenyl, naphthyl, indanyl, indenyl, dihydronaphthyl, or tetralinyl each of which is optionally substituted with 1, 2, 3, or 4 groups that are independently:
(i) $C_1$–$C_6$ alkyl optionally substituted with one, two or three substituents independently selected from the group consisting of $C_1$–$C_3$ alkyl, —F, —Cl, —Br, I, —OH, —SH, —$NR_{1-a}$ $R_{1-b}$, —C≡N, —$CF_3$, and $C_1$–$C_3$ alkoxy,
(ii) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$,
(iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$,
(iv) —F, Cl, —Br and —I,
(v) —$C_1$–$C_6$ alkoxy optionally substituted with 1, 2, or 3-F, (vi) —$NR_{N-2}R_{N-3}$,
(vii) —OH,
(viii) —C≡N,
(ix) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1-a}R_{1-b}$,
(x) —CO—($C_1$–$C_4$ alkyl),
(xi) —$SO_2$—$NR_{1-a}R_{1-b}$,
(xii) —CO—$NR_{1-a}R_{1-b}$, or
(xiii) —$SO_2$-($C_1$–$C_4$ alkyl), (k) —$R_{1-heteroaryl}$ wherein $R_{1-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1-heteroaryl}$ group is optionally substituted with 1, 2, 3, or 4 groups that are independently:
(i) $C_1$–$C_6$ alkyl optionally substituted with 1, 2, or 3 groups independently selected from the group consisting of $C_1$–$C_3$ alkyl, —F, —Cl, —Br, —I, —OH, —SH, —$NR_{1-a}R_{1-b}$, —C≡N, —$CF_3$, and $C_1$–$C_3$ alkoxy,
(ii) $C_2$–$C_6$ alkenyl optionally substituted with 1, 2, or 3 groups that are independently —F, —Cl, —OH, —SH, —C≡N, —$CF_3$, $C_1$–$C_3$ alkoxy, and —$NR_{1-a}R_{1-b}$,
(iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$,
(iv) —F, —Cl, —Br and —I,
(v) —$C_1$–$C_3$ alkoxy optionally substituted with one, two, or three —F,
(vi) —$(CH_2)_{0-4}$—$NR_{N-2}R_{N-3}$,
(vii) —OH,
(viii) —C≡N,
(ix) $(CH_2)_{0-4}$—$C_3$–$C_7$ cycloalkyl, optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$,
(x) $(CH_2)_{0-4}$—CO—($C_1$–$C_6$ alkyl),
(xi) $(CH_2)_{0-4}$—$SO_2$—$NR_{N-2}R_{N-3}$,
(xii) $(CH_2)_{0-4}$—CO—$R_{N-2}R_{N-3}$,
(xiii) $(CH_2)_{0-4}$—$SO_2$-($C_1$–$C_6$ alkyl),
(xiv) $(CH_2)_{0-4}$—N($R_{N-2}$)—$SO_2$—, and
(xv) $(CH_2)_{0-4}$—N($R_{N-2}$)—C(O)—, (8) —$(CH_2)_{0-4}$—CO—($C_1$–$C_{12}$ alkyl),
(9) —$(CH_2)_{0-4}$—CO—($C_2$–$C_{12}$ alkenyl)
(10) —$(CH_2)_{0-4}$—CO—($C_2$–$C_{12}$ alkynyl),
(11) —$(CH_2)_{0-4}$—CO—$(CH_2)_{0-4}$ ($C_3$–$C_7$ cycloalkyl),
(12) —$(CH_2)_{0-4}$—CO—$R_{1-aryl}$,
(13) —$(CH_2)_{0-4}$—CO—$R_{1-heteroaryl}$,
(14) —$(CH_2)_{0-4}$—CO—$R_{1-heterocycle}$ wherein $R_{1-heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the $R_{1-heterocycle}$ group is bonded by any atom of the parent $R_{1-heterocycle}$ group substituted by hydrogen such that the new bond to the $R_{1-heterocycle}$ group replaces the hydrogen atom and its bond, where heterocycle is optionally substituted with 1, 2, 3, or 4 groups that are independently:
(a) $C_1$–$C_6$ alkyl optionally substituted with one, two or three substituents independently selected from the group consisting of $C_1$–$C_3$ alkyl, halogen, —OH, —SH, —$NR_{1-a}R_{1-b}$ —C≡N, —$CF_3$, and $C_1$–$C_3$ alkoxy,
(b) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$,
(c) $C_2$–$C_6$ alkynyl with one or two triple bonds, optionally substituted with one, two or three substituents independently selected from the group consisting of —F, —Cl, —OH, —SH, —C≡N, —CF$_3$, C$_1$–C$_3$ alkoxy, and —NR$_{1-b}$R$_{1-b}$,
(d) halogen,
(e) C$_1$–C$_6$ alkoxy,
(f) —C$_1$–C$_6$ alkoxy optionally substituted with one, two, or three —F,
(g) —NR$_{N-2}$R$_{N-3}$,
(h) —OH,
(i) —C≡N,
(j) (CH$_2$)$_{0-4}$-(C$_3$–C$_7$ cycloalkyl), optionally substituted with 1, 2, or 3 groups independently selected from the group consisting of —F, —Cl, —OH, —SH, —C≡N, —CF$_3$, C$_1$–C$_3$ alkoxy, and —NR$_{1-a}$R$_{1-b}$,
(k) —(CH$_2$)$_{0-4}$—CO—(C$_1$–C$_4$ alkyl),
(l) —(CH$_2$)$_{0-4}$—SO$_2$—NR$_{1-a}$R$_{1-b}$,
(m) —(CH$_2$)$_{0-4}$—CO—NR$_{1-a}$R$_{1-b}$,
(n) —(CH$_2$)$_{0-4}$—SO$_2$-(C$_1$–C$_6$ alkyl), and
(o) =O,
(p) —(CH$_2$)$_{0-4}$—N(R$_{N-2}$)—SO$_2$—,
(q) —(CH$_2$)$_{0-4}$—N(R$_{N-2}$)—C(O)—,
(15) —(CH$_2$)$_{0-4}$—CO—R$_{N-4}$ wherein
R$_{N-4}$ at each occurrence is independently selected from the group consisting of morpholinyl, thiomorpholinyl, pyrrolidinonyl, pyrrolyl, pyrazolyl, thienyl, pyridyl N-oxide, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with 1, 2, 3, or 4 groups that are independently C$_1$–C$_6$ alkyl,
(16) —(CH$_2$)$_{0-4—CO2}$—R$_{N5}$ where
R$_{N-5}$ at each occurrence is independently selected from the group consisting of:
(a) C$_1$–C$_6$ alkyl,
(b) —(CH$_2$)$_{0-2}$—(R$_{1-aryl}$),
(c) C$_2$–C$_6$ alkenyl,
(d) C$_2$–C$_6$ alkynyl,
(e) C$_3$–C$_7$ cycloalkyl, and
(f) —(CH$_2$)$_{0-4}$—(R$_{1-heteroaryl}$),
(17) —(CH$_2$)$_{0-4}$—SO$_2$—NR$_{N-2}$R$_{N-3}$,
(18) —(CH$_2$)$_{0-4}$—SO—(C$_1$–C$_8$ alkyl),
(19) —(CH$_2$)$_{0-4}$—SO$_2$-(C$_1$–C$_{12}$ alkyl),
(20) —(CH$_2$)$_{0-4}$—SO$_2$-(C$_3$–C$_7$ cycloalkyl),
(21) —(CH$_2$)$_{0-4}$—N(H or R$_{N-5}$)—CO$_2$—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$–C$_6$ alkyl),
(28) —(CH$_2$)$_{0-4}$—O—P(O)—(OR$_{100}$)$_2$ where R$_{100}$ is independently H or C$_1$–C$_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$)
(34) —(CH$_2$)$_{0-4}$—O—(C$_1$–C$_6$ alkyl) wherein the alkyl group is optionally substituted with one, two, three, four, or five substituents independently selected from the group consisting of F, Cl, Br, and I,
(35) —(CH$_2$)$_{0-4}$-(C$_3$–C$_8$ cycloalkyl),
(36) C$_2$–C$_6$ alkenyl optionally substituted with C$_1$–C$_3$ alkyl, halogen, —OH, —SH, —C—N, —CF$_3$, C$_1$–C$_3$ alkoxy, or —NR$_{1-a}$R$_{1-b}$,
(37) C$_2$–C$_6$ alkynyl optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$, and
(38) —(CH$_2$)$_{0-4}$—N(—H or R$_{N-5}$)—SO$_2$—R$_{N-2}$;
(IV) —(CR$_{C-x}$R$_{C-y}$)$_{0-4}$—R$_{C-heteroaryl}$ wherein R$_{C-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzoisothiazolyl, benzimidazolyl, benzofuranyl, furanyl, thienyl, pyrrolyl, oxadiazolyl, thiadiazolyl, triazolyl, tetrazolyl, oxazolopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, imidazopyrazolyl, quinazolinonyl, pyrazopyridyl, benzooxadiazolyl, dihydropyrimidinonyl, dihydrobenzofuranonyl,
where the R$_{C-heteroaryl}$ group is bonded by any atom of the parent R$_{C-heteroaryl}$ group substituted by hydrogen such that the new bond to the R$_{C-heteroaryl}$ group replaces the hydrogen atom and its bond, where heteroaryl is optionally substituted 1, 2, 3, or 4 groups that are independently:
(1) C$_1$–C$_6$ alkyl, optionally substituted with 1, 2, or 3 groups independently selected from the group consisting of C$_1$–C$_3$ alkyl, —F, —Cl, —Br, —I, —OH, —SH, —C≡N, —CF$_3$, C$_1$–C$_3$ alkoxy, and —NR$_{1-a}$R$_{1-b}$,
(2) —OH,
(3) —NO$_2$,
(4) —F, —Cl, —Br, —I,
(5) —CO—OH,
(6) —C≡N,
(V) C$_2$–C$_{10}$ alkenyl optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(VI) C$_2$–C$_{10}$ alkynyl optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(VII) —(C$_1$–C$_6$ alkyl)-O-(C$_1$–C$_6$ alkyl)-OH,
(VIII) —CH$_2$—NH—CH$_2$—CH(—O—CH$_2$—CH$_3$)$_2$,
(IX) —(CH$_2$)$_{0-6}$—C(=NR$_{1-a}$)(NR$_{1-a}$R$_{1-b}$);
where R$_N$ is
(I) R$_{N-1}$—X$_N$— where X$_N$ is —CO—, and where R$_{N-1}$ is selected from the group consisting of:

(A) phenyl, which is optionally substituted with one, two or three of the following substituents which can be the same or different and are:
  (1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$, wherein R$_{1\text{-}a}$ and R$_{1\text{-}b}$ at each occurrence are independently H or $C_1$–$C_6$ alkyl,
  (2) —OH,
  (3) —NO$_2$,
  (4) —F, —Cl, —Br, —I,
  (5) —CO$_2$H,
  (6) —C≡N,
  (7) —(CH$_2$)$_{0\text{-}4}$—CO—NR$_{N\text{-}2}$R$_{N\text{-}3}$ where R$_{N\text{-}2}$ and R$_{N\text{-}3}$ are the same or different and are selected from the group consisting of:
    (a) —H,
    (b) —$C_1$–$C_8$ alkyl optionally substituted with one substituent selected from the group consisting of:
      (i) —OH,
      (ii) —NH$_2$,
      (iii) phenyl,
    (c) —$C_1$–$C_8$ alkyl optionally substituted with 1, 2, or 3 groups that are independently —F, —Cl, —Br, or —I,
    (d) —$C_3$–$C_8$ cycloalkyl,
    (e) —($C_1$–$C_2$ alkyl)-($C_3$–$C_8$ cycloalkyl),
    (f) —($C_1$–$C_6$ alkyl)-O-($C_1$–$C_3$ alkyl),
    (g) —$C_2$–$C_6$ alkenyl,
    (h) —$C_2$–$C_6$ alkynyl,
    (i) —$C_1$–$C_6$ alkyl chain with one double bond and one triple bond,
    (j) —R$_{1\text{-}aryl}$, wherein R$_{1\text{-}aryl}$ at each occurrence is independently phenyl, naphthyl, indanyl, indenyl, dihydronaphthyl, or tetralinyl each of which is optionally substituted with 1, 2, 3, or 4 groups that are independently:
      (i) $C_1$–$C_6$ alkyl optionally substituted with one, two or three substituents independently selected from the group consisting of $C_1$–$C_3$ alkyl, —F, —Cl, —Br, —I, —OH, —SH, —NR$_{1\text{-}a}$R$_{1\text{-}b}$, —C≡N, —CF$_3$, and $C_1$–$C_3$ alkoxy,
      (ii) $C_2$–$C_6$ alkenyl with one or two double bonds, optionally substituted with one, two or three substituents independently selected from the group consisting of —F, —Cl, —OH, —SH, —C≡N, —CF$_3$, $C_1$–$C_3$ alkoxy, and —NR$_{1\text{-}a}$R$_{1\text{-}b}$,
      (iii) $C_2$–$C_6$ alkynyl optionally substituted with 1, 2, or 3 groups that are independently selected from the group consisting of —F, —Cl, —OH, —SH, —C≡N, —CF$_3$, $C_1$–$C_3$ alkoxy, and —NR$_{1\text{-}a}$R$_{1\text{-}b}$,
      (iv) —F, Cl, —Br and —I,
      (v) —$C_1$–$C_6$ alkoxy optionally substituted with 1, 2, or 3 —F,
      (vi) —NR$_{N\text{-}2}$R$_{N\text{-}3}$,
      (vii) —OH,
      (viii) —C≡N,
      (ix) $C_3$–$C_7$ cycloalkyl, optionally substituted with 1, 2, or 3 groups that are selected from the; group consisting of —F, —Cl, —OH, —SH, —C≡N, —CF$_3$, $C_1$–$C_3$ alkoxy, and —NR$_{1\text{-}a}$R$_{1\text{-}b}$,
      (x) —CO-($C_1$–$C_4$ alkyl),
      (xi) —SO$_2$—NR$_{1\text{-}a}$R$_{1\text{-}b}$,
      (xii) —CO—NR$_{1\text{-}a}$R$_{1\text{-}b}$, or
      (xiii) —SO$_2$-($C_1$–$C_4$ alkyl),
    (k) —R$_{1\text{-}heteroaryl}$, wherein R$_{1\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide,
    where the R$_{1\text{-}heteroaryl}$ group is optionally substituted with 1, 2, 3, or 4 groups that are independently:
      (i) $C_1$–$C_6$ alkyl optionally substituted with 1, 2, or 3 groups independently selected from the group consisting of $C_1$–$C_3$ alkyl, —F, —Cl, —Br, —I, —OH, —SH, —NR$_{1\text{-}a}$R$_{1\text{-}b}$, —C≡N, —CF$_3$, and $C_1$–$C_3$ alkoxy,
      (ii) $C_2$–$C_6$ alkenyl optionally substituted with 1, 2, or 3 groups that are independently —F, —Cl, —OH, —SH, —C≡N, —CF$_3$, $C_1$–$C_3$ alkoxy, or —NR$_{1\text{-}a}$R$_{1\text{-}b}$,
      (iii) $C_2$–$C_6$ alkynyl optionally substituted with 1, 2, or 3 groups that are independently —F, —Cl, —OH, —SH, —C≡N, —CF$_3$, $C_1$–$C_3$ alkoxy, or —NR$_{1\text{-}a}$R$_{1\text{-}b}$,
      (iv) —F, —Cl, —Br and —I,
      (v) —$C_1$–$C_6$ alkoxy optionally substituted with one, two, or three —F,
      (vi) —(CH$_2$)$_{0\text{-}4}$—NR$_{N\text{-}2}$R$_{N\text{-}3}$,
      (vii) —OH,
      (viii) —C≡N,
      (ix) (CH$_2$)$_{0\text{-}4}$—$C_3$–$C_7$ cycloalkyl, optionally substituted with 1, 2, or 3 groups that are independently selected from the group consisting of —F, —Cl, —OH, —SH, —C≡N, —CF$_3$, C$_1$–C$_3$ alkoxy, and —NR$_{1-a}$R$_{1-b}$,
  (x) (CH$_2$)$_{0-4}$—CO—(C$_1$–C$_6$ alkyl),
  (xi) (CH$_2$)$_{0-4}$—SO$_2$—NR$_{N-2}$R$_{N-3}$,
  (xii) (CH$_2$)$_{0-4}$—CO—NR$_{N-2}$R$_{N-3}$,
  (xiii) (CH$_2$)$_{0-4}$—SO$_2$-(C$_1$–C$_6$ alkyl),
  (xiv) (CH$_2$)$_{0-4}$—N(R$_{N-2}$)—SO$_2$—, and
  (xv) (CH$_2$)$_{0-4}$—N(R$_{N-2}$)—C(O)—,
(l) —R$_{1\text{-}heterocyle}$, wherein R$_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the R$_{1\text{-}heterocycle}$ group is bonded by any atom of the parent R$_{1\text{-}heterocycle}$ group substituted by hydrogen such that the new bond to the R$_{1\text{-}heterocycle}$ group replaces the hydrogen atom and its bond, where heterocycle is optionally substituted with 1, 2, 3, or 4 groups that are independently:
(a) C$_1$–C$_6$ alkyl optionally substituted with one, two or three substituents independently selected from the group consisting of C$_1$–C$_3$ alkyl, halogen, —OH, —SH, —NR$_{1-a}$R$_{1-b}$ —C≡N, —CF$_3$, and C$_1$–C$_3$ alkoxy,
(b) C$_2$–C$_6$ alkenyl with one or two double bonds, optionally substituted with one, two or three substituents independently selected from the group consisting of —F, —Cl, —OH, —SH, —C≡N, —CF$_3$, C$_1$–C$_3$ alkoxy, and —NR$_{1-a}$R$_{1-b}$,
(c) C$_2$–C$_6$ alkynyl with one or two triple bonds, optionally substituted with one, two or three substituents independently selected from the group consisting of —F, —Cl, —OH, —SH, —C≡N, —CF$_3$, C$_1$–C$_3$ alkoxy, and —NR$_{1-a}$R$_{1-b}$,
(d) halogen,
(e) C$_1$–C$_6$ alkoxy,
(f) —C$_1$–C$_6$ alkoxy optionally substituted with one, two, or three —F,
(g) —NR$_{N-2}$R$_{N-3}$,
(h) —OH,
(i) —C≡N,
(j) (CH$_2$)$_{0-4}$-(C$_3$–C$_8$ cycloalkyl), optionally substituted with 1, 2, or 3 groups independently selected from the group consisting of —F, —Cl, —OH, —SH, —C≡N, —CF$_3$, C$_1$–C$_3$ alkoxy, and —NR$_{1-a}$R$_{1-b}$,
(k) —(CH$_2$)$_{0-4}$—CO—(C$_1$–C$_4$ alkyl),
(l) —(CH$_2$)$_{0-4}$—SO$_2$—NR$_{1-a}$R$_{1-b}$,
(m) —(CH$_2$)$_{0-4}$—CO—NR$_{1-a}$R$_{1-b}$,
(n) —(CH$_2$)$_{0-4}$—SO$_2$-(C$_1$–C$_6$ alkyl), and
(o) =O,
(p) —(CH$_2$)$_{0-4}$—N(R$_{N-2}$)—SO$_2$—,
(q) —(CH$_2$)$_{0-4}$—N(R$_{N-2}$)—C(O)—,
(8) —(CH$_2$)$_{0-4}$—CO—(C$_1$–C$_{12}$ alkyl),
(9) —(CH$_2$)$_{0-4}$—CO—(C$_2$–C$_{12}$ alkenyl)
(10) —(CH$_2$)$_{0-4}$—CO—(C$_2$–C$_{12}$ alkynyl),
(11) —(CH$_2$)$_{0-4}$—CO—(C$_3$–C$_8$ cycloalkyl),
(12) —(CH$_2$)$_{0-4}$—CO—R$_{1\text{-}aryl}$,
(13) —(CH$_2$)$_{0-4}$—CO—R$_{1\text{-}heteroaryl}$,
(14) —(CH$_2$)$_{0-4}$—CO—R$_{1\text{-}heterocycle}$,
(15) —(CH$_2$)$_{0-4}$—CO—R$_{N-4}$ wherein R$_{N-4}$ is selected from the group consisting of phenyl, morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl, thienyl, pyrazolyl, pyridyl N-oxide, oxazolyl, thiazolyl, imidazolyl, and pyrrolidinyl where each group is optionally substituted with one, two, three, or four groups that are independently C$_1$–C$_6$ alkyl,
(16) —(CH$_2$)$_{0-4}$—CO—O—R$_{N-5}$ where R$_{N-5}$ is selected from the group consisting of:
  (a) C$_1$–C$_6$ alkyl,
  (b) —(CH$_2$)$_{0-2}$—(R$_{1\text{-}aryl}$)
  (c) C$_2$–C$_6$ alkenyl,
  (d) C$_2$–C$_6$ alkynyl,
  (e) —(CH$_2$)$_{0-2}$—C$_3$–C$_8$ cycloalkyl,
  (f) —(CH$_2$)$_{0-2}$—(R$_{1\text{-}heteroaryl}$), and
  (g) —(CH$_2$)$_{0-2}$—(R$_{1\text{-}heterocycle}$)
(17) —(CH$_2$)$_{0-4}$—SO$_2$—NR$_{N-2}$R$_{N-3}$,
(18) —(CH$_2$)$_{0-4}$—SO—(C$_1$–C$_8$ alkyl),
(19) —(CH$_2$)$_{0-4}$—SO$_2$-(C$_1$–C$_{12}$ alkyl),
(20) —(CH$_2$)$_{0-4}$—SO$_2$-(C$_3$–C$_8$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$–C$_6$ alkyl),
(28) —(CH$_2$)$_{0-4}$—O—P(O)—(OR$_{100}$)$_2$ wherein R$_{100}$ at each occurrence is independently —H or C$_1$–C$_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—(C$_1$–C$_6$ alkyl optionally substituted with one, two, three, four, or five of —F),
(35) C$_3$–C$_8$ cycloalkyl,
(36) C$_2$–C$_6$ alkenyl optionally substituted with C$_1$–C$_3$ alkyl, —F, —Cl, —Br, —I, —OH, —SH, —C≡N, —CF$_3$, C$_1$–C$_3$ alkoxy, or NR$_{1-a}$R$_{1-b}$,
(37) C$_2$–C$_6$ alkynyl optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$,
(38) —(CH$_2$)$_{0-4}$—N(H or R$_{N-5}$)—SO$_2$—R$_{N-2}$,
(39) —(CH$_2$)$_{1-4}$-(C$_3$–C$_8$ cycloalkyl),
(B) —R$_{N\text{-}heteroaryl}$ where R$_{N\text{-}heteroaryl}$ is selected from the group consisting of pyridinyl, indolyl, indolinyl, isoindolyl, imidazolyl, isoxazolyl, oxazolyl, thiazolyl, indolizinyl and isochromanyl,
where the R$_{N\text{-}heteroaryl}$ group is bonded by any atom of the parent R$_{N\text{-}heteroaryl}$ group substituted by hydrogen such that the new bond to the R$_{N\text{-}heteroaryl}$ group replaces the hydrogen atom and its bond, where heteroaryl is optionally substituted with one, two, three, or four of:
  (1) C$_1$–C$_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$,
(2) —OH,
(3) —NO$_2$,
(4) —F, —Cl, —Br, —I,
(5) —CO$_2$H,
(6) —C≡N,
(7) —(CH$_2$)$_{0-4}$—CO—NR$_{N-2}$R$_{N-3}$,
(8) —(CH$_2$)$_{0-4}$—CO—($C_1$–$C_{12}$ alkyl),
(9) —(CH$_2$)$_{0-4}$—CO—($C_2$–$C_{12}$ alkenyl),
(10) —(CH$_2$)$_{0-4}$—CO—($C_2$–$C_{12}$ alkynyl),
(11) —(CH$_2$)$_{0-4}$—CO—($C_3$–$C_8$ cycloalkyl),
(12) —(CH$_2$)$_{0-4}$—CO—R$_{1-aryl}$,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$,
(16) —(CH$_2$)$_{0-4}$—CO—O—R$_{N-5}$,
(17) —(CH$_2$)$_{0-4}$—SO$_2$—NR$_{N-2}$R$_{N-3}$,
(18) —(CH$_2$)$_{0-4}$—SO—($C_1$–$C_8$ alkyl),
(19) —(CH$_2$)$_{0-4}$—SO$_2$—($C_1$–$C_{12}$ alkyl),
(20) —(CH$_2$)$_{0-4}$—SO$_2$—($C_3$–$C_8$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$, (26) —(CH$_2$)$_{0-4}$—R$_{N-4}$,
(27) —(CH$_2$)$_{0-4}$—O—CO—($C_1$–$C_6$ alkyl)
(28) —(CH$_2$)$_{0-4}$—O—P(O)—(OR$_{100}$)$_2$,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—($C_1$–$C_6$ alkyl optionally substituted with one, two, three, four, or five of —F),
(35) $C_3$–$C_8$ cycloalkyl,
(36) $C_2$–$C_6$ alkenyl optionally substituted with $C_1$–$C_3$ alkyl, —F, —Cl, —Br, —I, —OH, —SH, —C≡N, —CF$_3$, $C_1$–$C_3$ alkoxy, or —NR$_{1-a}$R$_{1-b}$,
(37) $C_2$–$C_6$ alkynyl optionally substituted with $C_1$–$C_3$ alkyl, —F, —Cl, —Br, —I, —OH, —SH, —C≡N, —CF$_3$, $C_1$–$C_3$ alkoxy, or —NR$_{1-a}$R$_{1-b}$,
(38) —(CH$_2$)$_{0-4}$—N(—H or R$_{N-5}$)—SO$_2$—R$_{N-2}$,
(39) —(CH$_2$)$_{1-4}$—$C_3$–$C_8$ cycloalkyl,
(C) R$_{1-aryl}$—W—R$_{N-aryl}$,
(D) R$_{N-aryl}$—W—R$_{N-heteroaryl}$,
(E) R$_{N-aryl}$—W—R$_{1-heterocycle}$,
(F) R$_{N-heteroaryl}$—W—R$_{N-aryl}$,
(G) R$_{N-heteroaryl}$—W—R$_{N-heteroaryl}$,
(H) R$_{N-heteroaryl}$—W—R$_{N-1-heterocycle}$,
(I) R$_{N-heterocycle}$—W—R$_{N-aryl}$,
(J) R$_{N-heterocycle}$—W—R$_{N-heteroaryl}$,
(K) R$_{N-heterocycle}$—W—R$_{N-1-heterocycle}$,
where W is
(7) —(CH$_2$)$_{1-4}$—,
(8) —O—,
(9) —S(O)$_{0-2}$—,
(10) —N(R$_{N-5}$)—,
(11) —CO—; or
(12) a bond;
(II) —CO—($C_1$–$C_6$ alkyl)-M-($C_1$–$C_6$ alkyl), where M is S, SO or SO$_2$, and wherein each alkyl is unsubstituted or substituted with one, two, or three of substituents independently selected from the group consisting of:
(A) —NH—CO—($C_1$–$C_6$ alkyl),
(B) —NH—CO—O—R$_{N-8}$,
(C) —NR$_{N-2}$R$_{N-3}$;
where R$_1$ is
—(CH$_2$)$_{n1}$-phenyl, where n$_1$ is zero or one, and which is optionally substituted with one, two, three or four of the following substituents on the phenyl ring:
(A) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$,
(B) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,
(C) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,
(D) —F, Cl, —Br or —I,
(F) —$C_1$–$C_6$ alkoxy optionally substituted with one, two or three of —F,
(G) —NR$_{N-2}$R$_{N-3}$ where R$_{N-2}$ and R$_{N-3}$ are as defined below,
(H) —OH,
(I) —C≡N,
(J) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,
(K) —CO—($C_1$–$C_4$ alkyl),
(L) —SO$_2$—NR$_{1-a}$R$_{1-b}$,
(M) —CO—NR$_{1-a}$R$_{1-b}$,
(N) —SO$_2$-($C_1$–$C_4$ alkyl); and
where R$_2$ is
(I) —(Z)-$C_1$–$C_6$ alkyl, where Z is a bond, —C(O), —CO$_2$— or —SO$_2$—, wherein the alkyl group is optionally substituted with one, two or three substituents selected from the group consisting of $C_1$–$C_3$ alkyl, $C_1$–$C_7$ alkyl (optionally substituted with $C_1$–$C_3$ alkyl and $C_1$–$C_3$ alkoxy), —F, —Cl, —Br, —I, —OH, —SH, —C≡N, —CF$_3$, $C_1$–$C_3$ alkoxy, —NR$_{1-a}$R$_{1-b}$ where R$_{1-a}$ and R$_{1-b}$ are independently —H or $C_1$–$C_6$ alkyl, and —OC=O NR$_{1-a}$R$_{1-b}$,
(II) —(Z)—CH$_2$—S(O)$_{0-2}$-($C_1$–$C_6$ alkyl),
(III) —(Z)—CH$_2$—CH$_2$—S(O)$_{0-2}$-($C_1$–$C_6$ alkyl),
(IV) —(Z)-$C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,
(V) —(Z)-$C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,
(VI) —(Z)—(CH$_2$)$_{n1}$—(R$_{1-aryl}$), where Z is a bond, CO, CO$_2$ or SO$_2$, where n, is zero or one and where R$_{1-aryl}$ is phenyl, 1-naphthyl, 2-naphthyl and indanyl, indenyl, dihydronaphthalyl, or tetralinyl optionally substituted with one, two, three or four of the following substituents on the aryl ring:
(A) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$, (B) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$, (C) $C_2$–$C_6$ alkynyl with one or two triple bonds, optionally substituted with one., two or three substituents selected from the group consisting of —F, —Cl, —OH, —SH, —C≡N, —CF$_3$, $C_1$–$C_3$ alkoxy, and —NR$_{1-a}$R$_{1-b}$, (D) —F, Cl, —Br or —I, (F) —$C_1$–$C_6$ alkoxy optionally substituted with one, two or three of —F, (G) —NR$_{N-2}$R$_{N-3}$ where R$_{N-2}$ and R$_{N-3}$ are as defined below, (H) —OH, (I) —C≡N, (J) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$, (K) —CO—($C_1$–$C_4$ alkyl), (L) —SO$_2$—NR$_{1-a}$R$_{1-b}$, (M) —CO—NR$_{1-a}$R$_{1-b}$, (N) —SO$_2$-($C_1$–$C_4$ alkyl), (VII) —(Z)—(CH$_2$)$_{n1}$—(R$_{1-heteroaryl}$) where n$_1$ is as defined above and where R$_{1-heteroaryl}$ is selected from the group consisting of:

pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, where the R$_{1-heteroaryl}$ group is bonded to —(CH$_2$)$_{n1}$— by any ring atom of the parent RN-heteroaryl group substituted by hydrogen such that the new bond to the R$_{1-heteroaryl}$ group replaces the hydrogen atom and its bond, where heteroaryl is optionally substituted with one, two, three or four of:

(1) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$, (2) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$, (3) $C_2$–$C_6$ alkynyl with one or two triple bonds, optionally substituted with one, two or three substituents selected from the group consisting of —F, —Cl, —OH, —SH, —C≡N, CF$_3$, $C_1$–$C_3$ alkoxy, and —NR$_{1-a}$R$_{1-b}$, (4) —F, Cl, —Br or —I, (6) —$C_1$–$C_6$ alkoxy optionally substituted with one, two, or three of —F, (7) —NR$_{N-2}$R$_{N-3}$ where R$_{N-2}$ and R$_{N-3}$ are as defined below, (8) —OH, (9) —C≡N,

(10) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$,

(11) —CO—($C_1$–$C_4$ alkyl),

(12) —SO$_2$—NR$_{1-a}$R$_{1-b}$,

(13) —CO—NR$_{1-a}$R$_{1-b}$, or

(14) —SO$_2$-($C_1$–$C_4$ alkyl), with the proviso that when n$_1$ is zero R$_{1-heteroaryl}$ is not bonded to the carbon chain by nitrogen, or (VIII) —(Z)—(CH$_2$)$_{n1}$—(R$_{1-heterocycle}$) where n$_1$ is as defined above and R$_{1-heterocycle}$ is selected from the group consisting of:

morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homomorpholinyl S-oxide, homothiomorpholinyl S,S-dioxide, oxazolidinonyl, dihydropyrazolyl, dihydropyrrolyl, dihydropyrazinyl dihydropyridinyl dihydropyrimidinyl, dihydrofuryl, dihydropyranyl, tetrahydrothienyl S-oxide, tetrahydrothienyl S,S-dioxide, homothiomorpholinyl S-oxide, where the R$_{1-heterocycle}$ group is bonded by any atom of the parent R$_{1-heterocycle}$ group substituted by hydrogen such that the new bond to the R$_{1-heterocycle}$ group replaces the hydrogen atom and its bond, where heterocycle is optionally substituted with one, two, three or four:

(1) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$, (2) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$, (3) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$, (4) —F, Cl, —Br, or —I, (5) $C_1$–$C_6$ alkoxy, (6) —$C_1$–$C_6$ alkoxy optionally substituted with one, two, or three —F,
(7) —$NR_{N-2}R_{N-3}$ where $R_{N-2}$ and $R_{N-3}$ are as defined below,
(8) —OH,
(9) —C≡N,
(10) $C_3$–$C_7$ cycloalkyl, optionally substituted with one, two or three substituents selected from the group consisting of —F, —Cl, —OH, —SH, —C≡N, —$CF_3$, $C_1$–$C_3$ alkoxy, and —$NR_{1-a}R_{1-b}$,
(11) —CO—($C_1$–$C_4$ alkyl),
(12) —$SO_2$—$NR_{1-a}R_{1-b}$,
(13) —CO—$NR_{1-a}R_{1-b}$,
(14) —$SO_2$-($C_1$–$C_4$ alkyl),
(15) =O, with the proviso that when $n_1$ is zero $R_{1-heterocycle}$ is not bonded to the carbon chain by nitrogen; and
where $R_{20}$ is H or $C_{1-6}$ alkyl or alkenyl.

In another preferred embodiment relative to formula II, Rc is —$(CR_{C-x}R_{C-y})_{0-4}$—$R_{C-aryl}$ where $R_{C-x}$ and $R_{C-y}$ are independently selected from the group consisting of
—H,
$C_1$–$C_4$ alkyl optionally substituted with 1 or 2 —OH,
$C_1$–$C_4$ alkoxy optionally substituted with 1, 2, or 3 halogen,
—$(CH_2)_{0-4}$—$C_3$–$C_8$ cycloalkyl,
$C_2$–$C_6$ alkenyl containing one or two double bonds,
$C_2$–$C_6$ alkynyl containing one or two triple bonds, and phenyl, or
$R_{C-x}$ and $R_{C-y}$ are taken together with the carbon to which they are attached to form a carbocycle of three, four, five, six or seven carbon atoms, where one carbon atom is optionally replaced by a group selected from —O—, —S—, —$SO_2$—, —$NR_{N-2}$— and $R_{C-aryl}$, wherein RC-arylis phenyl, which is optionally substituted with 1, 2, or 3 groups that are independently:
(1) $C_1$–$C_6$ alkyl, optionally substituted with one, two or three substituents selected from the group consisting of $C_1$–$C_3$ alkyl, halogen, —OH, —SH, —C≡N, —$CF_3$, $C_1$–$C_3$ alkoxy, and —$NR_{1-a}R_{1-b}$,
(2) —OH,
(3) —$NO_2$,
(4) halogen,
(5) —$CO_2H$,
(6) —C≡N.

In yet another preferred embodiment, Rc is —$(CR_{C-x}R_{C-y})_{0-4}$—$R_{C-aryl}$ where $R_{C-x}$ and $R_{C-y}$ are independently selected from the group consisting of
—H,
$C_1$–$C_4$ alkyl optionally substituted with 1 or 2 —OH,
$C_1$–$C_4$ alkoxy optionally substituted with 1, 2, or 3 halogen,
—$(CH_2)_{0-4}$—$C_3$–$C_8$ cycloalkyl,
$C_2$–$C_6$ alkenyl containing one or two double bonds,
$C_2$–$C_6$ alkynyl containing one or two triple bonds, and phenyl, or
$R_{C-x}$ and $R_{C-y}$ are taken together with the carbon to which they are attached to form a carbocycle of three, four, five, six or seven carbon atoms, where one carbon atom is optionally replaced by a group selected from —O—, —S—, —$SO_2$—, —$NR_{N-2}$— and $R_{C-aryl}$, wherein
—$(CR_{C-x}R_{C-y})_{0-4}$—$R_{C-heteroaryl}$ is selected from the group consisting of pyridinyl, indolyl, indolinyl, isoindolyl, imidazolyl, isoxazolyl, oxazolyl, thiazolyl, indolizinyl and isochromanyl.

In another preferred embodiment relative to formula II, $R_C$ is the optionally substituted —$C_1$–$C_{10}$ alkyl groups as described above.

Preferred compounds of the formula II include, amongst others:

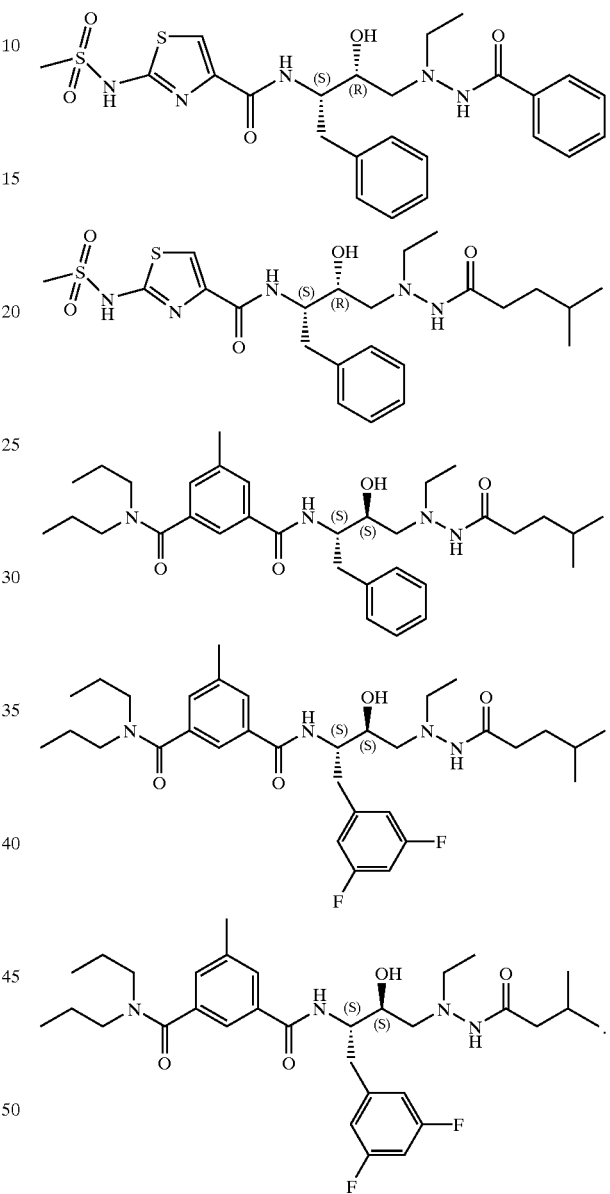

In another preferred embodiment, the invention provides compounds of formula III:

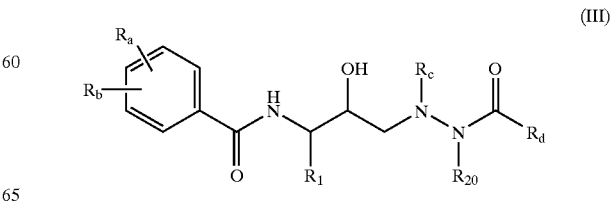

(III)

or a pharmaceutically acceptable salt thereof wherein $R_1$ represents phenyl ($C_1$–$C_6$)alkyl where the phenyl is optionally substituted with up to three groups independently selected from halogen, hydroxy, $C_1$–$C_2$ alkyl, $C_1$–$C_2$ alkoxy, amino, nitro, trifluoromethyl, cyano, mono ($C_1$–$C_2$)alkylamino and di ($C_1$–$C_2$) alkylamino;

$R_a$ and $R_b$ independently represent hydrogen, hydroxy, $C_1$–$C_6$ alkyl, $C_1$–$C_6$ alkoxy, $C_3$–$C_7$ cycloalkyl, $C_3$–$C_7$ cycloalkyl($C_1$–$C_6$)alkyl, $C_3$–$C_7$ cycloalkyl($C_1$–$C_6$)alkoxy, halogen, cyano, amino, mono($C_1$–$C_6$)alkylamino, di($C_1$–$C_6$)alkylamino, mono- or di($C_1$–$C_6$)alkylaminosulfonyl, $C_1$–$C_6$ alkyl sulfonylamino, $C_2$–$C_6$ alkenyl, $C_2$–$C_6$ alkynyl, trifluoromethyl, mono($C_1$–$C_6$)alkylaminocarbonyl, or di($C_1$–$C_6$)alkylaminocarbonyl and provided that not both $R_a$ and $R_b$ are hydrogen simultaneously;

$R_c$ represents hydrogen, or $C_1$–$C_6$ alkyl, $C_2$–$C_6$ alkenyl, or $C_2$–$C_6$ alkynyl each of which is optionally substituted with halogen, hydroxy, amino, cyano, or trifluoromethyl;

$R_d$ represents phenyl optionally substituted with hydroxy, $C_1$–$C_6$ alkyl, $C_1$–$C_6$ alkoxy, $C_3$–$C_7$ cycloalkyl, $C_3$–$C_7$ cycloalkyl($C_1$–$C_6$)alkyl, $C_3$–$C_7$ cycloalkyl($C_1$–$C_6$)alkoxy, halogen, cyano, amino, mono($C_1$–$C_6$)alkylamino, di($C_1$–$C_6$)alkylamino, mono- or di($C_1$–$C_6$)alkylaminosulfonyl, $c_1$–$C_6$ alkyl sulfonylamino, $C_2$–$C_6$ alkenyl, $C_2$–$C_6$ alkynyl; or $C_1$–$C_6$ alkyl optionally substituted with hydroxy, $C_1$–$C_6$ alkyl, $C_1$–$C_6$ alkoxy, halogen, cyano, amino, mono ($C_1$–$C_6$)alkylamino, di($C_1$–$C_6$)alkylamino, $C_2$–$C_6$ alkenyl, $C_2$–$C_6$ alkynyl, or trifluoromethyl; and $R_{20}$ represents hydrogen, $C_1$–$C_6$ alkyl, $C_2$–$C_6$ alkenyl, $C_2$–$C_6$ alkynyl, or trifluoromethyl.

In accordance witht this preferred embodiment, $R_1$ is benzyl where the phenyl is optionally substituted. Also preferably, the phenyl is substituted with one or two groups independently selected from halogen, hydroxy, $C_1$–$C_3$ alkyl, amino, and trifluoromethyl. In another preferred embodiment, phenyl is substituted with two groups independently selected from halogen, hydroxy, and trifluoromethyl. In an alternavie preferred embodiment, phenyl is disubstituted with halogen. Also preferably, $R_1$ is 3,5-difluorobenzyl. Preferably, $R_a$ and $R_b$ are different and $R_b$ represents mono- or di($C_1$–$C_6$) alkylaminocarbonyl. Also preferably, $R_d$ is phenyl optionally substituted with $C_1$–$C_3$ alkyl, $C_1$–$C_3$ alkoxy, amino, hydroxy, or halogen. In a further preferred embodiment, $R_c$ is hydrogen or $C_1$–$C_4$ alkyl. Also preferably, $R_c$ is $C_1$–$C_3$ alkyl. In yet another preferred embodiment, $R_d$ is $C_1$–$C_6$ lower alkyl and $R_{20}$ is hydrogen.

In another preferred embodiment, the invention provides for compounds of formula IV:

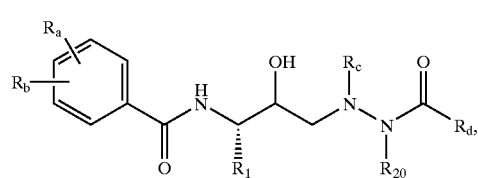

(IV)

where $R_a$, $R_b$, $R_1$ $R_c$, $R_{20}$ and $R_d$ are defined above for this preferred embodiment. In another preferred embodiment, $R_1$ is benzyl where the phenyl is disubstituted with chloro or fluoro; $R_c$ is $C_1$–$C_3$ alkyl; $R_d$ is $C_1$–$C_6$ lower alkyl; $R_{20}$ is hydrogen or $C_1$–$C_6$ alkyl; and $R_b$ is di($C_1$–$C_6$) alkylaminocarbonyl attached to the 3-position of the phenyl group.

In another preferred embodiment, the invention provides compounds of the formula V:

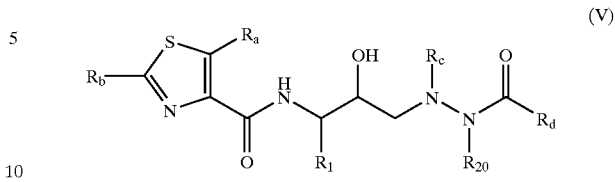

(V)

or a pharmaceutically acceptable salt thereof wherein $R_1$ represents phenyl ($C_1$–$C_6$)alkyl where the phenyl is optionally substituted with up to three groups independently selected from halogen, hydroxy, $C_1$–$C_2$ alkyl, $C_1$–$C_2$ alkoxy, amino, nitro, trifluoromethyl, cyano, mono ($C_1$–$C_2$)alkylamino and di ($C_1$–$C_2$) alkylamino;

$R_a$ and $R_b$ independently represent hydrogen, hydroxy, $C_1$–$C_6$ alkyl, $C_1$–$C_6$ alkoxy, $C_3$–$C_7$ cycloalkyl, $C_3$–$C_7$ cycloalkyl($C_1$–$C_6$)alkyl, $C_3$–$C_7$ cycloalkyl($C_1$–$C_6$) alkoxy, halogen, cyano, amino, mono($C_1$–$C_6$)alkylamino, di($C_1$–$C_6$)alkylamino, mono- or di($C_1$–$C_6$) alkylaminosulfonyl, $C_1$–$C_6$ alkyl sulfonylamino, $C_2$–$C_6$ alkenyl, $C_2$–$C_6$ alkynyl, trifluoromethyl, mono($C_1$–$C_6$) alkylaminocarbonyl, or di($C_1$–$C_6$) alkylaminocarbonyl and provided that not both $R_a$ and $R_b$ are hydrogen simultaneously;

$R_c$ represents hydrogen, or $C_1$–$C_6$ alkyl, $C_2$–$C_6$ alkenyl, or $C_2$–$C_6$ alkynyl each of which is optionally substituted with halogen, hydroxy, amino, cyano, or trifluoromethyl;

$R_d$ represents phenyl optionally substituted with hydroxy, $C_1$–$C_6$ alkyl, $C_1$–$C_6$ alkoxy, $C_3$–$C_7$ cycloalkyl, $C_3$–$C_7$ cycloalkyl ($C_1$–$C_6$)alkyl, $C_3$–$C_7$ cycloalkyl($C_1$–$C_6$)alkoxy, halogen, cyano, amino, mono($C_1$–$C_6$)alkylamino, di($C_1$–$C_6$)alkylamino, mono- or di($C_1$–$C_6$) alkylaminosulfonyl, $C_1$–$C_6$ alkyl sulfonylamino, $C_2$–$C_6$ alkenyl, $C_2$–$C_6$ alkynyl; or $C_1$–$C_6$ alkyl optionally substituted with hydroxy, $C_1$–$C_6$ alkyl, $C_1$–$C_6$ alkoxy, halogen, cyano, amino, mono ($C_1$–$C_6$)alkylamino, di($C_1$–$C_6$)alkylamino, $C_2$–$C_6$ alkenyl, $C_2$–$C_6$ alkynyl, or trifluoromethyl; and $R_{20}$ represents hydrogen, $C_1$–$C_6$ alkyl, $C_2$–$C_6$ alkenyl, $C_2$–$C_6$ alkynyl, or trifluoromethyl.

In accordance with this preferred embodiment, $R_1$ is benzyl where the phenyl is optionally substituted. Preferably, the phenyl is substituted with one or two groups independently selected from halogen, hydroxy, $C_1$–$C_3$ alkyl, amino, and trifluoromethyl. Also preferably, phenyl is substituted with two groups independently selected from halogen, hydroxy, and trifluoromethyl. Also preferably, phenyl is disubstituted with halogen. In another preferred embodiment, $R_1$ is 3,5-difluorobenzyl. Also preferably, $R_a$ and $R_b$ are different and Rb represents $C_1$–$C_6$)alkylsulfonylamino. Preferably, $R_d$ is phenyl optionally substituted with $C_1$–$C_3$ alkyl, $C_1$–$C_3$ alkoxy, amino, hydroxy, or halogen. Prefereably, $R_c$ is hydrogen or $C_1$–$C_4$ alkyl. Preferably, $R_c$ is $C_1$–$C_3$ alkyl. Also preferably, $R_d$ is $C_1$–$C_6$ lower alkyl and $R_{20}$ is hydrogen. Further in accordance with this preferred embodiement, the invention provides compounds of the formula VI;

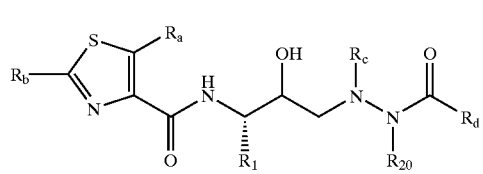

(VI)

where $R_a$, $R_b$, $R_1$, $R_c$, $R_{20}$ and $R_d$ are defined above for this preferred embodiment. In another preferred embodiment, $R_1$ is benzyl where the phenyl is disubstituted with chloro or fluoro; $R_c$ is $C_1$–$C_3$ alkyl; $R_d$ is $C_1$–$C_6$ lower alkyl; $R_{20}$ is hydrogen or $C_1$–$C_6$ alkyl; and $R_b$ is alkylsulfonylamino attached to the 2-position of the thiazolyl group.

Preferred compounds of the invention include:

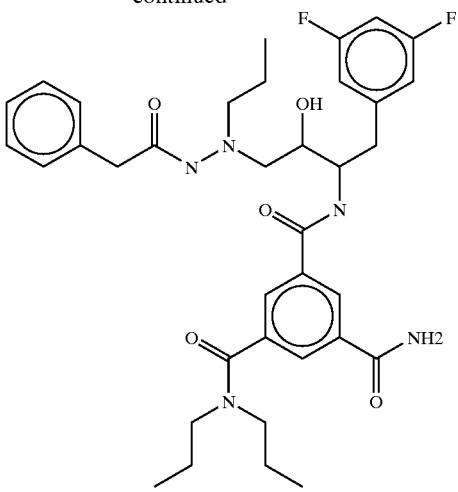

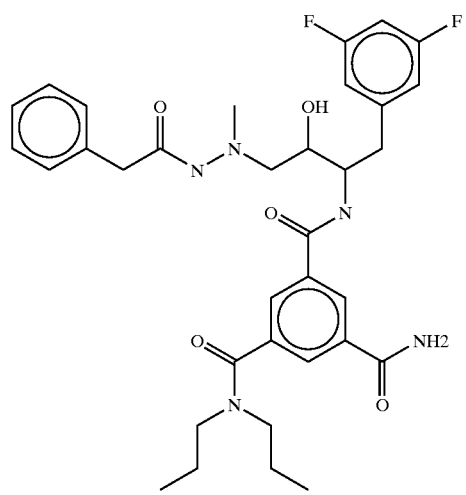

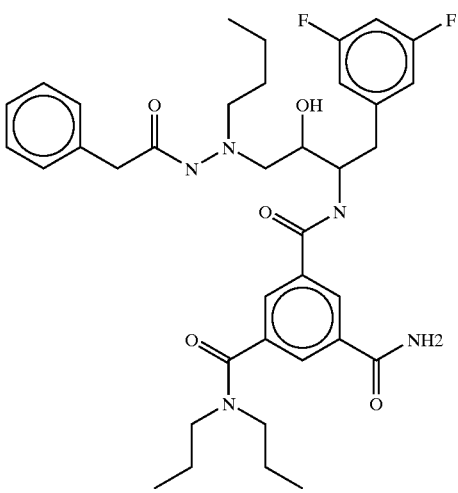

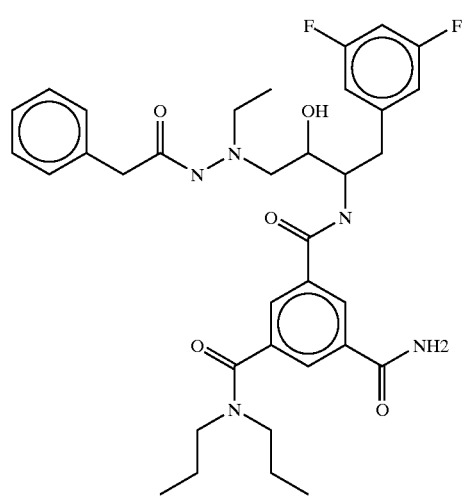

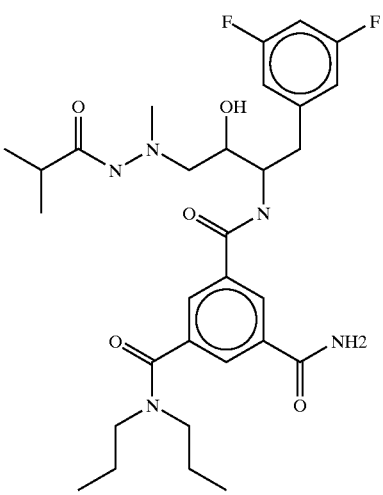

45
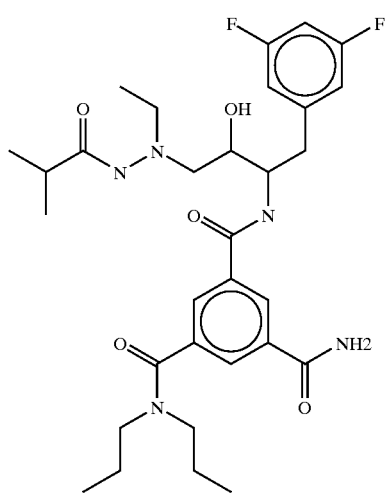
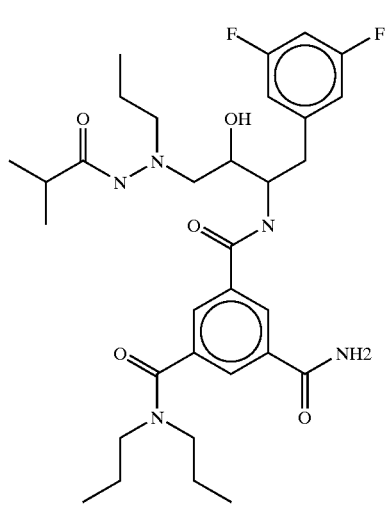
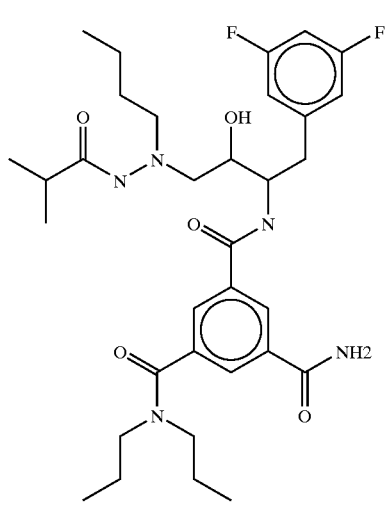
46
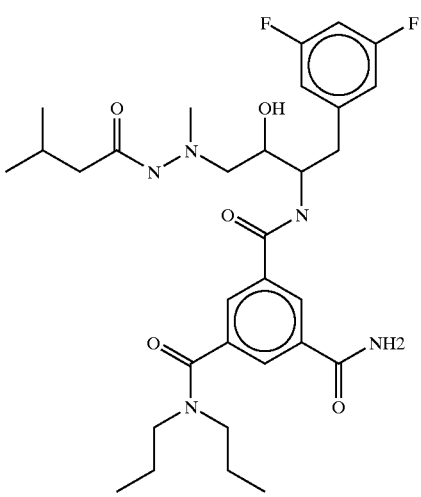
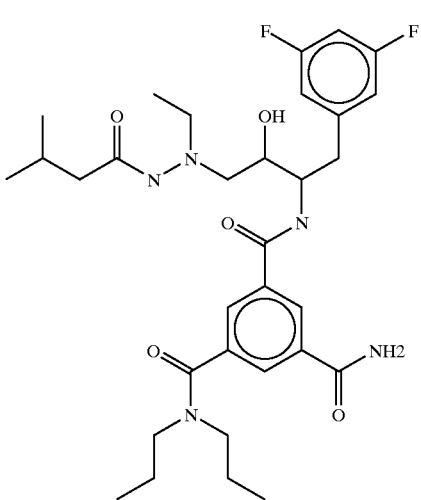
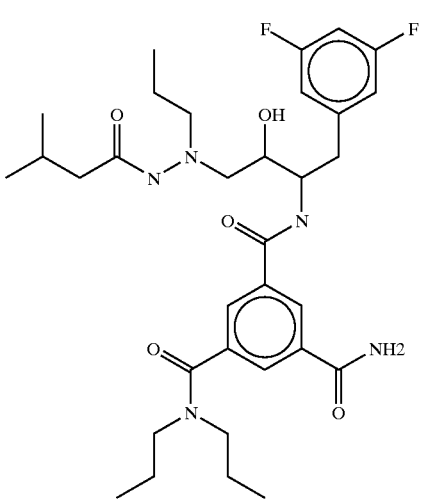

47
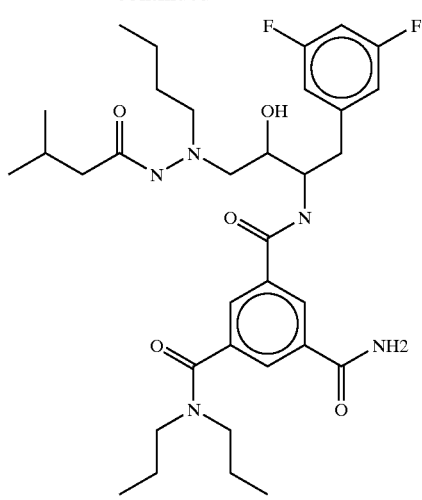
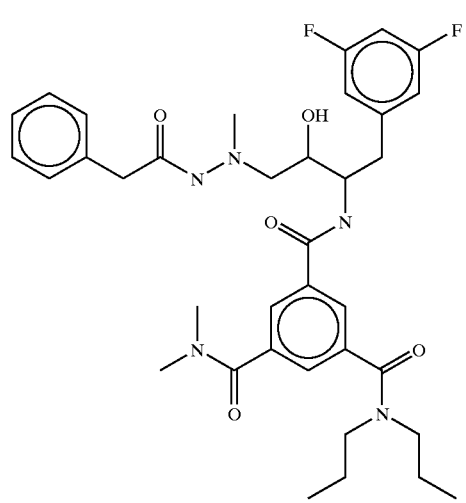
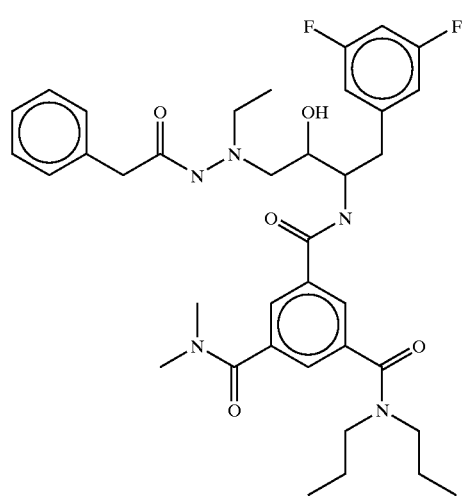
48
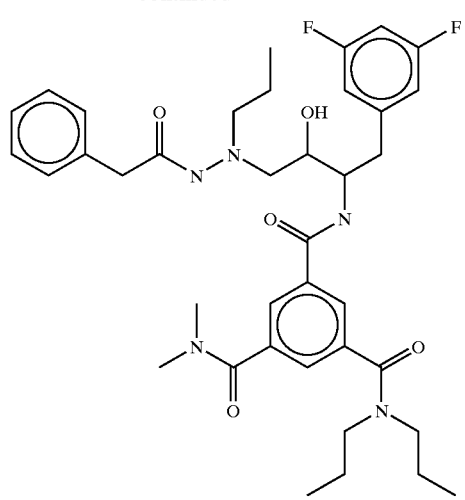
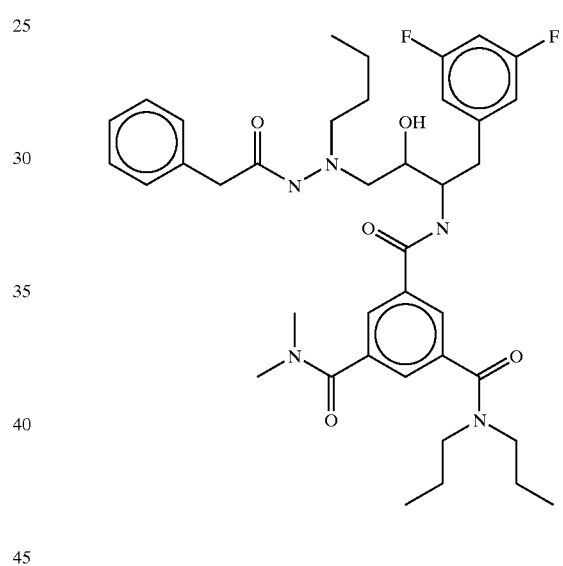
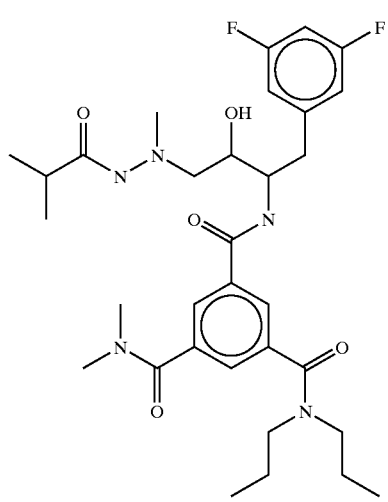

| 49 | 50 |
|---|---|
| -continued | -continued |
| 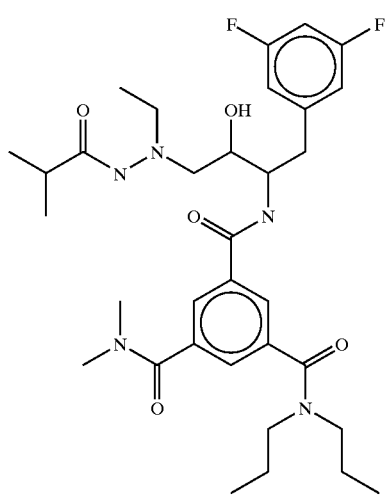 | 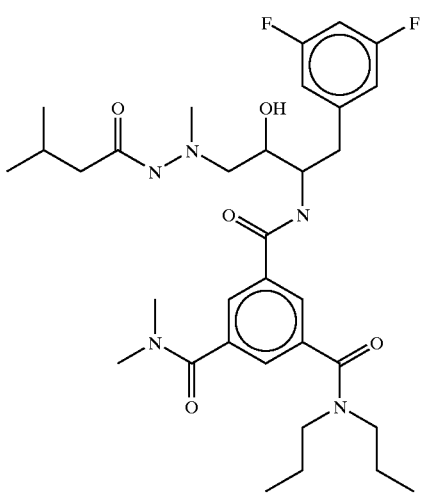 |
| 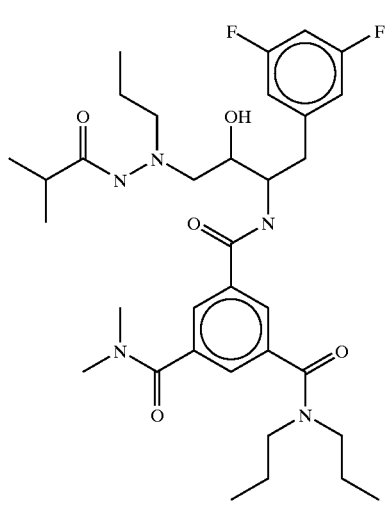 | 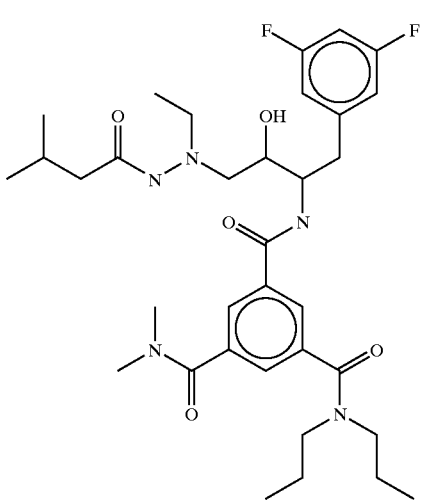 |
| 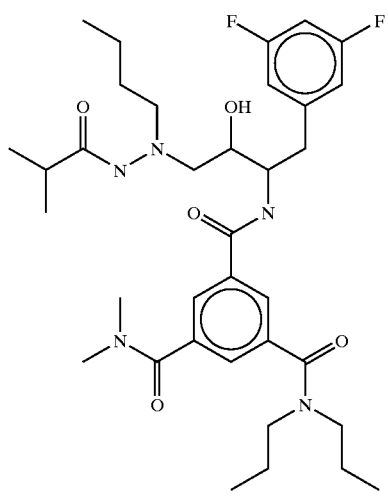 | 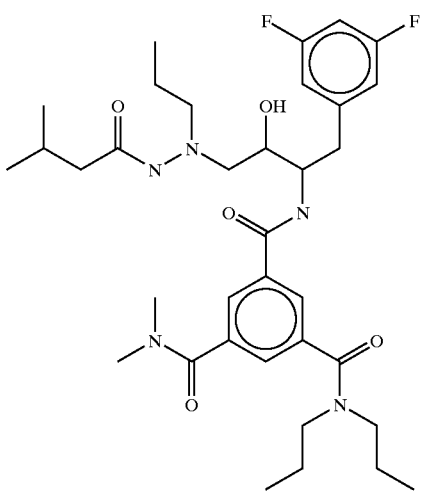 |

51
-continued
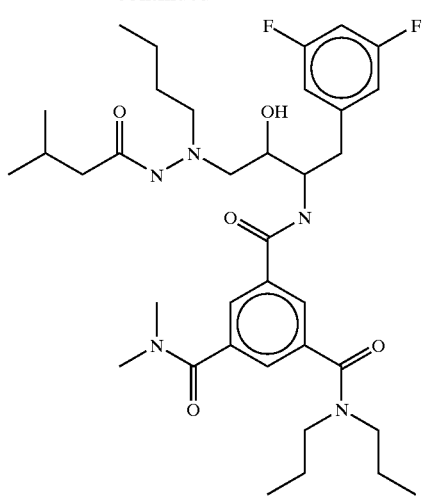
52
-continued
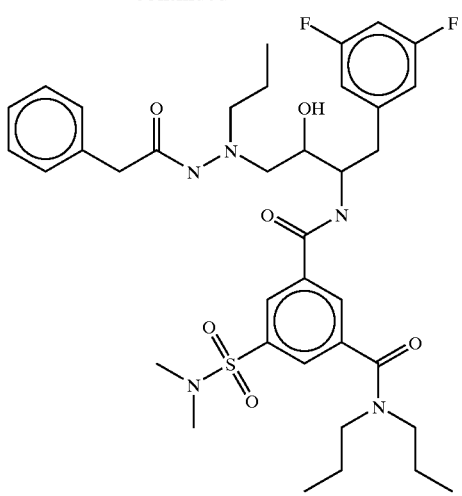
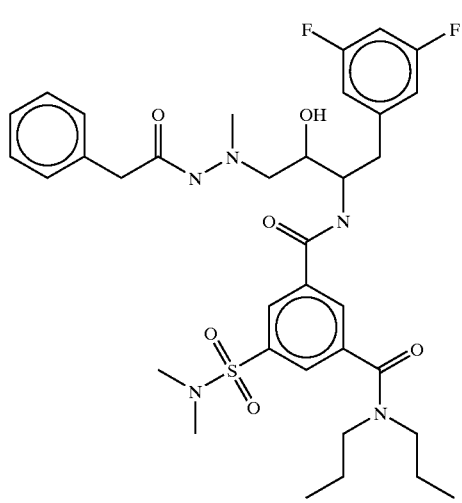
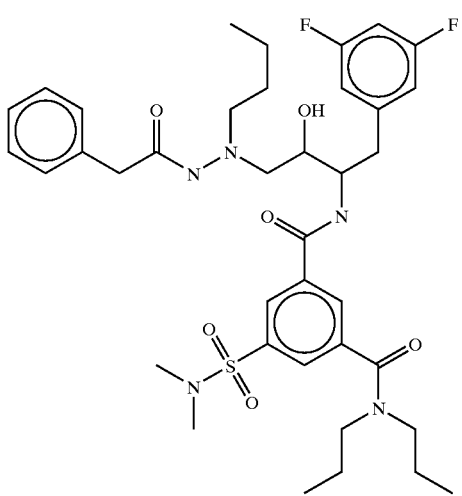
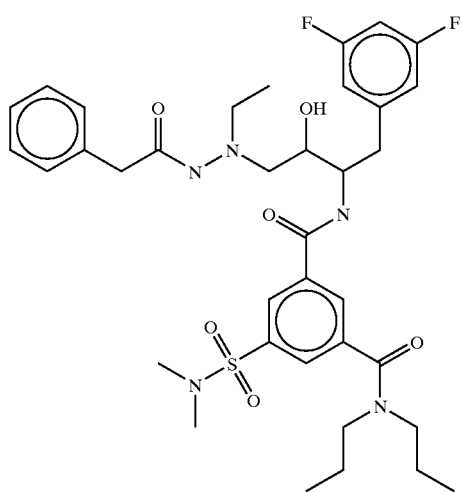
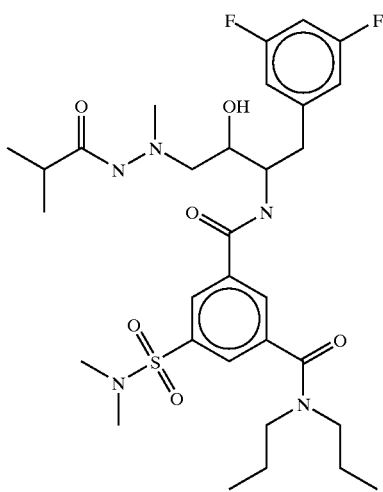

53
-continued
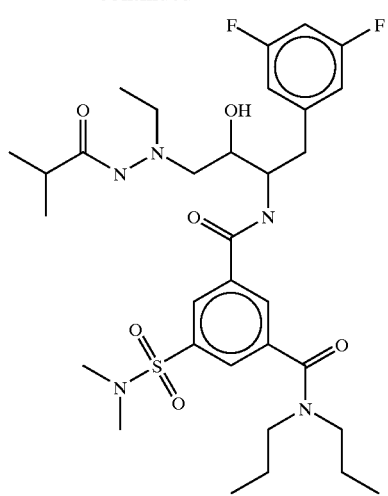
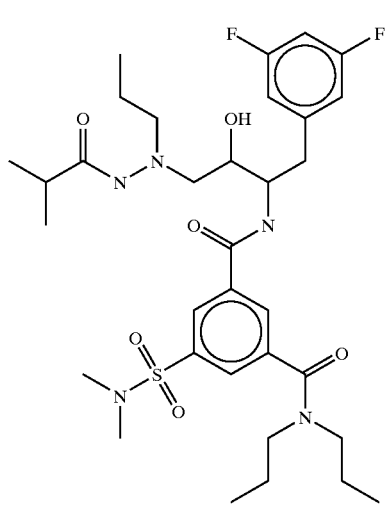
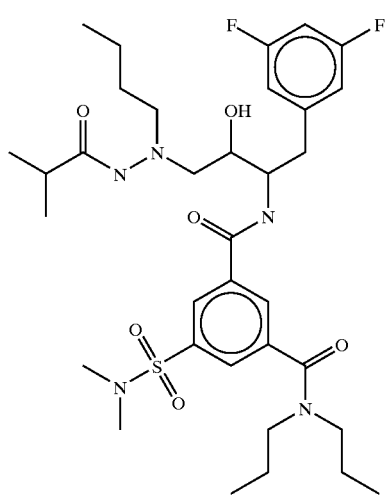
54
-continued
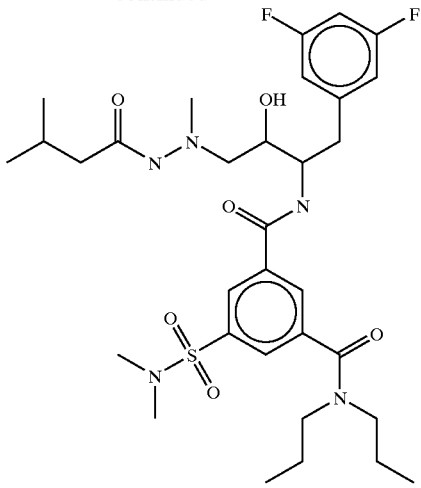
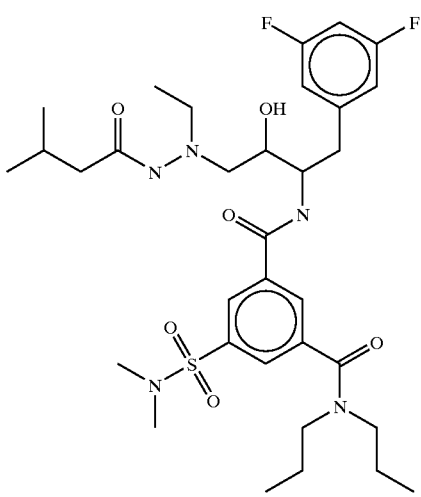
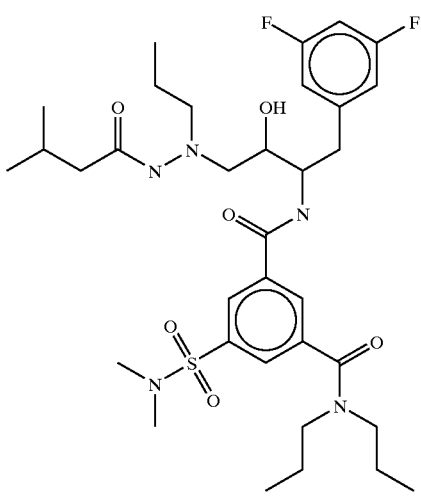

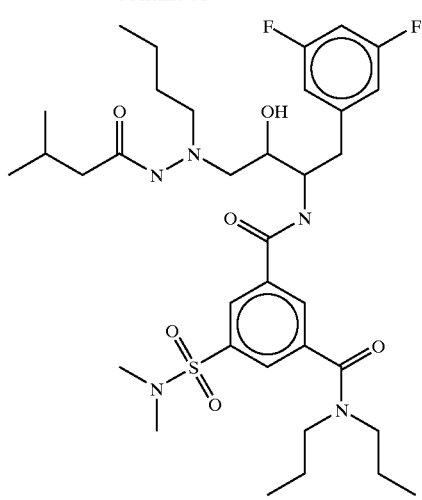
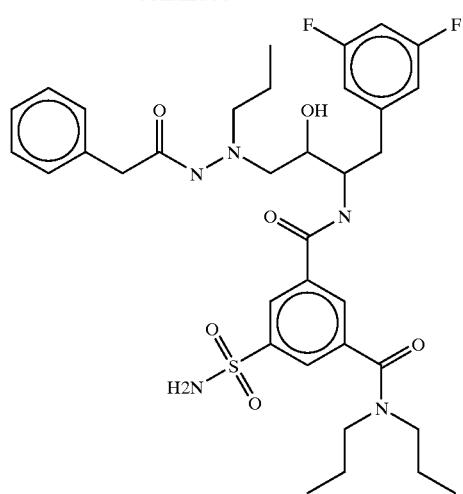
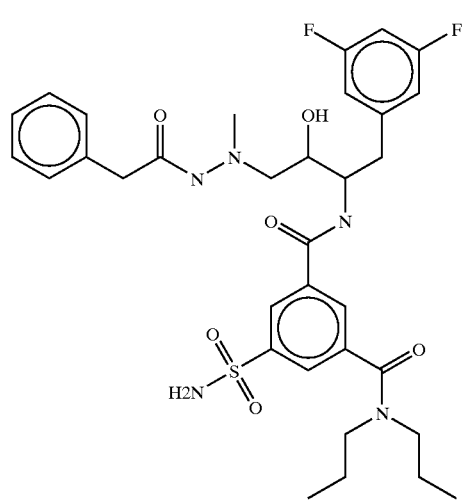
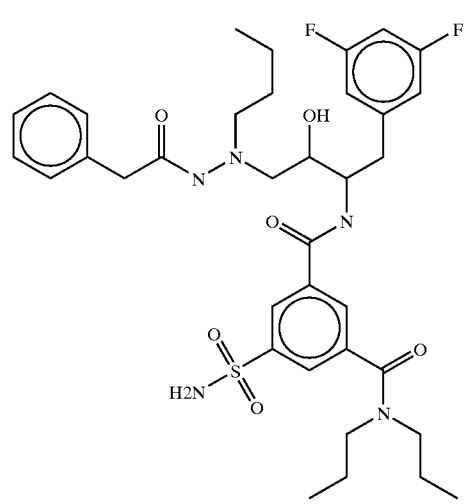
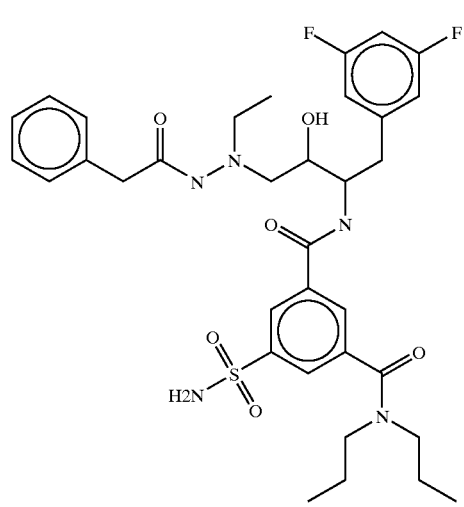
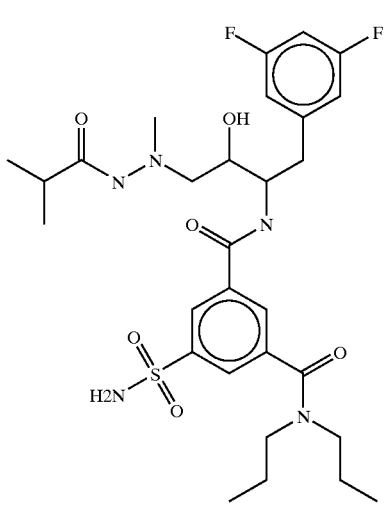

57
-continued
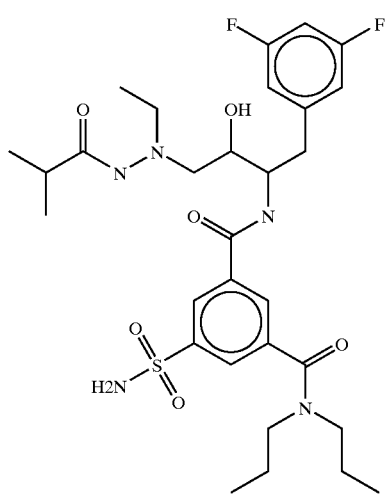
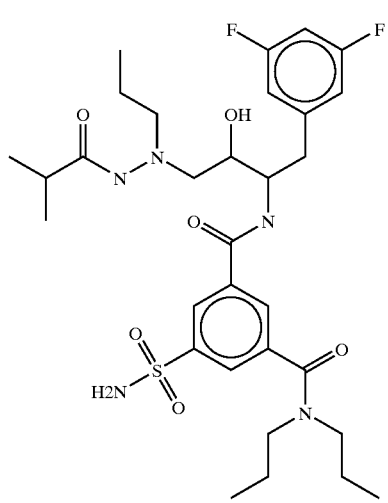
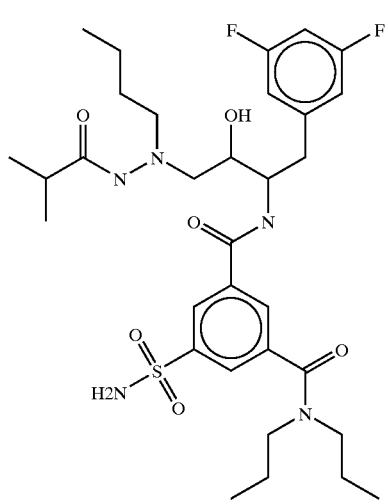
58
-continued
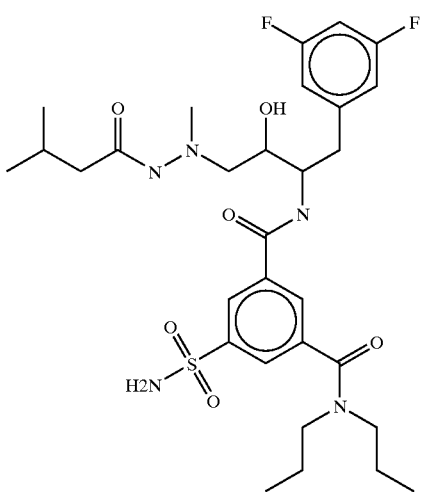
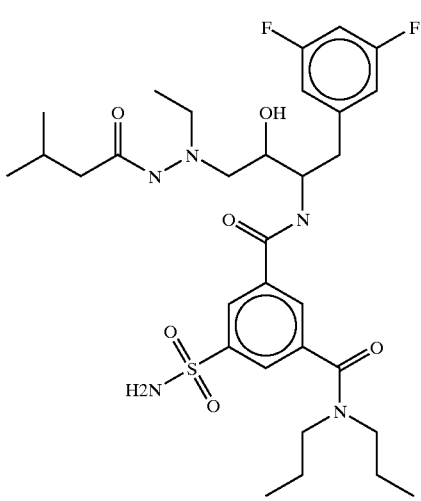
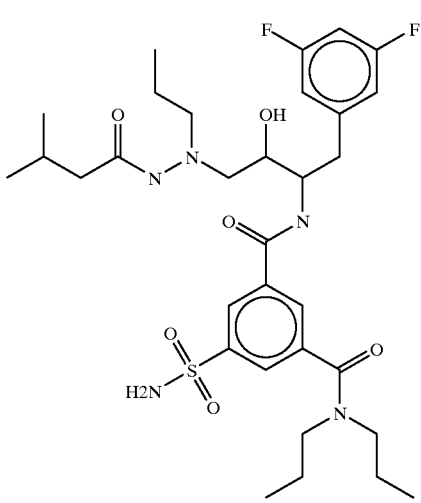

59
-continued
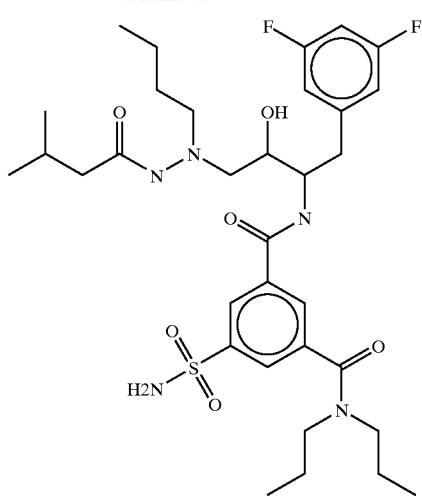
60
-continued
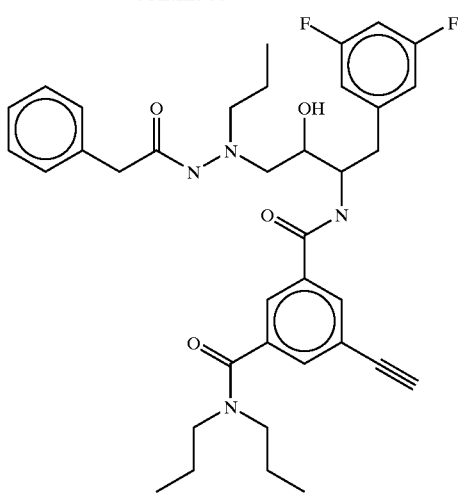
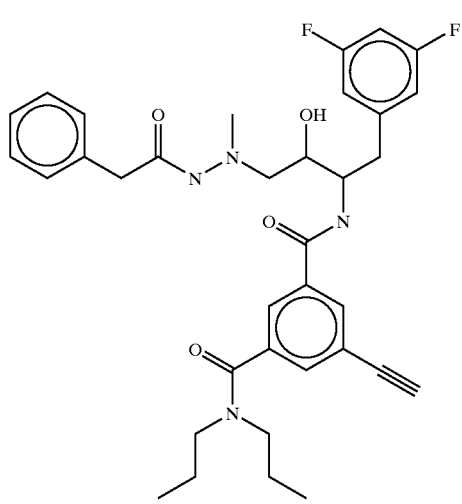
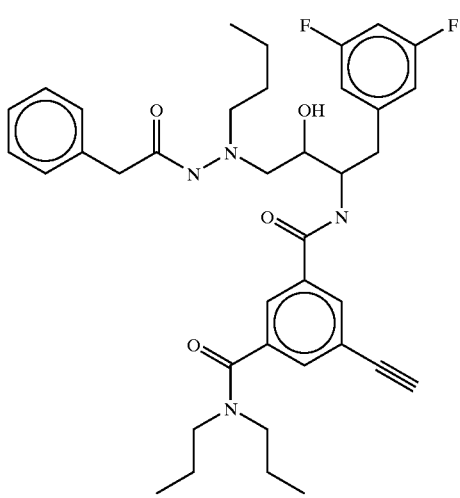
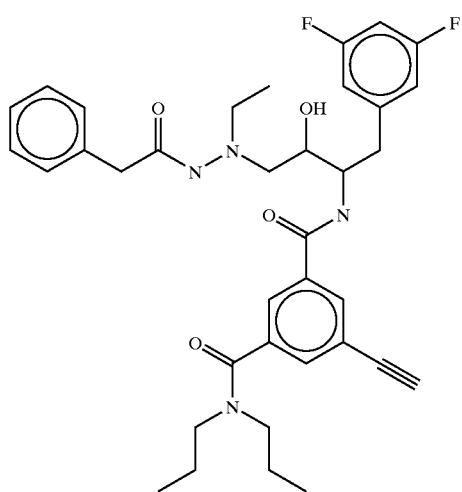
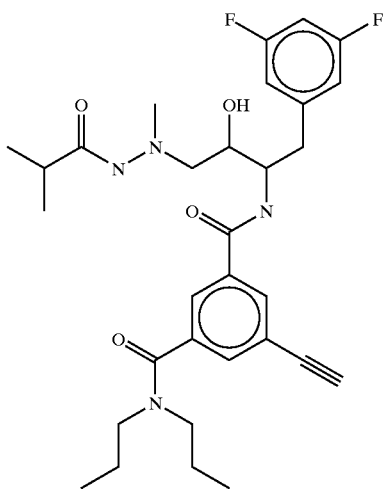

61
-continued
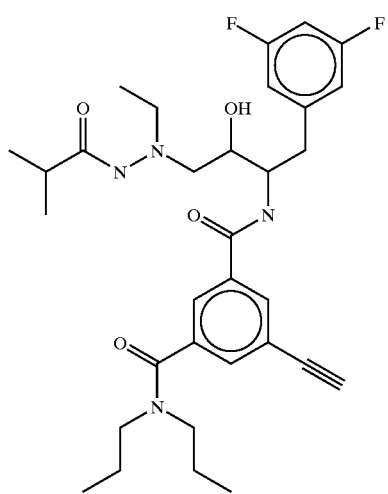
62
-continued
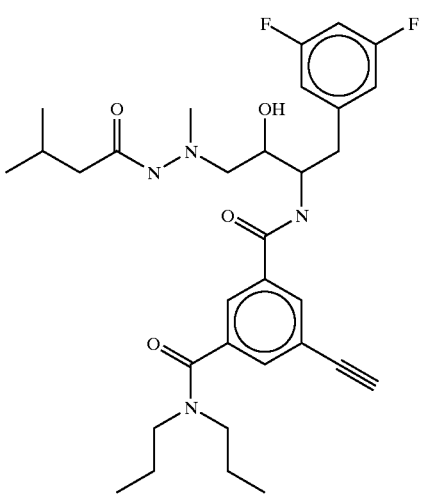
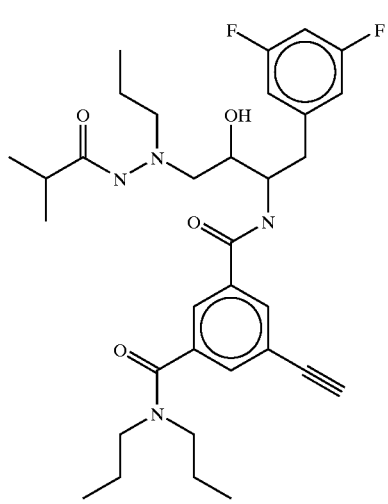
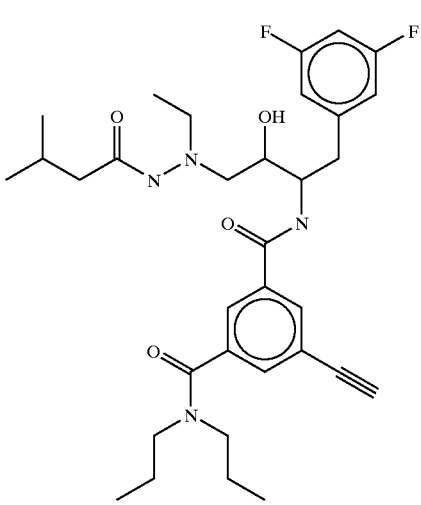
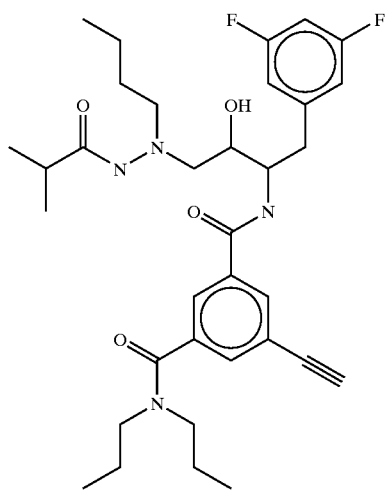
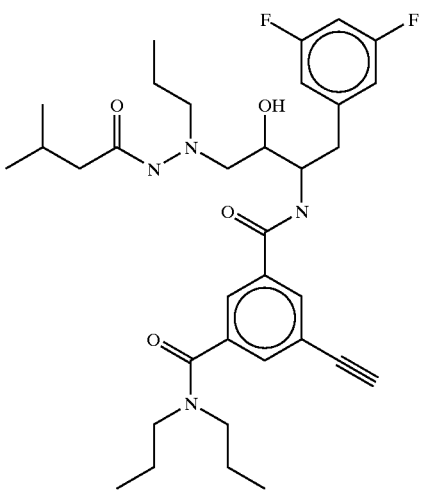

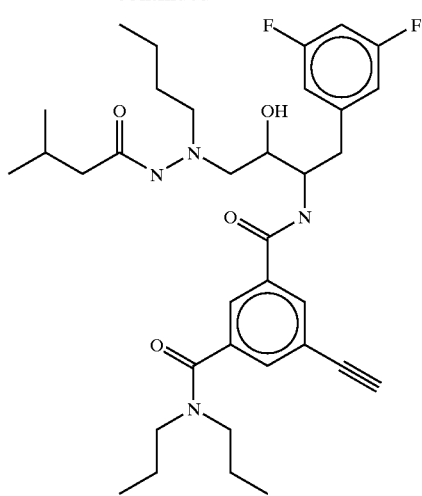
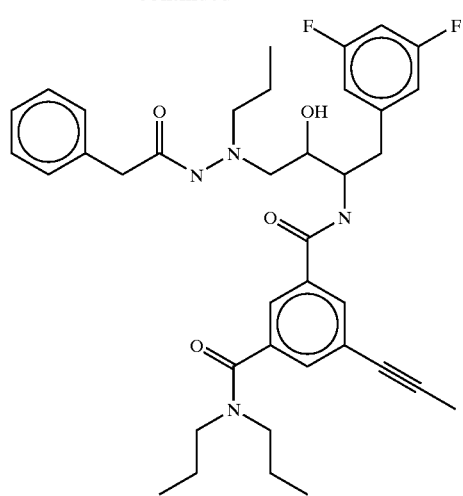
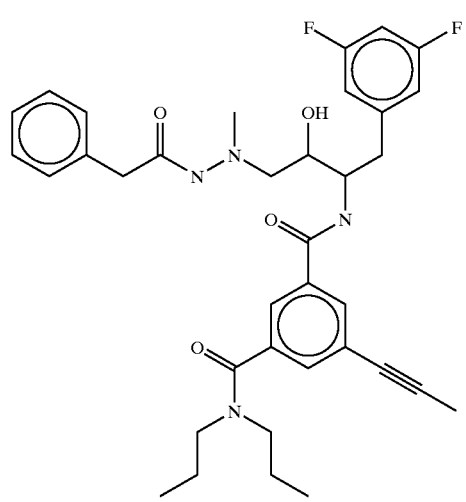
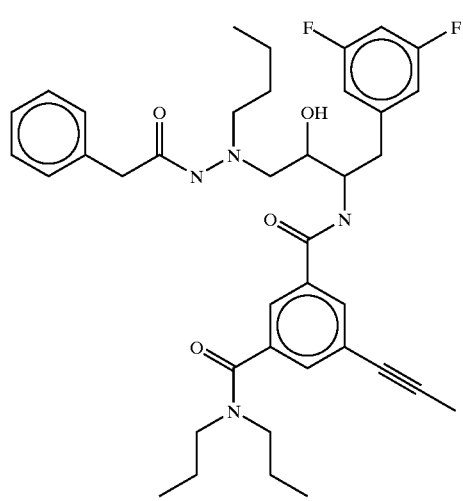
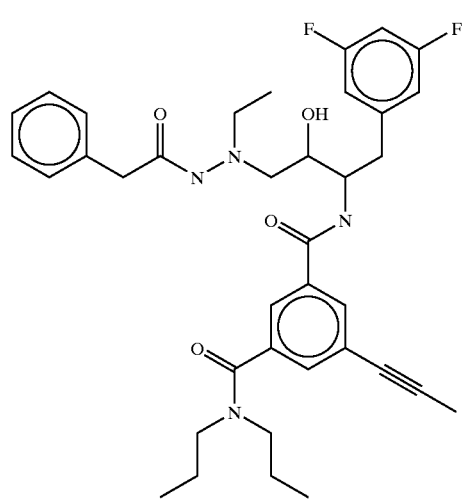
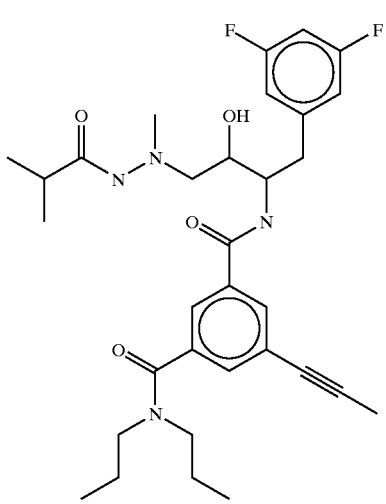

65
-continued
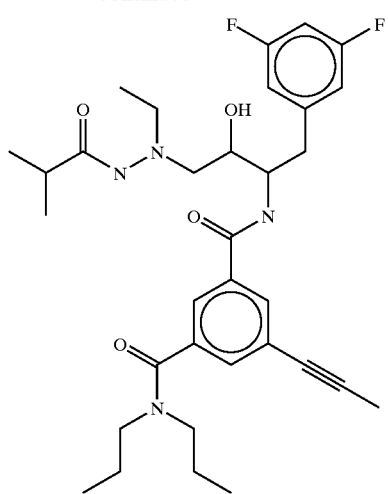
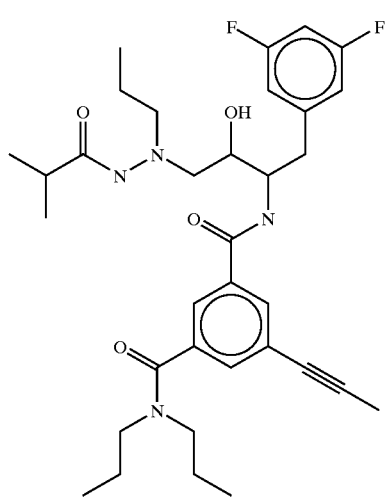
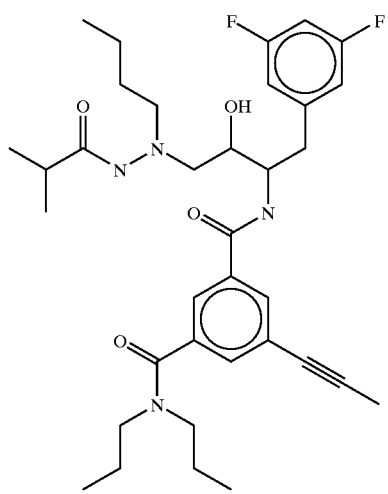
66
-continued
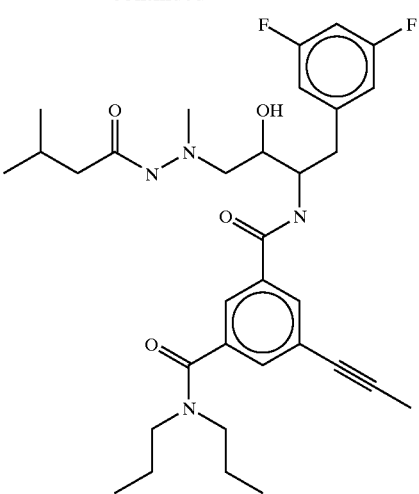
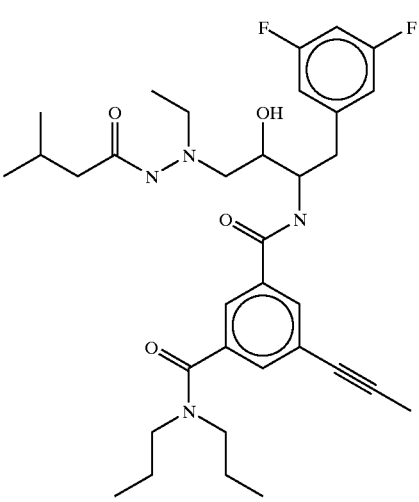
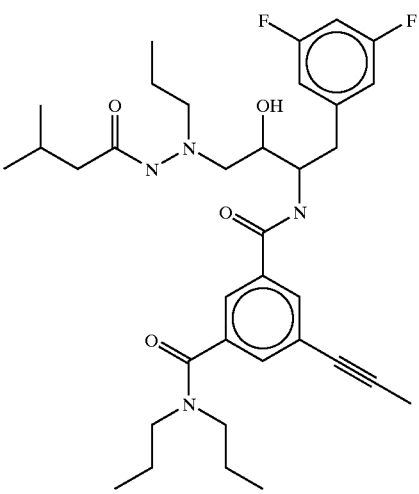

67
-continued
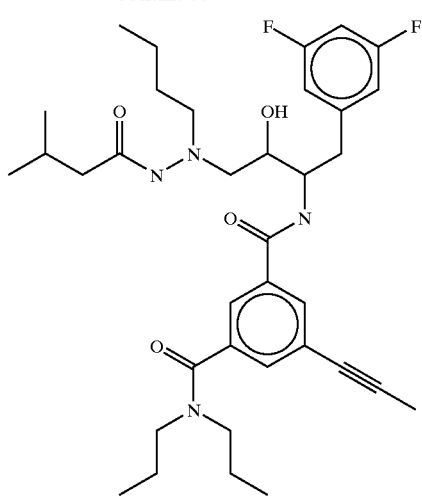
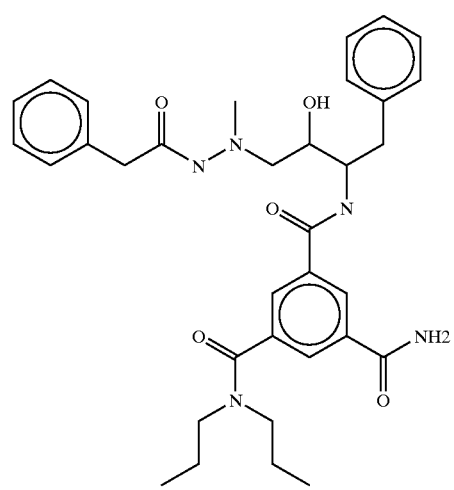
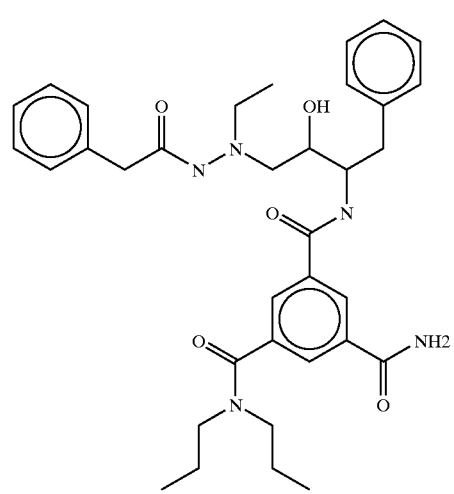
68
-continued
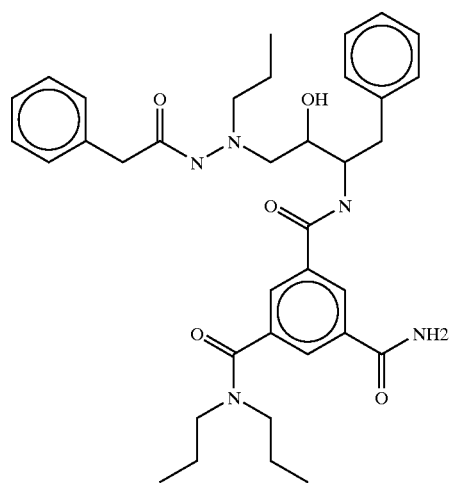
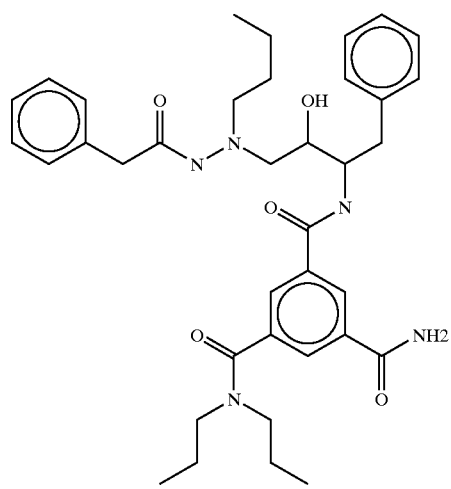
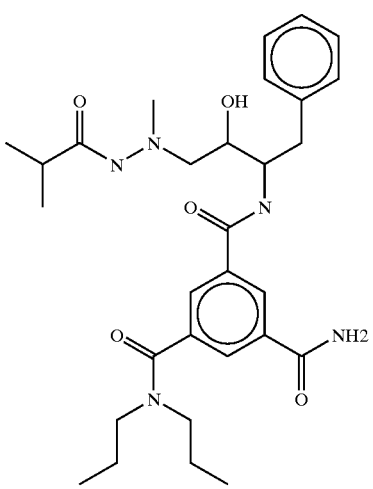

69
-continued
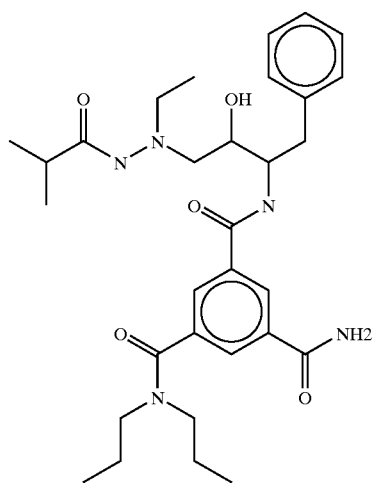
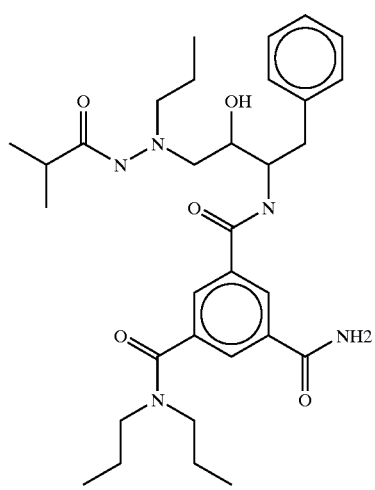
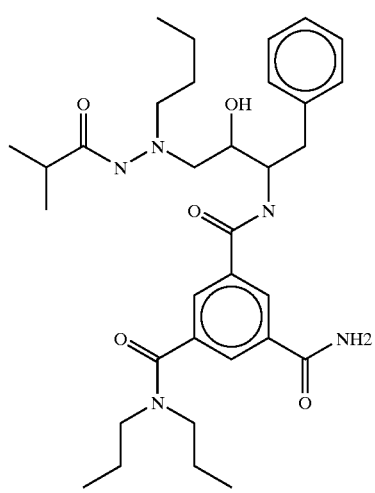
70
-continued
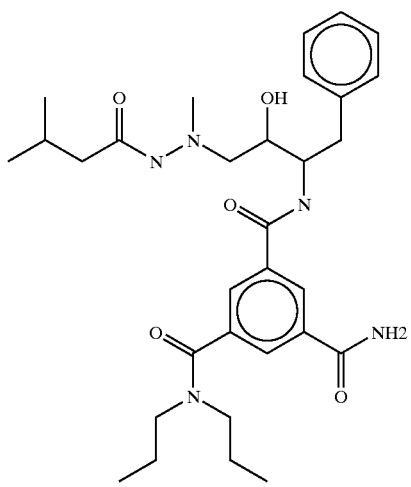
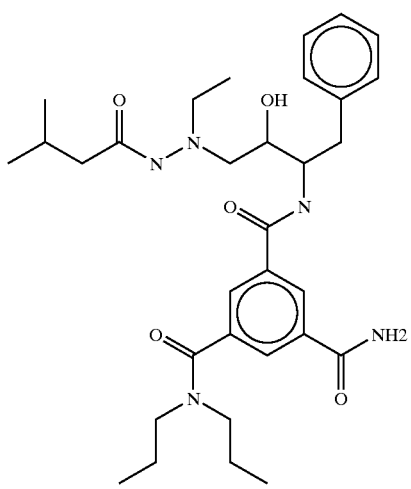
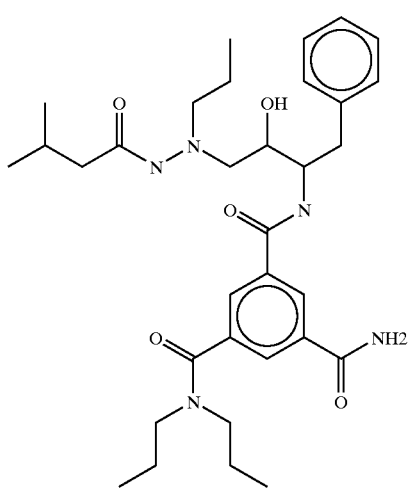

71
-continued
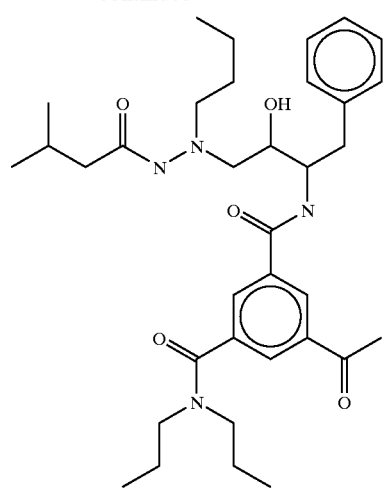
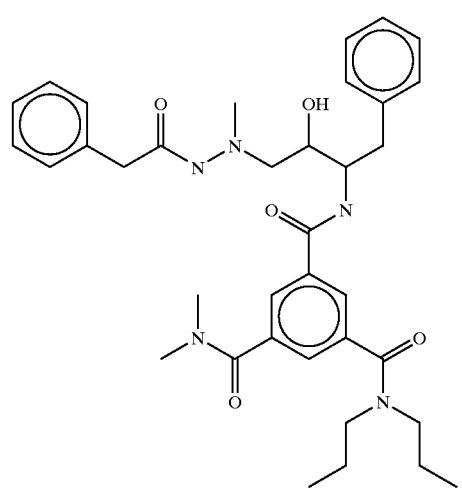
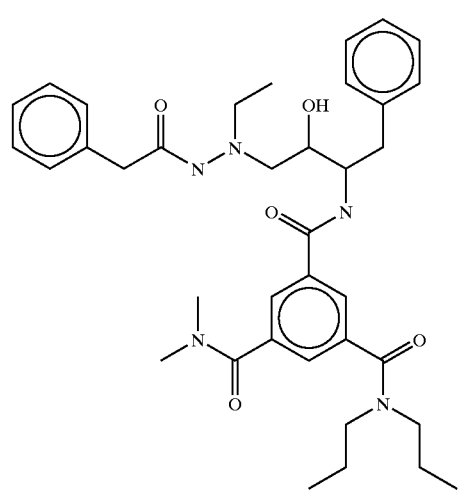
72
-continued
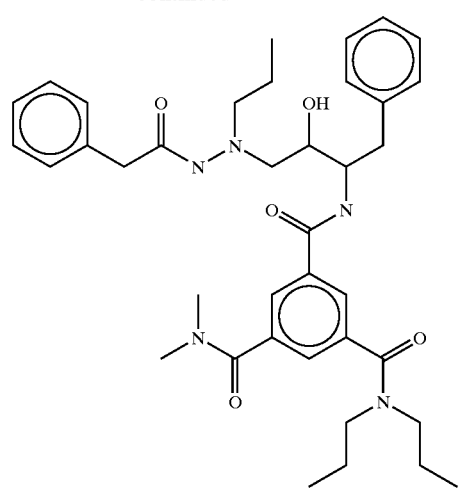
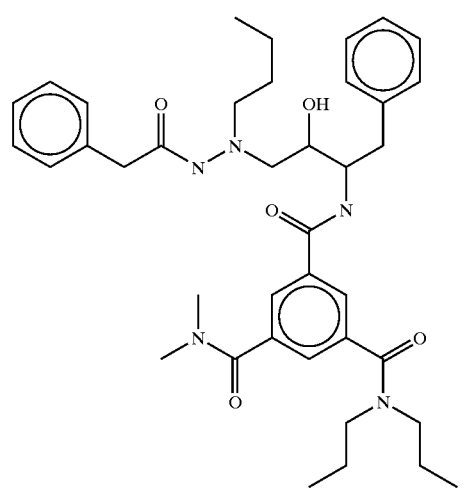
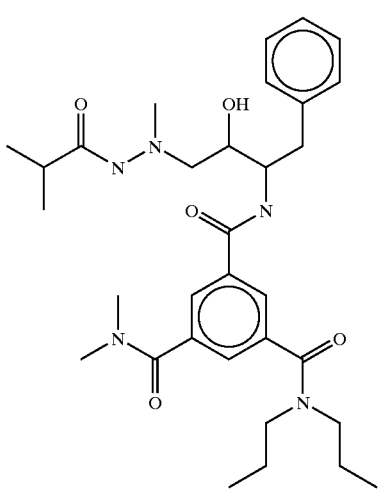

73
-continued
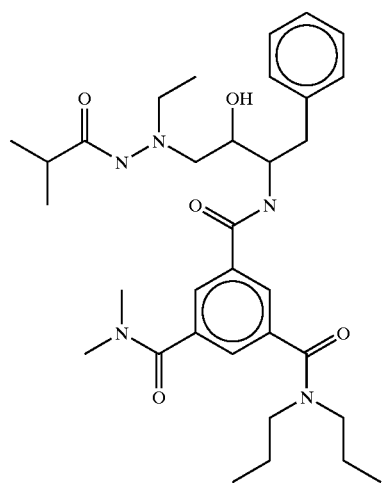
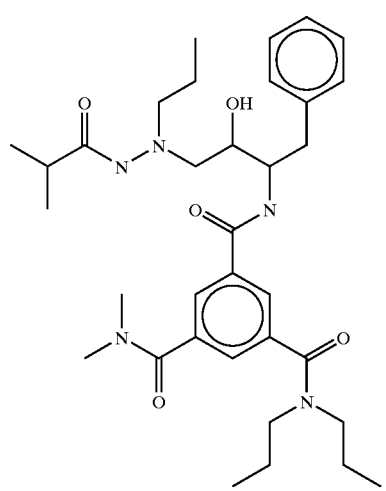
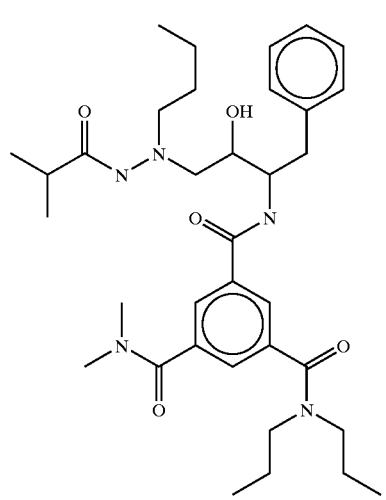
74
-continued
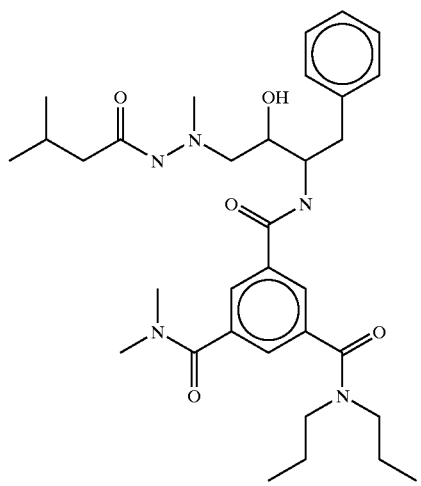
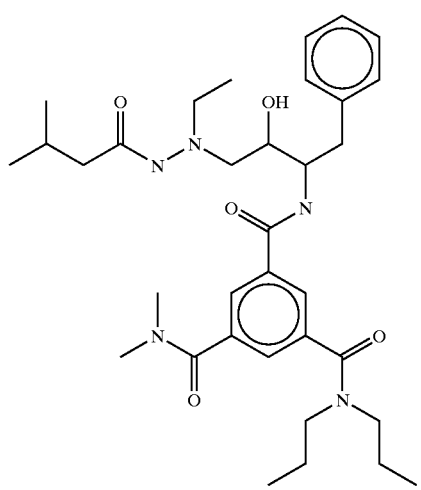
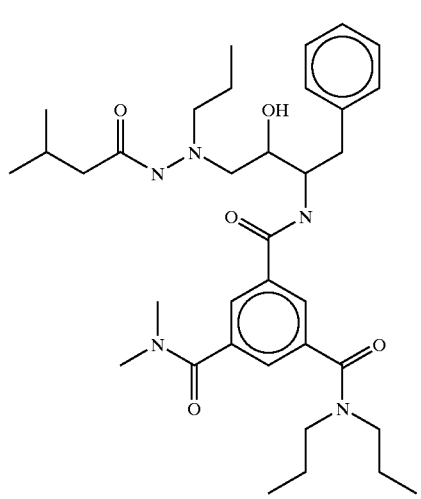

75
-continued
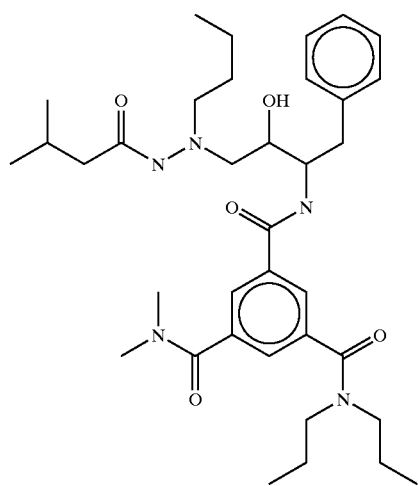
76
-continued
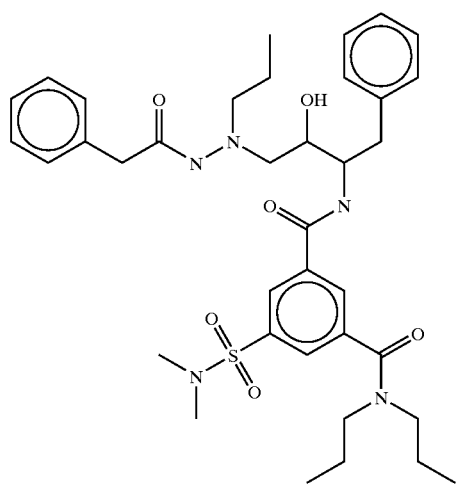
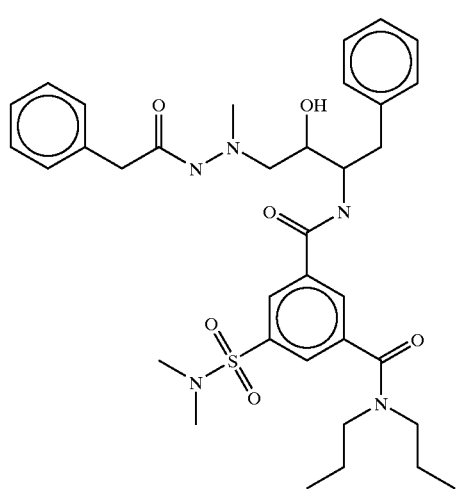
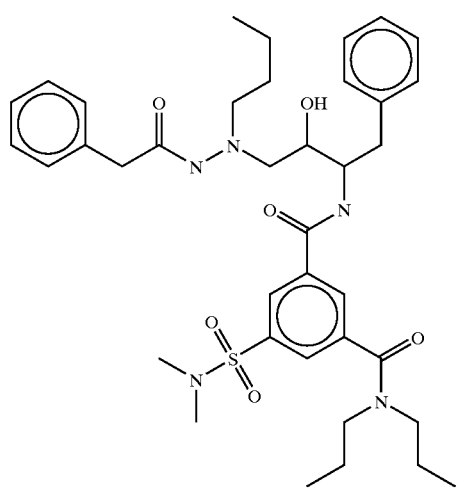
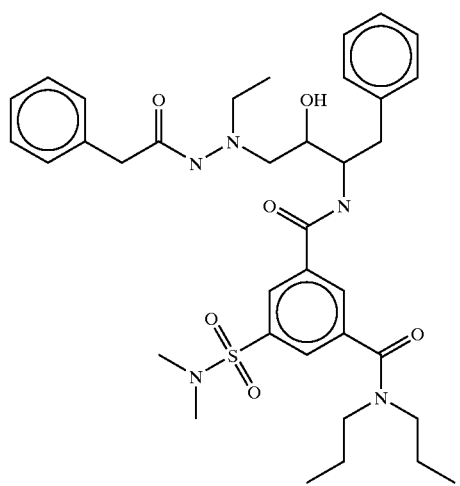
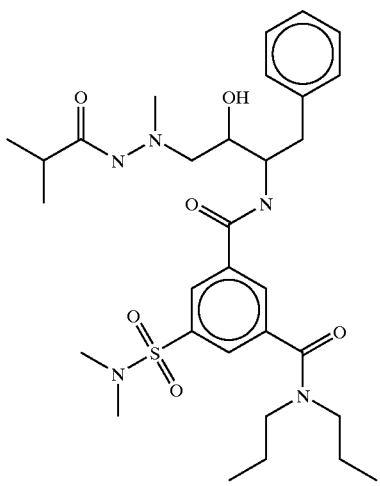

77
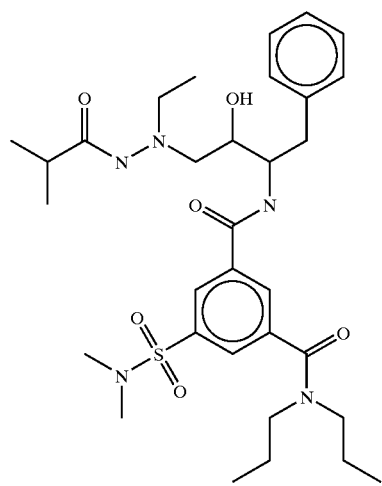
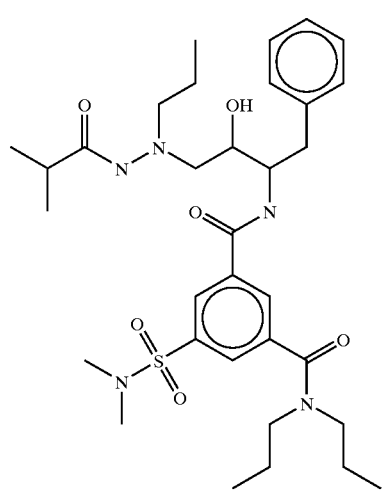
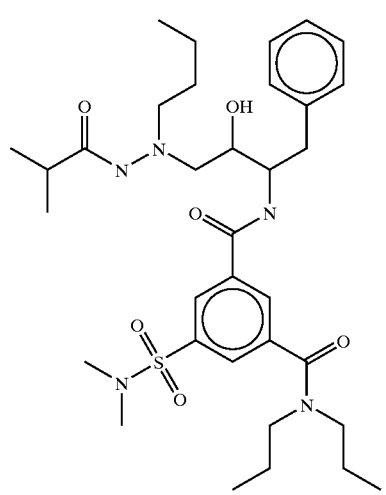
78
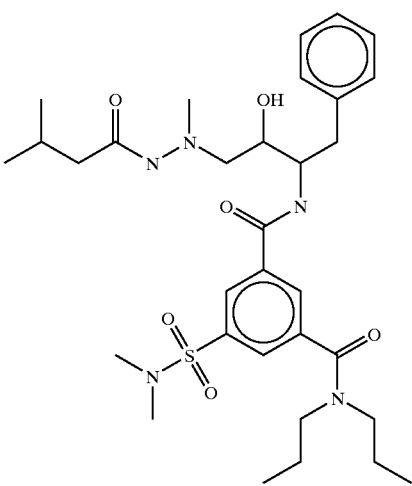
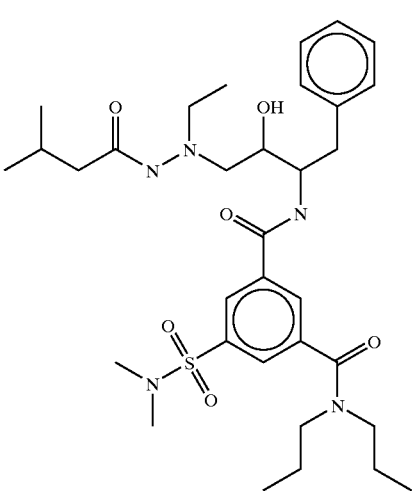

79
-continued
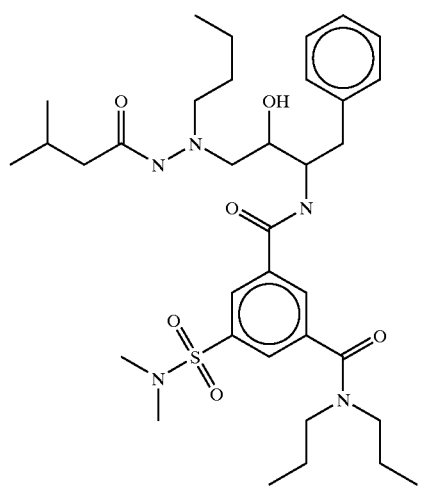
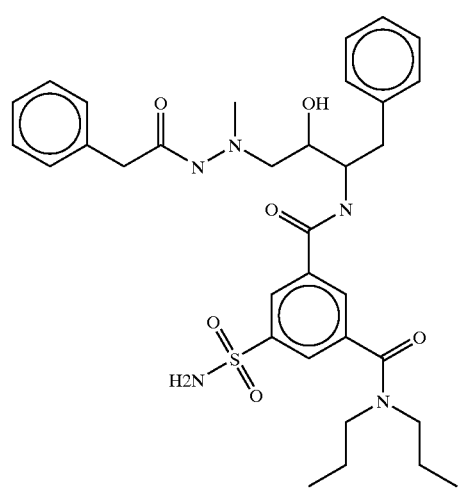
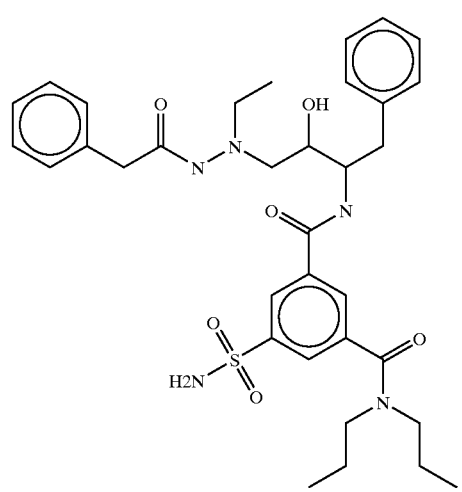
80
-continued
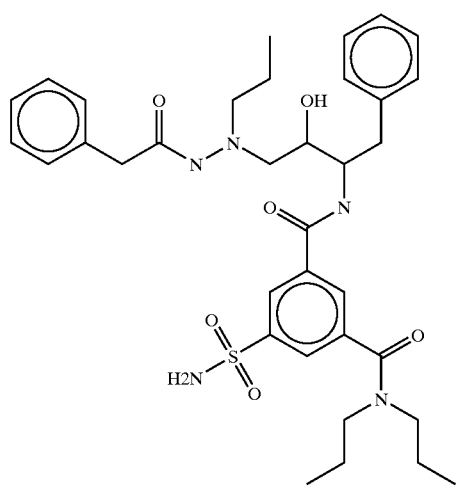
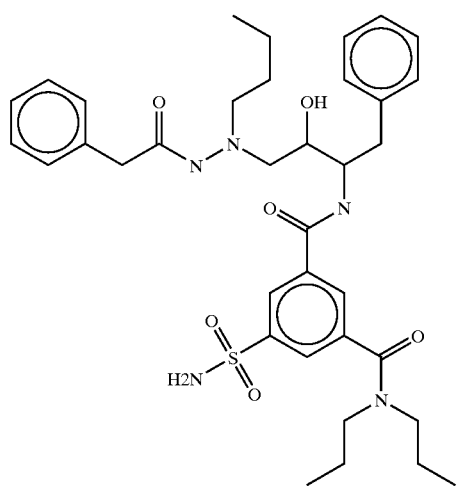
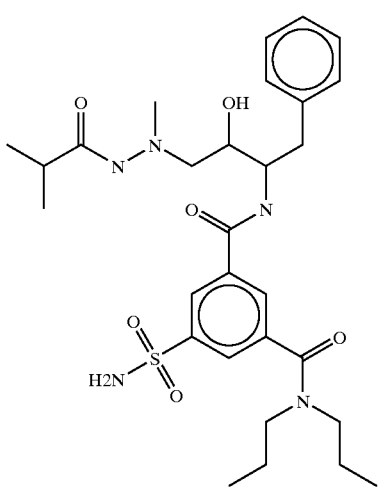

81
-continued
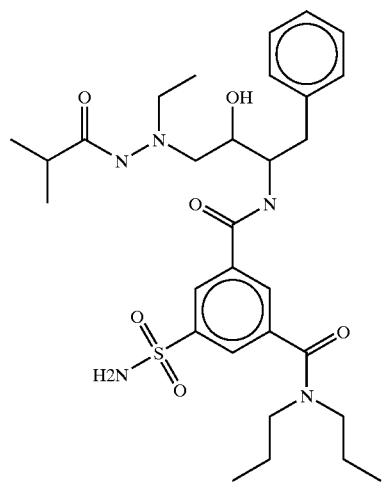
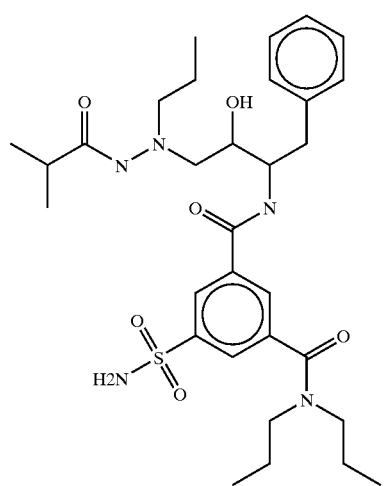
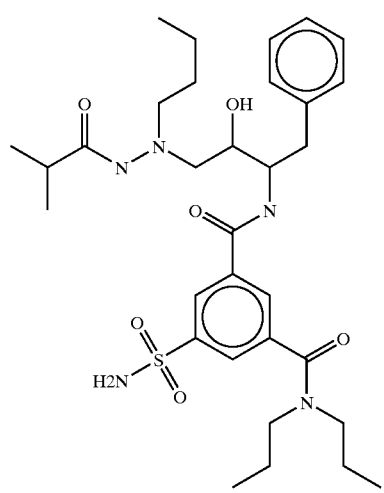
82
-continued
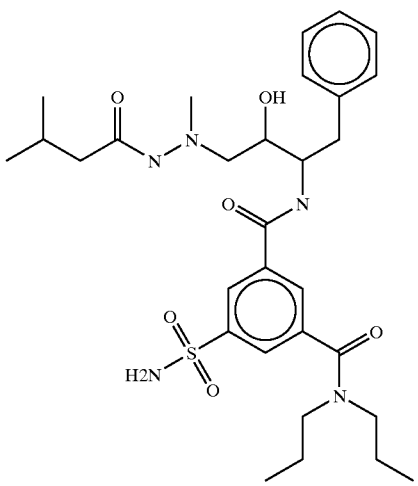
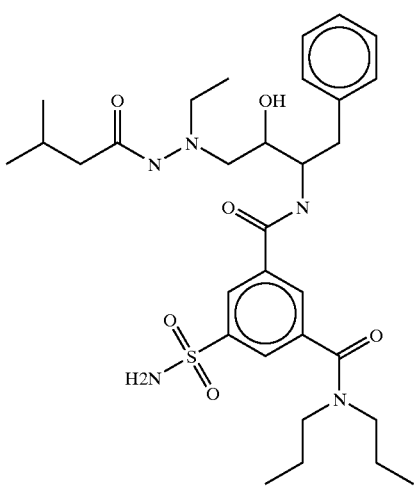
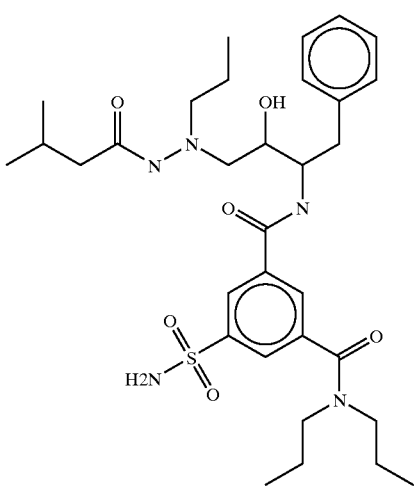

83
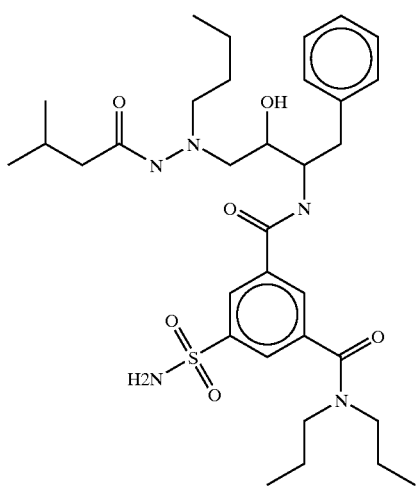
84
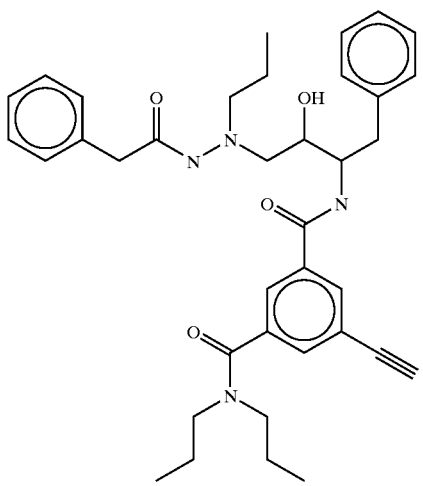
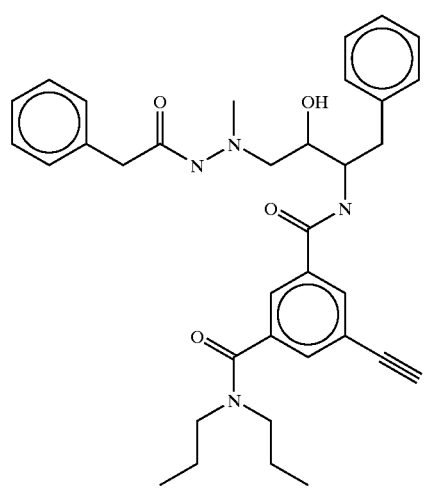
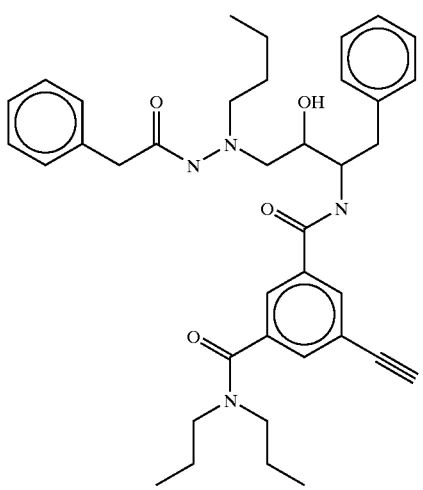
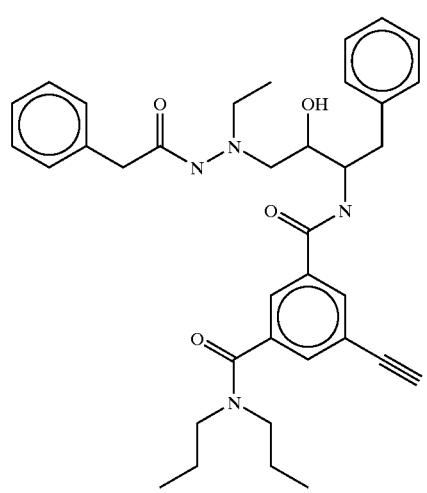
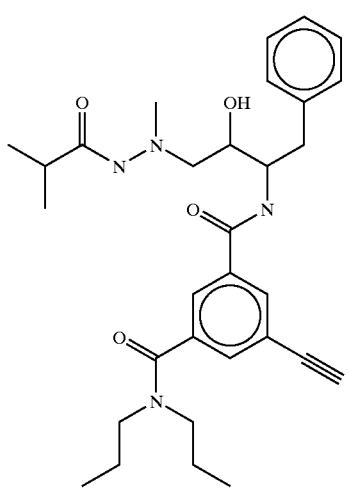

85
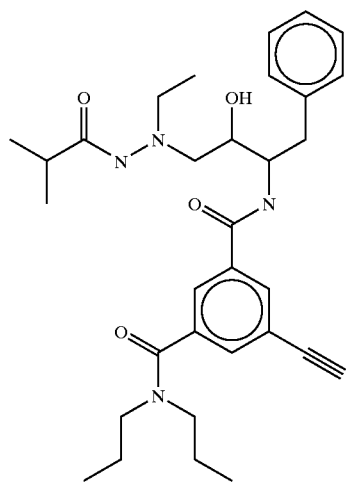
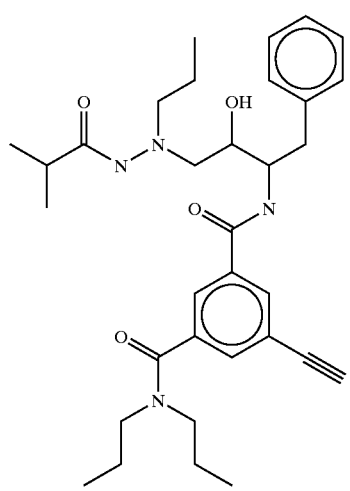
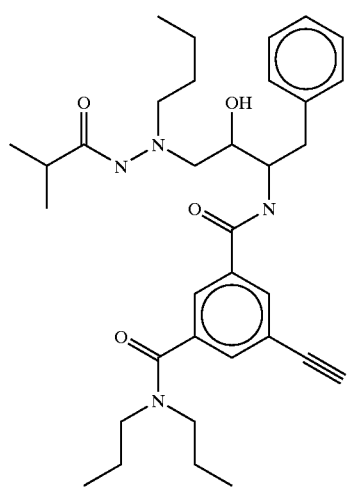
86
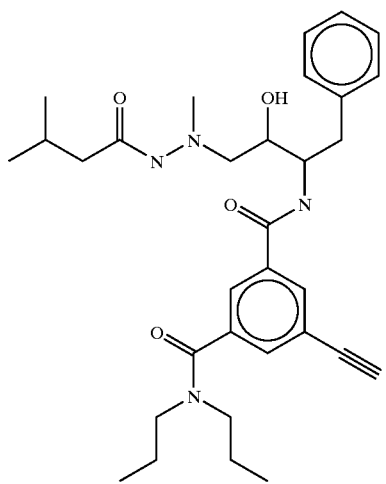
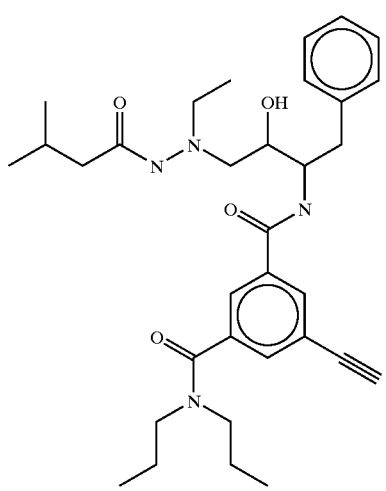
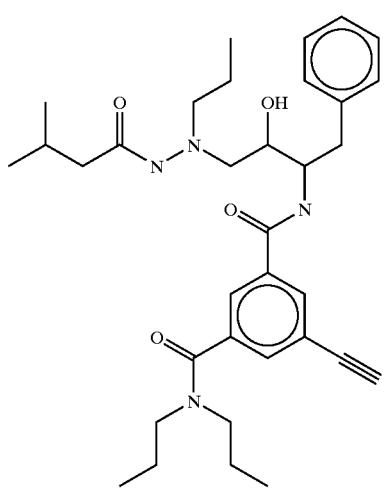

87
-continued
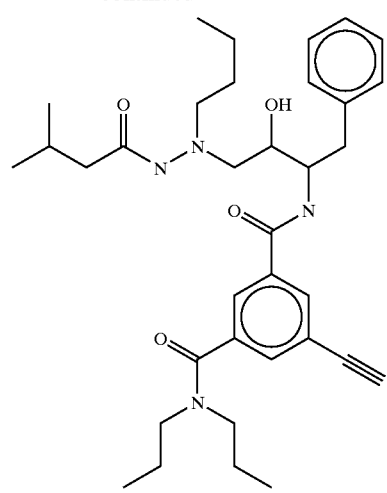
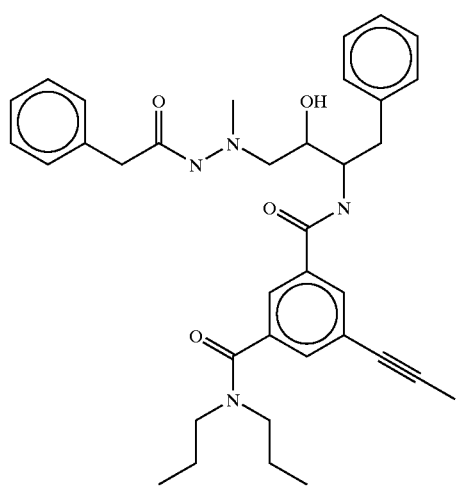
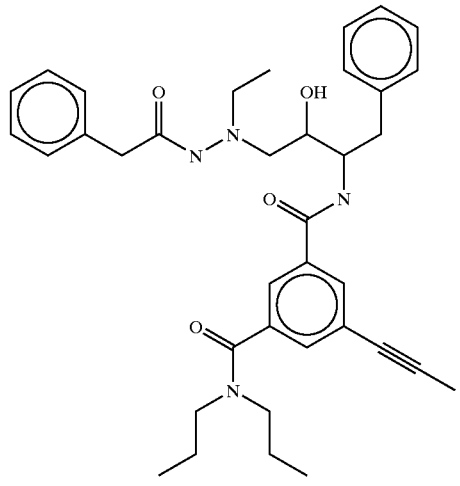
88
-continued
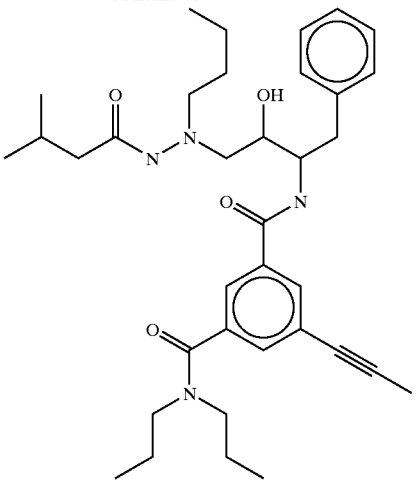
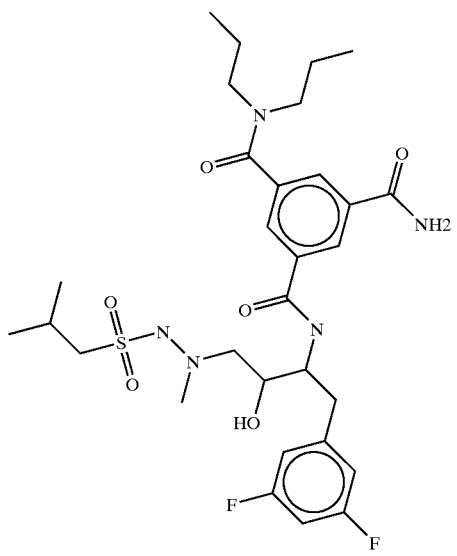
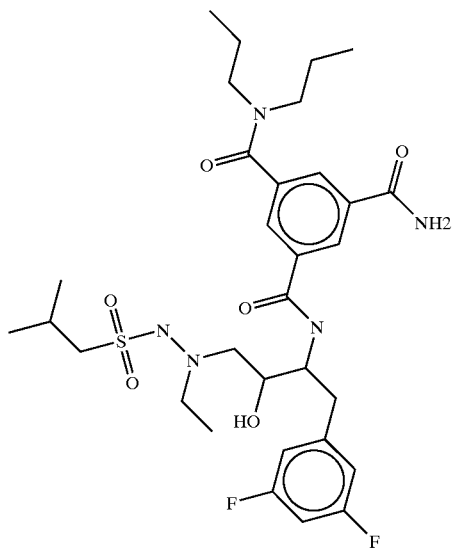

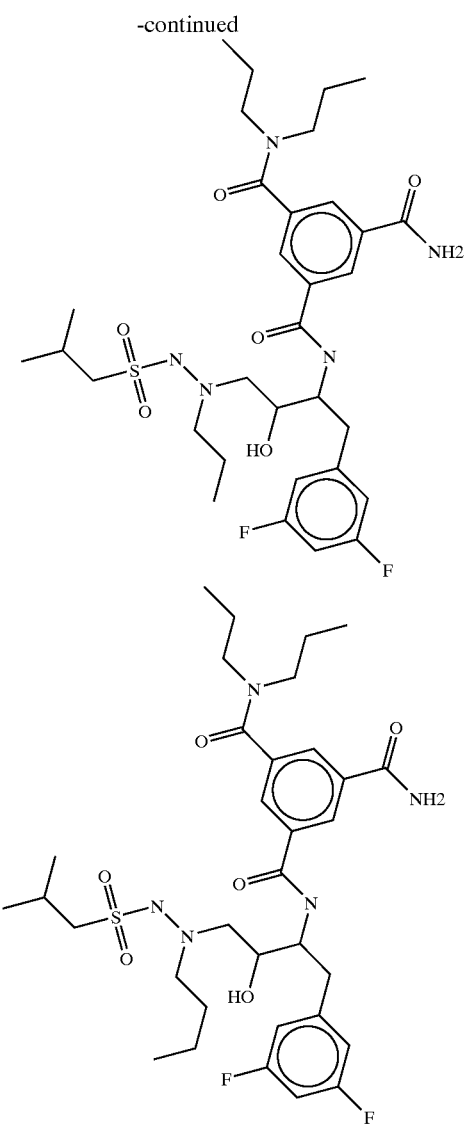

(II)

$$R_N\underset{R_1}{\overset{R_{20}}{N}}-\underset{}{\overset{OH}{C}}-\underset{R_{20}}{\overset{R_C}{N}}-N\underset{}{\overset{R_2}{}}$$

or a pharmaceutically acceptable salt thereof, where $R_c$ is (I) —$C_1$–$C_{10}$ alkyl optionally substituted with one, two or three groups independently selected from the group consisting of $C_1$–$C_3$ alkyl, halogen, —OH, —SH, —C≡N, —$CF_3$, $C_1$–$C_6$ alkoxy, —O-phenyl, —$NR_{1-a}R_{1-b}$, —OC=O $NR_{1-a}R_{1-b}$, —S(=O)$_{0-2}$ $R_{1-a}$, —$NR_{1-a}$C=O $NR_{1-a}R_{1-b}$, —C=O $NR_{1-a}R_{1-b}$, and —S(=O)$_2$ $NR_{1-a}R_{1-b}$ wherein $R_{1-a}$ and $R_{1-b}$ at each occurrence are independently H or $C_1$–$C_6$ alkyl, (II) —(CH$_2$)$_{0-3}$–(C$_3$–C$_8$) cycloalkyl where cycloalkyl can be optionally substituted with one, two or three substituents independently selected from the group consisting of $C_1$–$C_3$ alkyl, halogen, —OH, —SH, —C≡N, —$CF_3$, $C_1$–$C_6$ alkoxy, —O-phenyl, —$CO_2$H, —$CO_2$-($C_1$–$C_4$ alkyl), and —$NR_{1-a}R_{1-b}$, (III) —(C$R_{C-x}R_{C-y}$)$_{0-4}$—$R_{C-aryl}$ where $R_{C-x}$ and $R_{C-y}$ are independently selected from the group consisting of

—H, $C_1$–$C_4$ alkyl optionally substituted with 1 or 2 —OH, $C_1$–$C_4$ alkoxy optionally substituted with 1, 2, or 3 halogen, —(CH$_2$)$_{0-4}$—$C_3$–$C_8$ cycloalkyl, $C_2$–$C_6$ alkenyl containing one or two double bonds, $C_2$–$C_6$ alkynyl containing one or two triple bonds, and phenyl, or $R_{C-x}$ and $R_{C-y}$ are taken together with the carbon to which they are attached to form a carbocycle of three, four, five, six or seven carbon atoms, where one carbon atom is optionally replaced by a group selected from —O—, —S—, —SO$_2$—, —$NR_{N-2}$— and $R_{C-aryl}$, wherein $R_{C-aryl}$ is phenyl, which is optionally substituted with 1, 2, or 3 groups that are independently:

(1) $C_1$–$C_6$ alkyl, optionally substituted with one, two or three substituents selected from the group consisting of $C_1$–$C_3$ alkyl, halogen, —OH, —SH, —C≡N, —$CF_3$, $C_1$–$C_3$ alkoxy, and —$NR_{1-a}R_{1-b}$, (2) —OH, (3) —$NO_2$, (4) halogen, (5) —$CO_2$H, (6) —C≡N, (7) —(CH$_2$)$_{0-4}$—CO—$NR_{N-2}R_{N-3}$ where $R_{N-2}$ and $R_{N-3}$ are independently selected from the group consisting of:

(a) —H, (b) —$C_1$–$C_6$ alkyl optionally substituted with one substituent selected from the group consisting of:

(i) —OH, and (ii) —$NH_2$, (c) —$C_1$–$C_6$ alkyl optionally substituted with 1, 2, or 3 groups that are independently —F, —Cl, —Br, —I, or OH, (d) —$C_3$–$C_7$ cycloalkyl, (e) —($C_1$–$C_2$ alkyl)-($C_3$–$C_7$ cycloalkyl), (f) —($C_1$–$C_6$ alkyl)-O-($C_1$–$C_3$ alkyl), In another embodiment, the invention provides a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment which comprises administration of a therapeutically effective amount of a compound selected from the group consisting of an aza hydroxylated ethyl amine of the formula II:

(g) —$C_2$–$C_6$ alkenyl
(h) —$C_2$–$C_6$ alkynyl
(i) —$C_1$–$C_6$ alkyl chain with one double bond and one triple bond,
(j) $R_{1\text{-}aryl}$ wherein $R_{1\text{-}aryl}$ at each occurrence is independently phenyl, naphthyl, indanyl, indenyl, dihydronaphthyl, or tetralinyl each of which is optionally substituted with 1, 2, 3, or 4 groups that are independently:
  (i) $C_1$–$C_6$ alkyl optionally substituted with one, two or three substituents independently selected from the group consisting of $C_1$–$C_3$ alkyl, —F, —Cl, —Br, —I, —OH, —SH, —$NR_{1\text{-}a}R_{1\text{-}b}$, —C≡N, —$CF_3$, and $C_1$–$C_3$ alkoxy,
  (ii) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1\text{-}a}N_{1\text{-}b}$,
  (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (iv) —F, Cl, —Br and —I,
  (v) —$C_3$–$C_6$ alkoxy optionally substituted with 1, 2, or 3 —F,
  (vi) —$NR_{N\text{-}2}R_{N\text{-}3}$,
  (vii) —OH,
  (viii) —C≡N,
  (ix) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1\text{-}a}R_{1\text{-}b}$,
  (x) —CO—($C_1$–$C_4$ alkyl),
  (xi) —$SO_2$—$NR_{1\text{-}a}R_{1\text{-}b}$,
  (xii) —CO—$NR_{1\text{-}a}R_{1\text{-}b}$, or
  (xiii) —$SO_2$-($C_1$–$C_4$ alkyl),
(k) —$R_{1\text{-}heteroaryl}$ wherein $R_{1\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide,
where the $R_{1\text{-}heteroaryl}$ group is optionally substituted with 1, 2, 3, or 4 groups that are independently:
  (i) $C_1$–$C_6$ alkyl optionally substituted with 1, 2, or 3 groups independently selected from the group consisting of $C_1$–$C_3$ alkyl, —F, —Cl, —Br, —I, —OH, —SH, —$NR_{1\text{-}a}R_{1\text{-}b}$, —C≡N, —$CF_3$, and $C_1$–$C_3$ alkoxy,
  (ii) $C_2$–$C_6$ alkenyl optionally substituted with 1, 2, or 3 groups that are independently —F, —Cl, —OH, —SH, —C≡N, —$CF_3$, $C_1$–$C_3$ alkoxy, and —$NR_{1\text{-}a}R_{1\text{-}b}$,
  (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (iv) —F, —Cl, —Br and —I,
  (v) —$C_1$–$C_6$ alkoxy optionally substituted with one, two, or three —F,
  (vi) —$(CH_2)_{0\text{-}4}$—$NR_{N\text{-}2}R_{N\text{-}3}$,
  (vii) —OH,
  (viii) —C≡N,
  (ix) $(CH_2)_{0\text{-}4}$—$C_3$–$C_7$ cycloalkyl, optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (x) $(CH_2)_{0\text{-}4}$—CO—($C_1$–$C_6$ alkyl),
  (xi) $(CH_2)_{0\text{-}4}$—$SO_2$—$NR_{N\text{-}2}R_{N\text{-}3}$,
  (xii) $(CH_2)_{0\text{-}4}$—CO—$NR_{N\text{-}2}R_{N\text{-}3}$,
  (xiii) $(CH_2)_{0\text{-}4}$—$SO_2$-($C_1$–$C_6$ alkyl),
  (xiv) $(CH_2)_{0\text{-}4}$—N($R_{N\text{-}2}$)—$SO_2$—, and
  (xv) $(CH_2)_{0\text{-}4}$—N($R_{N\text{-}2}$)—C(O)—,
(8) —$(CH_2)_{0\text{-}4}$—CO—($C_1$–$C_{12}$ alkyl),
(9) —$(CH_2)_{0\text{-}4}$—CO—($C_2$–$C_{12}$ alkenyl),
(10) —$(CH_2)_{0\text{-}4}$—CO—($C_2$–$C_{12}$ alkynyl),
(11) —$(CH_2)_{0\text{-}4}$—CO—$(CH_2)_{0\text{-}4}$ ($C_3$–$C_7$ cycloalkyl),
(12) —$(CH_2)_{0\text{-}4}$—CO—$R_{1\text{-}heteroaryl}$,
(13) —$(CH_2)_{0\text{-}4}$—CO—$R_{1\text{-}heteroaryl}$,
(14) —$(CH_2)_{0\text{-}4}$—CO—$R_{1\text{-}heterocycle}$ wherein
  $R_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with 1, 2, 3, or 4 groups that are independently:
  (a) $C_1$–$C_6$ alkyl optionally substituted with one, two or three substituents independently selected from the group consisting of $C_1$–$C_3$ alkyl, halogen, —OH, —SH, —$NR_{1\text{-}a}R_{1\text{-}b}$ —C≡N, —$CF_3$, and $C_1$–$C_3$ alkoxy,
  (b) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and -$NR_{1\text{-}a}R_{1\text{-}b}$,
  (c) $C_2$–$C_6$ alkynyl with one or two triple bonds, optionally substituted with one, two or three substituents independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (d) halogen,
  (e) $C_1$–$C_6$ alkoxy,
  (f) —$C_1$–$C_6$ alkoxy optionally substituted with one, two, or three —F,
  (g) —$NR_{N\text{-}2}R_{N\text{-}3}$,
  (h) —OH,
  (i) —C≡N,
  (j) $(CH_2)_{0\text{-}4}$-($C_3$–$C_7$ cycloalkyl), optionally substituted with 1, 2, or 3 groups independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (k) —$(CH_2)_{0\text{-}4}$—CO—($C_1$–$C_4$ alkyl),
  (l) —$(CH_2)_{0\text{-}4}$—$SO_2$—$NR_{1\text{-}a}R_{1\text{-}b}$,
  (m) —$(CH_2)_{0\text{-}4}$—CO—$NR_{1\text{-}a}R_{1\text{-}b}$,
  (n) —$(CH_2)_{0\text{-}4}$—$SO_2$-($C_1$–$C_6$ alkyl), and
  (o) =O,
  (p) —$(CH_2)_{0\text{-}4}$—$N(R_{N\text{-}2})$—$SO_2$—,
  (q) —$(CH_2)_{0\text{-}4}$—$N(R_{N\text{-}2})$—C(O)—,
(15) —$(CH_2)_{0\text{-}4}$—CO—$R_{N\text{-}4}$ wherein
  $R_{N\text{-}4}$ at each occurrence is independently selected from the group consisting of morpholinyl, thiomorpholinyl, pyrrolidinonyl, pyrrolyl, pyrazolyl, thienyl, pyridyl N-oxide, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with 1, 2, 3, or 4 groups that are independently $C_1$–$C_6$ alkyl,
(16) —$(CH_2)_{0\text{-}4}$—$CO_2$—$R_{N\text{-}5}$ where
  $R_{N\text{-}5}$ at each occurrence is independently selected from the group consisting of:
    (a) $C_1$–$C_6$ alkyl,
    (b) —$(CH_2)_{0\text{-}2}$—$(R_{1\text{-}aryl})$,
    (c) $C_2$–$C_6$ alkenyl,
    (d) $C_2$–$C_6$ alkynyl,
    (e) $C_3$–$C_7$ cycloalkyl, and
    (f) —$(CH_2)_{0\text{-}4}$—$(R_{1\text{-}heteroaryl})$,
(17) —$(CH_2)_{0\text{-}4}$—$SO_2$—$NR_{N\text{-}2}R_{N\text{-}3}$,
(18) —$(CH_2)_{0\text{-}4}$—SO—($C_1$–$C_8$ alkyl),
(19) —$(CH_2)_{0\text{-}4}$—$SO_2$-($C_1$–$C_{12}$ alkyl),
(20) —$(CH_2)_{0\text{-}4}$—$SO_2$-($C_3$–$C_7$ cycloalkyl),
(21) —$(CH_2)_{0\text{-}4}$—N(H or $R_{N\text{-}5}$)—$CO_2$—$R_{N\text{-}5}$,
(22) —$(CH_2)_{0\text{-}4}$—N(H or $R_{N\text{-}5}$)—CO—$N(R_{N\text{-}5})_2$,
(23) —$(CH_2)_{0\text{-}4}$—N—CS—$N(R_{N\text{-}5})_2$,
(24) —$(CH_2)_{0\text{-}4}$—N(—H or $R_{N\text{-}5}$)—CO—$R_{N\text{-}2}$,
(25) —$(CH_2)_{0\text{-}4}$—$NR_{N\text{-}2}R_{N\text{-}3}$,
(26) —$(CH_2)_{0\text{-}4}$—$R_{N\text{-}4}$,
(27) —$(CH_2)_{0\text{-}4}$—O—CO—($C_1$–$C_6$ alkyl),
(28) —$(CH_2)_{0\text{-}4}$—O—P(O)—$(OR_{100})_2$ where $R_{100}$ is independently H or $C_1$–$C_4$ alkyl,
(29) —$(CH_2)_{0\text{-}4}$—O—CO—$N(R_{N\text{-}5})_2$,
(30) —$(CH_2)_{0\text{-}4}$—O—CS—$N(R_{N\text{-}5})_2$,
(31) —$(CH_2)_{0\text{-}4}$—O—$(R_{N\text{-}5})$,
(32) —$(CH_2)_{0\text{-}4}$—O—$(R_{N\text{-}5})$—COOH,
(33) —$(CH_2)_{0\text{-}4}$—S—$(R_{N\text{-}5})$,
(34) —$(CH_2)_{0\text{-}4}$—O—($C_1$–$C_6$ alkyl) wherein the alkyl group is optionally substituted with one, two, three, four, or five substituents independently selected from the group consisting of F, Cl, Br, and I,
(35) —$(CH_2)_{0\text{-}4}$-($C_3$–$C_8$ cycloalkyl),
(36) $C_2$–$C_6$ alkenyl optionally substituted with $C_1$–$C_3$ alkyl, halogen, —OH, —SH, —C≡N, —$CF_3$, $C_1$–$C_3$ alkoxy, or —$NR_{1\text{-}a}R_{1\text{-}b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1\text{-}a}R_{1\text{-}b}$, and
(38) —$(CH_2)_{0\text{-}4}$—N(—H or $R_{N\text{-}5}$)—$SO_2$—$R_{N\text{-}2}$;

(IV) —$(CR_{C\text{-}x}R_{C\text{-}y})_{0\text{-}4}$—$R_{C\text{-}heteroaryl}$ wherein $R_{C\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzoisothiazolyl, benzimidazolyl, benzofuranyl, furanyl, thienyl, pyrrolyl, oxadiazolyl, thiadiazolyl, triazolyl, tetrazolyl, oxazolopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, imidazopyrazolyl, quinazolinonyl, pyrazopyridyl, benzooxadiazolyl, dihydropyrimidinonyl, dihydrobenzofuranonyl, where the $R_{C\text{-}heteroaryl}$ group is bonded by any atom of the parent $R_{C\text{-}heteroaryl}$ group substituted by hydrogen such that the new bond to the $R_{C\text{-}heteroaryl}$ group replaces the hydrogen atom and its bond, where heteroaryl is optionally substituted 1, 2, 3, or 4 groups that are independently:
(1) $C_1$–$C_6$ alkyl, optionally substituted with 1, 2, or 3 groups independently selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
(2) —OH,
(3) —$NO_2$,
(4) —F, —Cl, —Br, —I,
(5) —CO—OH,
(6) —C≡N,
(V) $C_2$–$C_{10}$ alkenyl optionally substituted with one, two or three substituents independently selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$,
(VI) $C_2$–$C_{10}$ alkynyl optionally substituted with one, two or three substituents independently selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$,
(VII) —($C_1$–$C_6$ alkyl)-C-($C_1$–$C_6$ alkyl)-OH,
(VIII) —$CH_2$—NH—$CH_2$—CH(—O—$CH_2$—$CH_3$)$_2$,
(IX) —$(CH_2)_{0-6}$—C (=$NR_{1-a}$)($NR_{1-a}R_{1-b}$);
where $R_N$ is
(I) $R_{N-1}$—$X_N$— where $X_N$ is —CO—, and where $R_{N-1}$ is selected from the group consisting of:
(A) phenyl, which is optionally substituted with one, two or three of the following substituents which can be the same or different and are:
(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$, wherein $R_{1-a}$ and $R_{1-b}$ at each occurrence are independently H or $C_1$–$C_6$ alkyl,
(2) —OH,
(3) —$NO_2$,
(4) —F, —Cl, —Br, —I,
(5) —$CO_2$H,
(6) —C≡N,
(7) —$(CH_2)_{0-4}$—CO—$NR_{N-2}R_{N-3}$ where $R_{N-2}$ and $R_{N-3}$ are the same or different and are selected from the group consisting of:
(a) —H,
(b) —$C_1$–$C_8$ alkyl optionally substituted with one substituent selected from the group consisting of:
(i) —OH,
(ii) —$NH_2$,
(iii) phenyl,
(c) —$C_1$–$C_8$ alkyl optionally substituted with 1, 2, or 3 groups that are independently —F, —Cl, —Br, or —I,
(d) —$C_3$–$C_8$ cycloalkyl,
(e) —($C_1$–$C_2$ alkyl)-($C_3$–$C_8$ cycloalkyl),
(f) —($C_1$–$C_6$ alkyl)-O-($C_1$–$C_3$ alkyl),
(g) —$C_2$–$C_6$ alkenyl,
(h) —$C_2$–$C_6$ alkynyl,
(i) —$C_1$–$C_6$ alkyl chain with one double bond and one triple bond,
(j) —$R_{1-aryl}$, wherein $R_{1-aryl}$ at each occurrence is independently phenyl, naphthyl, indanyl, indenyl, dihydronaphthyl, or tetralinyl each of which is optionally substituted with 1, 2, 3, or 4 groups that are independently:

i) $C_1$–$C_6$ alkyl optionally substituted with one, two or three substituents independently selected from the group consisting of $C_1$–$C_3$ alkyl, —F, —Cl, —Br, —I, —OH, —SH, —$NR_{1-a}R_{1-b}$, —C≡N, —$CF_3$, and $C_1$–$C_3$ alkoxy,
(ii) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$,
(iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$,
(iv) —F, Cl, —Br and —I,
(v) —$C_1$–$C_6$ alkoxy optionally substituted with 1, 2, or 3 —F,
(vi) —$NR_{N-2}R_{N-3}$,
(vii) —OH,
(viii) —C≡N,
(ix) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1-a}R_{1-b}$,
(x) —CO—($C_1$–$C_4$ alkyl),
(xi) —$SO_2$—$NR_{1-a}R_{1-b}$,
(xii) —CO—$NR_{1-a}R_{1-b}$, or
(xiii) —$SO_2$-($C_1$–$C_4$ alkyl),
(k) —$R_{1-heteroaryl}$, wherein $R_{1-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1\text{-}heteroaryl}$ group is optionally substituted with 1, 2, 3, or 4 groups that are independently:
(i) $C_1\text{-}C_6$ alkyl optionally substituted with 1, 2, or 3 groups independently selected from the group consisting of $C_1\text{-}C_3$ alkyl, —F, —Cl, —Br, —I, —OH, —SH, —$NR_{1\text{-}a}R_{1\text{-}b}$, —C≡N, —$CF_3$, and $C_1\text{-}C_3$ alkoxy,
(ii) $C_2\text{-}C_6$ alkenyl optionally substituted with 1, 2, or 3 groups that are independently —F, —Cl, —OH, —SH, —C≡N, —$CF_3$, $C_1\text{-}C_3$ alkoxy, or —$NR_{1\text{-}a}R_{1\text{-}b}$,
(iii) $C_2\text{-}C_6$ alkynyl optionally substituted with 1, 2, or 3 groups that are independently —F, —Cl, —OH, —SH, —C≡N, —$CF_3$, $C_1\text{-}C_3$ alkoxy, or —$NR_{1\text{-}a}R_{1\text{-}b}$,
(iv) —F, —Cl, —Br and —I,
(v) —$C_1\text{-}C_6$ alkoxy optionally substituted with one, two, or three —F,
(vi) —$(CH_2)_{0\text{-}4}$—$NR_{N\text{-}2}R_{N\text{-}3}$,
(vii) —OH,
(viii) —C≡N,
(ix) $(CH_2)_{0\text{-}4}$—$C_3\text{-}C_7$ cycloalkyl, optionally substituted with 1, 2, or 3 groups that are independently selected from the group consisting of —F, —Cl, —OH, —SH, —C≡N, —$CF_3$, $C_1\text{-}C_3$ alkoxy, and —$NR_{1\text{-}a}R_{1\text{-}b}$,
(x) $(CH_2)_{0\text{-}4}$—CO—$(C_1\text{-}C_6$ alkyl),
(xi) $(CH_2)_{0\text{-}4}$—$SO_2$—$NR_{N\text{-}2}R_{N\text{-}3}$,
(xii) $(CH_2)_{0\text{-}4}$—CO—$NR_{N\text{-}2}R_{N\text{-}3}$,
(xiii) $(CH_2)_{0\text{-}4}$—$SO_2$-$(C_1\text{-}C_6$ alkyl),
(xiv) $(CH_2)_{0\text{-}4}$—$N(R_{N\text{-}2})$—$SO_2$—, and
(xv) $(CH_2)_{0\text{-}4}$—$N(R_{N\text{-}2})$—C(O)—, (l) —$R_{1\text{-}heterocyle}$, wherein
$R_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with 1, 2, 3, or 4 groups that are independently:
(a) $C_1\text{-}C_6$ alkyl optionally substituted with one, two or three substituents independently selected from the group consisting of $C_1\text{-}C_3$ alkyl, halogen, —OH, —SH, —$NR_{1\text{-}a}R_{1\text{-}b}$ —C≡N, —$CF_3$, and $C_1\text{-}C_3$ alkoxy,
(b) $C_2\text{-}C_6$ alkenyl with one or two double bonds, optionally substituted with one, two or three substituents independently selected from the group consisting of —F, —Cl, —OH, —SH, —C≡N, —$CF_3$, $C_1\text{-}C_3$ alkoxy, and —$NR_{1\text{-}a}R_{1\text{-}b}$,
(c) $C_2\text{-}C_6$ alkynyl with one or two triple bonds, optionally substituted with one, two or three substituents independently selected from the group consisting of —F, —Cl, —OH, —SH, —C≡N, —$CF_3$, $C_1\text{-}C_3$ alkoxy, and —$NR_{1\text{-}a}R_{1\text{-}b}$,
(d) halogen,
(e) $C_1\text{-}C_6$ alkoxy,
(f) —$C_1\text{-}C_6$ alkoxy optionally substituted with one, two, or three —F,
(g) —$NR_{N\text{-}2}R_{N\text{-}3}$,
(h) —OH,
(i) —C≡N,
(j) $(CH_2)_{0\text{-}4}$-$(C_3\text{-}C_8$ cycloalkyl), optionally substituted with 1, 2, or 3 groups independently selected from the group consisting of —F, —Cl, —OH, —SH, —C≡N, —$CF_3$, $C_1\text{-}C_3$ alkoxy, and —$NR_{1\text{-}a}R_{1\text{-}b}$,
(k) —$(CH_2)_{0\text{-}4}$—CO—$(C_1\text{-}C_4$ alkyl),
(l) —$(CH_2)_{0\text{-}4}$—$SO_2$—$NR_{1\text{-}a}R_{1\text{-}b}$,
(m) —$(CH_2)_{0\text{-}4}$—CO—$NR_{1\text{-}a}R_{1\text{-}b}$,
(n) —$(CH_2)_{0\text{-}4}$—$SO_2$-$(C_1\text{-}C_6$ alkyl), and
(o) =O,
(p) —$(CH_2)_{0\text{-}4}$—$N(R_{N\text{-}2})$—$SO_2$—,
(q) —$(CH_2)_{0\text{-}4}$—$N(R_{N\text{-}2})$—C(O)—,
(8) —$(CH_2)_{0\text{-}4}$—CO—$(C_1\text{-}C_{12}$ alkyl),
(9) —$(CH_2)_{0\text{-}4}$—CO—$(C_2\text{-}C_{12}$ alkenyl),
(10) —$(CH_2)_{0\text{-}4}$—CO—$(C_2\text{-}C_{12}$ alkynyl),
(11) —$(CH_2)_{0\text{-}4}$—CO—$(C_3\text{-}C_8$ cycloalkyl),
(12) —$(CH_2)_{0\text{-}4}$—CO—$R_{1\text{-}aryl}$,
(13) —$(CH_2)_{0\text{-}4}$—CO—$R_{1\text{-}heteroaryl}$,
(14) —$(CH_2)_{0\text{-}4}$—CO—$R_{1\text{-}heterocycle}$,
(15) —$(CH_2)_{0\text{-}4}$—CO—$R_{N\text{-}4}$ wherein $R_{N\text{-}4}$ is selected from the group consisting of phenyl, morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl, thienyl, pyrazolyl, pyridyl N-oxide, oxazolyl, thiazolyl, imidazolyl, and pyrrolidinyl where each group is optionally substituted with one, two, three, or four groups that are independently $C_1\text{-}C_6$ alkyl,
(16) —$(CH_2)_{0\text{-}4}$—CO—O—$R_{N\text{-}5}$ where $R_{N\text{-}5}$ is selected from the group consisting of:
(a) $C_1\text{-}C_6$ alkyl,
(b) —$(CH_2)_{0\text{-}2}$—$(R_{1\text{-}aryl})$,
(c) $C_2\text{-}C_6$ alkenyl,
(d) $C_2\text{-}C_6$ alkynyl,
(e) —$(CH_2)_{0\text{-}2}$—$C_3\text{-}C_8$ cycloalkyl,
(f) —$(CH_2)_{0\text{-}2}$—$(R_{1\text{-}heteroaryl})$, and
(g) —$(CH_2)_{0\text{-}2}$—$(R_{1\text{-}heterocycle})$,
(17) —$(CH_2)_{0\text{-}4}$—$SO_2$—$NR_{N\text{-}2}R_{N\text{-}3}$,
(18) —$(CH_2)_{0\text{-}4}$—SO—$(C_1\text{-}C_8$ alkyl),
(19) —$(CH_2)_{0\text{-}4}$—$SO_2$-$(C_1\text{-}C_{12}$ alkyl),
(20) —$(CH_2)_{0\text{-}4}$—$SO_2$-$(C_3\text{-}C_8$ cycloalkyl),
(21) —$(CH_2)_{0\text{-}4}$—N(H or $R_{N\text{-}5}$)—CO—O—$R_{N\text{-}5}$,
(22) —$(CH_2)_{0\text{-}4}$—N(H or $R_{N\text{-}5}$)—CO—$N(R_{N\text{-}5})_2$,
(23) —$(CH_2)_{0\text{-}4}$—N—CS—$N(R_{N\text{-}5})_2$,
(24) —$(CH_2)_{0\text{-}4}$—N(H or $R_{N\text{-}5}$)—CO—$R_{N\text{-}2}$,

(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO—($C_1$–$C_6$ alkyl),
(28) —$(CH_2)_{0-4}$—O—P(O)—$(OR_{100})_2$ wherein $R_{100}$ at each occurrence is independently —H or $C_1$–$C_4$ alkyl,
(29) —$(CH_2)_{0-4}$—O—CO—$N(R_{N-5})_2$,
(30) —$(CH_2)_{0-4}$—O—CS—$N(R_{N-5})_2$,
(31) —$(CH_2)_{0-4}$—O—$(R_{N-5})$,
(32) —$(CH_2)_{0-4}$—O—$(R_{N-5})$—COOH,
(33) —$(CH_2)_{0-4}$—S—$(R_{N-5})$,
(34) —$(CH_2)_{0-4}$—O—($C_1$–$C_6$ alkyl optionally substituted with one, two, three, four, or five of —F),
(35) $C_3$–$C_8$ cycloalkyl,
(36) $C_2$–$C_6$ alkenyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(38) —$(CH_2)_{0-4}$—N(H or $R_{N-5}$)—$SO_2$—$R_{N-2}$,
(39) —$(CH_2)_{0-4}$-($C_3$–$C_8$ cycloalkyl),
(B) —$R_{N-heteroaryl}$ where $R_{N-heteroaryl}$ is selected from the group consisting of pyridinyl, indolyl, indolinyl, isoindolyl, imidazolyl, isoxazolyl, oxazolyl, thiazolyl, indolizinyl and isochromanyl,
where the $R_{N-heteroaryl}$ group is bonded by any atom of the parent $R_{N-heteroaryl}$ group substituted by hydrogen such that the new bond to the $R_{N-heteroaryl}$ group replaces the hydrogen atom and its bond, where heteroaryl is optionally substituted with one, two, three, or four of:
(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
(2) —OH,
(3) —$NO_2$,
(4) —F, —Cl, —Br, —I,
(5) —$CO_2H$,
(6) —C≡N,
(7) —$(CH_2)_{0-4}$—CO—$NR_{N-2}R_{N-3}$,
(8) —$(CH_2)_{0-4}$—CO—($C_1$–$C_{12}$ alkyl),
(9) —$(CH_2)_{0-4}$—CO—($C_2$–$C_{12}$ alkenyl),
(10) —$(CH_2)_{0-4}$—CO—($C_2$–$C_{12}$ alkynyl),
(11) —$(CH_2)_{0-4}$—CO—($C_3$–$C_8$ cycloalkyl),
(12) —$(CH_2)_{0-4}$—CO—$R_{1-aryl}$,
(13) —$(CH_2)_{0-4}$—CO—$R_{1-heteroaryl}$,
(14) —$(CH_2)_{0-4}$—CO—$R_{1-heterocycle}$,
(15) —$(CH_2)_{0-4}$—CO—$R_{N-4}$,
(16) —$(CH_2)_{0-4}$—CO—O—$R_{N-5}$,
(17) —$(CH_2)_{0-4}$—$SO_2$—$NR_{N-2}R_{N-3}$,
(18) —$(CH_2)_{0-4}$—SO—($C_1$–$C_8$ alkyl),
(19) —$(CH_2)_{0-4}$—$SO_2$-($C_1$–$C_{12}$ alkyl),
(20) —$(CH_2)_{0-4}$—$SO_2$-($C_3$–$C_8$ cycloalkyl),
(21) —$(CH_2)_{0-4}$—N(H or $R_{N-5}$)—CO—O—$R_{N-5}$,
(22) —$(CH_2)_{0-4}$—N(H or $R_{N-5}$)—CO—$N(R_{N-5})_2$,
(23) —$(CH_2)_{0-4}$—N—CS—$N(R_{N-5})_2$,
(24) —$(CH_2)_{0-4}$—N(—H or $R_{N-5}$)—CO—$R_{N-2}$,
(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO—($C_1$–$C_1$ alkyl),
(28) —$(CH_2)_{0-4}$—O—P(O)—$(OR_{100})_2$,
(29) —$(CH_2)_{0-4}$—O—CO—$N(R_{N-5})_2$,
(30) —$(CH_2)_{0-4}$—O—CS—$N(R_{N-5})_2$,
(31) —$(CH_2)_{0-4}$—O—$(R_{N-5})$,
(32) —$(CH_2)_{0-4}$—O—$(R_{N-5})$—COOH,
(33) —$(CH_2)_{0-4}$—S—$(R_{N-5})$,
(34) —$(CH_2)_{0-4}$—O—($C_1$–$C_6$ alkyl optionally substituted with one, two, three, four, or five of —F),
(35) $C_3$–$C_8$ cycloalkyl,
(36) $C_2$–$C_6$ alkenyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$,
(38) —$(CH_2)_{0-4}$—N(—H or $R_{N-5}$)—$SO_2$—$R_{N-2}$,
(39) —$(CH_2)_{1-4}$—$C_3$–$C_8$ cycloalkyl,
(C) $R_{N-aryl}$—W—$R_{N-aryl}$,
(D) $R_{N-aryl}$—W—$R_{N-heteroaryl}$,
(E) $R_{N-aryl}$—W—$R_{1-heterocycle}$,
(F) $R_{N-heteroaryl}$—W—$R_{N-aryl}$,
(G) $R_{N-heteroaryl}$—W—$R_{N-heteroaryl}$,
(H) $R_{N-heteroaryl}$—W—$R_{N-1-heterocycle}$,
(I) $R_{N-heterocycle}$—W—$R_{N-aryl}$,
(J) $R_{N-heterocycle}$—W—$R_{N-heteroaryl}$,
(K) $R_{N-heterocycle}$—W—$R_{N-1-heterocycle}$,
where W is
(13) —$(CH_2)_{1-4}$—,
(14) —O—,
(15) —$S(O)_{0-2}$—,
(16) —$N(R_{N-5})$—,
(17) —CO—; or
(18) a bond;
(II) —CO—($C_1$–$C_6$ alkyl)-M-($C_1$–$C_6$ alkyl), where M is S, SO or $SO_2$, and wherein each alkyl is unsubstituted or substituted with one, two, or three of substituents independently selected from the group consisting of:
(A) —NH—CO—($C_1$–$C_6$ alkyl),
(B) —NH—CO—O—$R_{N-8}$,
(C) —$NR_{N-2}R_{N-3}$;
where $R_1$ is
—$(CH_2)_{n1}$-phenyl, where $n_1$ is zero or one, and which is optionally substituted with one, two, three or four of the following substituents on the phenyl ring:
(A) $C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
(B) $C_2$–$C_6$ alkenyl with one or two double bonds, optionally substituted with one, two or three substituents selected from the group consisting of —F, —Cl, —OH, —SH, —C≡N, —$CF_3$, $C_1$–$C_3$ alkoxy, and —$NR_{1-a}R_{1-b}$,
(C) $C_2$–$C_5$ alkynyl with one or two triple bonds, optionally substituted with one, two or three substituents selected from the group consisting of —F, —Cl, —OH, —SH, —C≡N, —$CF_3$, $C_1$–$C_3$ alkoxy, and —$NR_{1-a}R_{1-b}$,
(D) —F, Cl, —Br or —I,
(F) —$C_1$–$C_6$ alkoxy optionally substituted with one, two or three of —F,
(G) —$NR_{N-2}R_{N-3}$ where $R_{N-2}$ and $R_{N-3}$ are as defined below,
(H) —OH,
(I) —C≡N,
(J) $C_3$–$C_7$ cycloalkyl, optionally substituted with one, two or three substituents selected from the group consisting of —F, —Cl, —OH, —SH, —C≡N, —$CF_3$, $C_1$–$C_3$ alkoxy, and —$NR_{1-a}R_{1-b}$,
(K) —CO—($C_1$–$C_4$ alkyl),
(L) —$SO_2$—$NR_{1-a}R_{1-b}$, (M) —CO—NR$_{1-a}$R$_{1-b}$,
(N) —SO$_2$-(C$_1$-C$_4$ alkyl); and where R$_2$ is (I) —(Z)-C$_1$-C$_6$ alkyl, where Z is a bond, —C(O), —CO$_2$— or —SO$_2$—, wherein the alkyl group is optionally substituted with one, two or three substituents selected from the group consisting of C$_1$-C$_3$ alkyl, C$_1$-C$_7$ alkyl (optionally substituted with C$_1$-C$_3$ alkyl and C$_1$-C$_3$ alkoxy), —F, —Cl, —Br, —I, —OH, —SH, —C≡N, —CF$_3$, C$_1$-C$_3$ alkoxy, —NR$_{1-a}$R$_{1-b}$ where R$_{1-a}$ and R$_{1-b}$ are independently —H or C$_1$-C$_6$ alkyl, and —OC=NR$_{1-a}$R$_{1-b}$, (II) —(Z)-CH$_2$—S(O)$_{0-2}$-(C$_1$-C$_6$ alkyl), (III) —(Z)-CH$_2$—CH$_2$—S(O)$_{0-2}$-(C$_1$-C$_6$ alkyl), (IV) —(Z)-C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (V) —(Z)-C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (VI) —(Z)—(CH$_2$)$_{n1}$—(R$_{1-aryl}$), where Z is a bond, CO, CO$_2$ or SO$_2$, where n, is zero or one and where R$_{1-aryl}$ is phenyl, 1-naphthyl, 2-naphthyl and indanyl, indenyl, dihydronaphthalyl, or tetralinyl optionally substituted with one, two, three or four of the following substituents on the aryl ring:

(A) C$_1$-C$_6$ alkyl optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$, (B) C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (C) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (D) —F, Cl, —Br or —I, (F) —C$_1$-C$_6$ alkoxy optionally substituted with one, two or three of —F, (G) —NR$_{N-2}$R$_{N-3}$ where R$_{N-2}$ and R$_{N-3}$ are as defined below, (H) —OH, (I) —C≡N, (J) C$_3$-C$_7$ cycloalkyl, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (K) —CO—(C$_1$-C$_4$ alkyl), (L) —SO$_2$—NR$_{1-a}$R$_{1-b}$, (M) —CO—NR$_{1-a}$R$_{1-b}$, (N) —SO$_2$-(C$_1$-C$_4$ alkyl), (VII) —(Z)—(CH$_2$)$_{n1}$—(R$_{1-heteroaryl}$) where n$_1$ is as defined above and where R$_{1-heteroaryl}$ is selected from the group consisting of:

pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, where the R$_{1-heteroaryl}$ group is bonded to —(CH$_2$)$_{n1}$— by any ring atom of the parent R$_{N-heteroaryl}$ group substituted by hydrogen such that the new bond to the R$_{1-heteroaryl}$ group replaces the hydrogen atom and its bond, where heteroaryl is optionally substituted with one, two, three or four of:

(1) C$_1$-C$_6$ alkyl optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$, (2) C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (3) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$, (4) —F, Cl, —Br or —I, (6) —C$_1$-C$_6$ alkoxy optionally substituted with one, two, or three of —F, (7) —NR$_{N-2}$R$_{N-3}$ where R$_{N-2}$ and R$_{N-3}$ are as defined below, (8) —OH, (9) —C≡N,

(10) C$_3$-C$_7$ cycloalkyl, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$,

(11) —CO—(C$_1$-C$_4$ alkyl),

(12) —SO$_2$—NR$_{1-a}$R$_{1-b}$,

(13) —CO—NR$_{1-a}$R$_{1-b}$, or

(14) —SO$_2$-(C$_1$-C$_4$ alkyl), with the proviso that when n$_1$ is zero R$_{1-heteroaryl}$ is not bonded to the carbon chain by nitrogen, or (VIII) —(Z)—(CH$_2$)$_{n1}$—(R$_{1\text{-}heterocycle}$) where n$_1$ is as defined above and R$_{1\text{-}heterocycle}$ is selected from the group consisting of;

morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homomorpholinyl S-oxide, homothiomorpholinyl S,S-dioxide, oxazolidinonyl, dihydropyrazolyl, dihydropyrrolyl dihydropyrazinyl dihydropyridinyl dihydropyrimidinyl, dihydrofuryl, dihydropyranyl, tetrahydrothienyl S-oxide, tetrahydrothienyl S,S-dioxide, homothiomorpholinyl S-oxide, where the R$_{1\text{-}heterocycle}$ group is bonded by any atom of the parent R$_{1\text{-}heterocycle}$ group substituted by hydrogen such that the new bond to the R$_{1\text{-}heterocycle}$ group replaces the hydrogen atom and its bond, where heterocycle is optionally substituted with one, two, three or four:

(1) C$_1$–C$_6$ alkyl optionally substituted with one, two or three substituents selected from the group consisting of C$_3$–C$_3$ alkyl, —F, —Cl, —Br, —I, —OH, —SH, —C≡N, —CF$_3$, C$_1$–C$_3$ alkoxy, and —NR$_{1\text{-}a}$R$_{1\text{-}b}$, (2) C$_2$–C$_6$ alkenyl with one or two double bonds, optionally substituted with one, two or three substituents selected from the group consisting of —F, —Cl, —OH, —SH, —C≡N, —CF$_3$, C$_1$–C$_3$ alkoxy, and —NR$_{1\text{-}a}$R$_{1\text{-}b}$, (3) C$_2$–C$_6$ alkynyl with one or two triple bonds, optionally substituted with one, two or three substituents selected from the group consisting of —F, —Cl, —OH, —SH, —C≡N, —CF$_3$, C$_1$–C$_3$ alkoxy, and —NR$_{1\text{-}a}$R$_{1\text{-}b}$, (4) —F, Cl, —Br, or —I, (5) C$_1$–C$_6$ alkoxy, (6) —C$_1$–C$_6$ alkoxy optionally substituted with one, two, or three —F, (7) —NR$_{N\text{-}2}$R$_{N\text{-}3}$ where R$_{N\text{-}2}$ and R$_{N\text{-}3}$ are as defined below, (8) —OH, (9) —C≡N,

(10) C$_3$–C$_7$ cycloalkyl, optionally substituted with one, two or three substituents selected from the group consisting of —F, —Cl, —OH, —SH, —C≡N, —CF$_3$, C$_1$–C$_3$ alkoxy, and —NR$_{1\text{-}a}$R$_{1\text{-}b}$,

(11) —CO—(C$_1$–C$_4$ alkyl),

(12) —SO$_2$—NR$_{1\text{-}a}$R$_{1\text{-}b}$,

(13) —CO—NR$_{1\text{-}a}$R$_{1\text{-}b}$,

(14) —SO$_2$-(C$_1$–C$_4$ alkyl),

(15) =O, with the proviso that when n$_1$ is zero R$_{1\text{-}heterocycle}$ is not bonded to the carbon chain by nitrogen; and where R$_{20}$ is H or C$_{1\text{-}6}$ alkyl or alkenyl.

The compounds of the invention, and pharmaceutically acceptable salts or esters thereof, are useful for treating humans who have Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease. It is preferred that the disease is Alzheimer's disease.

The compounds of the invention are also useful to inhibit beta-secretase and reduce or inhibit the formation of placque.

When treating these diseases, compounds of the invention can either be used individually or together as is best for the patient.

With regard to these diseases the term "treating" means that compounds of the invention can be used in humans with existing disease. The compounds of the invention will not necessarily cure the patient who has the disease but will delay or slow the progression of the disease thereby giving the individual a more useful life span.

The term "preventing" means that that if the compounds of the invention are administered to those who do not now have the disease but who would normally get the disease or be at increased risk for the disease, they will not get the disease. In addition, "preventing" also includes delaying the development of the disease in an individual who will ultimately get the disease or would be at risk for the disease. By delaying the onset of the disease, compounds of the invention have prevented the individual from getting the disease during the period in which the individual would normally have gotten the disease or reduce the rate of development of the disease or some of its effects but for the administration of compounds of the invention up to the time the individual ultimately gets the disease.

In treating or preventing the above diseases the compounds of the invention are administered in a therapeutically effective amount. The therapeutically effective amount will vary depending on the particular compound used and the route of administration as is known to those skilled in the art.

In treating a patient with any of the diagnosed above conditions a physician should begin administration of one or more of the compounds of the invention immediately and continue indefinitely.

In treating patients who do not at the have Alzheimer's disease, but who are believed to be at substantial risk for getting Alzheimer's disease in the future, the physician should start treatment when the patient first experiences early pre-Alzheimer'symptoms such as, memory or cognitive problems associated with aging. In addition, there are some patients who are at high risk because of having the genetic marker APOE4 which is predictive for Alzheimer's disease. In these situations, even though the patient does not have the disease, the administration of the compounds of the invention should be started before disease symptoms appear and treatment continued indefinitely to prevent or delay them from possibly getting the disease.

The compounds of the invention can be administered orally, parenterally (IV, IM, depo-IM, SQ and depo-SQ), sublingually, intranasally (inhalation), intrathecally, topically and rectally. The invention here is the compounds of the invention. There is nothing new about the routes of administration nor the dosage forms. Dosage forms known to those skilled in the art are suitable for delivery of the compounds of the invention.

When administered orally, the compounds of the invention can be administered in usual dosage forms for oral administration as is well known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the compounds of the invention need to be administered only once or twice daily.

The oral dosage forms are administered to the patient one thru four times daily. It is preferred that the compounds of the invention be administered either three or fewer time, more preferably once or twice daily. Hence, it is preferred that the compounds of the invention be administered in solid dosage form and further it is preferred that the solid dosage form be a sustained release form which permits once or twice daily dosing. It is preferred that whatever dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art. When administered orally the therapeutically effective amount is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started on one dose, that dose may have to be varied over time as the patient's condition changes.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be given sublingually. When given sublingually, the compounds of the invention should be given one thru four times daily in the same amount as for IM administration.

The compounds of the invention can be given intranasally. When given by this route of administration, the appropriate dosage forms are a nasal spray or dry powder as is known to those skilled in the art. The dosage of the compounds of the invention for intranasal administration is the same as for IM administration.

The compounds of the invention can be given intrathecally. When given by this route of administration the appropriate dosage form can be a parenteral dosage form as is known to those skilled in the art. The dosage of the compounds of the invention for intrathecal administration is the same as for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the same as for depot administration.

The compounds of the invention are used in the same manner by the same routes of administration using the same pharmaceutical dosage forms and at the same dosing schedule for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease.

The compounds of the invention can be used with each other or with other agents used to treat or prevent the conditions listed above. Such agents include gamma-secretase inhibitors, anti-amyloid vaccines and pharmaceutical agents such as donepezil hydrochloride (ARICEPT Tablets), tacrine hydrochloride (COGNEX Capsules) or other acetylcholine esterase inhibitors and with direct or indirectneurotropic agents of the future.

In addition, the compounds of the invention can also be used with inhibitors of P-glycoproten (P-gp). The use of P-gp inhibitors is known to those skilled in the art. See for example, Cancer Research, 53, 4595–4602 (1993), Clin. Cancer Res., 2, 7–12 (1996), Cancer Research, 56, 4171–4179 (1996), International Publications WO99/64001 and WO01/10387. The important thing is that the blood level of the P-gp inhibitor be such that it exerts its effect in inhibiting P-gp from decreasing brain blood levels of the compounds of the invention. To that end the P-gp inhibitor and the compounds of the invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,1 1-methanodibenzosuberane, phenothiazines, acridine derivatives such as GF120918, FK506, VX-710, LY335979, PSC-833, GF-102,918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect From the acidic stomach, are also well known to those skilled in the art.

In addition, the P-gp inhibitors can be administered parenterally. When administered parenterally they can be administered IV, IM, depo-IM, SQ or depo-SQ. The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

Route of administration and the dosage forms for administering the P-gp inhibitors are known in the art. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, other medication the individual may be taking as is well known to those skilled in the art.

The compounds of the invention are also useful to inhibit beta-secretase and reduce or inhibit the formation of plaque.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site".

While not wishing to be bound by a particular theory, inhibition of beta-secretase activity is thought to inhibit production of beta amyloid peptide (A-beta or Abeta). Inhibitory activity is demonstrated in one of a variety of inhibition assays, whereby cleavage of an APP substrate in the presence of A-beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the examples below.

The enzymatic activity of beta-secretase and the production of Abeta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Mol. Cell. Neurosci. 14:419–427 (1999); Science 286:735–741 (1999); Nature 402:533–537 (1999); Nature 40:537–540 (1999); and PNAS USA 97:1456–1460 (2000)). Synthetic forms of the enzyme have also been described (WO98/22597 and WO00/17369). Beta-secretase can be extracted and purified from human brain tissue and can be produced in cells, for example mammalian cells expressing recombinant enzyme.

Prefered compounds of the invention are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described in Nature 325:733–6 (1987), the 770 amino acid isotype described Nature 331:530–532 (1981), and variants such as the Swedish Mutation (KM670-1NL) (APP-SW), the London Mutation (V7176F), and others. See, for example U.S. Pat. No. 5,766,846 and also Nature Genet. 1:233–234 (1992), for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful forenzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Neuro. Lett. 249:21–4 (1999) and in U.S. Pat. No. 5,612,486.

Useful antibodies to detect Abeta include, for example, the monoclonal antibody 6E10 (Senetek, St. Louis, Mo.) that specifically recognizes an epitope on amino acids 1–16 of the Abeta peptide; antibodies 162 and 164 (New York State Institute for Basic Research, Staten Island, N.Y.) that are specific for human A-beta 1–40 and 1–42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590–596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the EXAMPLES below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing A-beta-secretase and an APP substrate having A-beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4–7, at approximately 37° C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A-beta. Contact of an APP substrate with A-beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process Abeta from APP provide a useful means to assay inhibitory activities of the compounds of the invention. Production and release of A-beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as Abeta.

Although both neural and non-neural cells process and release A-beta, levels of endogenous beta-secretase activity are low and often difficult to detect by EIA. The use of cell types known to have enhanced beta-secretase activity, enhanced processing of APP to Abeta, and/or enhanced production of A-beta are therefore preferred. For example, transfection of cells with the Swedish Mutant form of APP (APP-SW); with APP-KK; or with APP-SW-KK provides cells having enhanced beta-secretase activity and producing amounts of A-beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of Abeta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and /or processing of APP to release Abeta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399, 5,612,486, 5,387,742, 5,720,936, 5,850,003, 5,877,015 and 5,811,633, and Nature 373:523 (1995)). Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of Abeta release can be analyzed in these animals by measure of cleavage fragments in the animal's body fluids such as cerebral fluid or tissues. Analysis of brain tissues for Abeta deposits or plaques is preferred.

On contacting an APP substrate with A-beta-secretase enzyme in the presence of an inhibitory compound of the invention and under conditions sufficient to permit enzymatic mediated cleavage of APP and/or release of Abeta from the substrate, the compounds of the invention are effective to reduce beta-secretase-mediated cleavage of APP at the beta-secretase cleavage site and/or effective to reduce released amounts of Abeta. Where such contacting is the administration of the inhibitory compounds of the invention to an animal model, for example, as described above, the compounds are effective to reduce Abeta deposition in brain tissues of the animal, and to reduce the number and/or size of beta amyloid plaques. Where such administration is to a human subject, the compounds are effective to inhibit or slow the progression of disease characterized by enhanced amounts of Abeta to slow the progression of AD in the, and/or to prevent onset or development of AD in a patient at risk for the disease.

Unless defined otherwise, all scientific and technical terms used herein have the same meaning as commonly understood by one of skill in the art to which this invention belongs.

Definitions and Conventions

The definitions and explanations below are for the terms as used throughout this entire document including both the specification and the claims.

Definitions

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

AD refers to Alzheimer's disease.

APP, amyloid precursor protein, is defined as any APP polypeptide, including APP variants, mutations, and isoforms, for example, as disclosed in U.S. Pat. No. 5,766,846.

A-beta (or Abeta), amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (beta-secretase, BACE1, Asp2, Memapsin 2) is an aspartyl protease that mediates cleavage of APP at the amino-terminal edge of Abeta. Human beta-secretase is described, for example, in WO00/17369.

DMSO refers to dimethyl sulfoxide.

All temperatures are in degrees Centigrade.

HPLC refers to high pressure liquid chromatography.

BOC refers to 1,1-dimethylethoxy carbonyl or t-butoxycarbonyl, —CO—O—C(CH$_3$)$_3$.

Protecting group generally refers to any suitable protecting groups, compatible with the synthetic routes for preparing the compounds herein. Generally, suitable protecting groups are those found in *Protective Groups in Organic Synthesis*, Greene, et. al., 2$^{nd}$ ed., John Wiley & Sons, 1991; and 3$^{rd}$ ed., John Wiley & Sones, 1999 More specific protecting groups are α-methyl benzyl, t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcycoopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobrornyloxycarbonyl and 1-piperidyloxycarbonyl, 9-fluoroenylmethyl carbonate, —CH—CH═CH$_2$ and phenyl-C(═N—)—H.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

Pharmaceutically acceptable refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs.

All patents and publications referred to herein are hereby incorporated by reference for all purposes.

Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$," where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)(R_j)H_2$. When chemical formulas are drawn in a linear fashion, such as those above, variable substituents contained in parentheses are bonded to the atom immediately to the left of the variable substituent enclosed in parentheses. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*$=$C(CH_3)$—CH=CCl—CH=$C^*H$ with the convention that the atoms marked with an asterisk (*) are bonded to each other resulting in the formation of a ring. Likewise, the cyclic molecular fragment, 4-(ethyl)-1-piperazinyl can be represented by —$N^*$—$(CH_2)_2$—$N(C_2H_5)$—$CH_2$—$C^*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha configuration and is identified by a broken, dashed or dotted line attachment to the carbon atom, i.e., by the symbol "- - -" or " . . . ". The corresponding substituent attached "above" ($X_2$) the other ($X_1$) is identified as being in the beta configuration and is indicated by an unbroken line attachment to the carbon atom. When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents alpha-$R_{i-j}$ and beta-$R_{i-k}$. When a bivalent variable, $R_i$, is defined to consist of two monovalent variable substituents, the convention used to define the bivalent variable is of the form "alpha-$R_{i-j}$:beta-$R_{i-k}$" or some variant thereof. In such a case both alpha-$R_{i-j}$ and beta-$R_{i-k}$ are attached to the carbon atom to give -C(alpha-$R_{i-j}$)(beta-$R_{i-k}$)-. For example, when the bivalent variable $R_6$, —$C(=R_6)$— is defined to consist of two monovalent variable substituents, the two monovalent variable substituents are alpha-$R_{6-1}$:beta-$R_{6-2}$, . . . alpha-$R_{6-9}$:beta-$R_{6-10}$, etc, giving -C(alpha-$R_{6-1}$) (beta-$R_{6-2}$)-, . . . -C(alpha-$R_{6-9}$) (beta-$R_{6-10}$)—, etc. Likewise, for the bivalent variable $R_{11}$, —$C(=R_{11})$—, two monovalent variable substituents are alpha-$R_{11}$:beta-$R_{11-2}$. For a ring substituent for which separate alpha and beta orientations do not exist (e.g. due to the presence of a carbon carbon double bond in the ring), and for a substituent bonded to a carbon atom which is not part of a ring the above convention is still used, but the alpha and beta designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide.

When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —CH$_2$—CH$_2$—O—CO— . . . " means a lactone in which the carbonyl is bonded to $C_2$. However, when designated " . . . $R_j$ and $R_i$ are taken together to form —CO—O—CH$_2$—CH$_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group CH$_3$—(CH$_2$)$_n$—O—CO— where n is zero, one or two. By the second method the carbon atom content of only each portion of the definition is indicated separately by enclosing the "$C_i$—$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

Modes of Preparation

Compounds of the invention can be prepared utilizing a variety of known chemical transformations. In essence, the preparation of the compounds of formula I may be achieved using techniques and chemical processes analogous to those known in the art; the choice of the specific route being dependent upon the usual factors in pharmaceutical research institutions such as availability and cost of starting materials, time and difficulties in separation and purification of intermediates and final compounds and such other factors well known and generally appreciated by those of ordinary skill in the art. In fact, there will generally be more than one process to prepare the compounds of the invention. Those having skill in the art will recognize that the starting materials may be varied and additional steps employed to produce compounds encompassed by the present invention, as demonstrated by the following examples.

The starting materials and various intermediates may be obtained from commercial sources, prepared from commercially available organic compounds, or prepared using well known synthetic methods. In some cases, protection of reactive functionalities may be necessary to achieve some of the transformations. In general, the need for such protecting groups as well as the conditions necessary to attach and remove such groups will be apparent to those skilled in the art of organic synthesis.

Representative synthetic methodologies suitable for preparing the compounds of the invention are disclosed in: *Tetrahedron Letters*, 39, 4925–4928 (1998); *Journal of Medicinal Chemistry*, 41, 3387–3401 (1998); *Journal of Medicinal Chemistry*, 39, 3203–3216 (1996); and/or *Journal of the Chemical Society Chemical Communications*, 1052–1053 (1993).

Examples of syntheses for preparing compounds of the invention are set forth below in Scheme 1, Scheme 2, Scheme 3 and Scheme 4. Specific exemplary descriptions of the routes depicted in Schemes 1–4 are found in the synthetic examples given for Intermediates A–D, general compound couplings E–G, and examples 1–5 below.

Scheme 1: Intermediate Synthesis

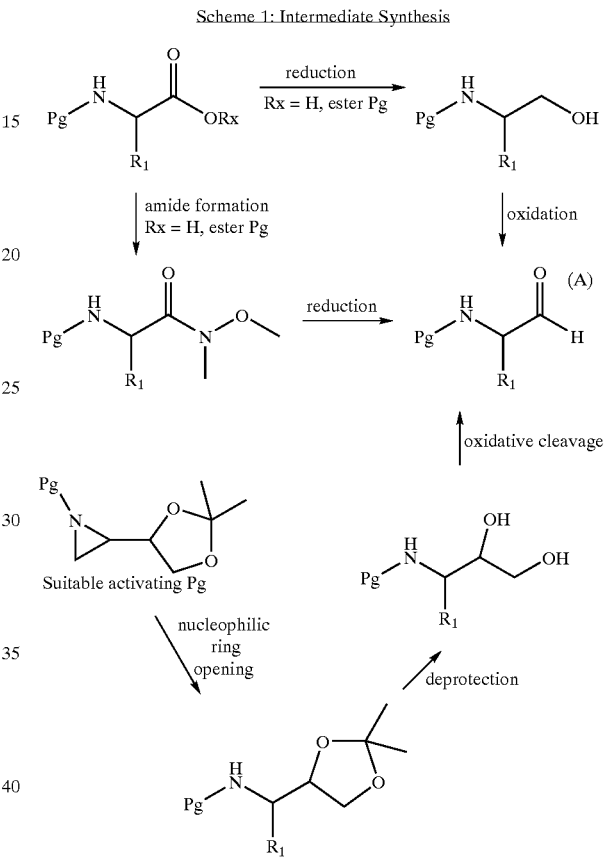

As used herein, Pg means protecting group, which is as defined herein; for exemplary synthesis of N-protected a-amino aldehydes see: Chem. Rev. 1989, 89, 149.

Scheme 2: Intermediate Synthesis

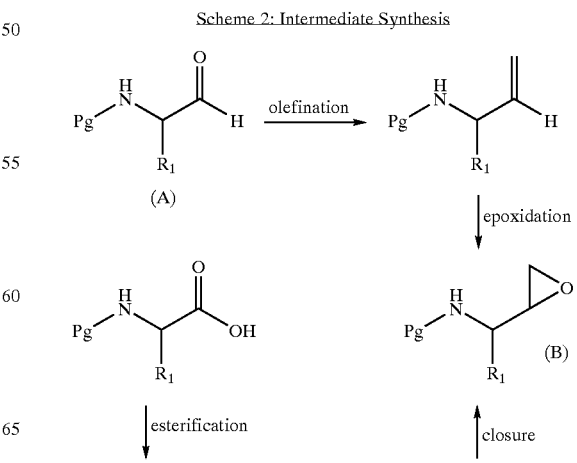

-continued

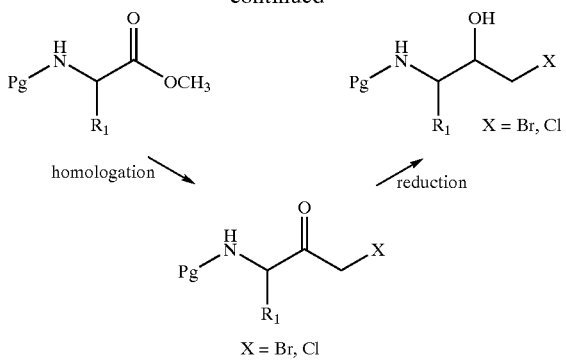

homologation / reduction

X = Br, Cl

Scheme 3: General Compound Synthesis

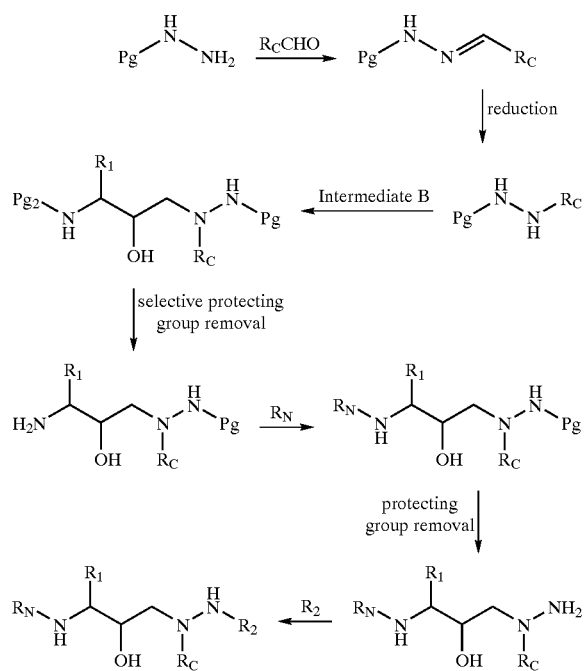

The invention is illustrated further by the following examples which are not to be construed as limiting the invention in scope or spirit to the specific procedures described in them.

Intermediate Syntheses

A. 2-Methanesulfonylamino-thiazole-4-carboxylic Acid

2-Methanesulfonylamino-thiazole-4-carboxylic acid methyl ester: To a well stirred solution of methyl 2-aminothiazole-4-carboxylate hydrobromide (*Justus Liebigs Ann. Chem.* 1951, 571, 44, *Heterocycles* 1997, 45, 1299) (13 g, 51 mmol) and TEA (40 mL, 290 mmol) in DCM (130 mL) at rt was added methanesulfonyl chloride (11 mL, 140 mmol) dropwise. After stirring for 1 h, the reaction mixture was filtered and the filtrate concentrated. The residue was re-suspended in ethyl acetate, filtered and chromatographed on silica gel (ethyl acetate/ethanol, 97:3) to provide 2-methanesulfonylamino-thiazole-4-carboxylic acid methyl ester (5.5 g). MS (ESI−) for $C_6H_8N_2O_4S_2$ m/z 234.9 (M−H)⁻.

2-Methanesulfonylamino-thiazole-4-carboxylic acid: A mixture of 2-methanesulfonylamino-thiazole-4-carboxylic acid methyl ester (5.5 g, 22 mmol) in 1M NaOH(50 mL) was stirred at rt for 1 h. The reaction mixture was extracted with ethyl acetate, concentrated and chromatographed on silica gel (ethyl acetate/ethanol, 97:3) to provide 2-methanesulfonylamino-thiazole-4-carboxylic acid (3.7 g) as a solid. MS (ESI−) for $C_5H_6N_2O_4S_2$ m/z 220.9 (M−H)⁻.

B. tert-Butyl 2-((2R,3S)-3-amino-2-hydroxy-4-phenylbutyl)-2-ethylhydrazinecarboxylate N'-Ethylidene-hydrazinecarboxylic acid tert-butyl ester: A solution of tert-butyl carbazate (50.0 g, 0.38 mole) and acetaldehyde (17.5 g, 0.4 mole) in ethanol (250 mL) was refluxed for 72 h. The solution was concentrated in vacuo and dissolved in ethyl acetate. The solution was washed with water, dried (anhydrous sodium sulfate) and concentrated to afford N'-ethylidene-hydrazinecarboxylic acid tert-butyl ester (56 g) as a light yellow oil that solidified on standing. MS (ESI+) for $C_7H_{14}N_2O_2$ m/z 159.0 (M+H)⁺.

N'-Ethylhydrazinecarboxylic acid tert-butyl ester: A slurry of N'-ethylidene-hydrazinecarboxylic acid tert-butyl ester (5.0 g, 32 mmol), acetic acid (48 μL) and PtO₂ (250 mg) in ethanol (50 mL) was shaken under a 40 psi pressure of H₂ in a Parr hydrogenator for 24 h. The mixture was filtered through Celite to provide N'-ethylhydrazinecarboxylic acid tert-butyl ester (5 g) as a clear oil. MS (ESI+) for $C_7H_{16}N_2O_2$ m/z 161.0 (M+H)⁺.

tert-Butyl 2-((2R,3S)-3-{[(benzyloxy)carbonyl]amino}-2-hydroxy-4-phenylbutyl)-2-ethylhydrazinecarboxylate (*J. Med. Chem.* 1998, 41, 3387–3401): To a well stirred solution of [(1S)-1-(2S)-oxiranyl-2-phenylethyl]-carbamic acid phenylmethyl ester (6.07 g, 20.4 mmol) in isopropanol (100 mL) was added N'-ethylhydrazinecarboxylic acid tert-butyl ester (3.93 g, 24.5 mmol) and the reaction refluxed for 67 h. The reaction was concentrated and chromatographed on silica gel (elution with a gradiant from hexane to dichloromethane to 1% methanol saturated with ammonia in dichloromethane) to give tert-butyl 2-((2R,3S)-3-{[(benzyloxy)carbonyl]amino}-2-hydroxy-4-phenylbutyl)-2-ethylhydrazinecarboxylate (7.9 g) as a white solid. MS (ESI+) for $C_{25}H_{35}N_3O_5$ m/z 458.3 (M+H)⁺.

tert-Butyl 2-((2R,3S)-3-amino-2-hydroxy-4-phenylbutyl)-2-ethylhydrazinecarboxylate: A solution of tert-butyl 2-((2R,3S)-3-{[(benzyloxy)carbonyl]amino}-2-hydroxy-4-phenylbutyl)-2-ethylhydrazinecarboxylate (3.11 g, 6.8 mmol) in methanol (50 mL) was added to 10% Pd/C (0.32 g) and stirred in a hydrogen atmosphere (@ ambient pressure) for 5 h. The reaction was filtered through Celite and the filtrate concentrated under reduced pressure to yield tert-butyl 2-((2R,3S)-3-amino-2-hydroxy-4-phenylbutyl)-2-ethylhydrazinecarboxylate (2.2 g) as an oil. MS (ESI+) for $C_{17}H_{29}N_3O_3$ m/z 324.3 (M+H)⁺.

C. tert-Butyl 2-((2S,3S)-3-amino-2-hydroxy-4-phenylbutyl)-2-ethylhydrazinecarboxylate tert-Butyl 2-((2S,3S)-3-{[(benzyloxy)carbonyl]amino}-2-hydroxy-4-phenylbutyl)-2-ethylhydrazinecarboxylate: To a well stirred solution of [(1S)-1-(2R)-oxiranyl-2-phenylethyl]-carbamic acid phenylmethyl ester (312 mg, 1.0 mmol) in isopropanol (3 mL) was added N'-ethylhydrazinecarboxylic acid tert-butyl ester (202 mg, 1.3 mmol) and the reaction refluxed for 24 h. The reaction was concentrated to give crude tert-butyl 2-((2S,3S)-3-{[(benzyloxy)carbonyl]amino]-2-hydroxy-4-phenylbutyl)-2-ethylhydrazinecarboxylate (537 mg). MS (ESI+) for $C_{25}H_{35}N_3O_5$ m/z 458.1 (M+H)⁺.

tert-Butyl 2-((2S,3S)-3-amino-2-hydroxy-4-phenylbutyl)-2-ethylhydrazinecarboxylate: A solution of crude tert-butyl 2-((2S,3S)-3-{[(benzyloxy)carbonyl]amino}-2-hydroxy-4-phenylbutyl)-2-ethylhydrazinecarboxylate (502 mg, 1.1 mmol) in MeOH (10 mL) was added to 10% Pd/C (5.2 mg) and stirred in a hydrogen atmosphere (@ ambient pressure) for 6 h. The reaction was filtered through Celite and the filtrate concentrated under reduced pressure to yield crude tert-butyl 2-((2S,3S)-3-amino-2-hydroxy-4-phenylbutyl)-2-ethylhydrazinecarboxylate (293 mg). MS (ESI+) for $C_{17}H_{29}N_3O_3$ m/z 324.2 (M+H)$^+$.

D. tert-Butyl 2-((2S,3S)-3-amino-2-hydroxy-4-(3,5-difluorophenyl)butyl)-2-ethylhydrazinecarboxylate (Z)-2-Benzyloxycarbonylamino-3-phenyl-acrylate: A well stirred solution of 3,5-difluorobenzaldehyde (1.92 g, 13.5 mmol) and methyl benzyloxycarbonylamino-(dimethoxyphosphoryl)acetate (5.37 g, 16.2 mmol) in dry THF (20 mL), under $N_2$, was cooled to 0° C. and 1,1,3,3-tetramethylgaunidine (1.38 g, 16.2 mmol) added via syringe. The reaction was allowed to warm to rt and stir for 6 h, quenched with saturated ammonium chloride and extracted with ethyl acetate. After concentration, the residue was chromatographed on silica gel (elution with 20% ethyl acetate/heptane) to give methyl (Z)-2-benzyloxycarbonylamino-3-phenyl-acrylate (3.55 g) as a white solid. MS (ESI+) for $C_{18}H_{15}F_2NO_4$ m/z 348.2 (M+H)$^+$.

CBZ-L-3,5-Difluorophenylalanine Methyl Ester: A Parr Hastelloy bomb was charged with (Z)-2-benzyloxycarbonylamino-3-phenyl-acrylate (21 g, 48 mmol) in degassed methanol (315 mL) and pressurized with $H_2$ @ 80 psi. After 1 h, (S)-EtDuPHOSRh(COD)BF$_4$ (476 mg, 1.5 mol %) in degassed methanol (15 mL) was added and the reaction stirred at rt under 40 psi $H_2$ for 16 h. The solution was filtered through Celite, concentrated and chromatographed on silica gel (elution with 20% ethyl acetate/heptane) to give 20 g of CBZ-L-3,5-difluorophenylalanine methyl ester as a white solid. MS (ESI+) for $C_{18}H_{17}F_2NO_4$ M/z 350.1 (M+H)$^+$.

[1S-(1-(3,5-Difluorobenzyl)-2-hydroxy-ethyl)]-carbamic acid benzyl ester: To a well stirred solution of L-3,5-difluorophenylalanine methyl ester (795 mg, 2.3 mmol) and lithium chloride (97 mg, 2.3 mmol) in THF/ethanol (10 mL, 1:1), under $N_2$, was added solid sodium borohydride (86 mg, 2.3 mmol) and the reaction stirred at rt overnight. The mixture was quenched with saturated ammonium chloride, extracted with ethyl acetate and the extracts combined, dried (anhydrous sodium sulfate) and concentrated. The residue was chromatographed an silica gel (elution with 20% ethyl acetate/heptane) to give [1S-(1-(3,5-difluorobenzyl)-2-hydroxy-ethyl)]-carbamic acid benzyl ester (660 mg) as a white solid. MS (ESI+) for $C_{17}H_{17}F_2NO_3$ m/z 322.2 (M+H)$^+$.

[1S-(1-(3,5-difluorobenzyl)-2-oxo-ethyl)]-carbamic acid benzyl ester: To a cold (−78° C.) well-stirred solution of oxalyl chloride (0.16 mL, 1.8 mmol) in methylene chloride (20 mL) was added DMSO (0.13 mL, 1.8 mmol) followed by the slow addition of [1S-(1-(3,5-difluoro-benzyl)-2-hydroxy-ethyl)]-carbamic acid benzyl ester (1.5 mmol) as a solution in $CH_2Cl_2$ (10 mL). The reaction mixture was stirred at −78° C. for 10 minutes followed by the addition of $Et_3N$ (0.63 mL, 4.5 mmol, 3.0 equiv). The mixture was stirred at −78° C. until no starting material was observed by TLC (2 h). The reaction mixture was then washed with 10% citric acid (aq) and dried over $MgSO_4$, filtered and condensed. The white solid was purified by silica chromatography (20% to 50% EtOAc/Heptane) to yield [1S-(1-(3,5-difluorobenzyl)-2-oxo-ethyl)]-carbamic acid benzyl ester (445 mg) as a white solid. MS (ESI+) for $C_{17}H_{15}F_2NO_3$ m/z 320 (M+H)$^+$.

[1S-(1-(3,5-Difluorobenzyl)-2-propenyl)]-carbamic acid benzyl ester: To a slurry of diethyl ether (5 mL) and Mg turnings (0.17 g, 7.1 mmol) was added $ClCH_2Si(CH_3)_3$ (0.97 mL, 7.0 mmol) and the mixture was heated to reflux. After initiation (0.5 h @ reflux), the reaction mixture was removed from heating and stirred for an additional 1 h, then cooled to rt. To the cooled solution was [1S-(1-(3,5-difluorobenzyl)-2-oxo-ethyl)]-carbamic acid benzyl ester (0.45 g, 1.4 mmol) as a solution in distilled THF (10 mL). The reaction mixture was stirred at rt for 1 h, cooled to 0° C. and $BF_3(OEt)_2$ (0.97 mL, 7.0 mmol) added. The reaction mixture was further stirred at rt for 16 h, quenched with 10% NaOH (aq) (50 mL) and stirring continued for 1 h. The reaction mixture was extracted with $CH_2Cl_2$, dried over $MgSO_4$, filtered and condensed to yield a clear oil. The oil was purified by silica chromatography (20% to 50% EtOAc/heptane) to yield [1S-(1-(3,5-difluorobenzyl)-2-propenyl)]-carbamic acid benzyl ester (270 mg) as a white solid. MS (ESI+) for $C_{18}H_{18}F_2NO_2$ m/z 318 (M+H)$^+$.

[(1S)-1-(2R)-oxiranyl-2-(3,5-difluorophenyl)ethyl]-carbamic acid phenylmethyl ester: To $CH_2Cl_2$ (20 mL) was added [1S-(1-(3,5-difluoro-benzyl)-2-propenyl)]-carbamic acid benzyl ester (270 mg, 0.85 mmol) followed by M-CPBA (77%, 458 mg, 1.0 mmol). The reaction mixture was stirred at rt for 24 h. The reaction was diluted with $CH_2Cl_2$ and then washed with 10% sodium thiosulfate (aq), dried over $Na_2SO_4$, filtered and condensed. Preparative chromatography (5×50 cm Chiralcel OD, 30° C., 70 ml/min. 25% IPA/75% heptane) provided [(1S)-1-(2R)-oxiranyl-2-(3,5-difluorophenyl)ethyl]-carbamic acid phenylmethyl ester. MS (ESI+) for $C_{18}H_{18}F_2NO_3$ m/z 334.2 (M+H)$^+$.

tert-Butyl 2-((2S,3S)-3-([(benzyloxy)carbonyl]amino)-2-hydroxy-4-(3,5-difluorophenyl)butyl)-2-ethylhydrazinecarboxylate: To a well stirred solution of [(1S)-1-(2R)-oxiranyl-2-(3,5-difluorophenyl)ethyl]-carbamic acid phenylmethyl ester (496 mg, 1.5 mmol) in isopropanol (4.25 mL) was added N'-ethylhydrazinecarboxylic acid tert-butyl ester (575 mg, 3.6 mmol) and the reaction refluxed for 48 h. The reaction was concentrated to provide crude tert-butyl 2-((2S,3S)-3-{[(benzyloxy)carbonyl]amino}-2-hydroxy-4-(3,5-difluorophenyl)butyl)-2-ethylhydrazine-carboxylate. MS (ESI+) for $C_{25}H_{33}F_2N_3O_5$ m/Z 516.2 (M+Na)$^+$.

tert-Butyl 2-((2S,3S)-3-amino-2-hydroxy-4-(3,5-difluorophenyl)butyl)-2-ethylhydrazinecarboxylate: A solution of crude tert-butyl 2-((2S,3S)-3-{[(benzyloxy)carbonyl]-amino}-2-hydroxy-4-(3,5-difluorophenyl)butyl)-2-ethylhydrazinecarboxylate (906 mg, 1.8 mmol) in MeOH (15 mL) was added to 10% Pd/C (95 mg) and stirred in a hydrogen atmosphere (ambient pressure) for 4 h. The catalyst was filtered off over Celite and the filtrate was concentrated under reduced pressure to yield crude tert-butyl 2-((2S, 3S)-3-amino-2-hydroxy-4-(3,5difluorophenyl)butyl)-2-ethylhydrazinecarboxylate. MS (ESI+) for $C_{17}H_{27}F_2N_3O_3$ m/z 360.2 (M+H)$^+$.

Scheme 4: General Preparation Procedure

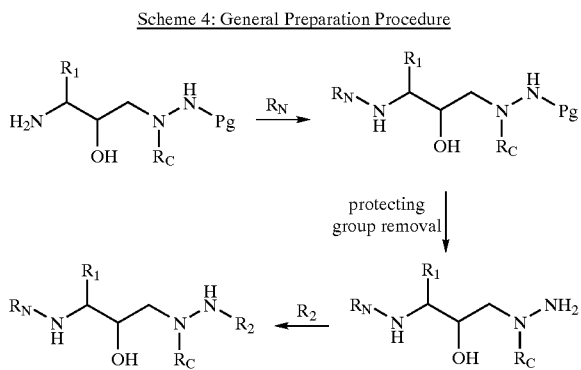

E. N-terminal Acid Coupling ($R_N$)

Solutions of each acid ($R_N$) were prepared (1.08 mmol) in DMF (3 mL) (enough for 6 cartridges per acid). Solutions of PyBOP (3.74 g, 7.2 mmol) and HOBT (0.96 g, 7.2 mmol) in DMF (24 mL) were prepared. To each cartridge on a Bohdan block was added acid solution (0.5 niL, 0.18 mmol) according to product layout (6 cartridges of each of the 8 acids). To each cartridge was added the PyBOP/HOBT solution (0.5 mL, 0.078 g PYBOP, 0.15 mmol/0.02g HOBT, 0.15 mmol) and DIEA (0.052 mL, 0.30 mmol). The Bohdan block was agitated on a Bohdan shaker at 700–800 rpm for 1 h. A solution of amine was prepared (2.30 g, 7.2 mmol) in 24 mL of $CH_2Cl_2$. To each cartridge was added 0.5 mL of amine solution (0.48 g, 0.15 mmol). The Bohdan block was agitated on the Bohdan shaker at 700–800 rpm for 16 h. The reaction mixtures were drained into 48 well Robbin's blocks. Each cartridge was rinsed with 0.5 mL DMF into another 48 well Robbin's block. The reaction mixtures were concentrated in the Robbin's blocks under reduced pressure at 50° C. for 6 h in a Jouan centrifugal evaporator. Products were carried on crude to next reaction.

F. Deprotection (J. Org. Chem. 1998, 63, 3471)

Add Dowex 50Wx2-400 ion-exchange resin (~230 mg) to each clean cartridge on a Bohdan block using an Argo Scoop. The previous product was pipetted as a solution in 2 mL MeOH into each cartridge. The Bohdan block was agitated on a Bohdan shaker at 50° C. at 700–800 rpm for 4 h. Each cartridge was rinsed with $CH_2Cl_2$ (2×2.5 mL) and MeOH (10×2.5 mL). The products were eluted using 3.5M $NH_3$ in MeOH (2×3 mL) into 2 separate 48 well Robbin's blocks. Reaction mixtures were concentrated in the Robbin's blocks under reduced pressure at 40° C. for 4 h in a Jouan.

G. C-Terminal Acid Coupling ($R_2$)

Solutions of each acid ($R_2$) were prepared (1.80 mmol) in DMF (2 mL) (enough for 8 cartridges per acid). A solution of HATU (4.13 g, 10.8 mmol) in DMF (12 mL) was prepared. To each cartridge on a Bohdan block was added acid solution (0.25 mL, 0.225 mmol) according to product layout (8 cartridges of each of the 6 acids). To each cartridge was added 0.25 mL of the HATU solution (0.086 g, 0.225 mmol) and DIEA (0.163 mL, 0.94 mmol). The Bohdan block was agitated on a Bohdan shaker at 700–800 rpm for 1 h. Solution of the amines were prepared (0.15 mmol/mL) in DMF. To each cartridge was added the amine solution (0.15 mmol,) according to the product layout. The Bohdan block was agitated on the Bohdan shaker at 700–800 rpm for 16 h. The reaction mixtures were drained into 48 well Robbin's blocks. Each cartridge was rinsed with 0.5 mL DMF into another 48 well Robbin's block. The reaction mixtures were concentrated in the Robbin's blocks under reduced pressure at 50° C. for 6 h in a Jouan. Products were dissolved in 2 mL MeOH and each transferred to a Varian Mega BE-SCX (2 gm, 12 mL) cartridge that had been presoaked with MeOH (5 mL). After products were loaded onto SCX cartridges by gravity, each cartridge was washed with MeOH (9×5 mL) using vacuum filtration. Final products were eluted off by gravity using 3.5M $NH_3$ in MeOH (3×3 mL) into pre-tared vials.

EXAMPLES

Example 1

N-[(1S,2R)-3-(2-benzoyl-1-ethylhydrazino)-1-benzyl-2-hydroxypropyl]-2-[(methylsulfonyl)amino]-1,3-thiazole-4-carboxamide: Synthesized as described above from tert-butyl 2-((2R,3S)-3-amino-2-hydroxy-4-phenylbutyl)-2-ethylhydrazinecarboxylate, benzoic acid and 2-methanesulfonylamino-thiazole-4-carboxylic acid. MS (ESI+) for $C_{24}H_{29}N_5O_5S_2$ m/z 532.7 $(M+H)^+$.

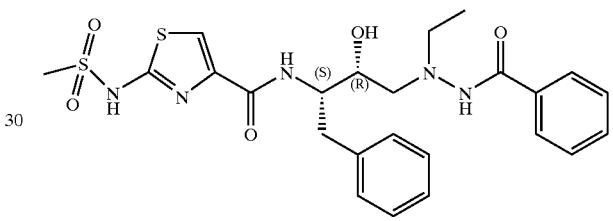

Example 2

N-{(1S,2R)-1-benzyl-3-[1-ethyl-2-(4-methylpentanoyl) hydrazino]-2-hydroxypropyl}-2-[(methylsulfonyl)amino]-1,3-thiazole-4-carboxamide: Synthesized as described above from tert-butyl 2-((2R,3S)-3-amino-2-hydroxy-4-phenylbutyl)-2-ethylhydrazinecarboxylate, 4-methylpentanoic acid and 2-methanesulfonylamino-thiazole-4-carboxylic acid. MS (ESI+) for $C_{23}H_{35}N_5O_5S_2$ m/z 526.7 $(M+H)^+$.

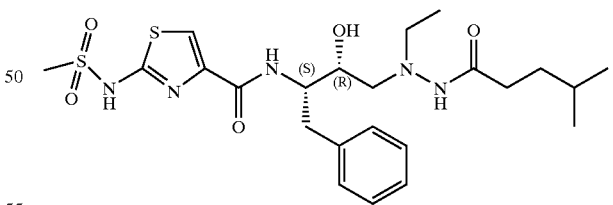

Example 3

$N^1$-{(1S,2S)-1-benzyl-3-[1-ethyl-2-(4-methylpentanoyl) hydrazino]-2-hydroxypropyl}-5-methyl-$N^3$,$N^3$-dipropylisophthalamide: Synthesized as described above from tert-butyl 2-((2S,3S)-3-amino-2-hydroxy-4-phenylbutyl)-2-ethylhydrazinecarboxylate, 4-methylpentanoic acid and 5-methyl-N,N-dipropyl-isophthalamic acid (WO 02/02512). MS (ESI+) for $C_{33}H_{50}N_4O_4$ m/z 567.3 $(M+H)^+$.

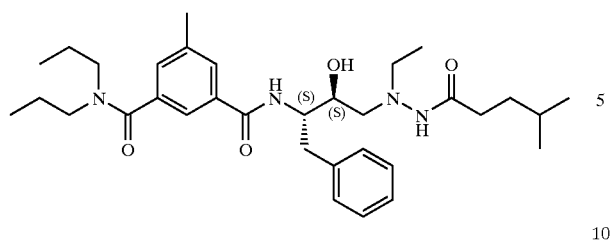

Example 4

N[1]-{(1S,2S)-1-(3,5-difluorobenzyl)-3-[1-ethyl-2-(4-methylpentanoyl)hydrazino]-2-hydroxypropyl}-5-methyl-N[3],N[3]-dipropylisophthalamide: Synthesized as described above from tert-butyl 2-((2S,3S)-3-amino-2-hydroxy-4-(3,5difluorophenyl)butyl)-2-ethylhydrazinecarboxylate, 3-methylpentanoic acid and 5-methyl-N,N-dipropylisophthalamic acid. MS (ESI+) for $C_{33}H_{48}F_2N_4O_4$ m/z 603.3 (M+H)+.

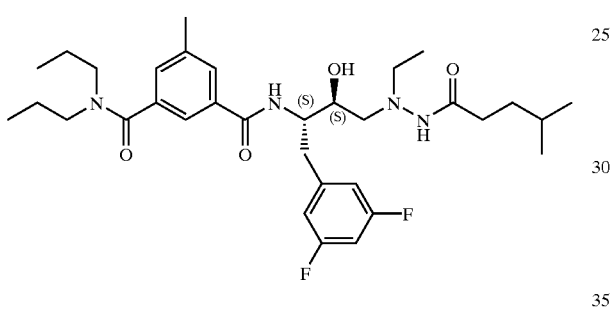

Example 5

N[1]-{(1S,2S)-1-(3,5-difluorobenzyl)-3-[1-ethyl-2-(4-methylbutanoyl)hydrazino]-2-hydroxypropyl}-5-methyl-N[3],N[3]-dipropylisophthalamide: Synthesized as described above from tert-butyl 2-((2S,3S)-3-amino-2-hydroxy-4-(3,5difluorophenyl)butyl)-2-ethylhydrazinecarboxylate, 3-methylbutanoic acid and 5-methyl-N,N-dipropylisophthalamic acid. MS (ESI+) for $C_{32}H_{46}F_2N_4O_4$ m/z 589.3 (M+H)+.

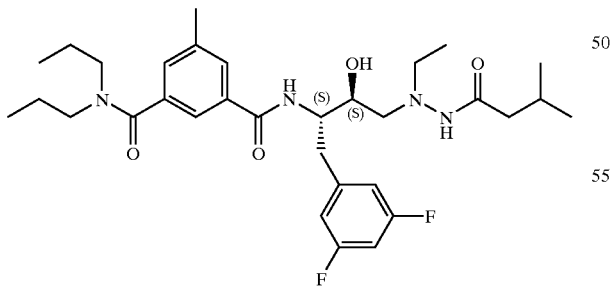

Example 6

The following compounds, as shown in Table 1 below, are prepared essentially according to the procedures outlined in Schemes 1–4 and according to examples 1–5:

TABLE 1

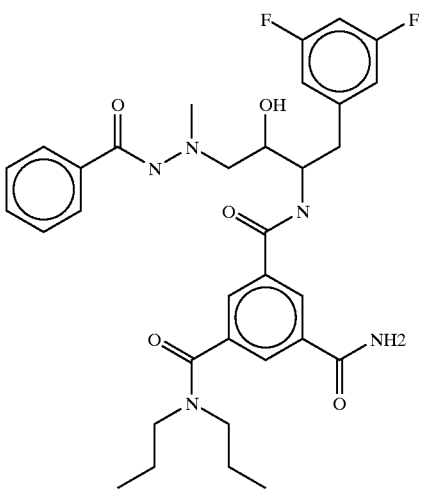

1:A1 1, 1, 1, 1

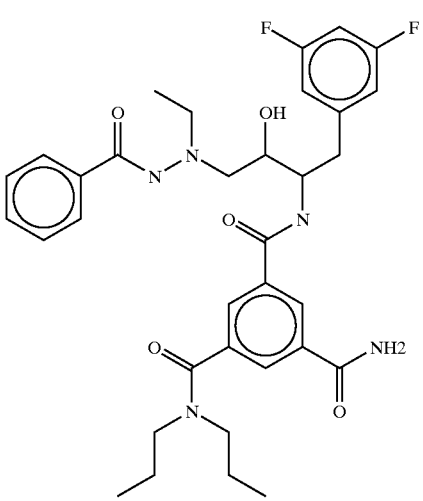

1:A2 1, 1, 1, 2

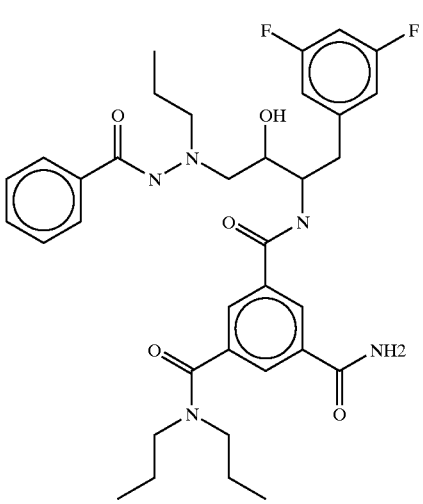

1:A3 1, 1, 1, 3

TABLE 1-continued
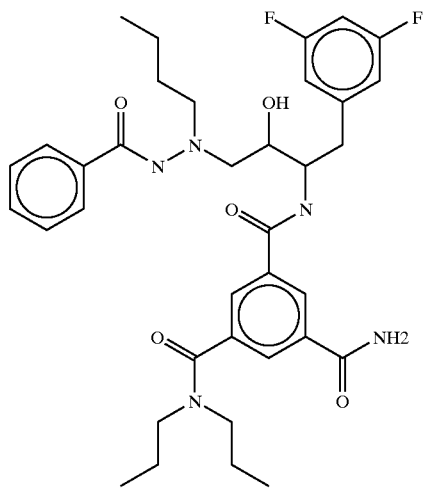
1:A4 1, 1, 1, 4
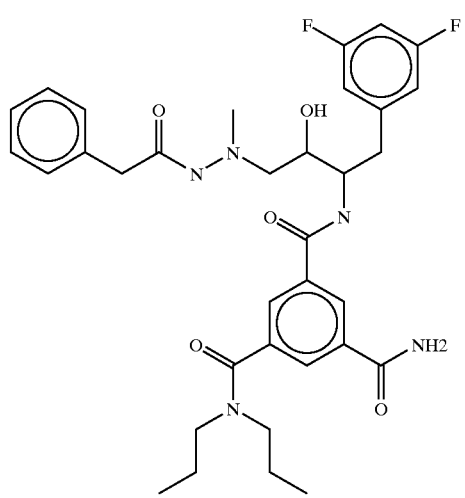
1:A5 1, 1, 2, 1
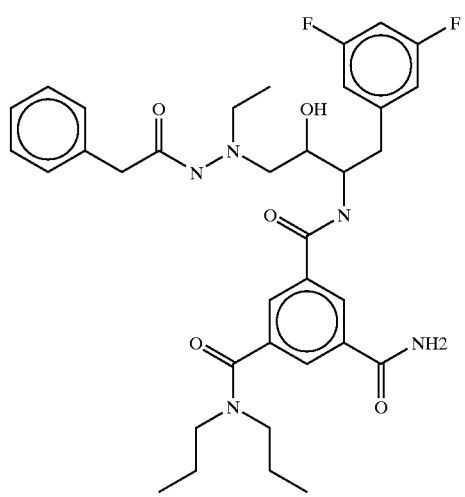
1:A6 1, 1, 2, 2
TABLE 1-continued
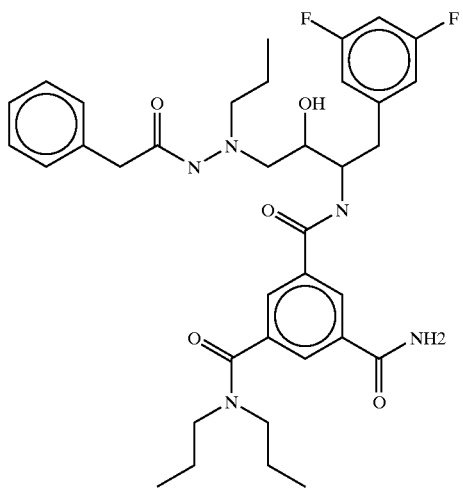
1:A7 1, 1, 2, 3
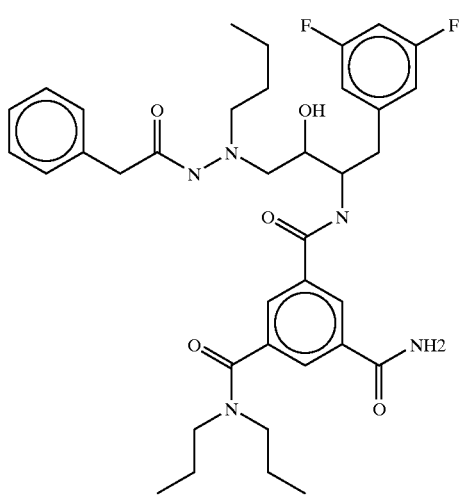
1:A8 1, 1, 2, 4
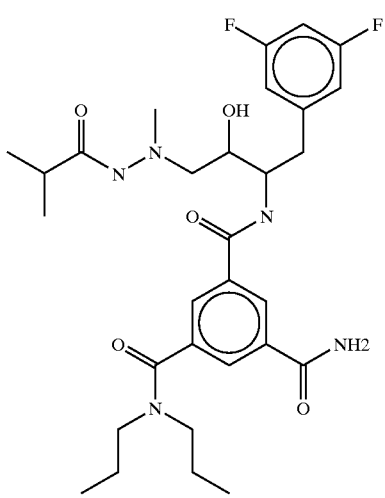
1:A9 1, 1, 3, 1

TABLE 1-continued
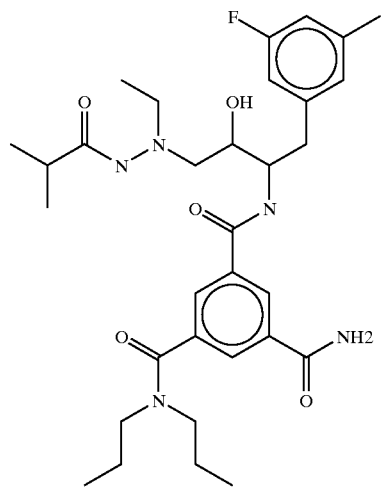
1:A10 1, 1, 3, 2
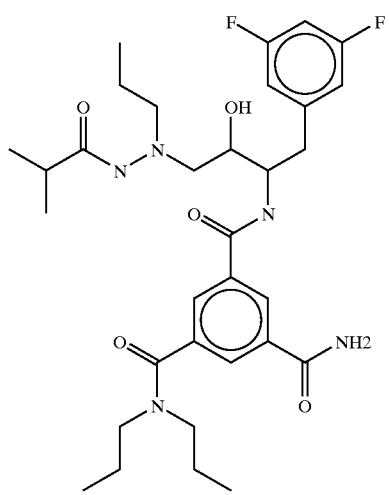
1:A11 1, 1, 3, 3
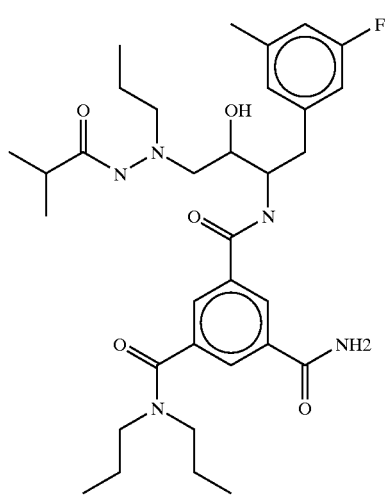
1:A12 1, 1, 3, 4
TABLE 1-continued
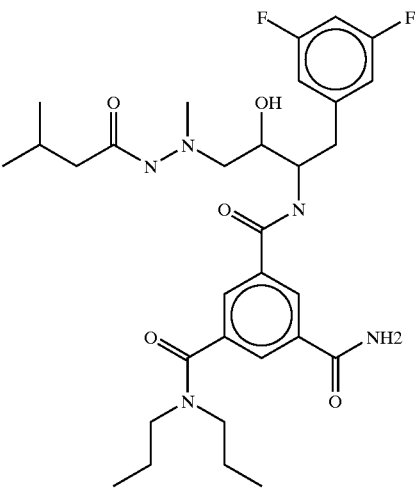
1:B1 1, 1, 4, 1
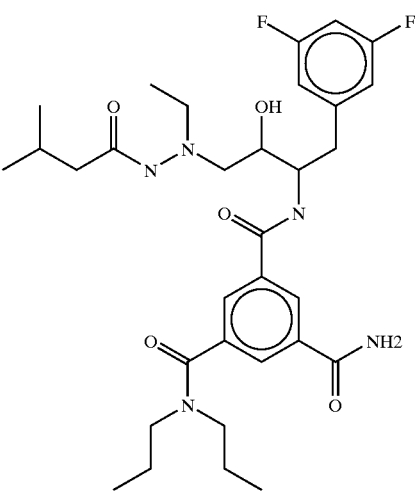
1:B2 1, 1, 4, 2
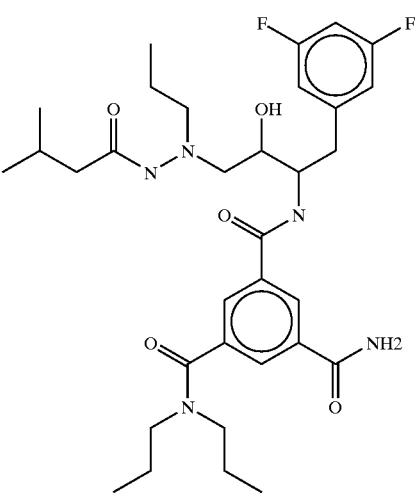
1:B3 1, 1, 4, 3

TABLE 1-continued
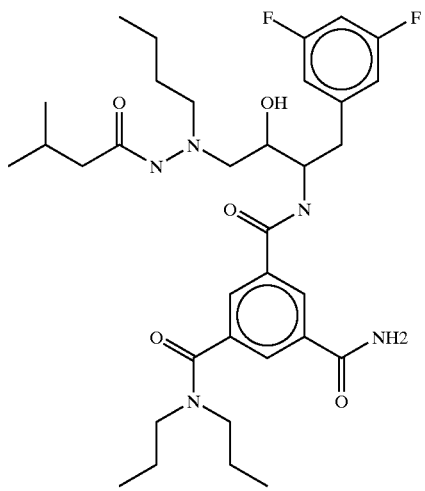
1:B4 1, 1, 4, 4
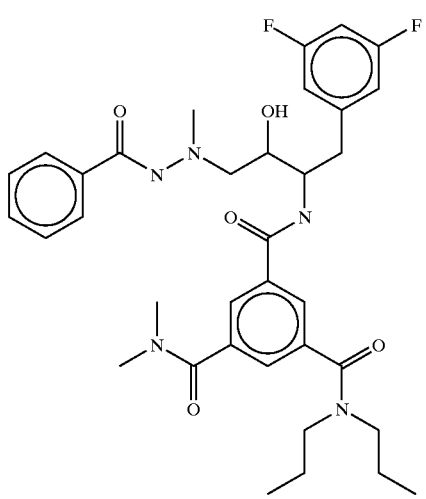
1:B5 1, 2, 1, 1
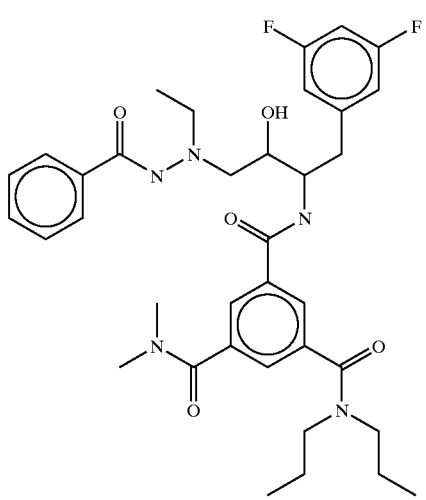
1:B6 1, 2, 1, 2
TABLE 1-continued
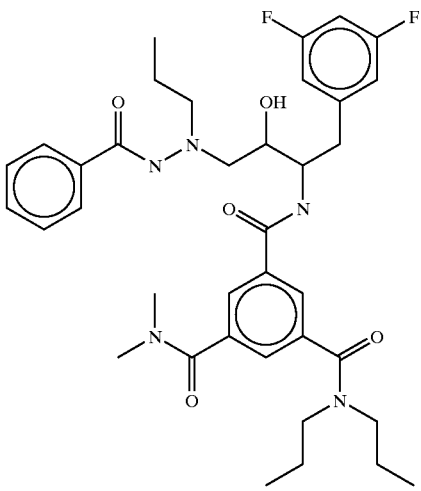
1:B7 1, 2, 1, 3
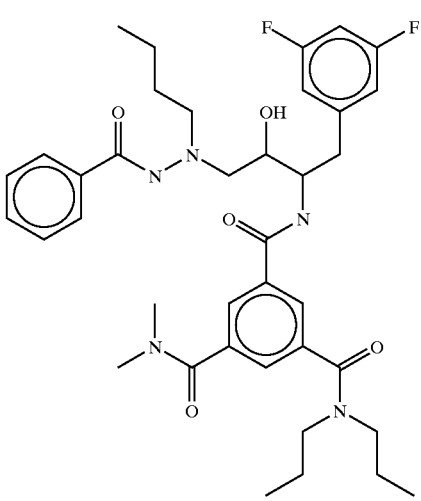
1:B8 1, 2, 1, 4
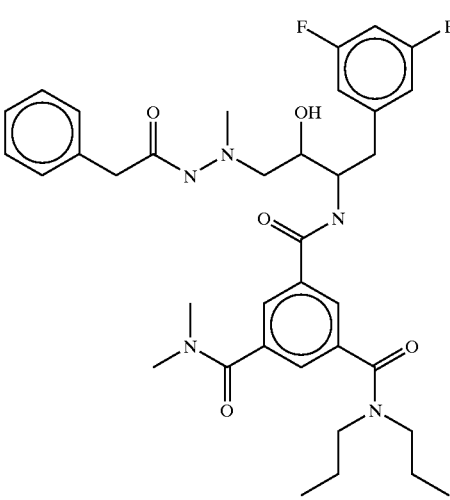
1:B9 1, 2, 2, 1

TABLE 1-continued
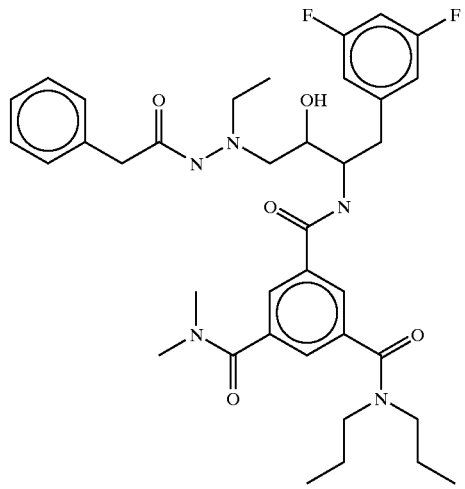
1:B10 1, 2, 2, 2
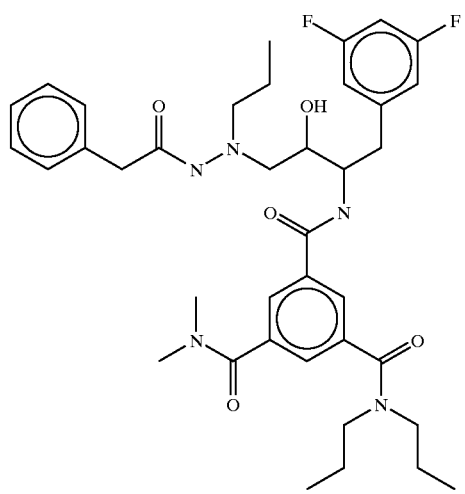
1:B11 1, 2, 2, 3
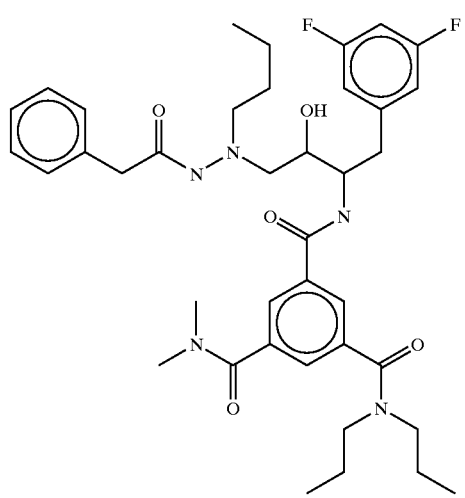
1:B12 1, 2, 2, 4
TABLE 1-continued
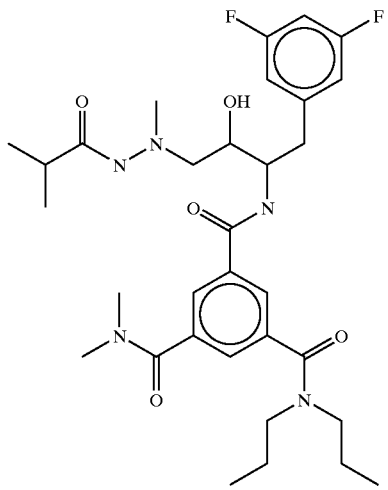
1:C1 1, 2, 3, 1
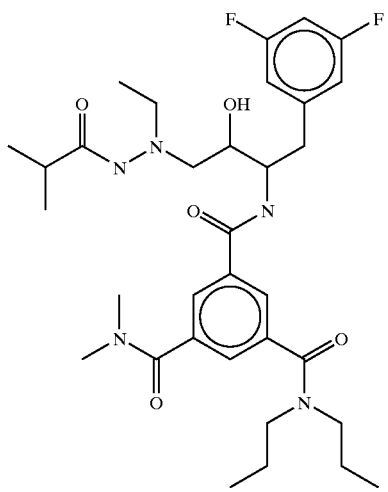
1:C2 1, 2, 3, 2
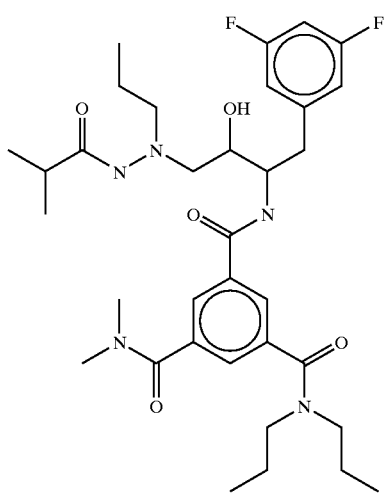
1:C3 1, 2, 3, 3

TABLE 1-continued
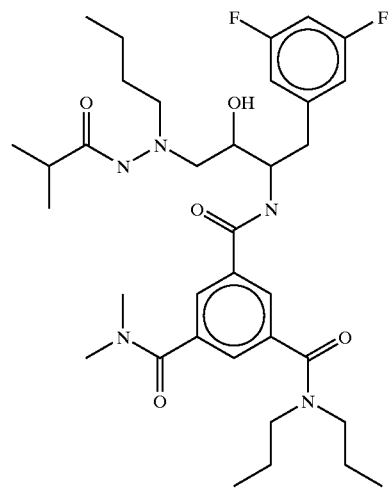
1:C4 1, 2, 3, 4
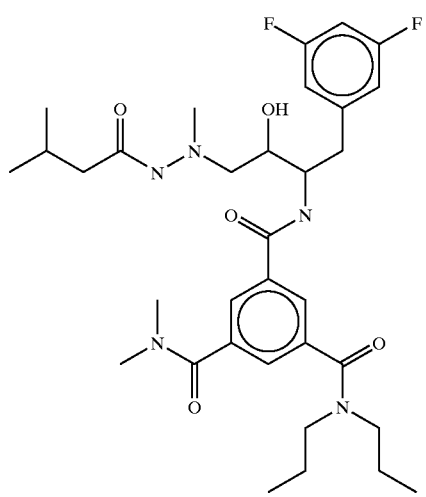
1:C5 1, 2, 4, 1
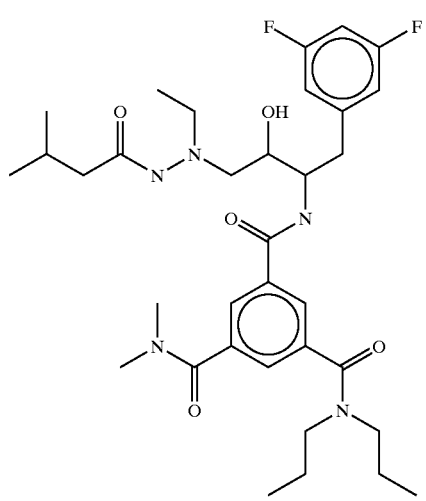
1:C6 1, 2, 4, 2
TABLE 1-continued
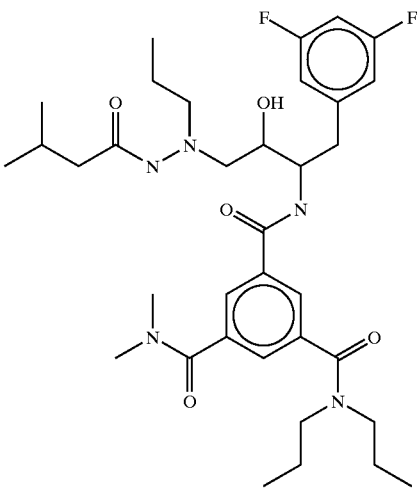
1:C7 1, 2, 4, 3
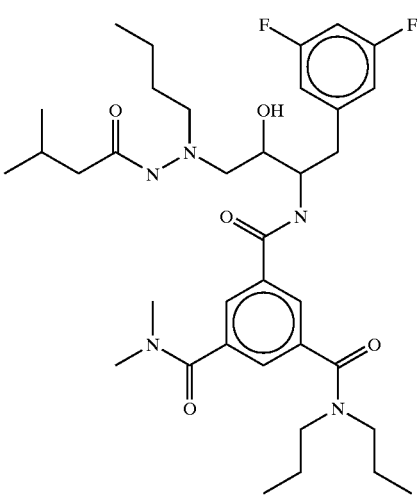
1:C8 1, 2, 4, 4
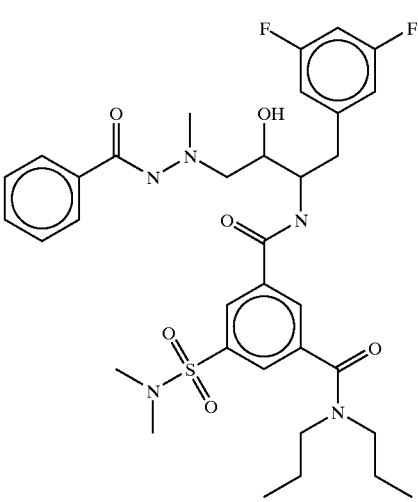
1:C9 1, 3, 1, 1

TABLE 1-continued
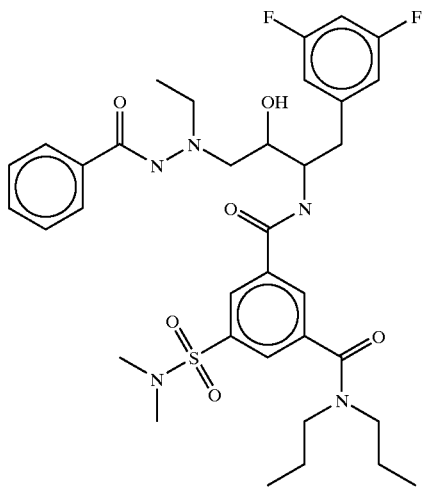
1:C10 1, 3, 1, 2
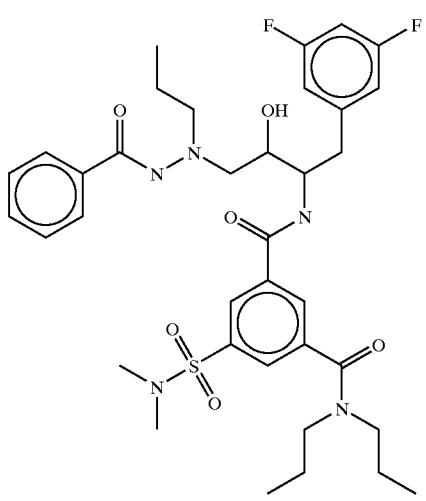
1:C11 1, 3, 1, 3
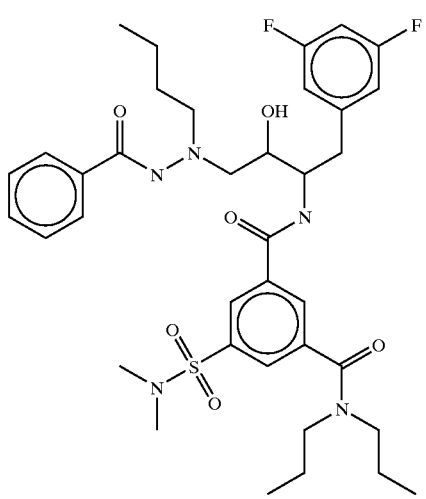
1:C12 1, 3, 1, 4
TABLE 1-continued
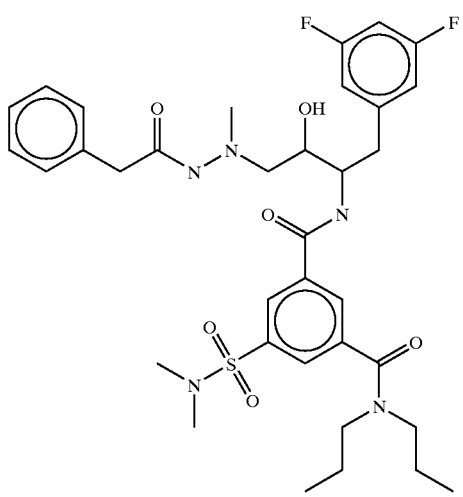
1:D1 1, 3, 2, 1
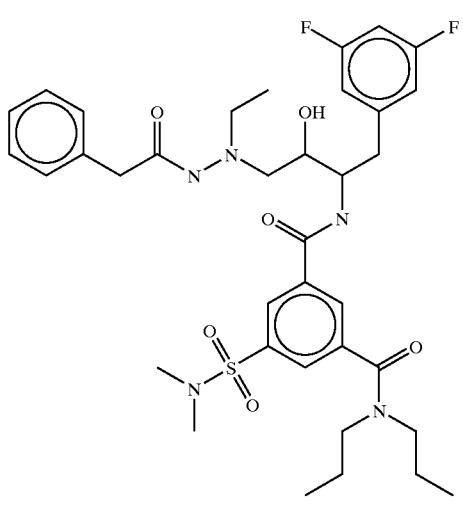
1:D2 1, 3, 2, 2
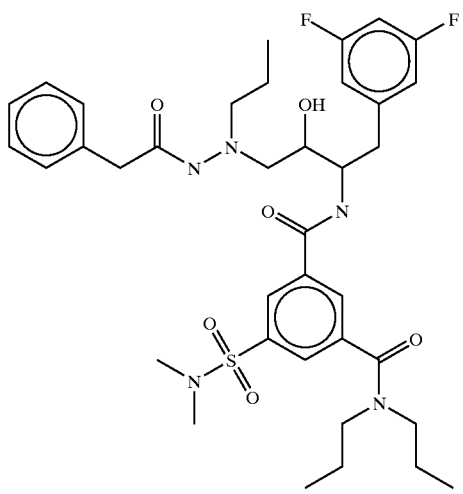
1:D3 1, 3, 2, 3

TABLE 1-continued
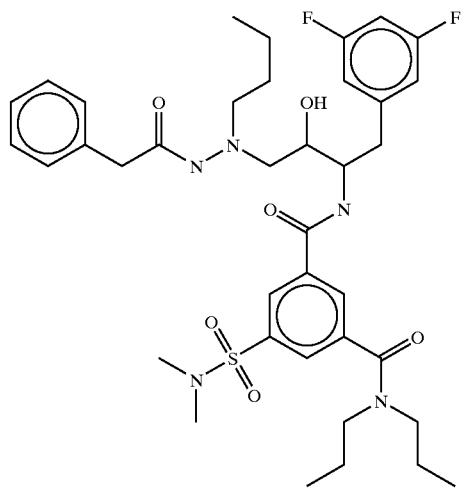
1:D4 1, 3, 2, 4
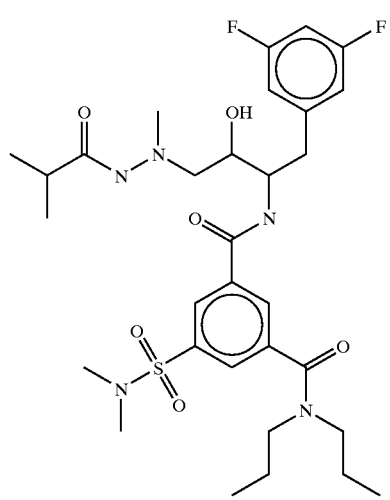
1:D5 1, 3, 3, 1
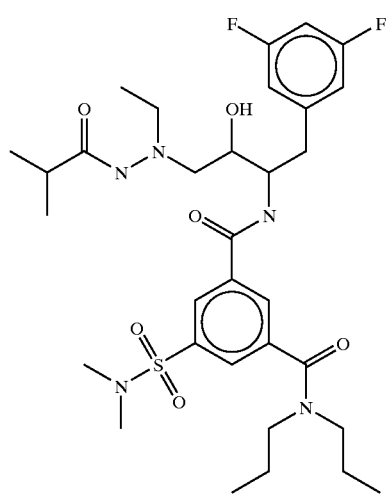
1:D6 1, 3, 3, 2
TABLE 1-continued
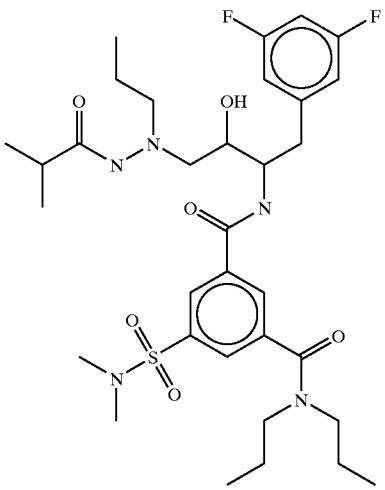
1:D7 1, 3, 3, 3
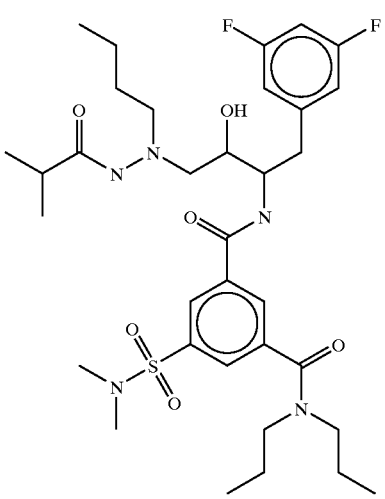
1:D8 1, 3, 3, 4
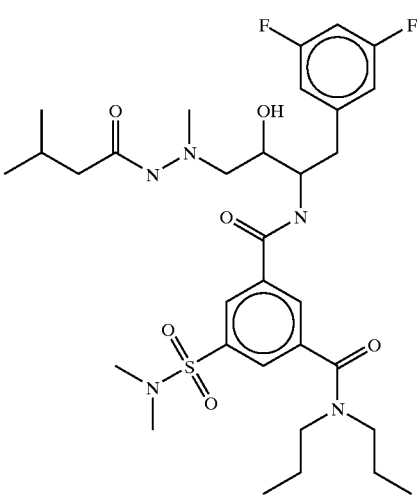
1:D9 1, 3, 4, 1

TABLE 1-continued
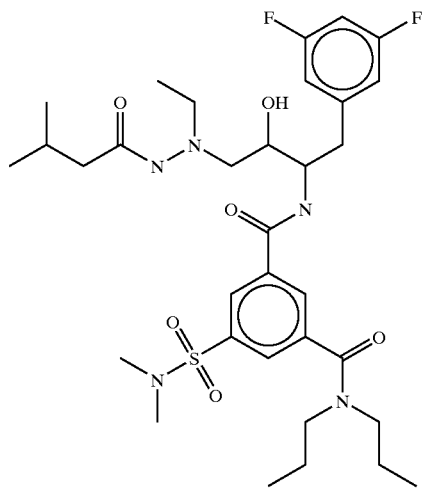
1:D10 1, 3, 4, 2
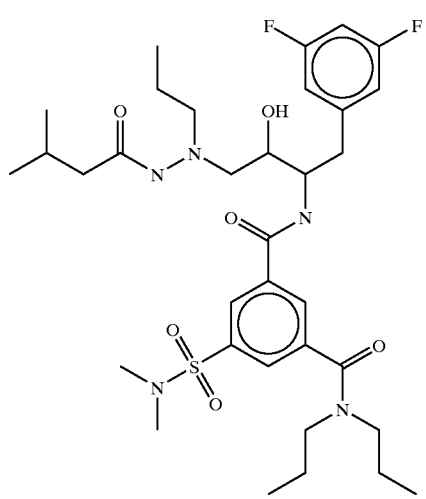
1:D11 1, 3, 4, 3
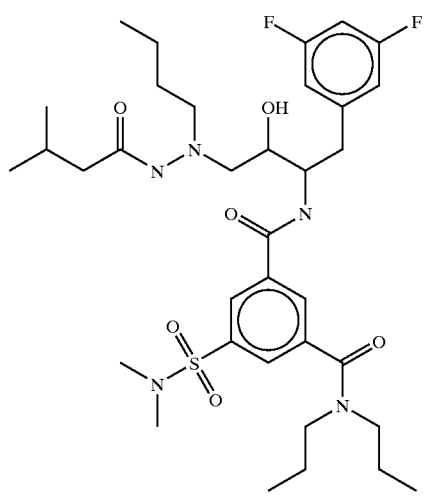
1:D12 1, 3, 4, 4
TABLE 1-continued
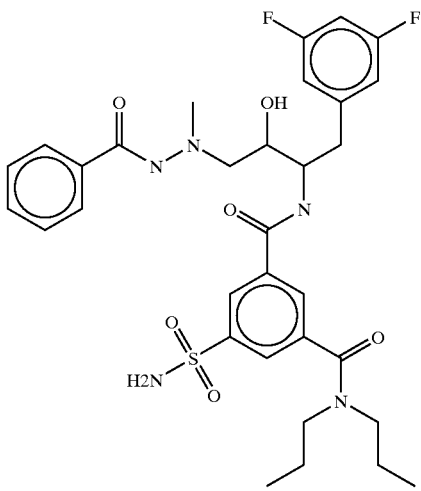
1:E1 1, 4, 1, 1
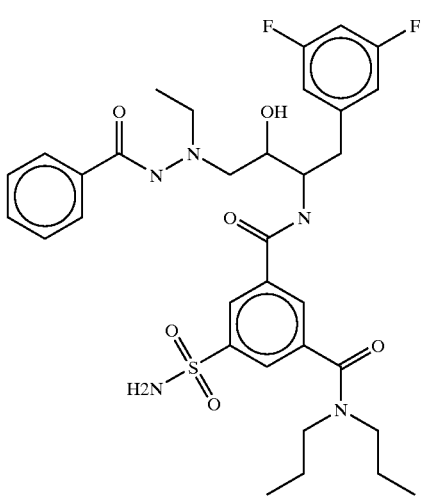
1:E2 1, 4, 1, 2
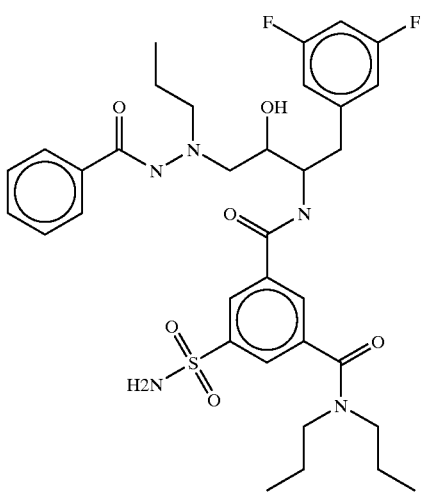
1:E3 1, 4, 1, 3

TABLE 1-continued
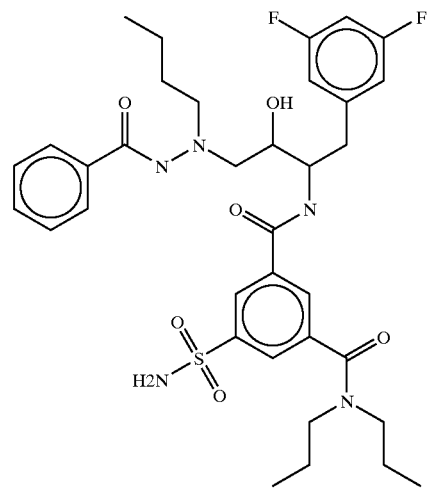
1:E4 1, 4, 1, 4
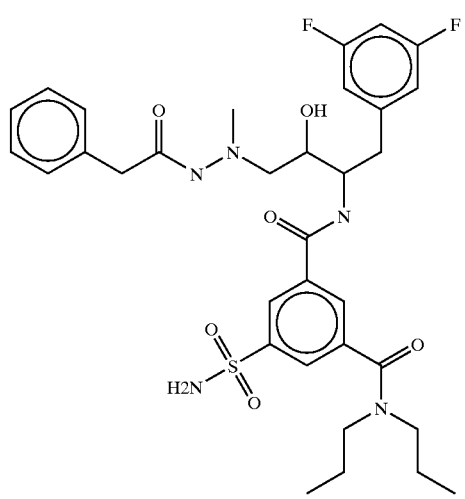
1:E5 1, 4, 2, 1
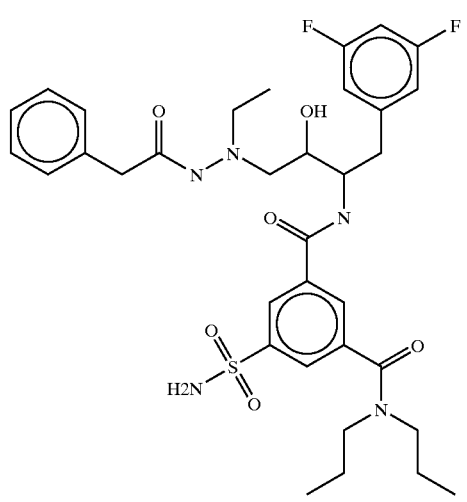
1:E6 1, 4, 2, 2
TABLE 1-continued
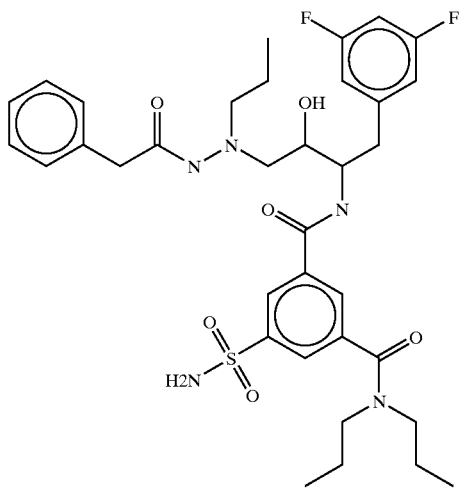
1:E7 1, 4, 2, 3
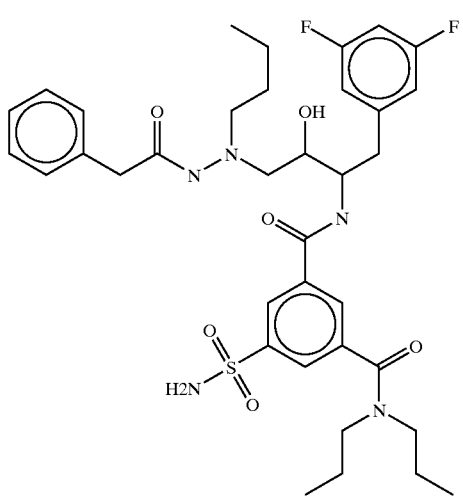
1:E8 1, 4, 2, 4
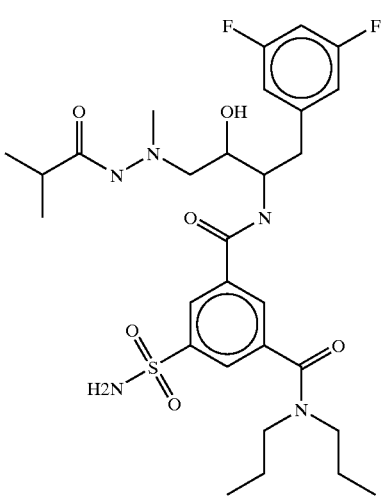
1:E9 1, 4, 3, 1

TABLE 1-continued
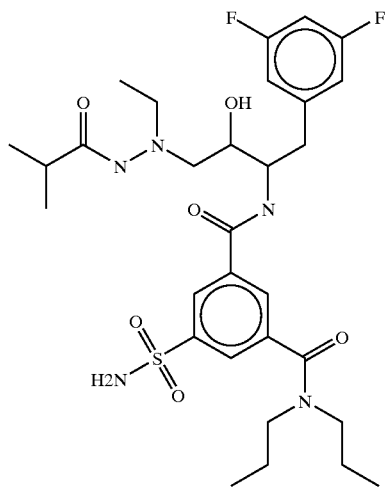
1:E10 1, 4, 3, 2
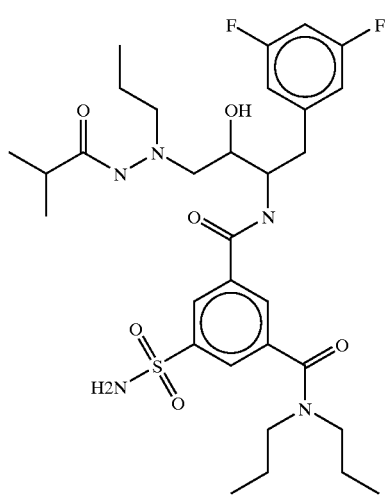
1:E11 1, 4, 3, 3
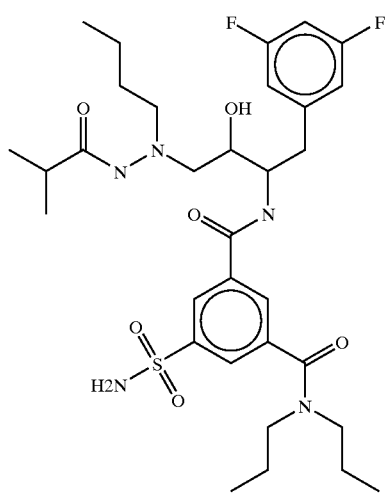
1:E12 1, 4, 3, 4
TABLE 1-continued
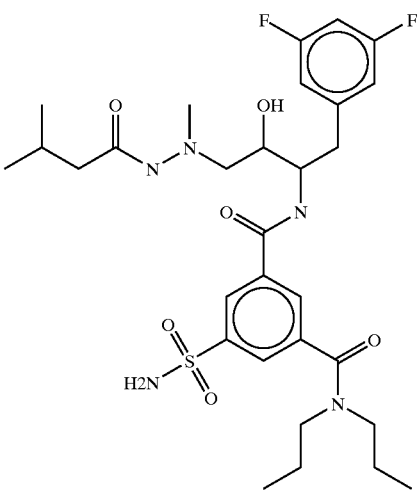
1:F1 1, 4, 4, 1
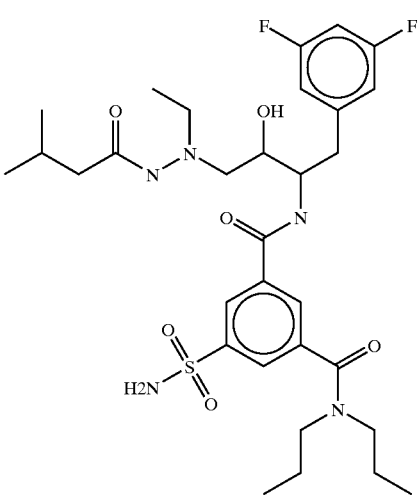
1:F2 1, 4, 4, 2
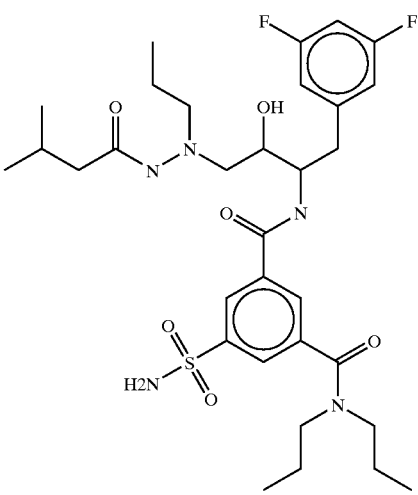
1:F3 1, 4, 4, 3

TABLE 1-continued
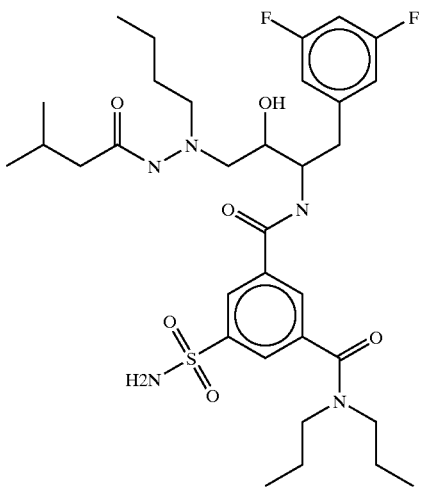
1:F4 1, 4, 4, 4
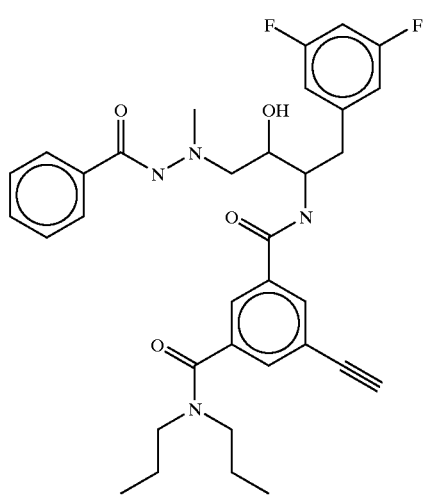
1:F5 1, 5, 1, 1
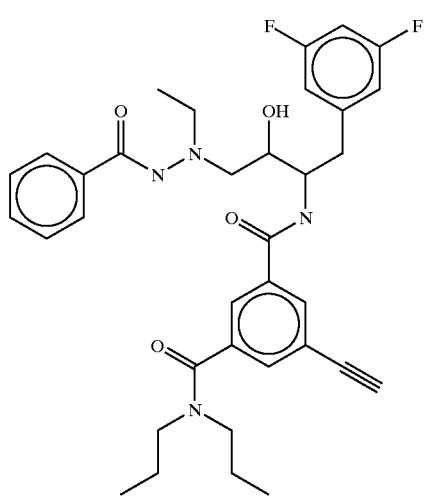
1:F6 1, 5, 1, 2
TABLE 1-continued
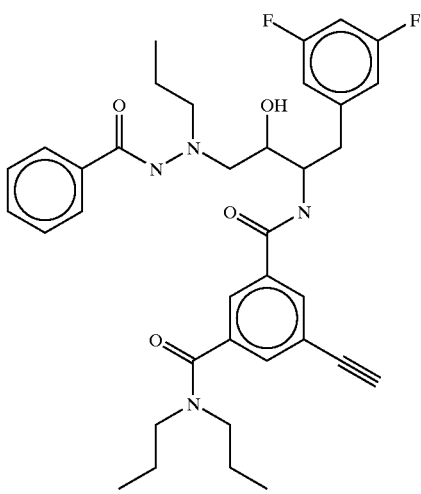
1:F7 1, 5, 1, 3
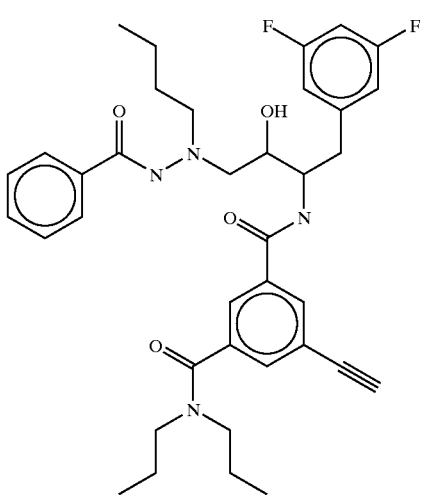
1:F8 1, 5, 1, 4
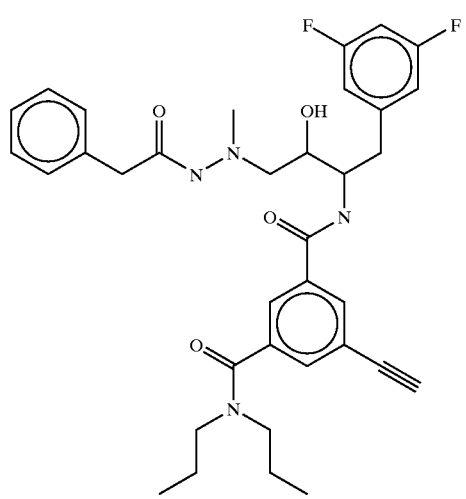
1:F9 1, 5, 2, 1

TABLE 1-continued
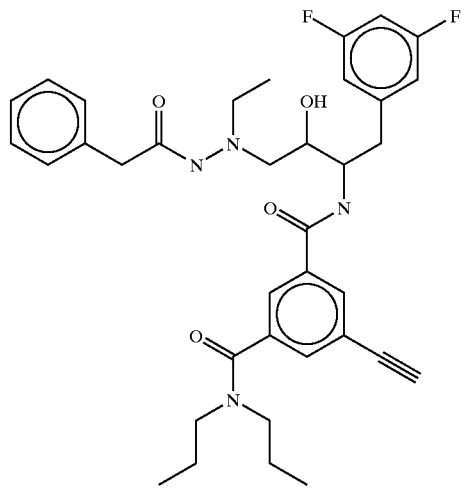
1:F10 1, 5, 2, 2
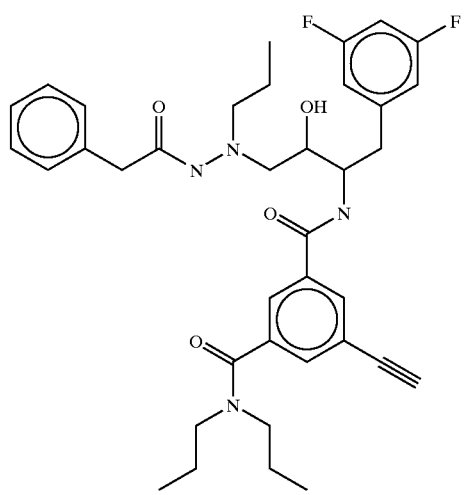
1:F11 1, 5, 2, 3
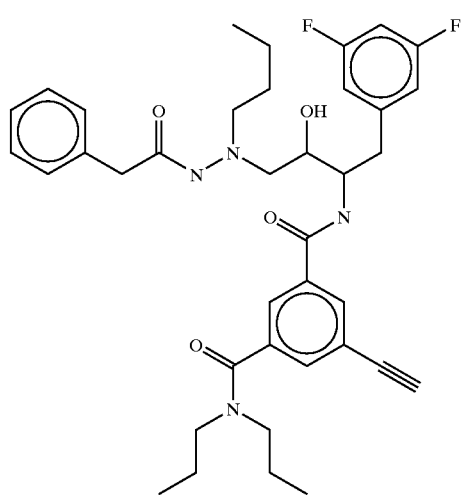
1:F12 1, 5, 2, 4
TABLE 1-continued
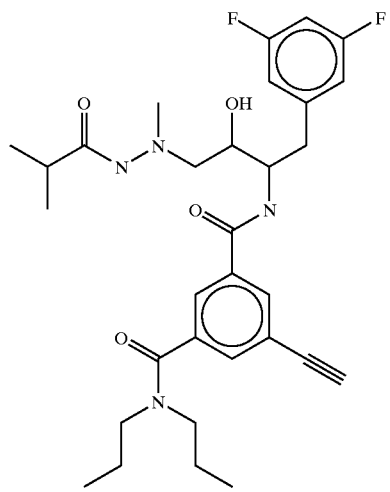
1:G1 1, 5, 3, 1
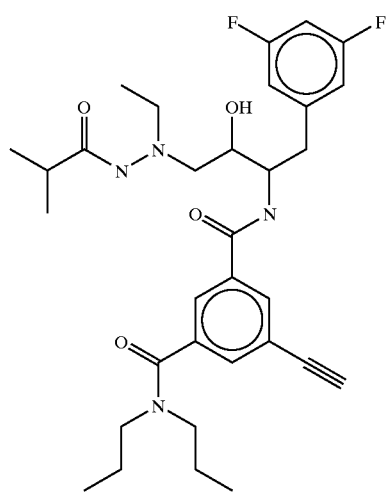
1:G2 1, 5, 3, 2
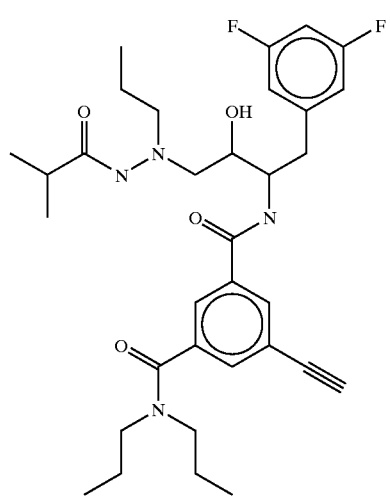
1:G3 1, 5, 3, 3

TABLE 1-continued
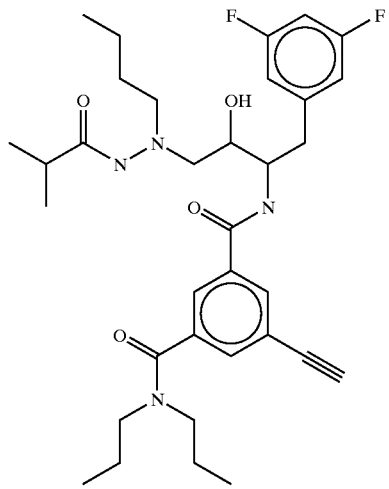
1:G4 1, 5, 3, 4
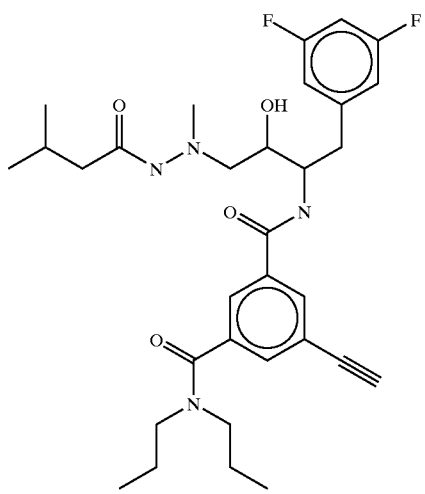
1:G5 1, 5, 4, 1
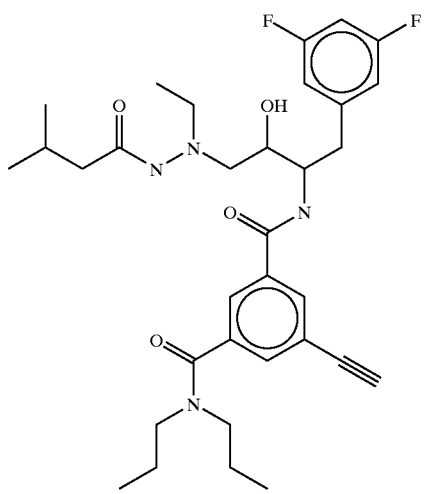
1:G6 1, 5, 4, 2
TABLE 1-continued
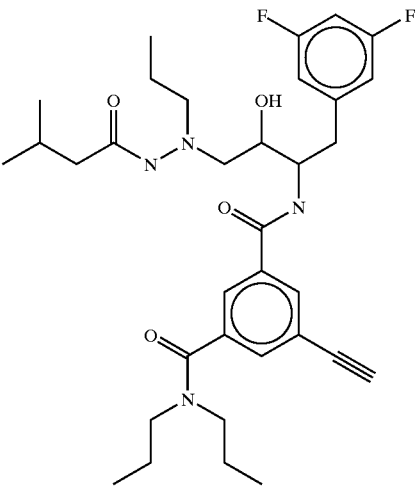
1:G7 1, 5, 4, 3
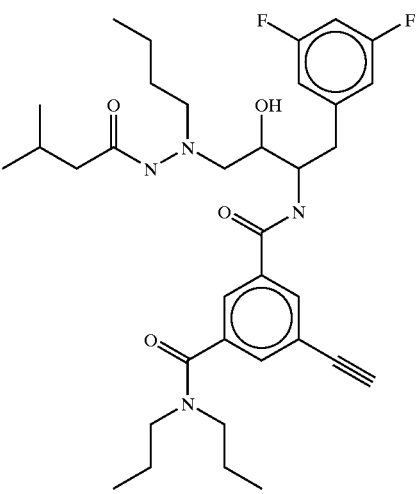
1:G8 1, 5, 4, 4
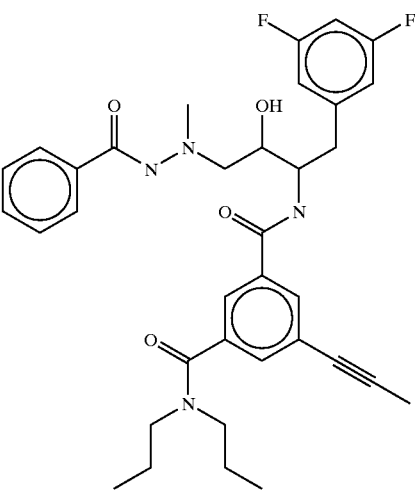
1:G9 1, 6, 1, 1

TABLE 1-continued
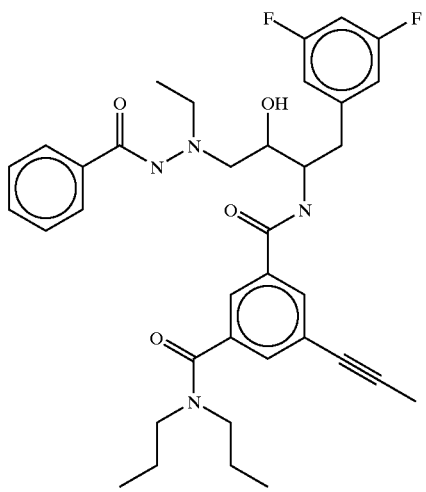
1:G10 1, 6, 1, 2
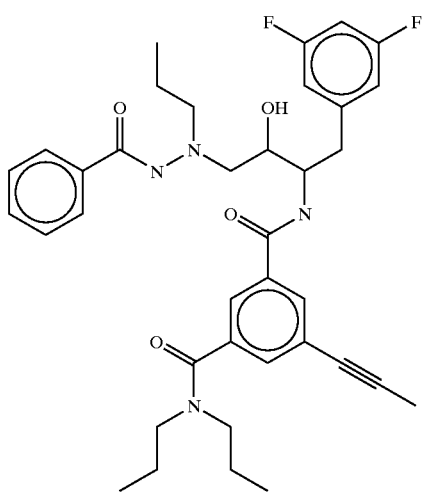
1:G11 1, 6, 1, 3
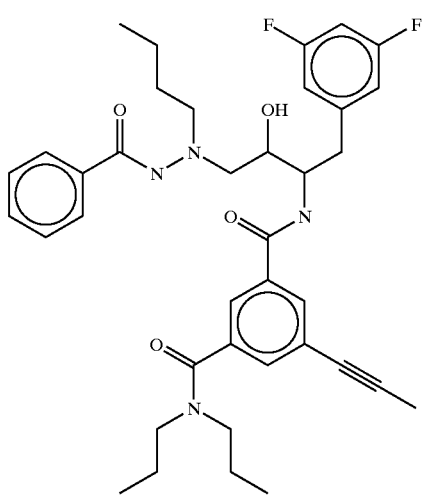
1:G12 1, 6, 1, 4
TABLE 1-continued
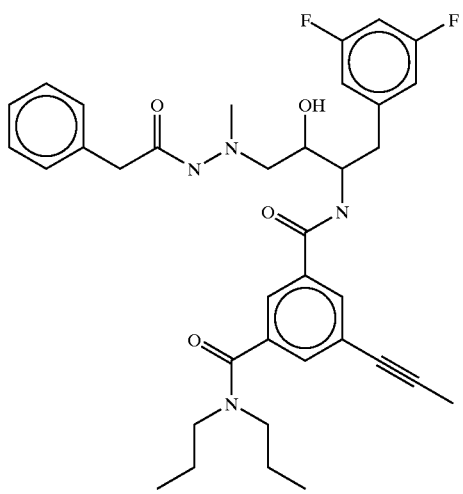
1:H1 1, 6, 2, 1
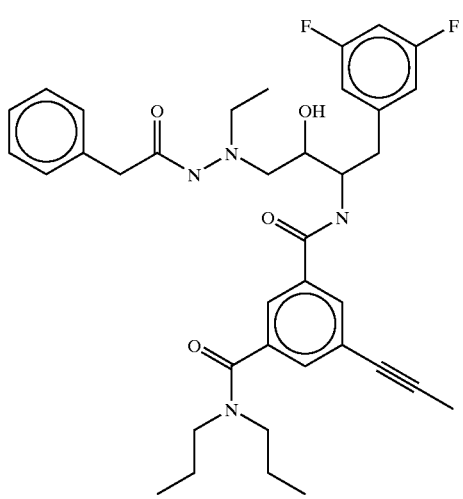
1:H2 1, 6, 2, 2
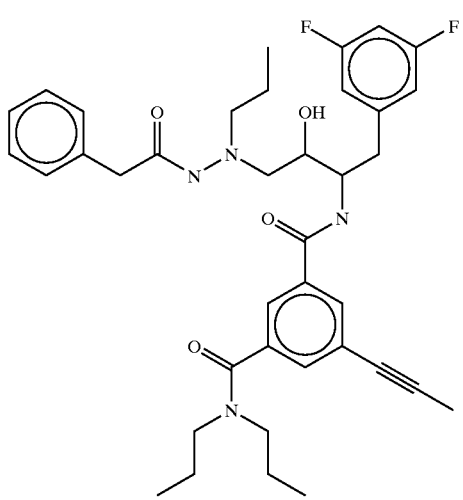
1:H3 1, 6, 2, 3

TABLE 1-continued
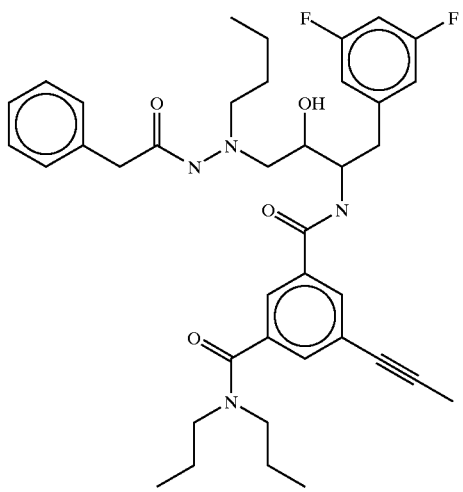
1:H4 1, 6, 2, 4
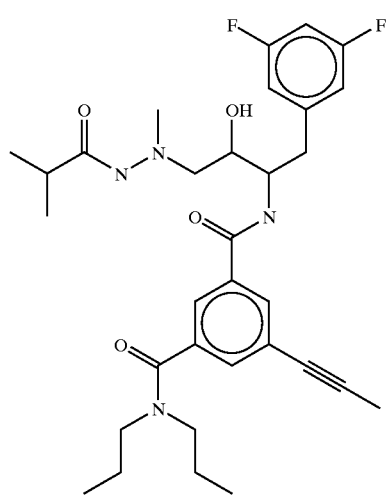
1:H5 1, 6, 3, 1
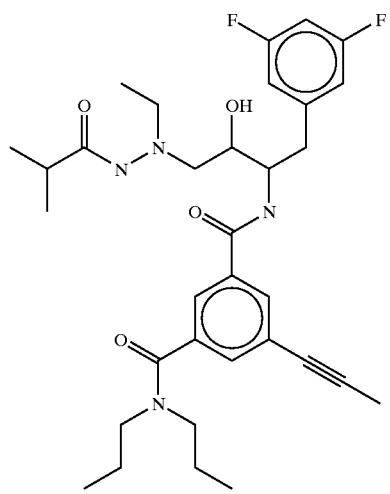
1:H6 1, 6, 3, 2
TABLE 1-continued
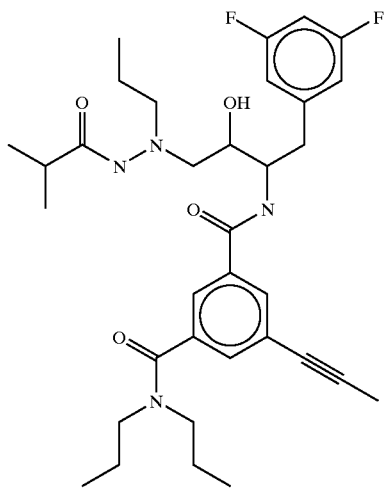
1:H7 1, 6, 3, 3
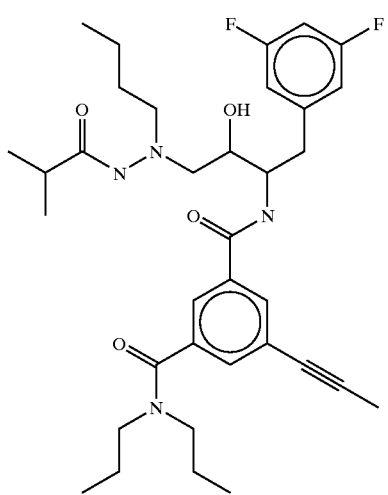
1:H8 1, 6, 3, 4
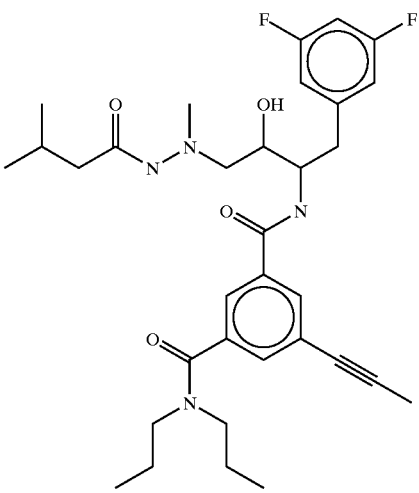
1:H9 1, 6, 4, 1

TABLE 1-continued
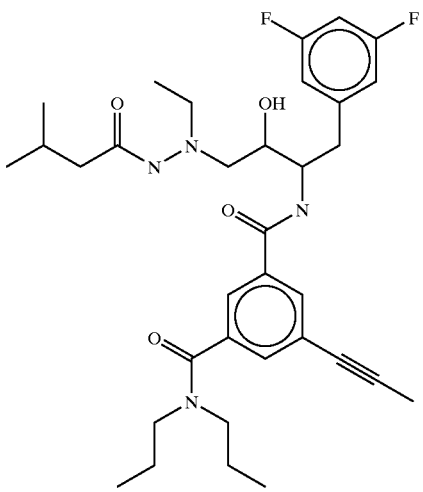
1:H10 1, 6, 4, 2
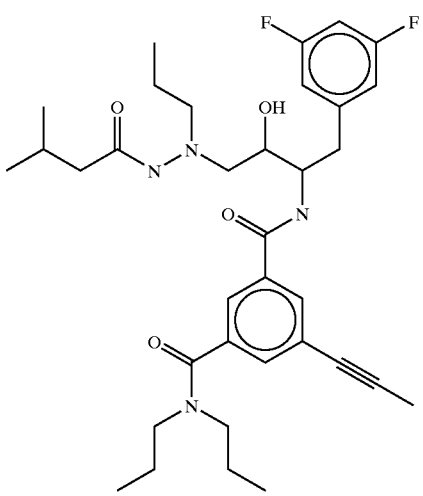
1:H11 1, 6, 4, 3
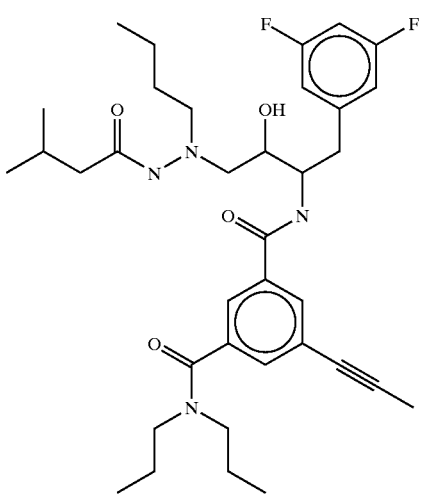
1:H12 1, 6, 4, 4
TABLE 1-continued
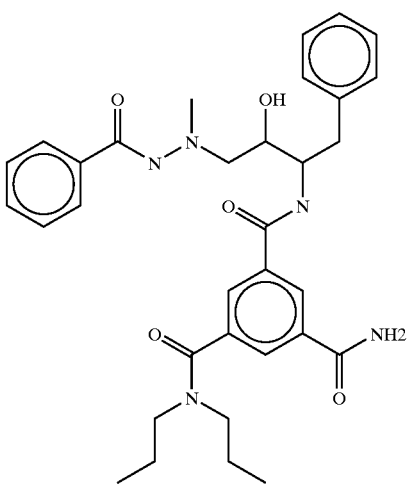
2:A1 2, 1, 1, 1
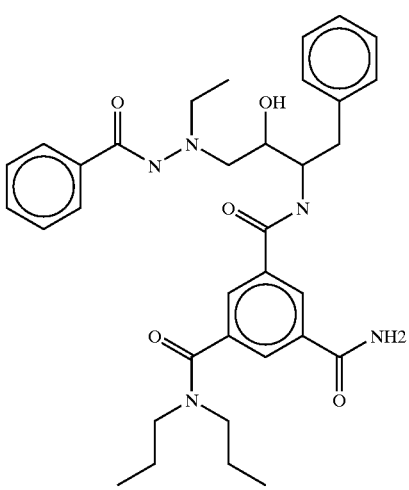
2:A2 2, 1, 1, 2
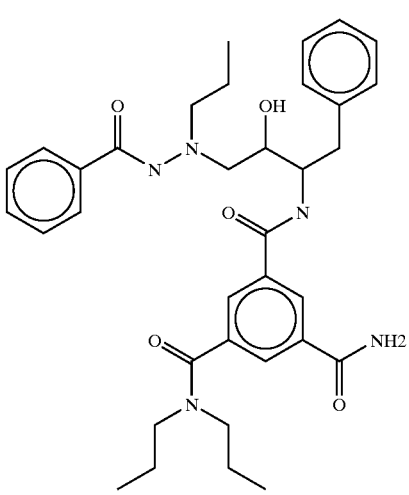
2:A3 2, 1, 1, 3

TABLE 1-continued
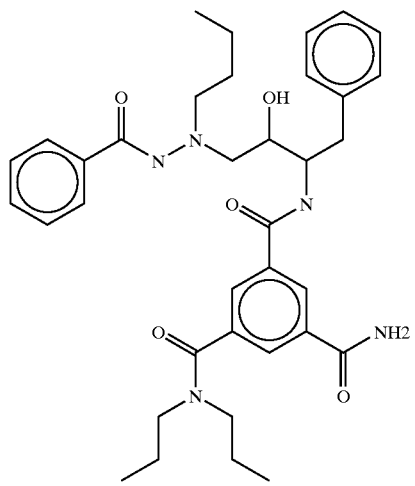
2:A4 2, 1, 1, 4
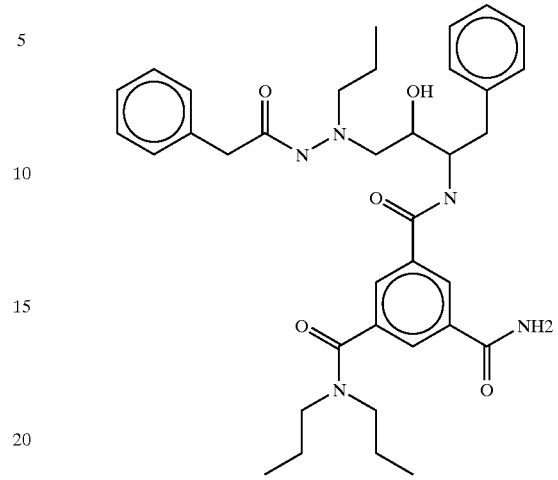
2:A7 2, 1, 2, 3
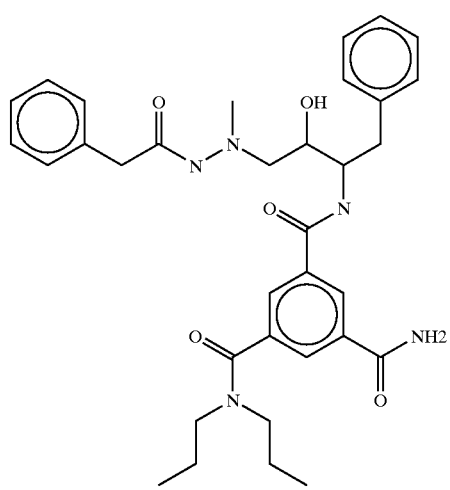
2:A5 2, 1, 2, 1
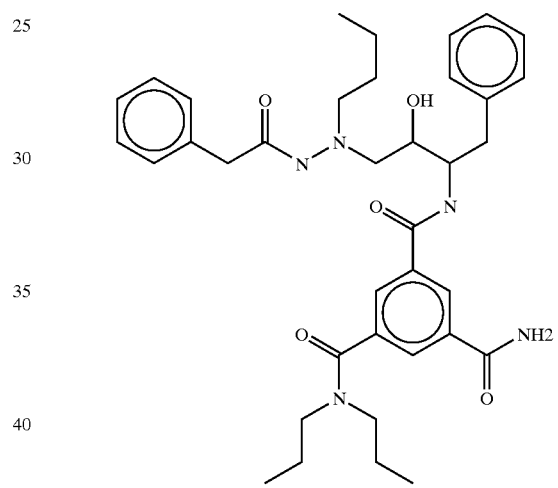
2:A8 2, 1, 2, 4
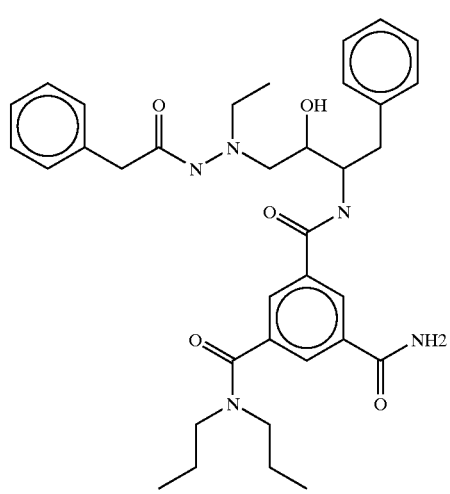
2:A6 2, 1, 2, 2
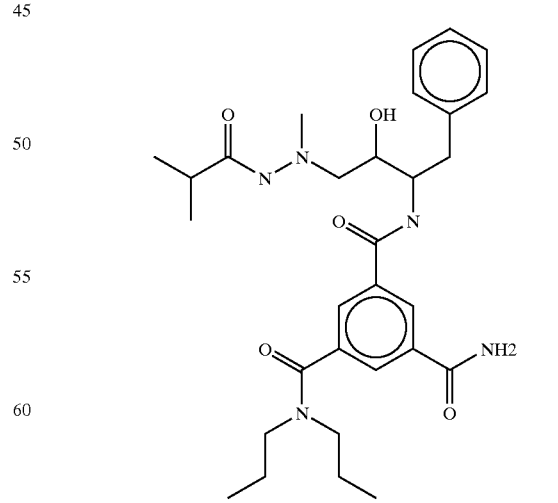
2:A9 2, 1, 3, 1

TABLE 1-continued
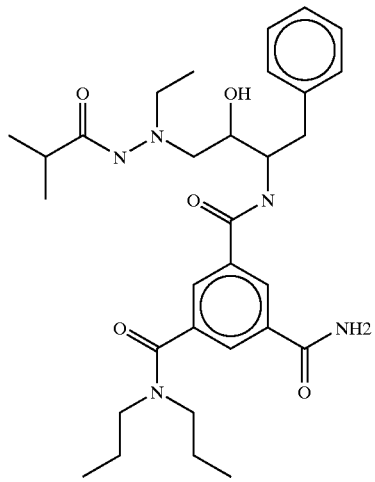
2:A10 2, 1, 3, 2
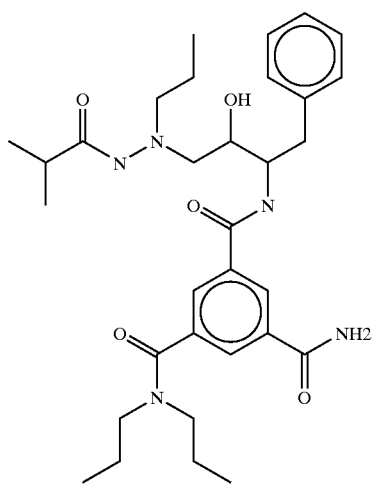
2:A11 2, 1, 3, 3
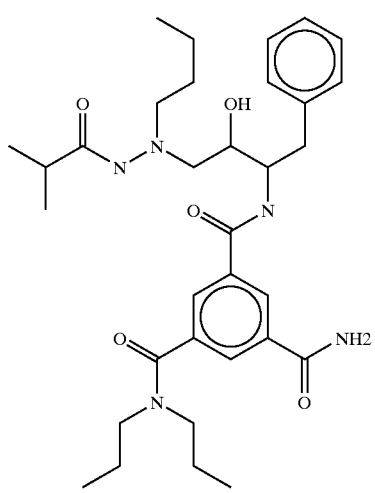
2:A12 2, 1, 3, 4
TABLE 1-continued
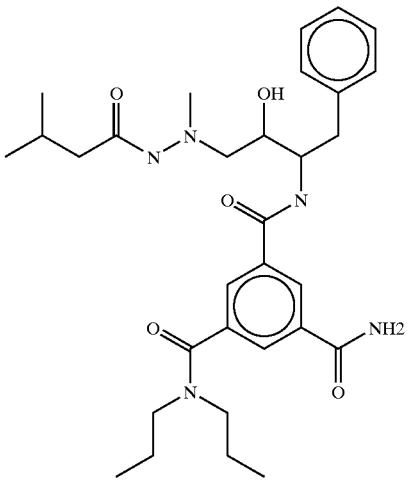
2:B1 2, 1, 4, 1
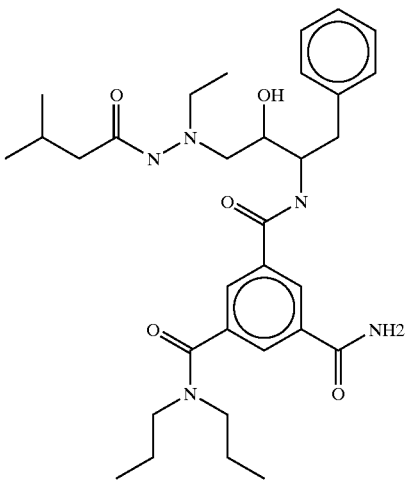
2:B2 2, 1, 4, 2
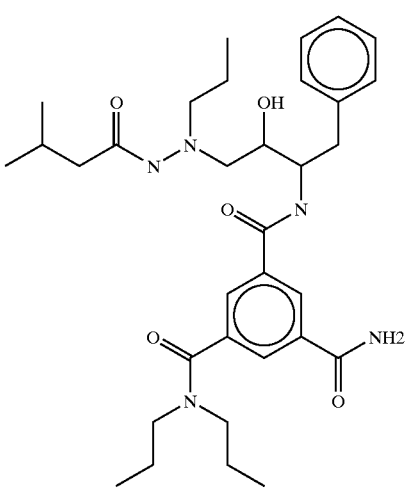
2:B3 2, 1, 4, 3

TABLE 1-continued
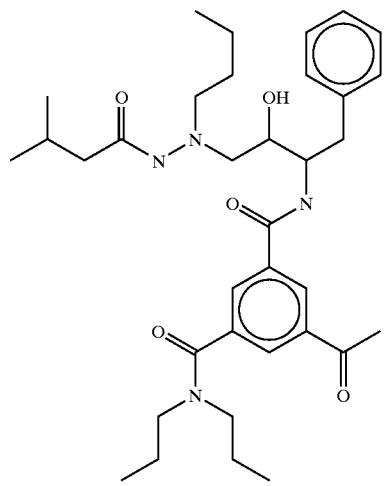
2:B4 2, 1, 4, 4
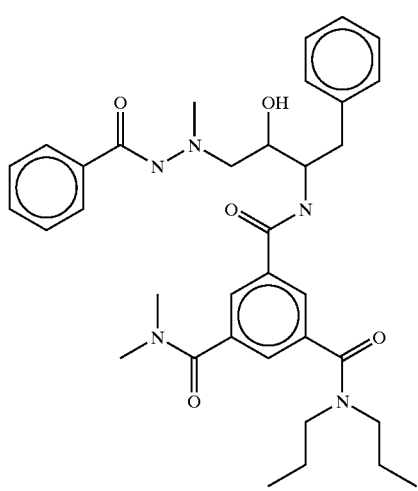
2:B5 2, 2, 1, 1
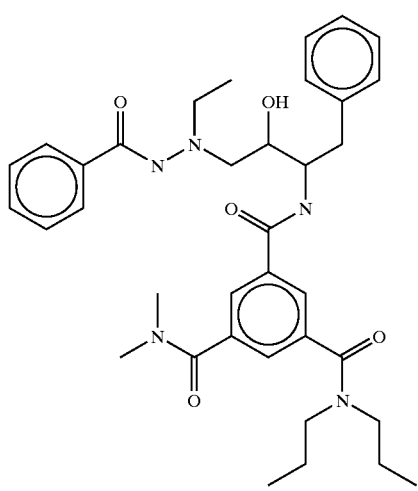
2:B6 2, 2, 1, 2
TABLE 1-continued
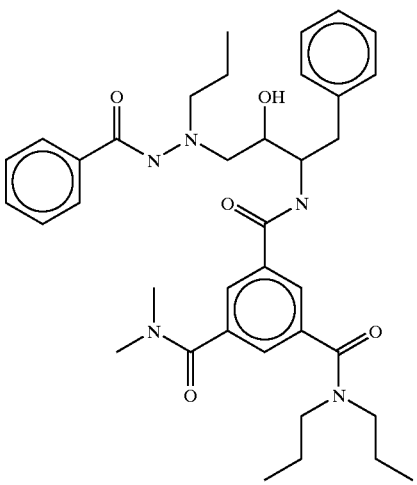
2:B7 2, 2, 1, 3
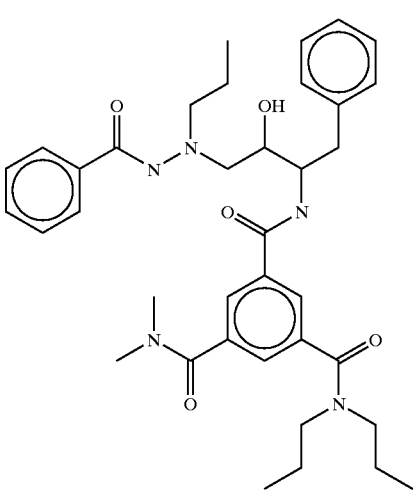
2:B8 2, 2, 1, 4
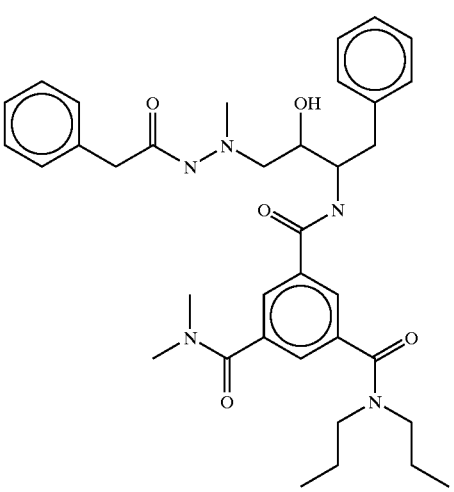
2:B9 2, 2, 2, 1

TABLE 1-continued
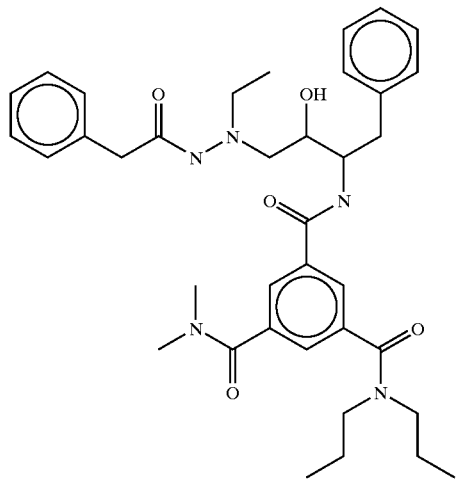
2:B10 2, 2, 2, 2
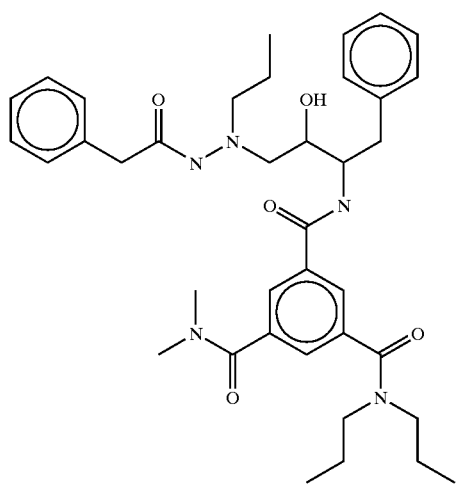
2:B11 2, 2, 2, 3
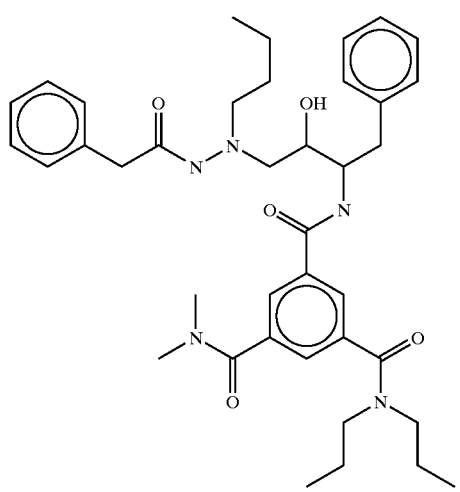
2:B12 2, 2, 2, 4
TABLE 1-continued
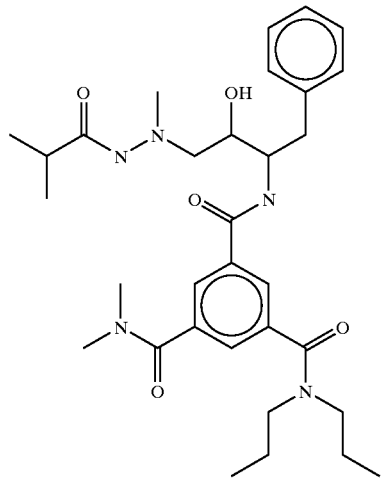
2:C1 2, 2, 3, 1
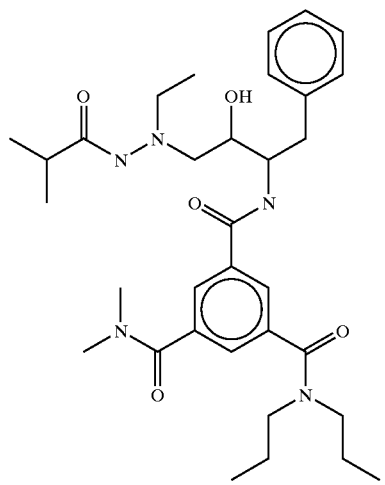
2:C2 2, 2, 3, 2
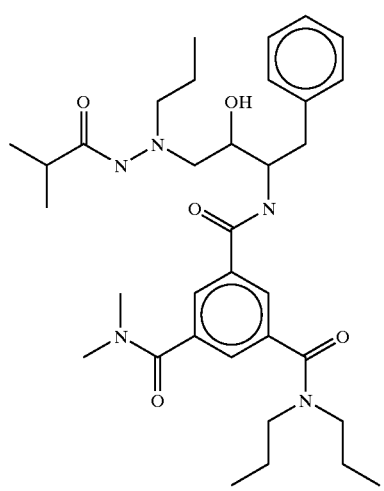
2:C3 2, 2, 3, 3

TABLE 1-continued
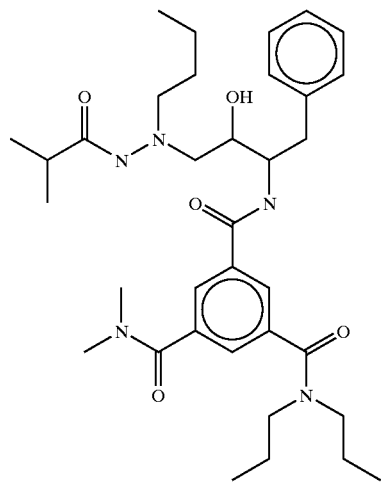
2:C4 2, 2, 3, 4
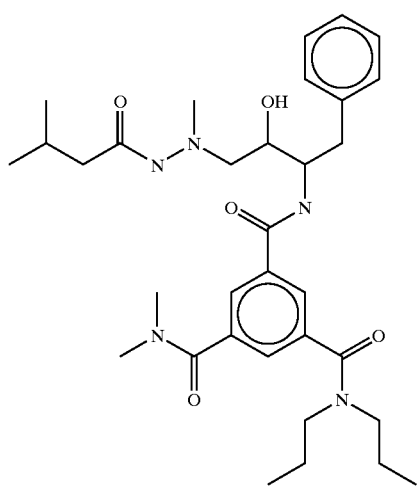
2:C5 2, 2, 4, 1
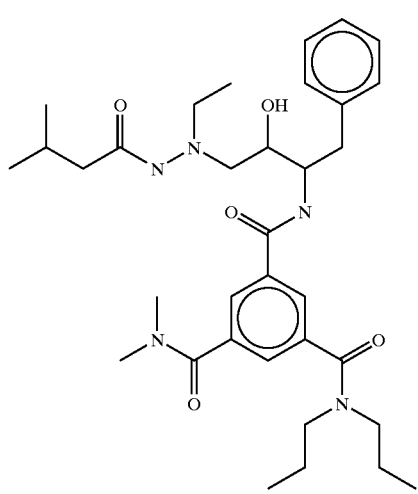
2:C6 2, 2, 4, 2
TABLE 1-continued
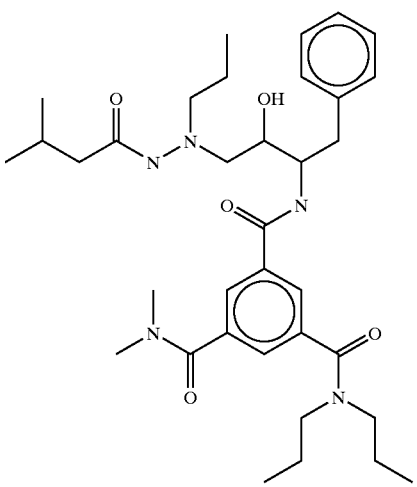
2:C7 2, 2, 4, 3
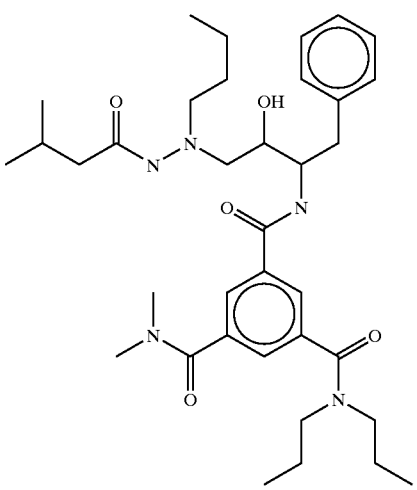
2:C8 2, 2, 4, 4
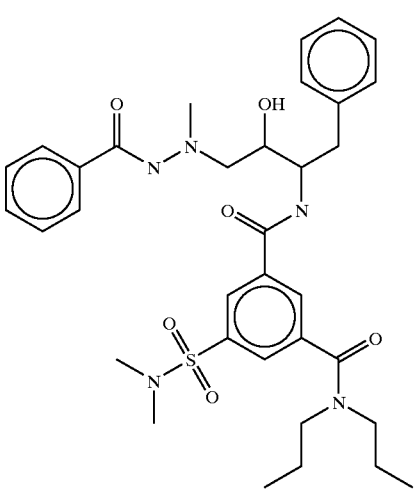
2:C9 2, 3, 1, 1

TABLE 1-continued
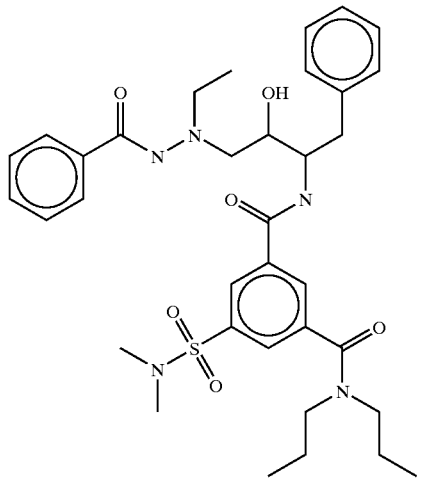
2:C10 2, 3, 1, 2
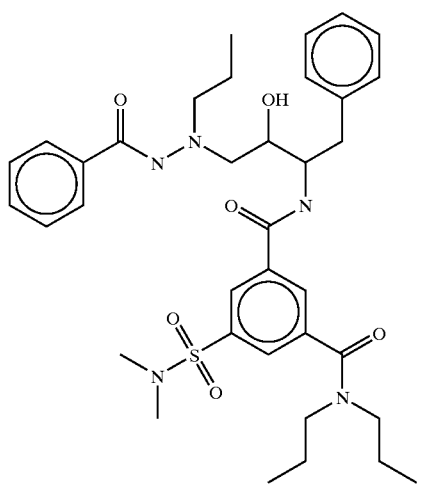
2:C11 2, 3, 1, 3
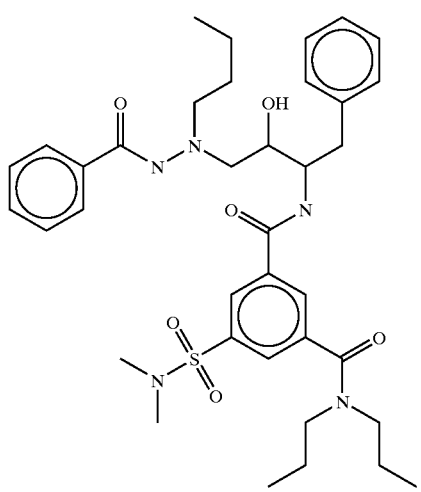
2:C12 2, 3, 1, 4
TABLE 1-continued
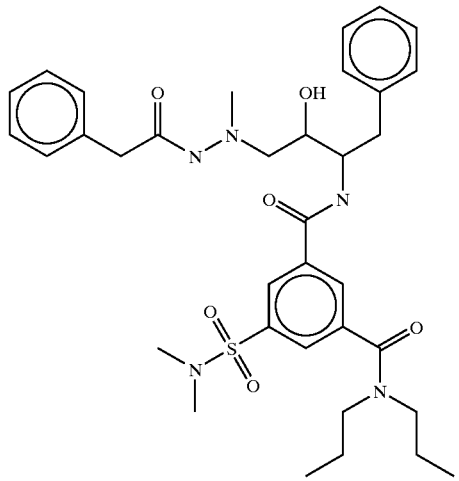
2:D1 2, 3, 2, 1
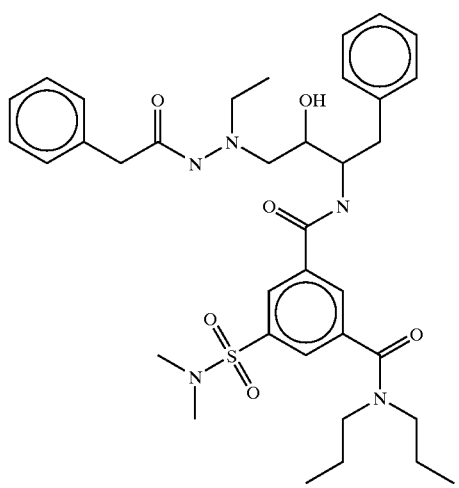
2:D2 2, 3, 2, 2
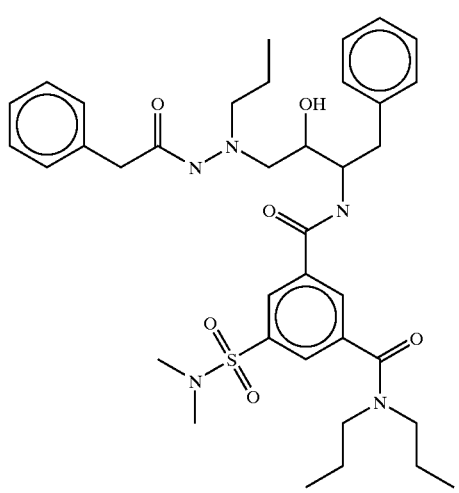
2:D3 2, 3, 2, 3

TABLE 1-continued
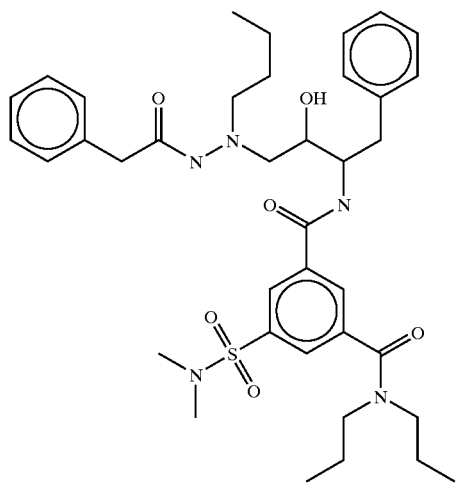
2:D4 2, 3, 2, 4
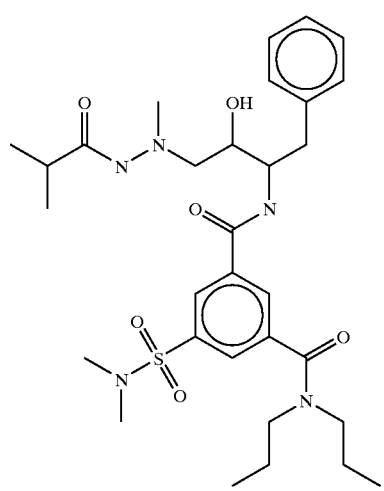
2:D5 2, 3, 3, 1
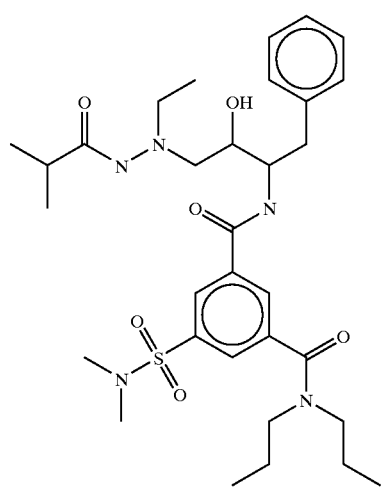
2:D6 2, 3, 3, 2
TABLE 1-continued
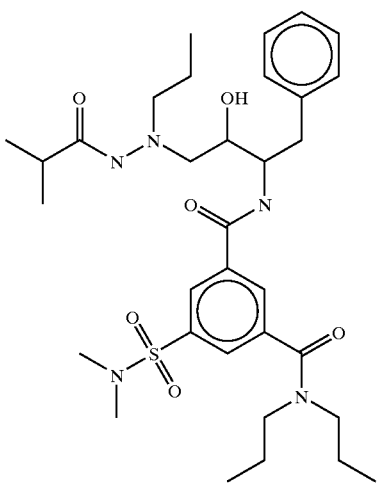
2:D7 2, 3, 3, 3
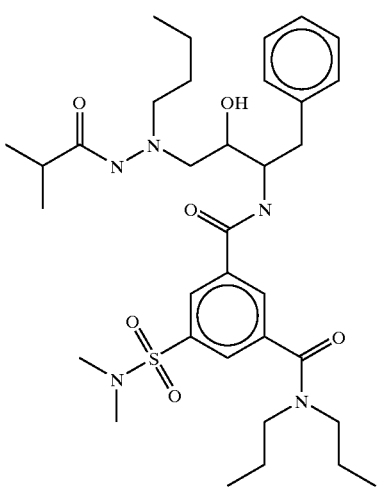
2:D8 2, 3, 3, 4
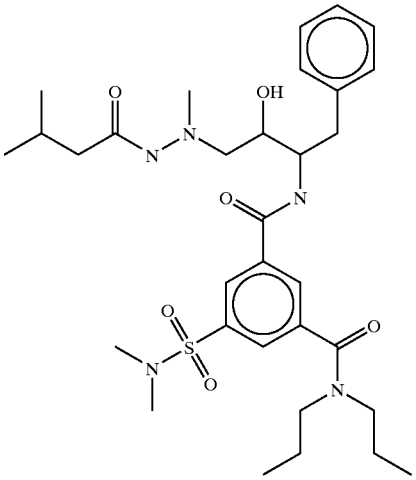
2:D9 2, 3, 4, 1

TABLE 1-continued
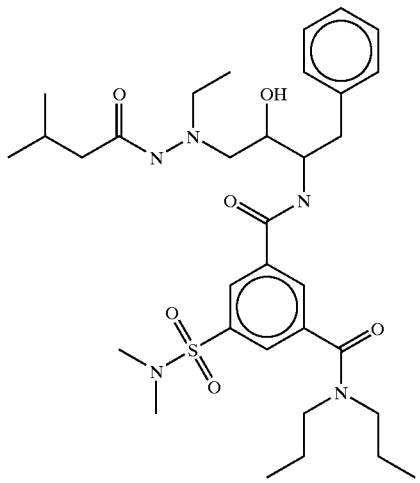
2:D10 2, 3, 4, 2
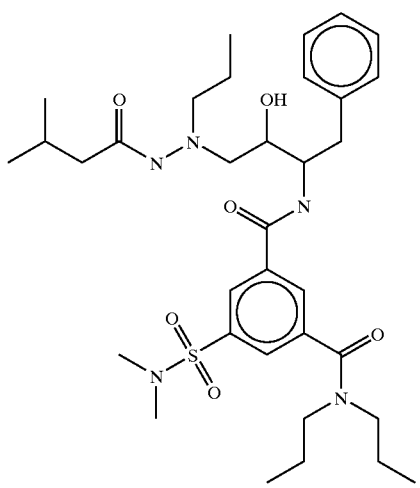
2:D11 2, 3, 4, 3
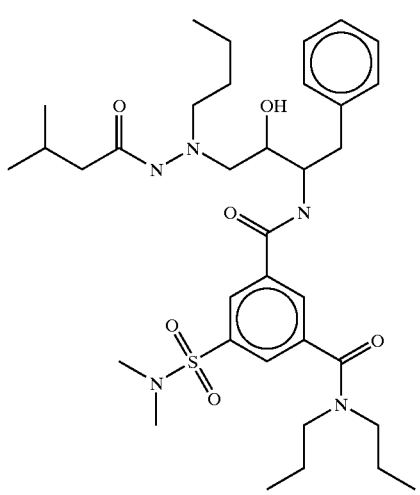
2:D12 2, 3, 4, 4
TABLE 1-continued
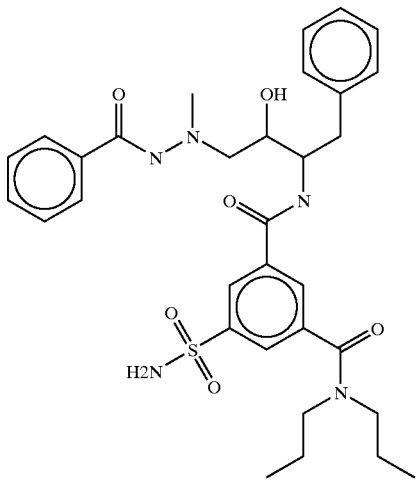
2:E1 2, 4, 1, 1
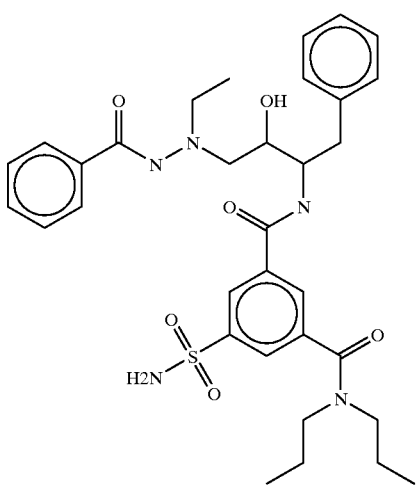
2:E2 2, 4, 1, 2
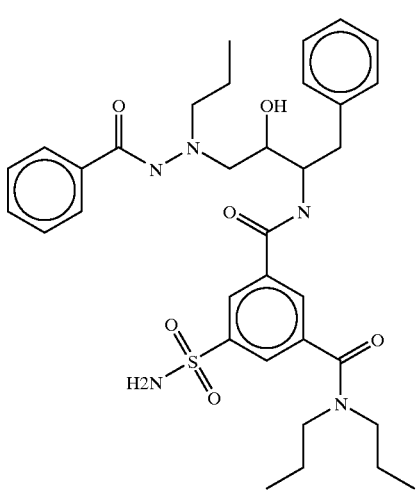
2:E3 2, 4, 1, 3

TABLE 1-continued
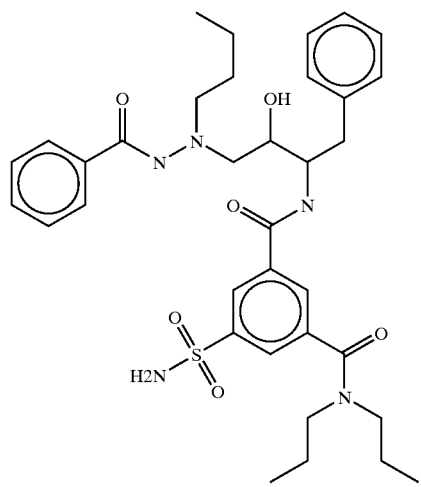
2:E4 2, 4, 1, 4
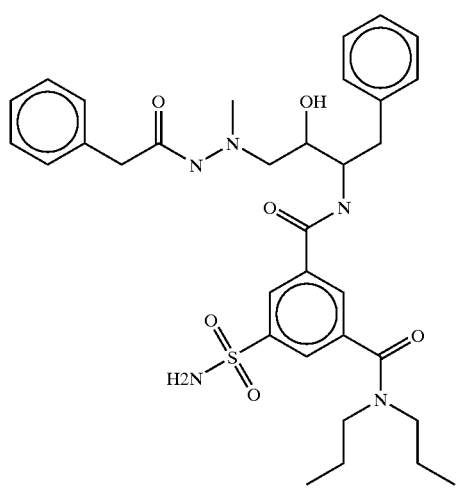
2:E5 2, 4, 2, 1
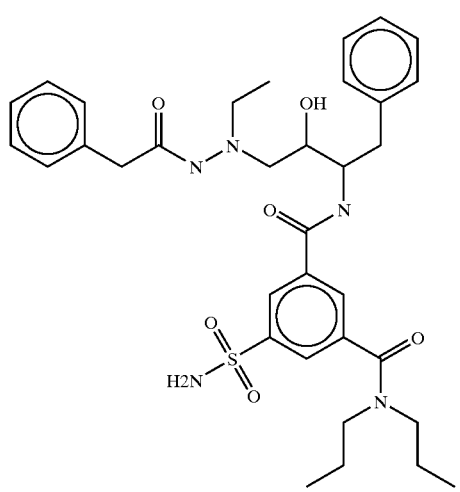
2:E6 2, 4, 2, 2
TABLE 1-continued
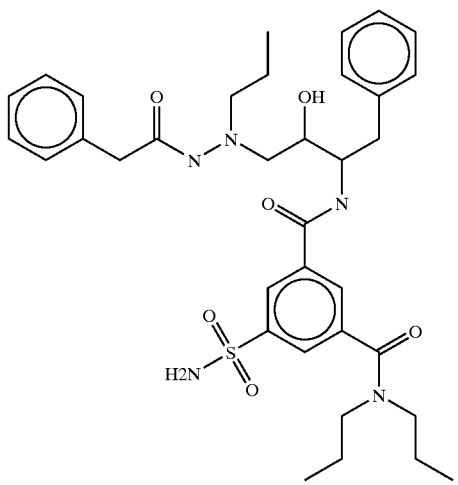
2:E7 2, 4, 2, 3
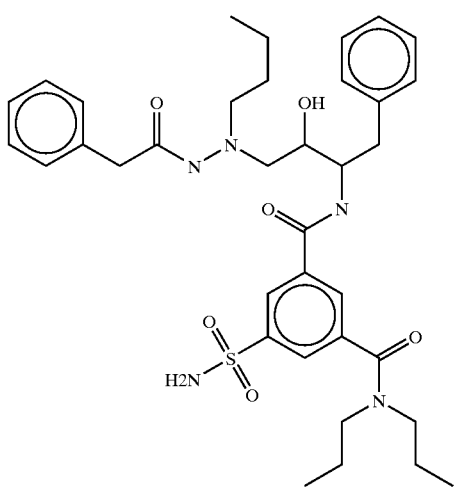
2:E8 2, 4, 2, 4
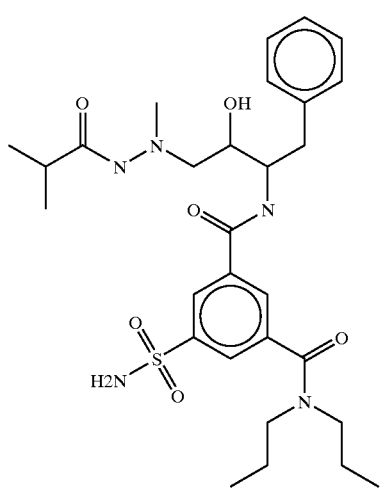
2:E9 2, 4, 3, 1

TABLE 1-continued
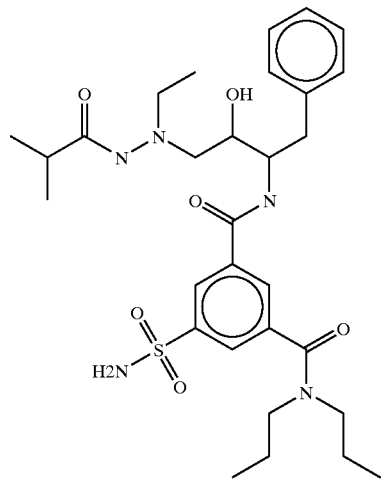
2:E10 2, 4, 3, 2
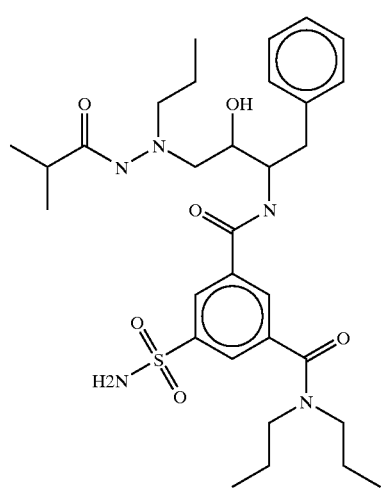
2:E11 2, 4, 3, 3
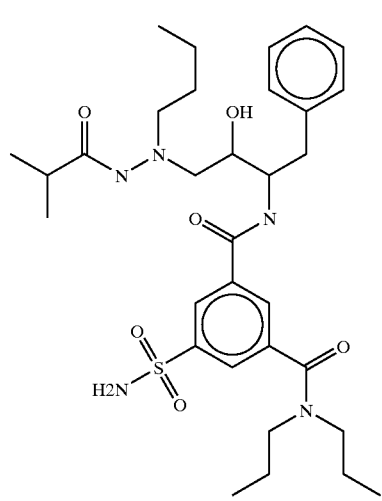
2:E12 2, 4, 3, 4
TABLE 1-continued
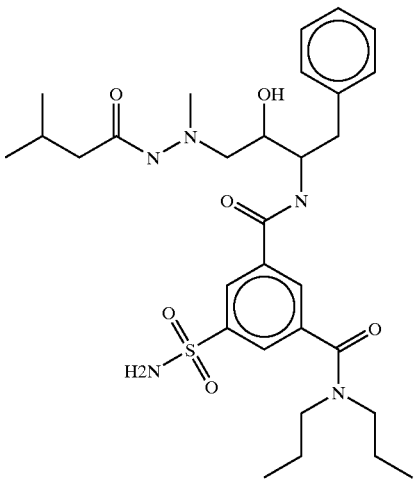
2:F1 2, 4, 4, 1
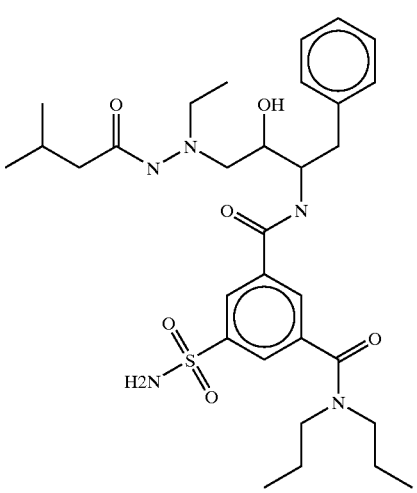
2:F2 2, 4, 4, 2
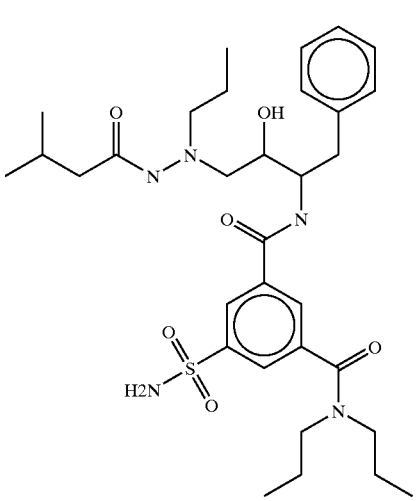
2:F3 2, 4, 4, 3

TABLE 1-continued
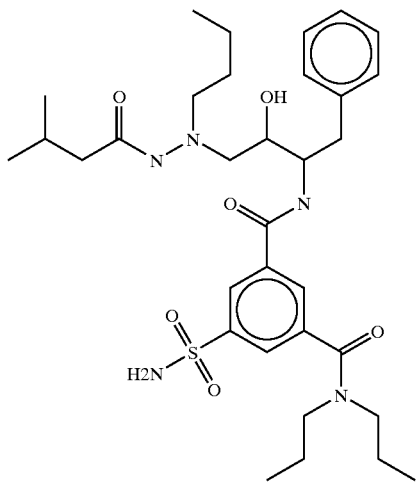
2:F4 2, 4, 4, 4
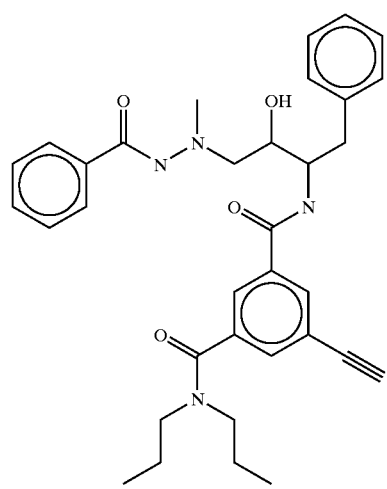
2:F5 2, 5, 1, 1
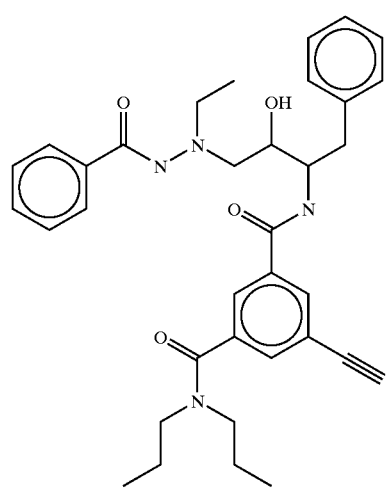
2:F6 2, 5, 1, 2
TABLE 1-continued
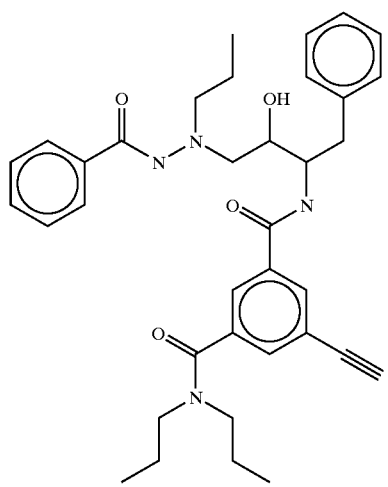
2:F7 2, 5, 1, 3
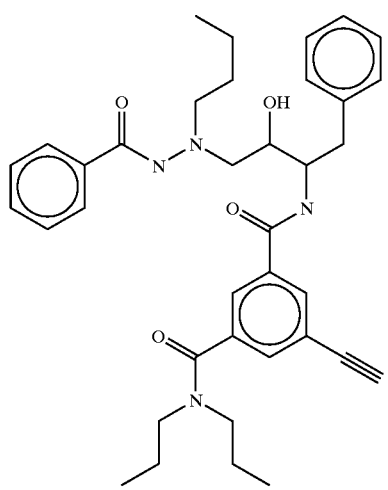
2:F8 2, 5, 1, 4
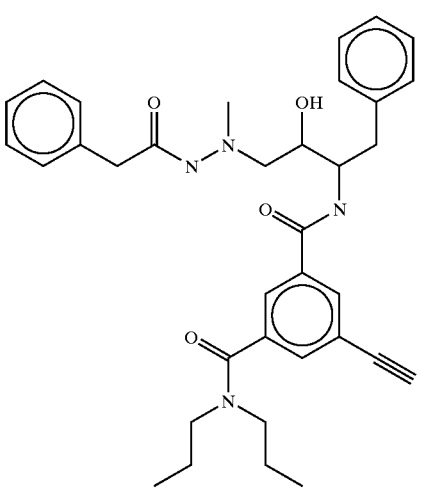
2:F9 2, 5, 2, 1

TABLE 1-continued
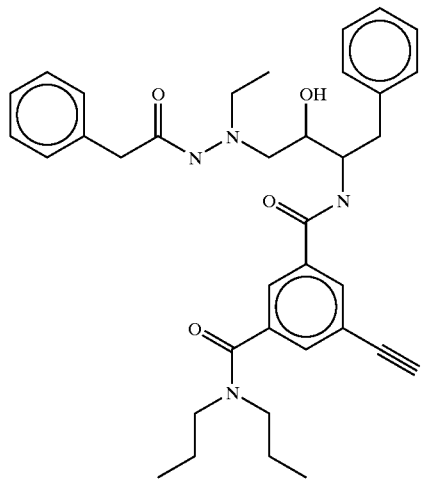
2:F10 2, 5, 2, 2
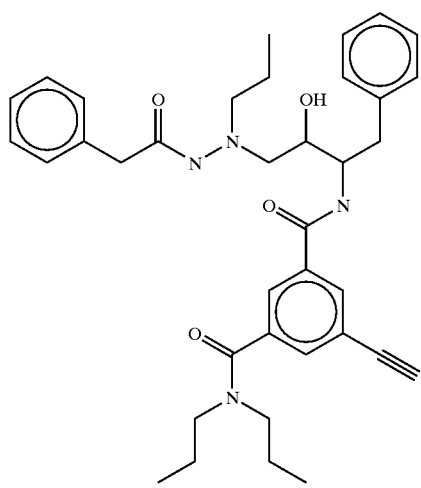
2:F11 2, 5, 2, 3
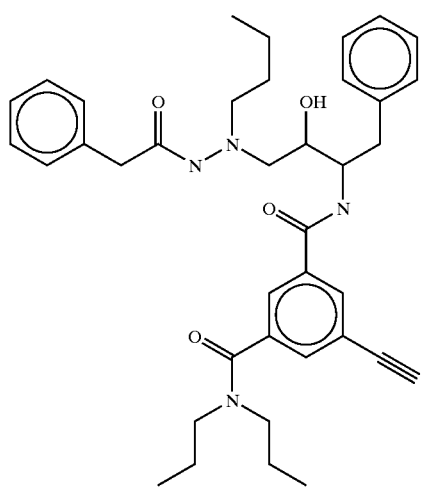
2:F12 2, 5, 2, 4
TABLE 1-continued
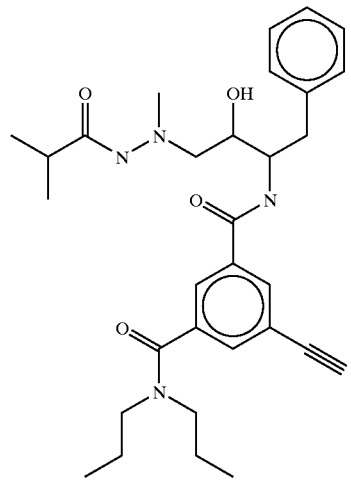
2:G1 2, 5, 3, 1
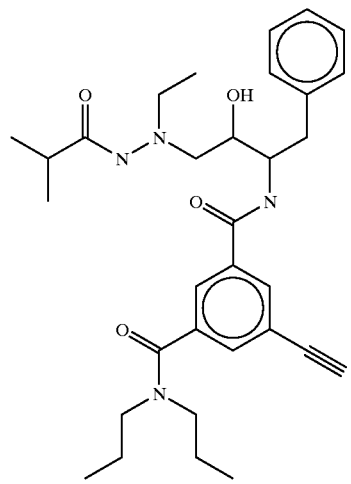
2:G2 2, 5, 3, 2
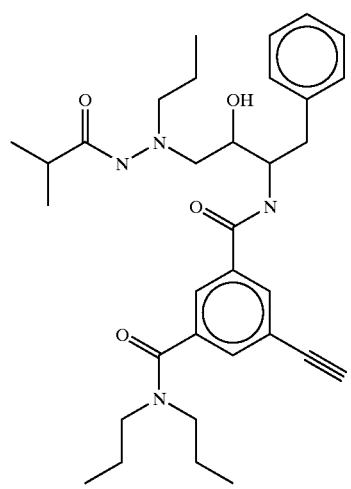
2:G3 2, 5, 3, 3

TABLE 1-continued
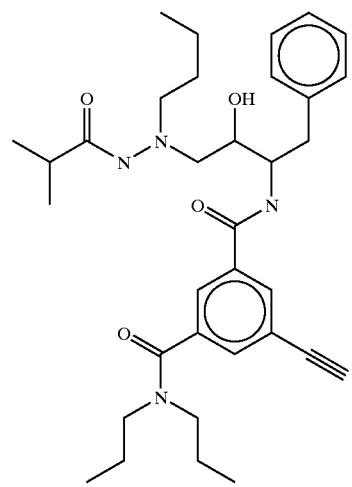
2:G4 2, 5, 3, 4
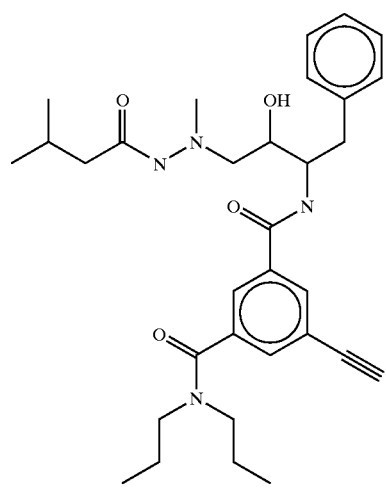
2:G5 2, 5, 4, 1
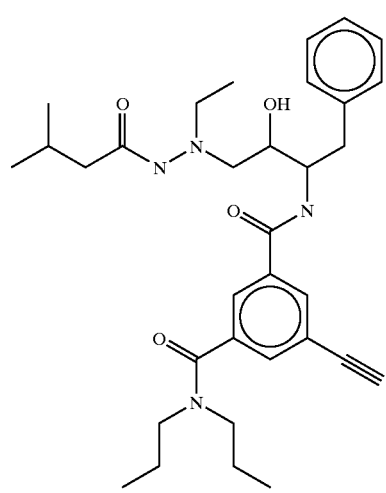
2:G6 2, 5, 4, 2
TABLE 1-continued
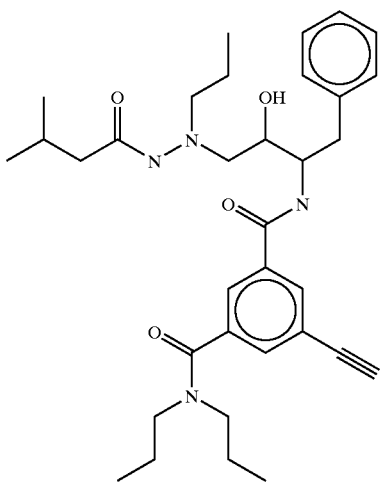
2:G7 2, 5, 4, 3
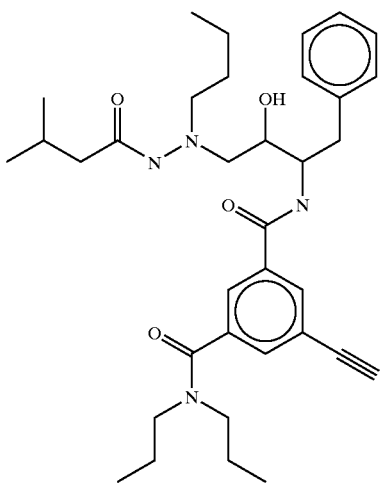
2:G8 2, 5, 4, 4
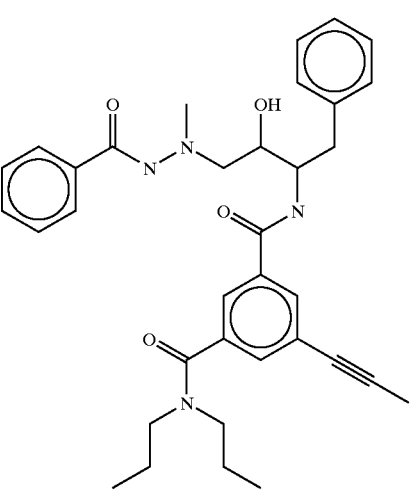
2:G9 2, 6, 1, 1

TABLE 1-continued
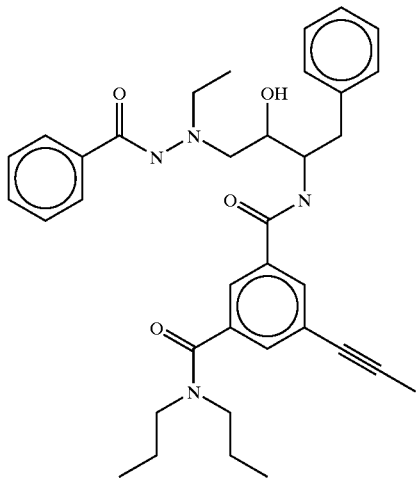
2:G10 2, 6, 1, 2
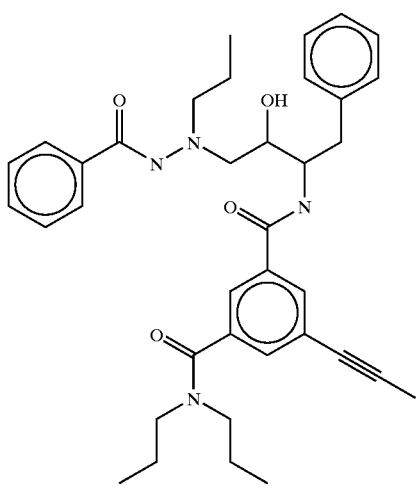
2:G11 2, 6, 1, 3
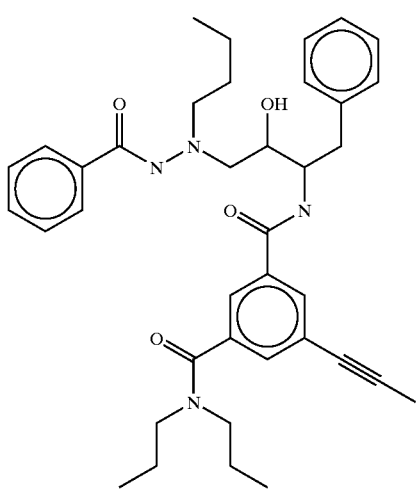
2:G12 2, 6, 1, 4
TABLE 1-continued
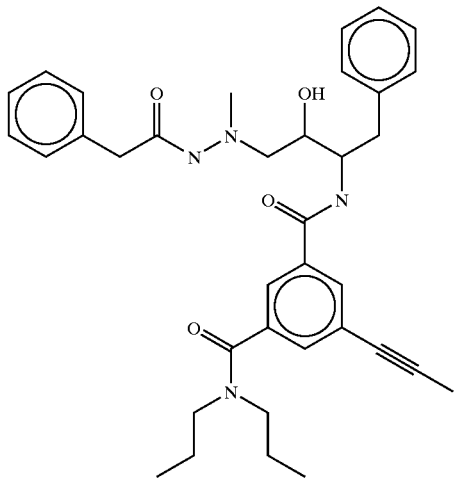
2:H1 2, 6, 2, 1
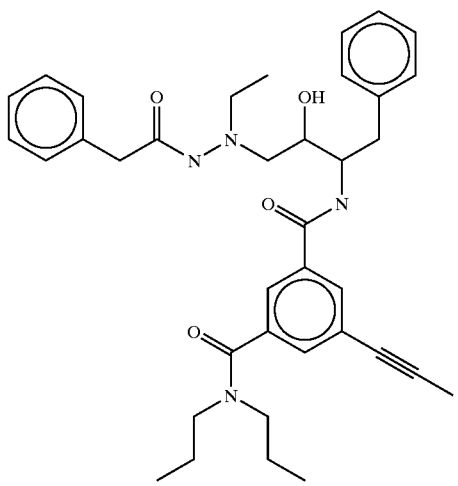
2:H2 2, 6, 2, 2
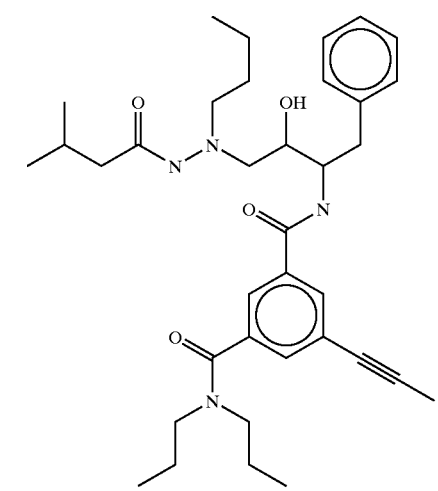
2:H12 2, 6, 4, 4

TABLE 1-continued
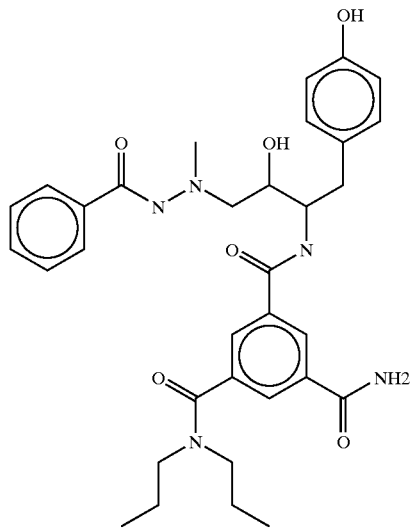
3:A1 3, 1, 1, 1
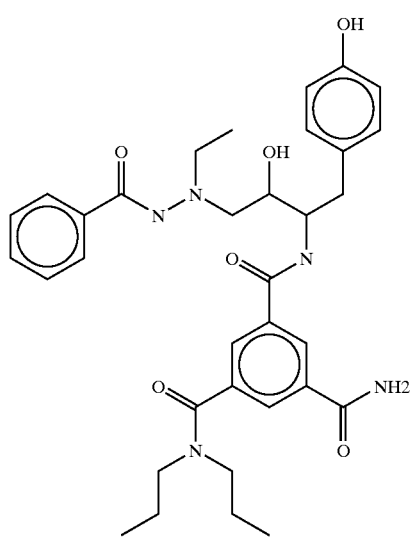
3:A2 3, 1, 1, 2
TABLE 1-continued
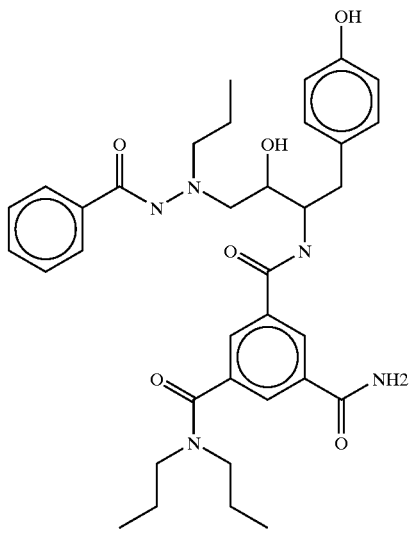
3:A3 3, 1, 1, 3
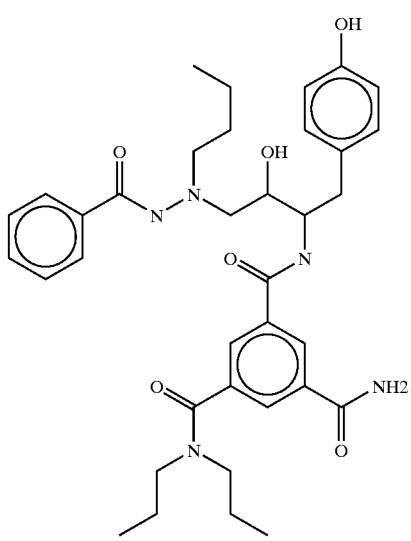
3:A4 3, 1, 1, 4

TABLE 1-continued
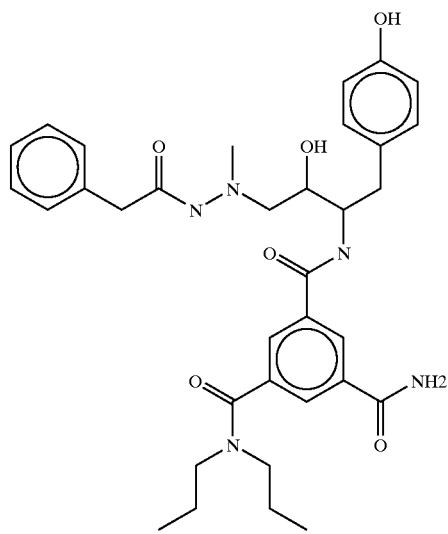
3:A5 3, 1, 2, 1
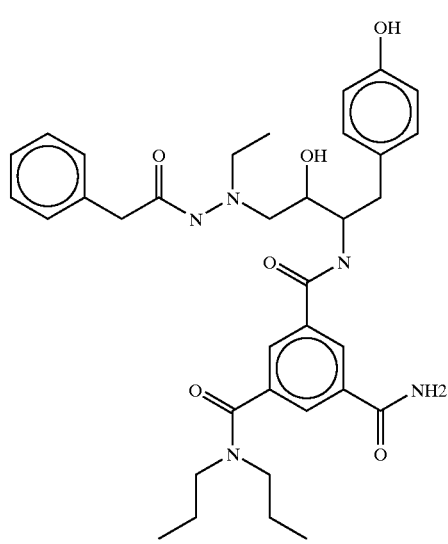
3:A6 3, 1, 2, 2
TABLE 1-continued
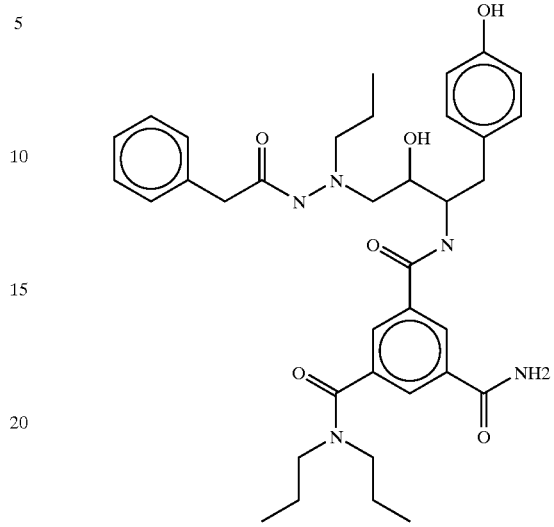
3:A7 3, 1, 2, 3
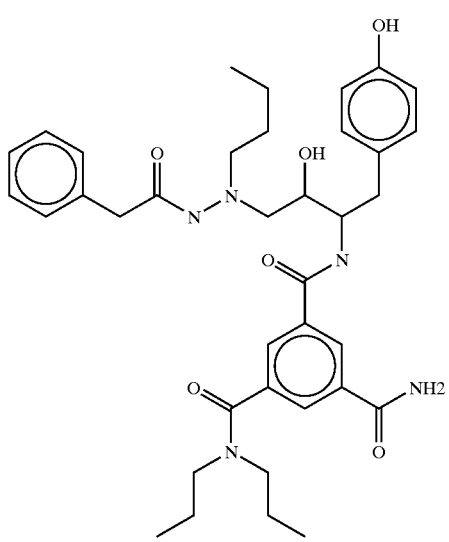
3:A8 3, 1, 2, 4

TABLE 1-continued
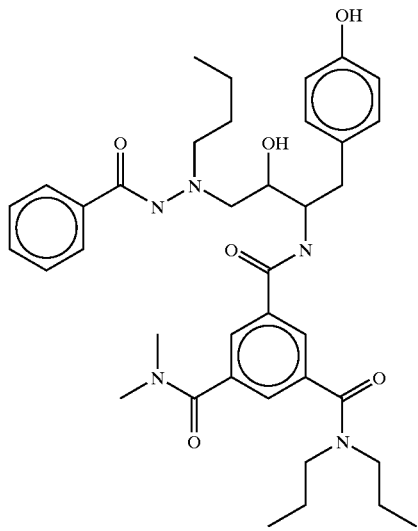
3:B8 3, 2, 1, 4
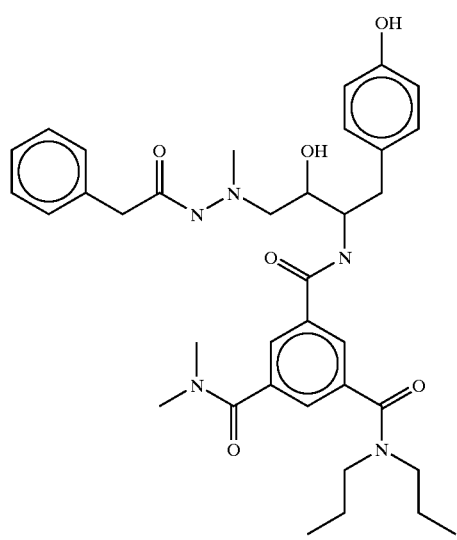
3:B9 3, 2, 2, 1
TABLE 1-continued
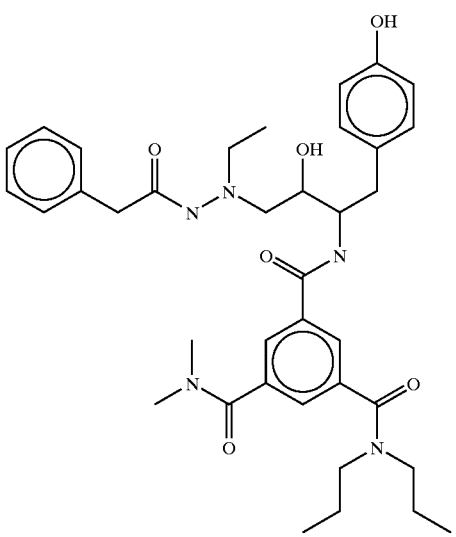
3:B10 3, 2, 2, 2
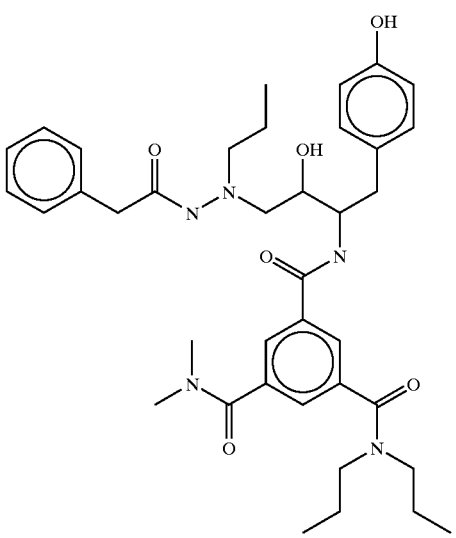
3:B11 3, 2, 2, 3

TABLE 1-continued
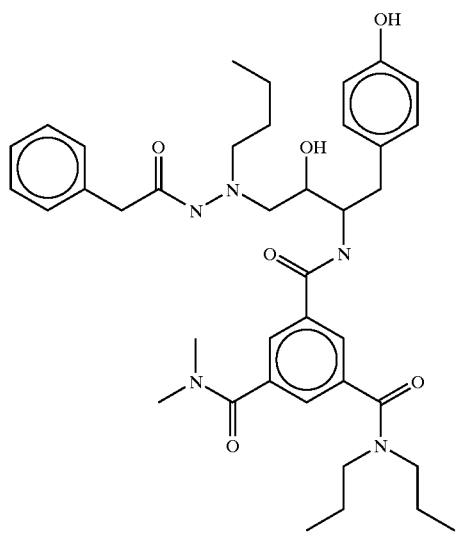
3:B12 3, 2, 2, 4
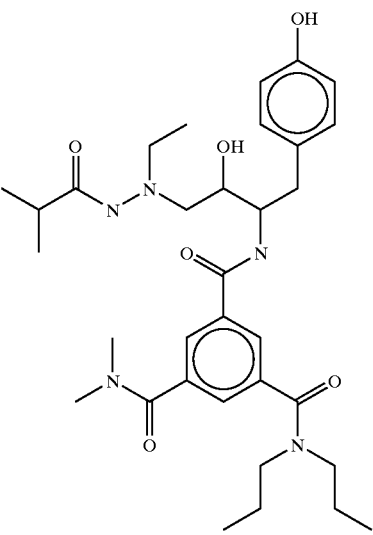
3:C2 3, 2, 3, 2
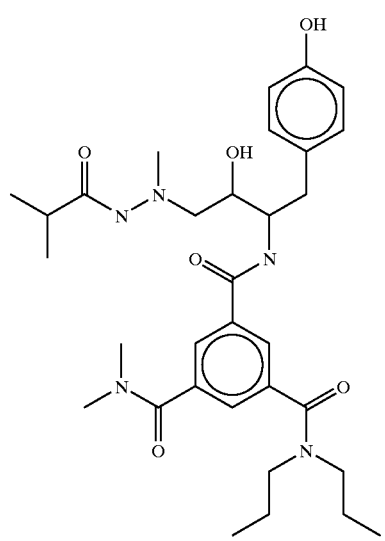
3:C1 3, 2, 3, 1
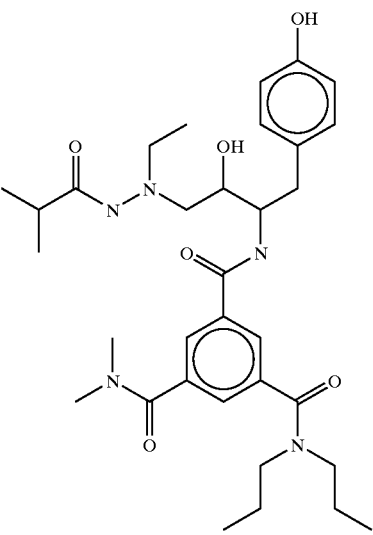
3:C3 3, 2, 3, 3

TABLE 1-continued
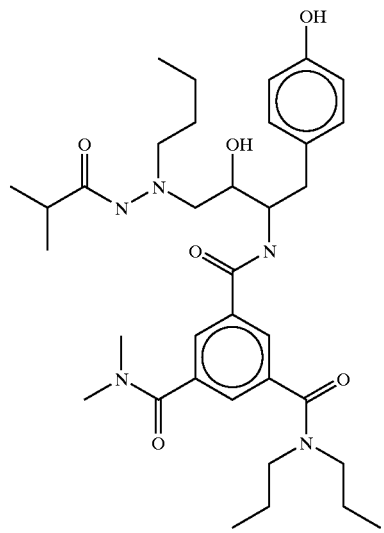
3:C4 3, 2, 3, 4
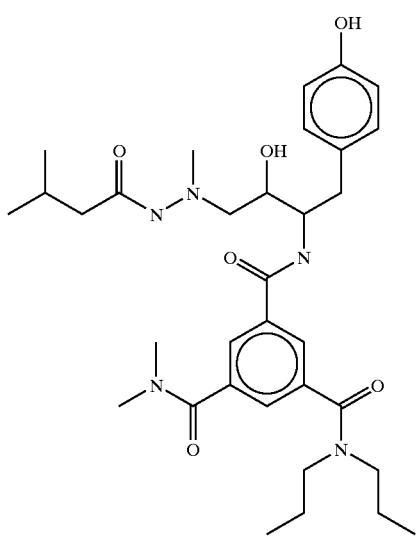
3:C5 3, 2, 4, 1
TABLE 1-continued
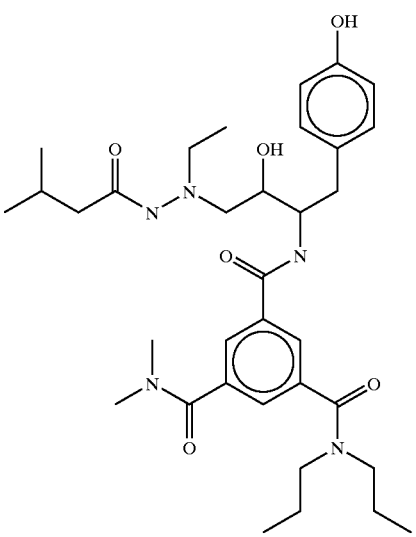
3:C6 3, 2, 4, 2
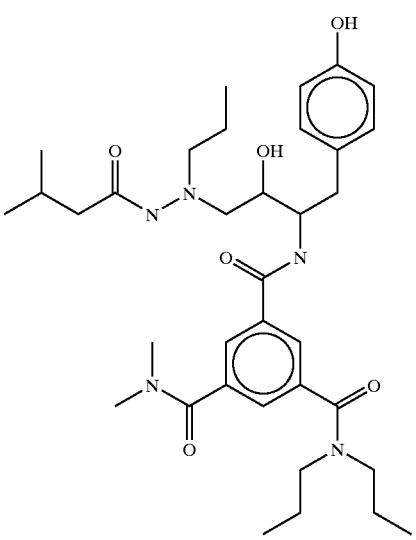
3:C7 3, 2, 4, 3

TABLE 1-continued
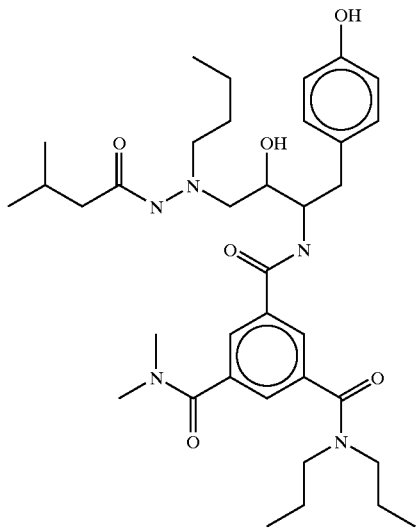
3:C8 3, 2, 4, 4
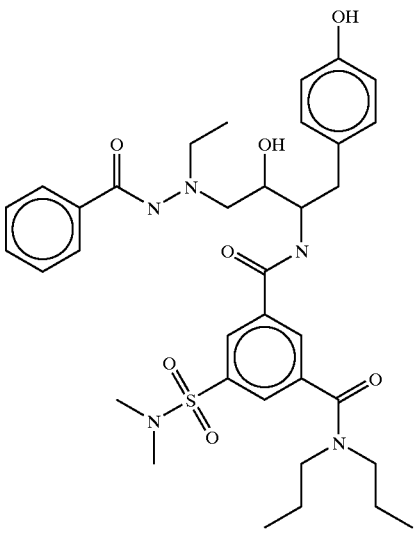
3:C10 3, 3, 1, 2
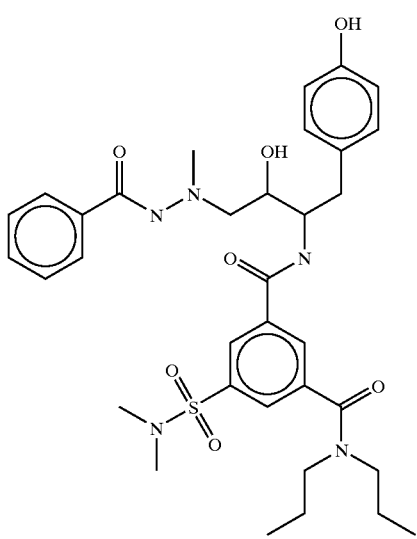
3:C9 3, 3, 1, 1
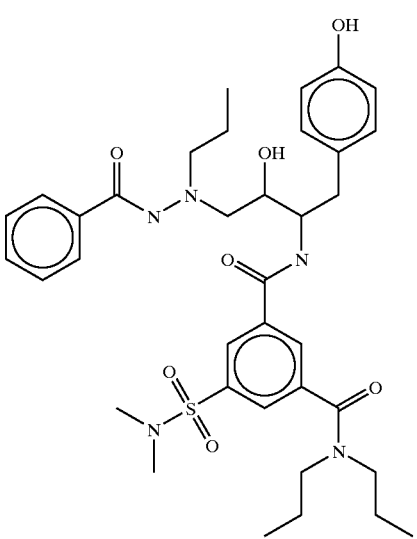
3:C11 3, 3, 1, 3

TABLE 1-continued
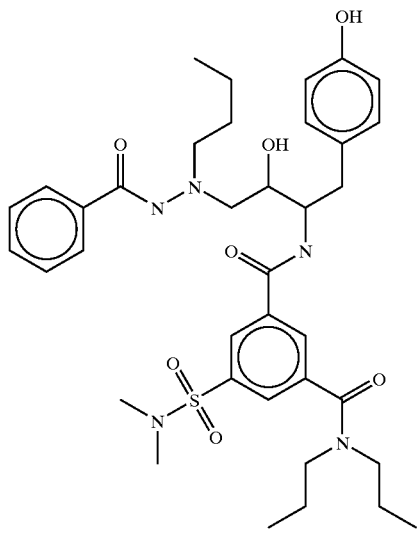
3:C12 3, 3, 1, 4
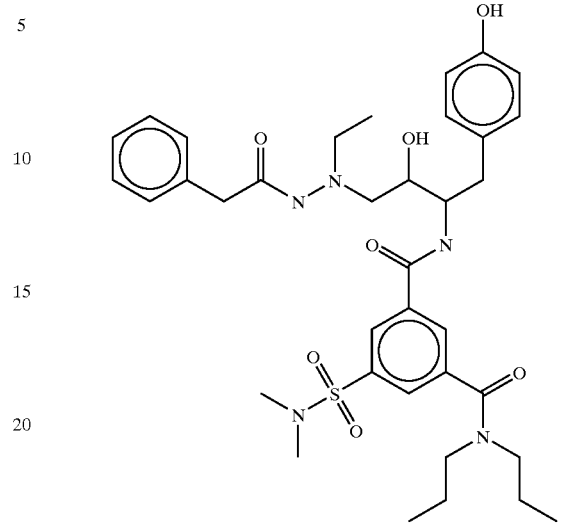
3:D2 3, 3, 2, 2
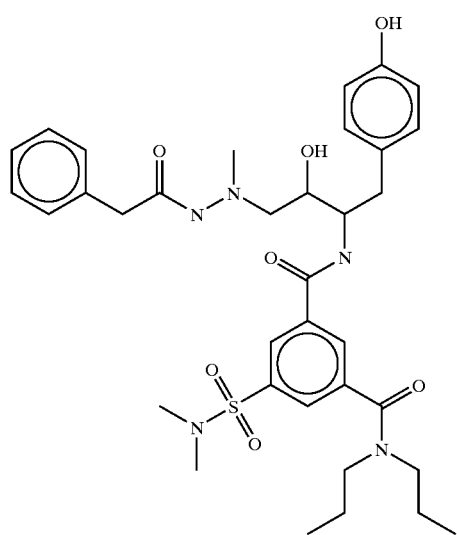
3:D1 3, 3, 2, 1
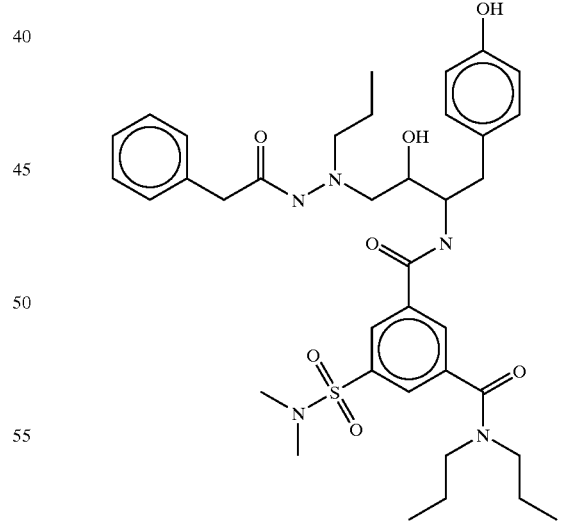
3:D3 3, 3, 2, 3

TABLE 1-continued
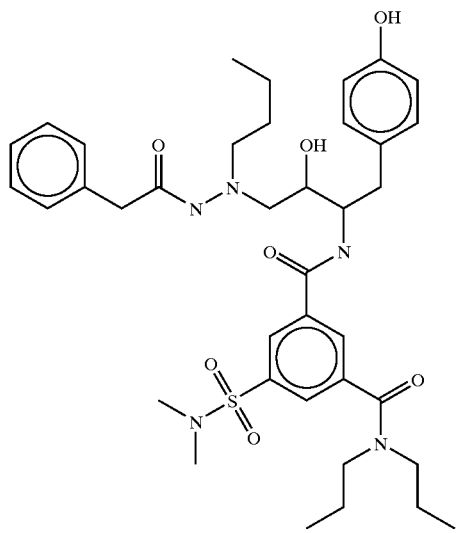
3:D4 3, 3, 2, 4
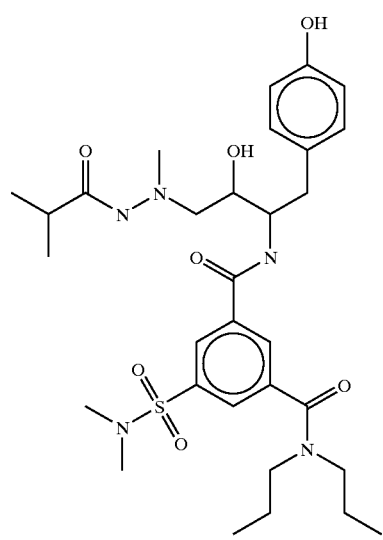
3:D5 3, 3, 3, 1
TABLE 1-continued
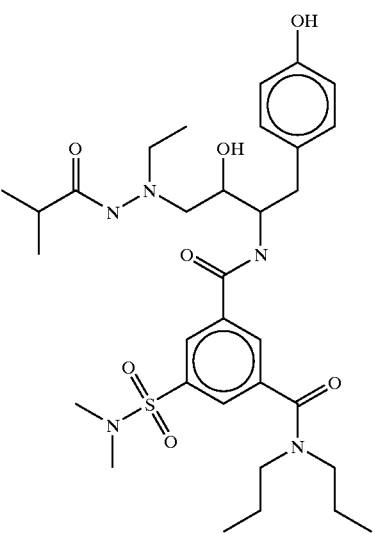
3:D6 3, 3, 3, 2
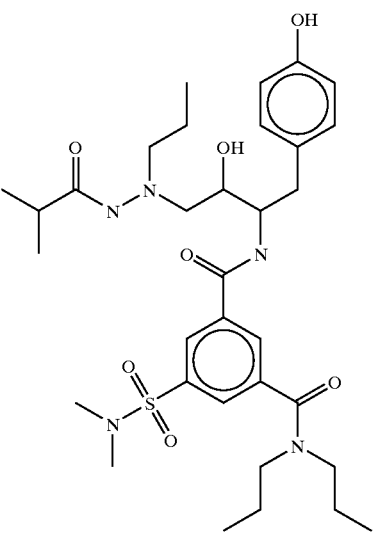
3:D7 3, 3, 3, 3

TABLE 1-continued
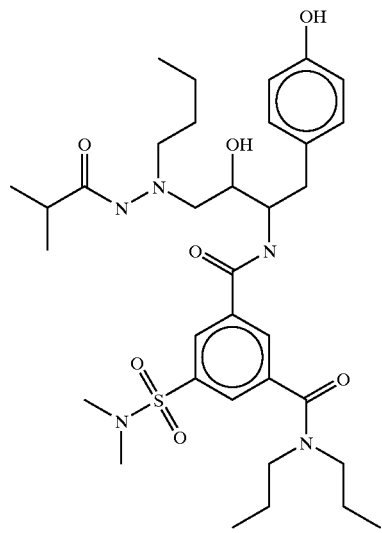
3:D8 3, 3, 3, 4
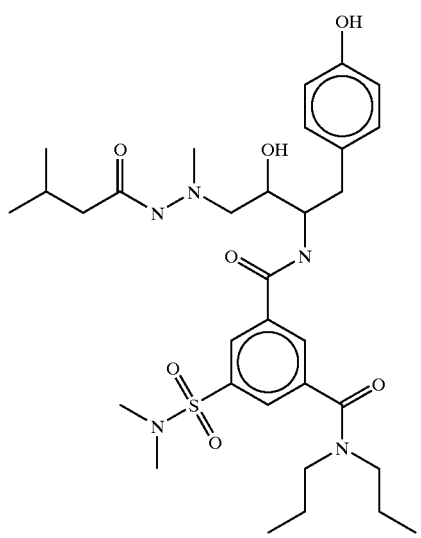
3:D9 3, 3, 4, 1
TABLE 1-continued
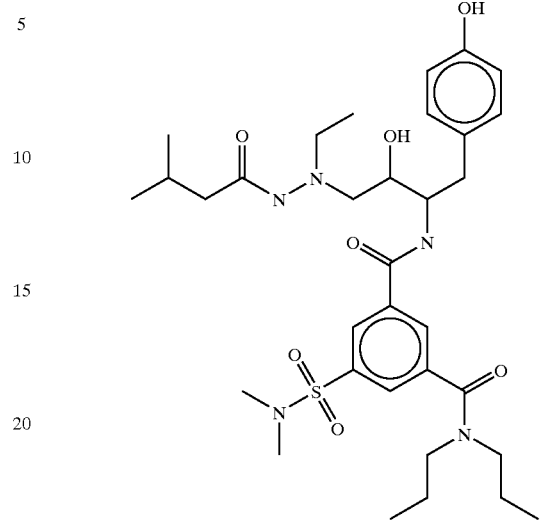
3:D10 3, 3, 4, 2
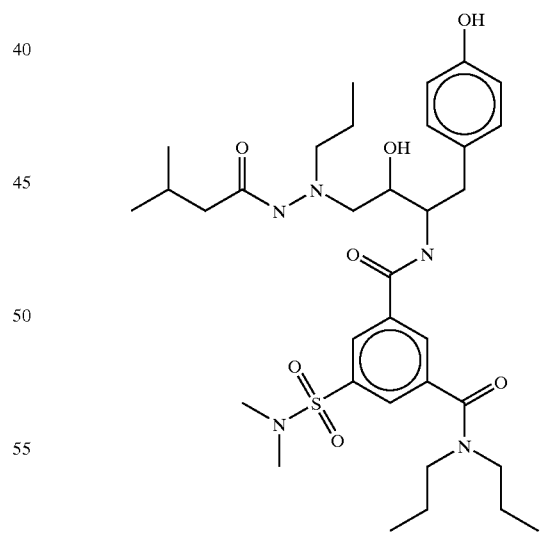
3:D11 3, 3, 4, 3

TABLE 1-continued
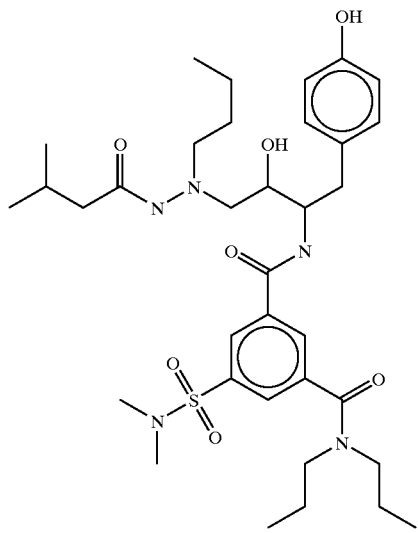
3:D12 3, 3, 4, 4
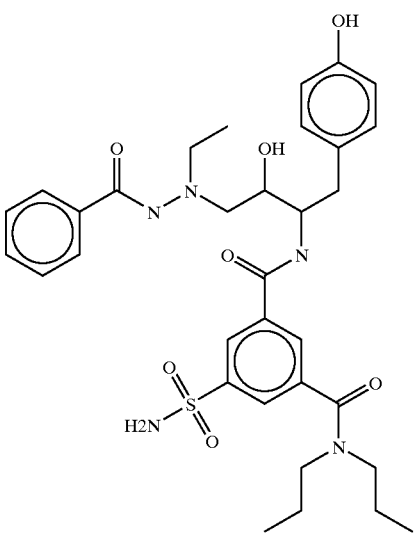
3:E2 3, 4, 1, 2
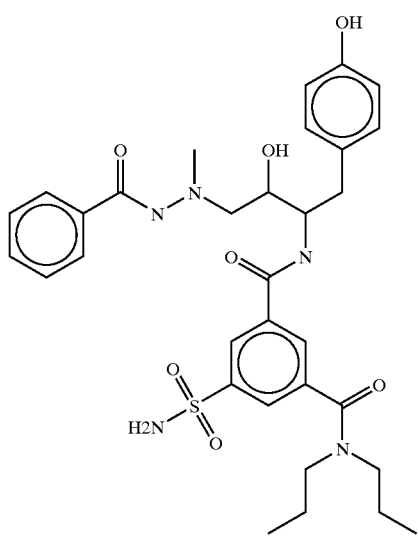
3:E1 3, 4, 1, 1
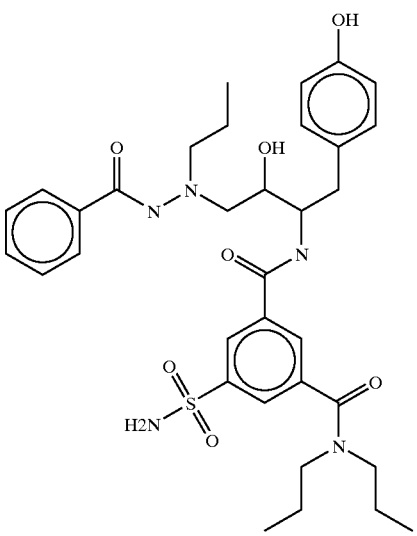
3:E3 3, 4, 1, 3

TABLE 1-continued
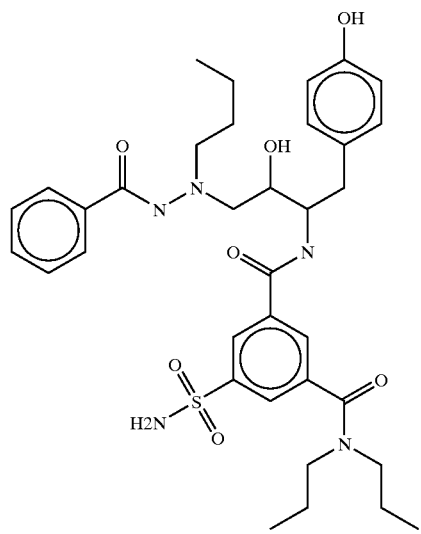
3:E4 3, 4, 1, 4
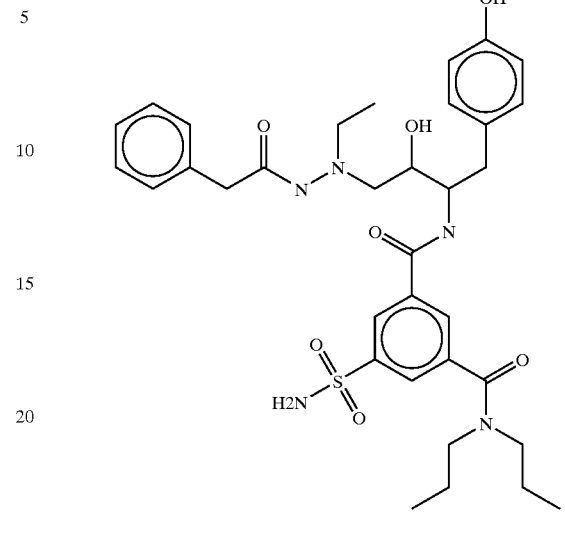
3:E6 3, 4, 2, 2
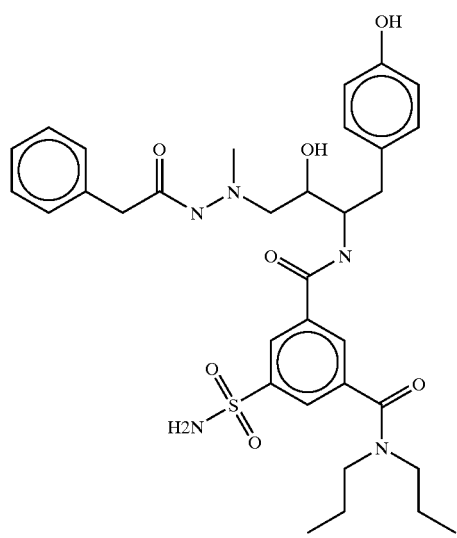
3:E5 3, 4, 2, 1
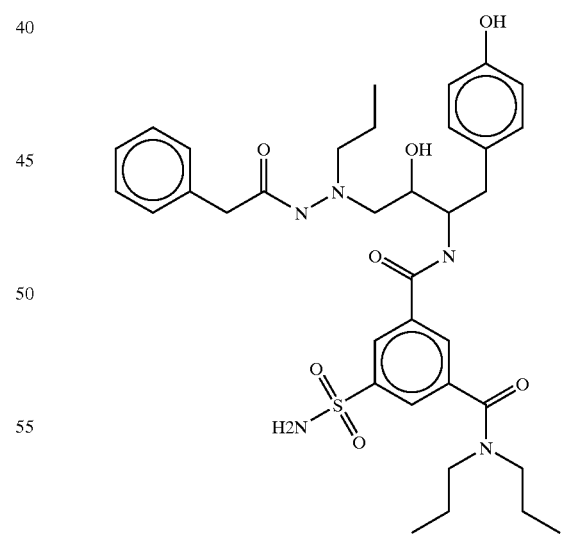
3:E7 3, 4, 2, 3

TABLE 1-continued
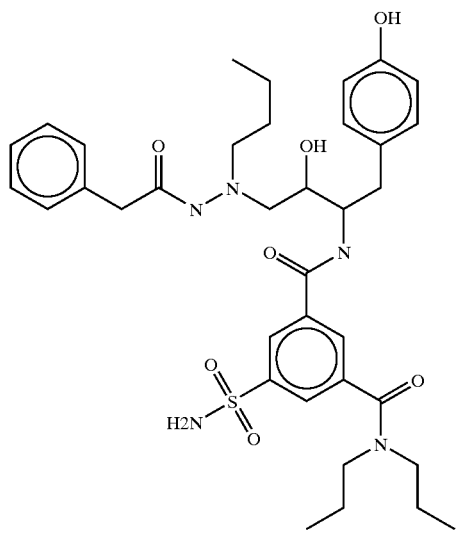
3:E8 3, 4, 2, 4
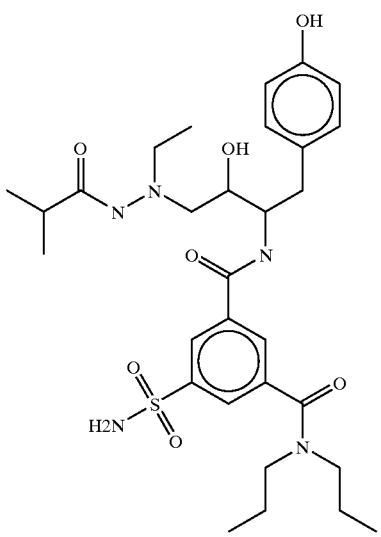
3:E10 3, 4, 3, 2
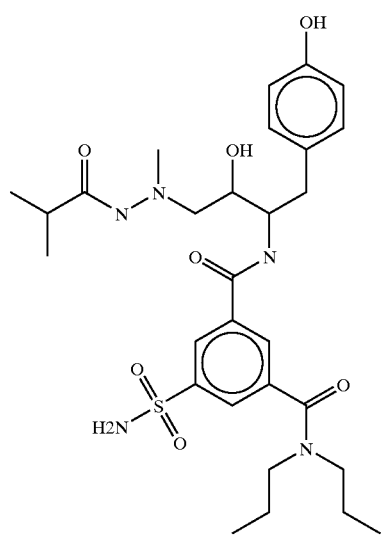
3:E9 3, 4, 3, 1
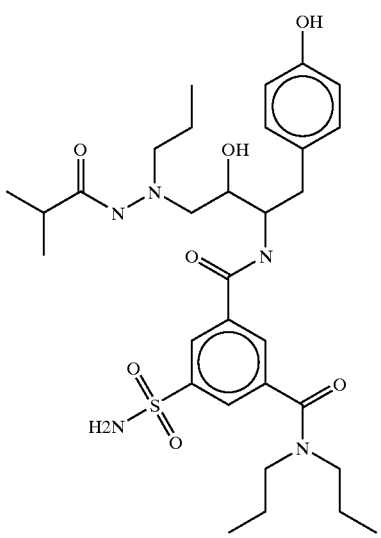
3:E11 3, 4, 3, 3

TABLE 1-continued
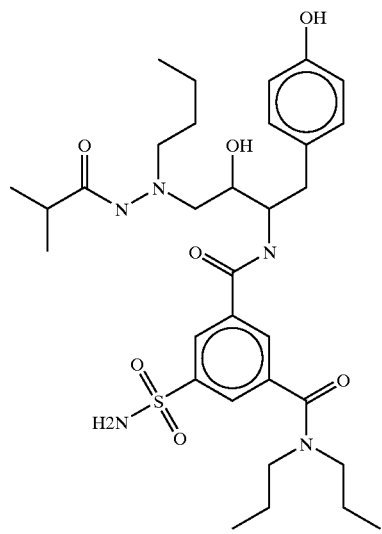
3:E12 3, 4, 3, 4
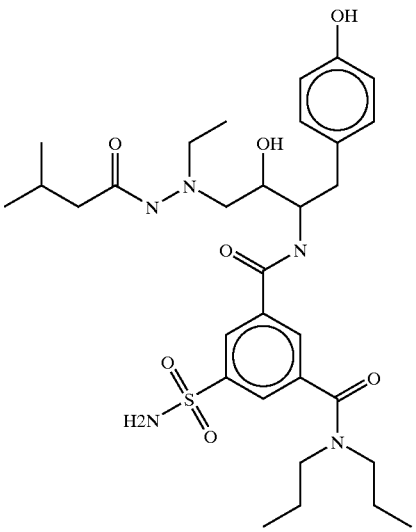
3:F2 3, 4, 4, 2
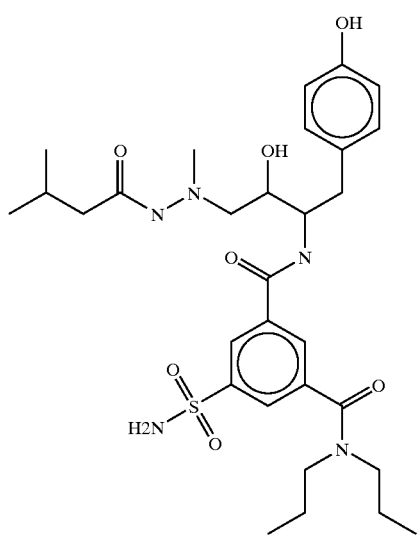
3:F1 3, 4, 4, 1
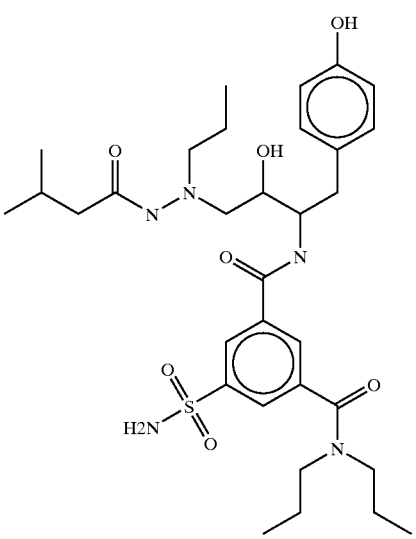
3:F3 3, 4, 4, 3

TABLE 1-continued
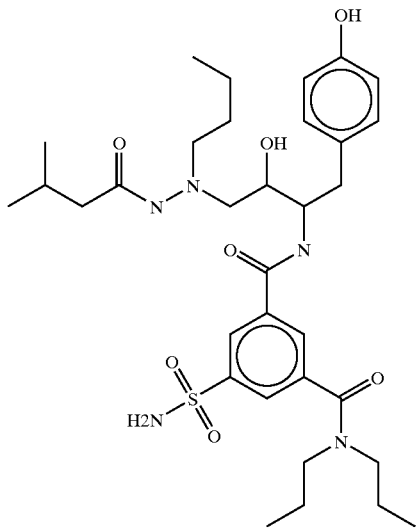
3:F4 3, 4, 4, 4
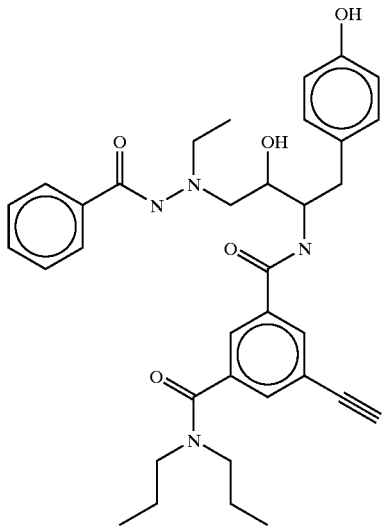
3:F6 3, 5, 1, 2
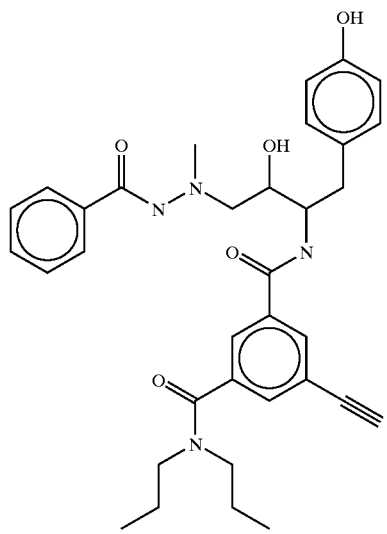
3:F5 3, 5, 1, 1
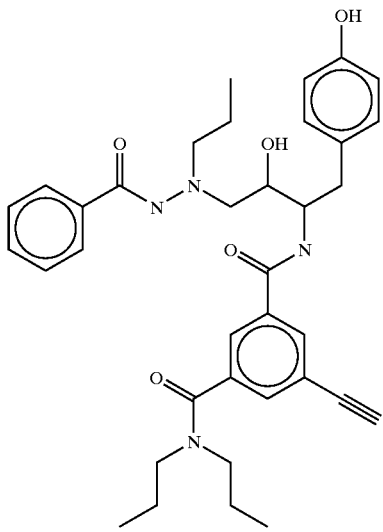
3:F7 3, 5, 1, 3

TABLE 1-continued
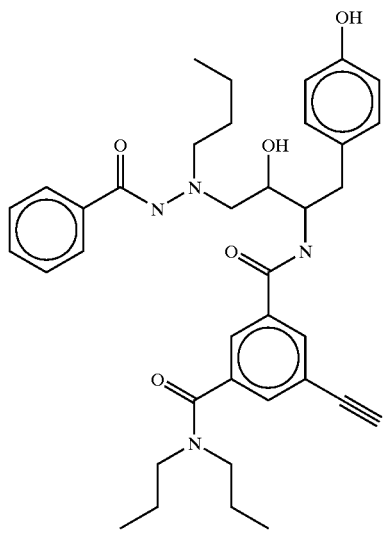
3:F8 3, 5, 1, 4
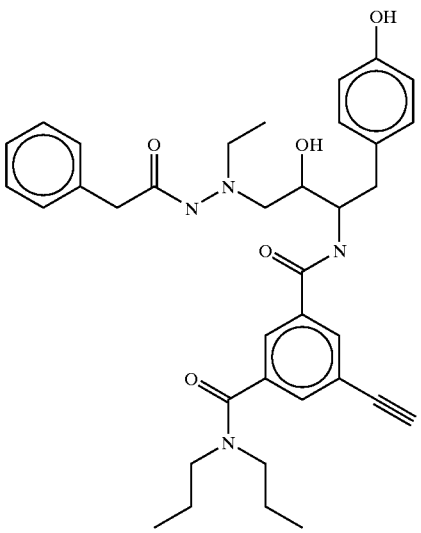
3:F10 3, 5, 2, 2
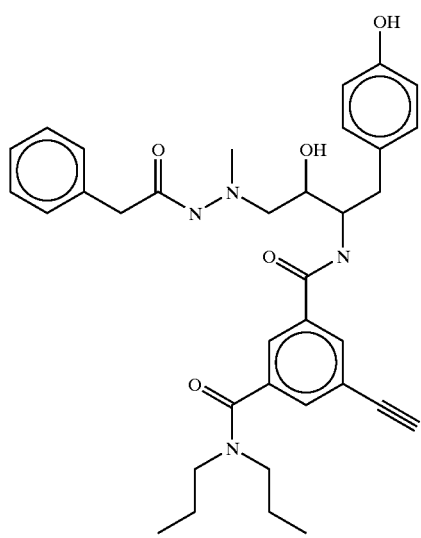
3:F9 3, 5, 2, 1
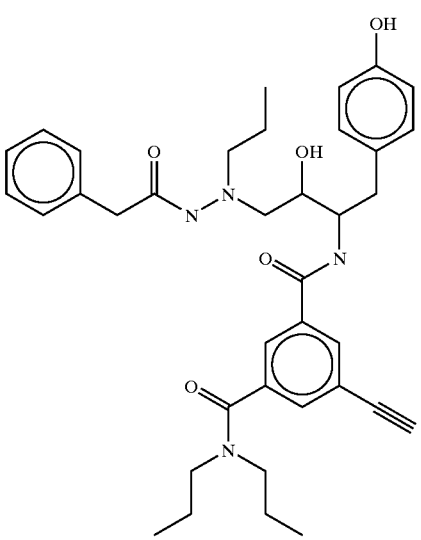
3:F11 3, 5, 2, 3

TABLE 1-continued
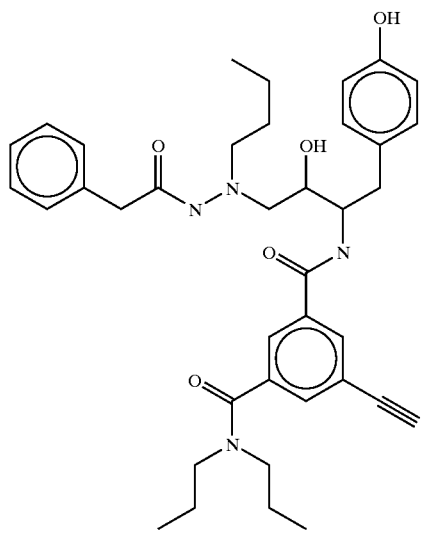
3:F12 3, 5, 2, 4
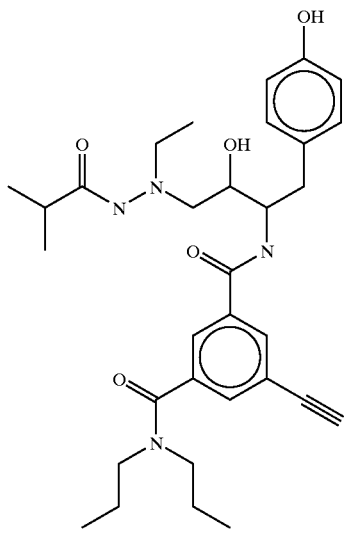
3:G2 3, 5, 3, 2
3:G1 3, 5, 3, 1
3:G3 3, 5, 3, 3

TABLE 1-continued
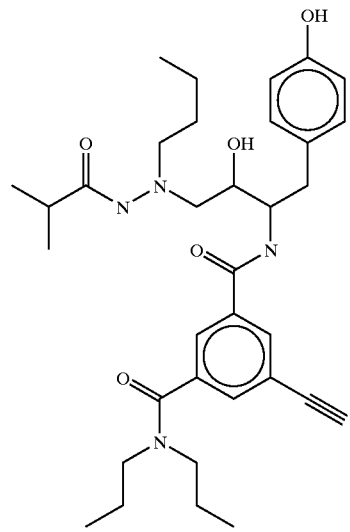
3:G4 3, 5, 3, 4
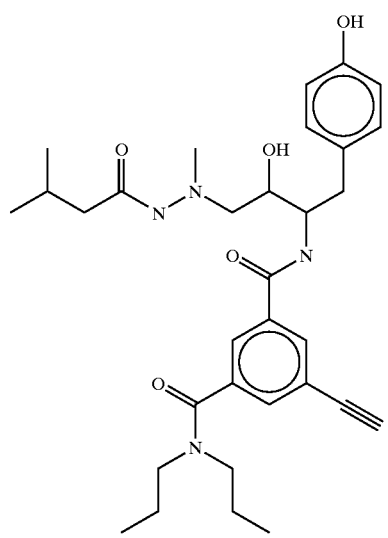
3:G5 3, 5, 4, 1
TABLE 1-continued
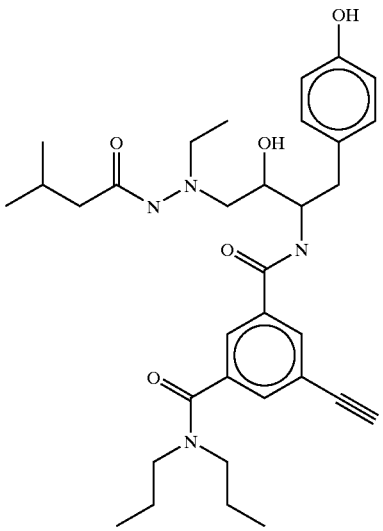
3:G6 3, 5, 4, 2
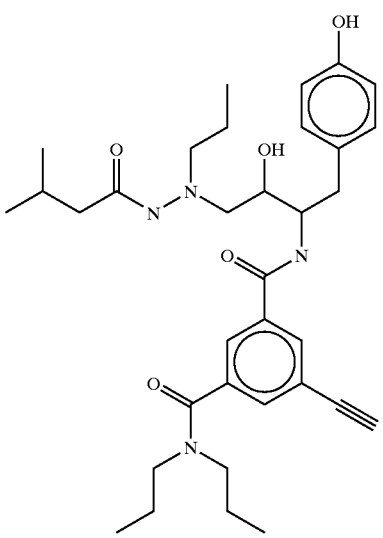
3:G7 3, 5, 4, 3

TABLE 1-continued
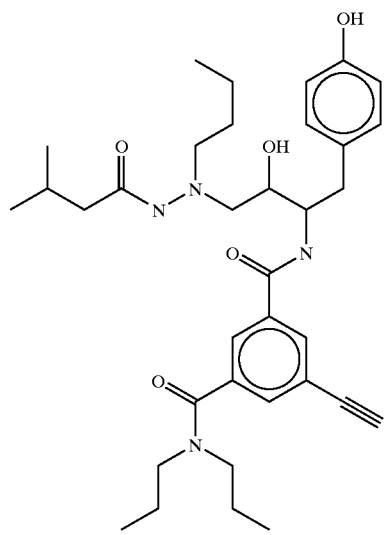
3:G8 3, 5, 4, 4
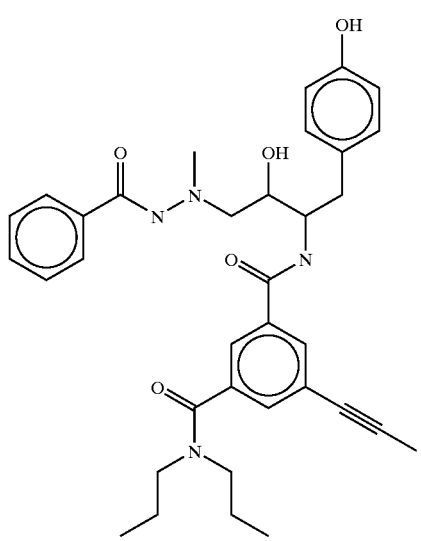
3:G9 3, 6, 1, 1
TABLE 1-continued
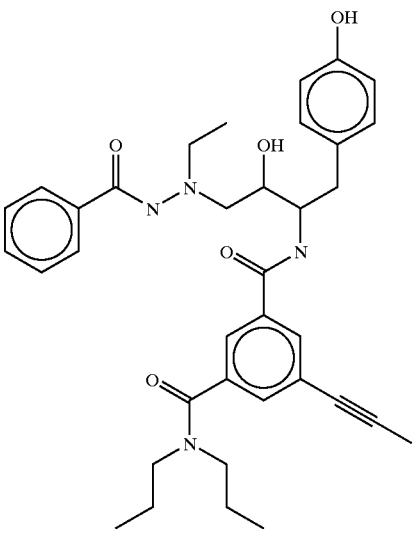
3:G10 3, 6, 1, 2
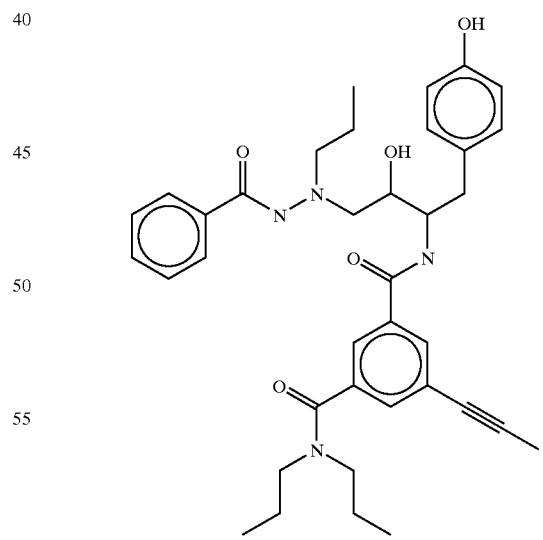
3:G11 3, 6, 1, 3

TABLE 1-continued
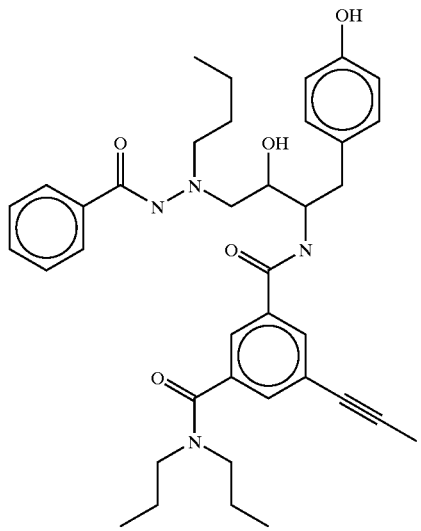
3:G12 3, 6, 1, 4
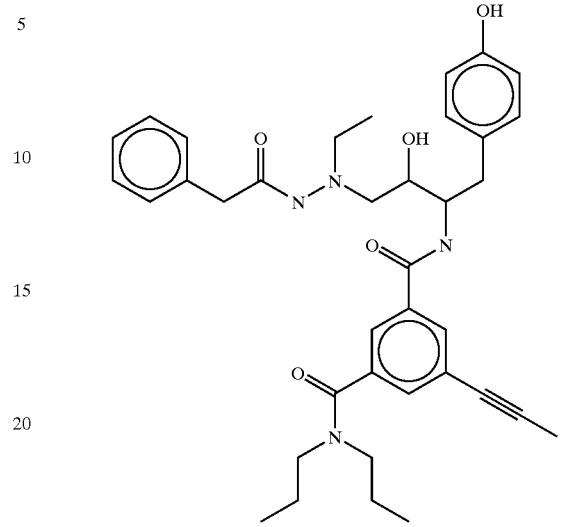
3:H2 3, 6, 2, 2
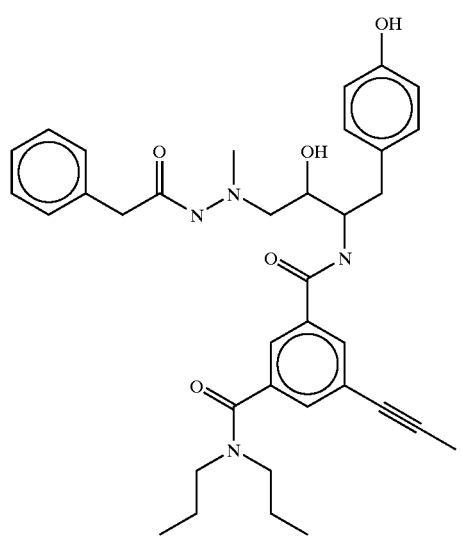
3:H1 3, 6, 2, 1
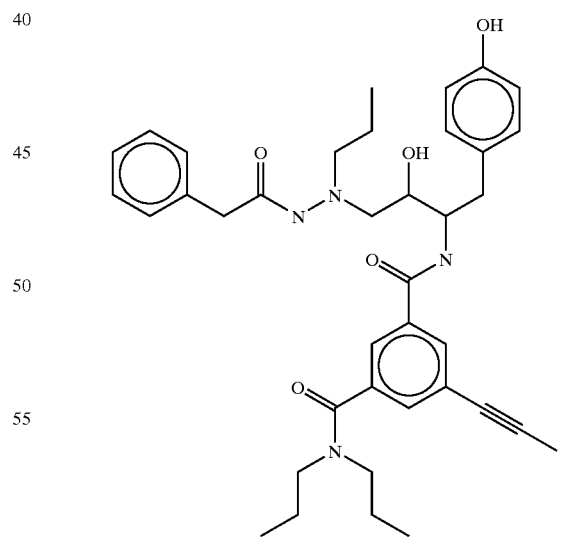
3:H3 3, 6, 2, 3

TABLE 1-continued
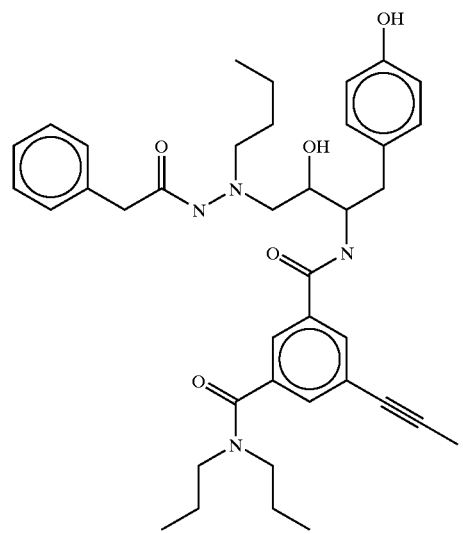
3:H4 3, 6, 2, 4
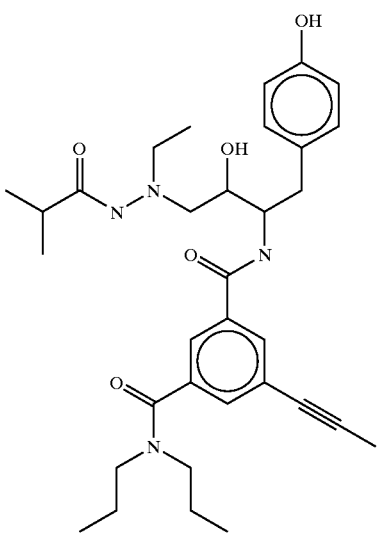
3:H6 3, 6, 3, 2
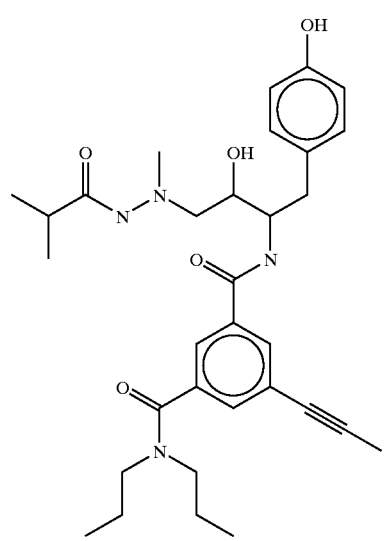
3:H5 3, 6, 3, 1
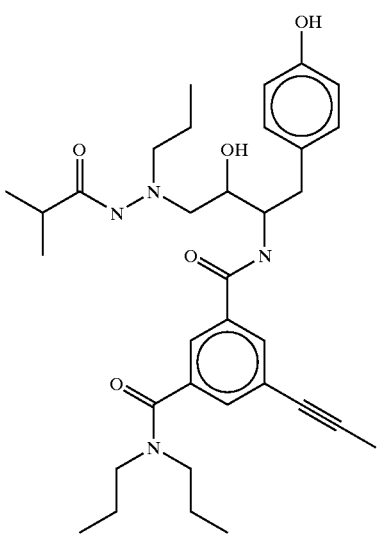
3:H7 3, 6, 3, 3

TABLE 1-continued
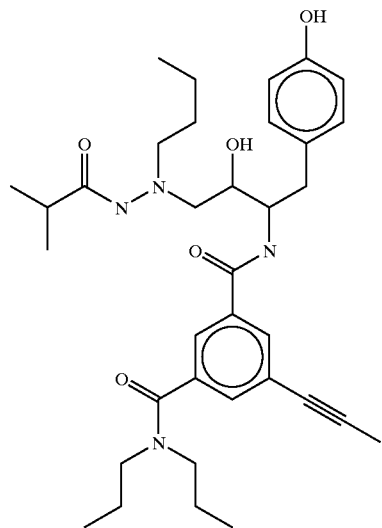
3:H8 3, 6, 3, 4
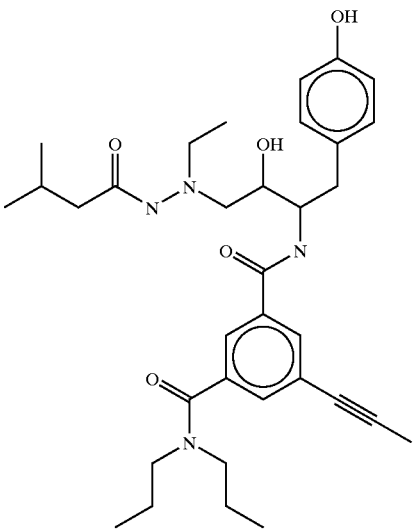
3:H10 3, 6, 4, 2
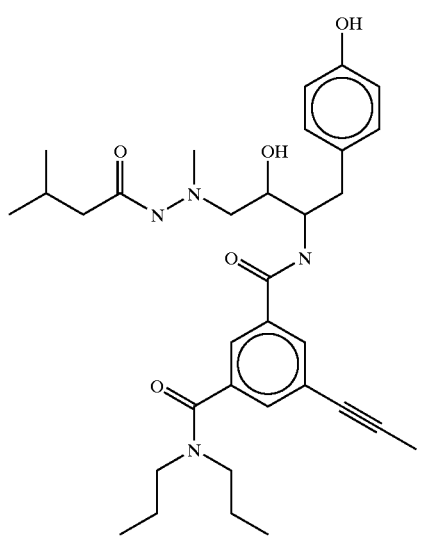
3:H9 3, 6, 4, 1
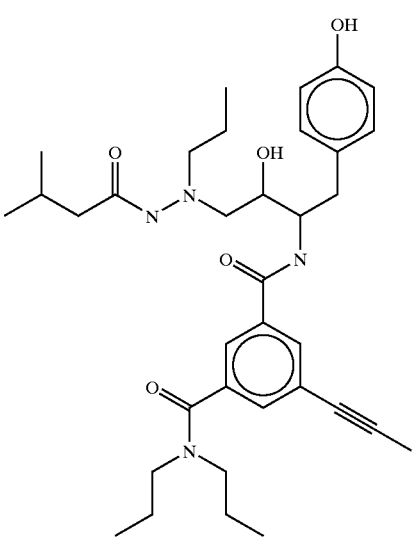
3:H11 3, 6, 4, 3

TABLE 1-continued
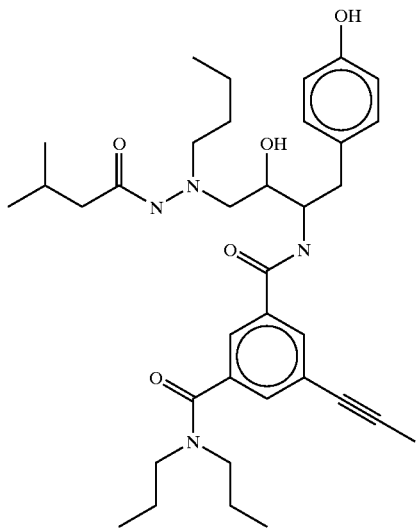
3:H12 3, 6, 4, 4
Change of itinerary "FCA681.2"
With location, precursor
TABLE 1-continued
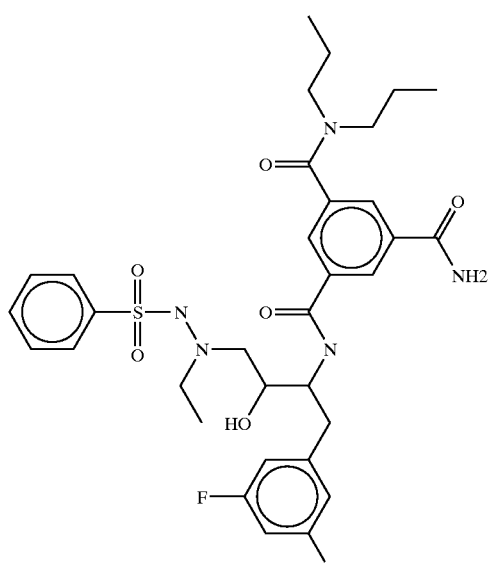
1:A2 1, 1, 1, 2
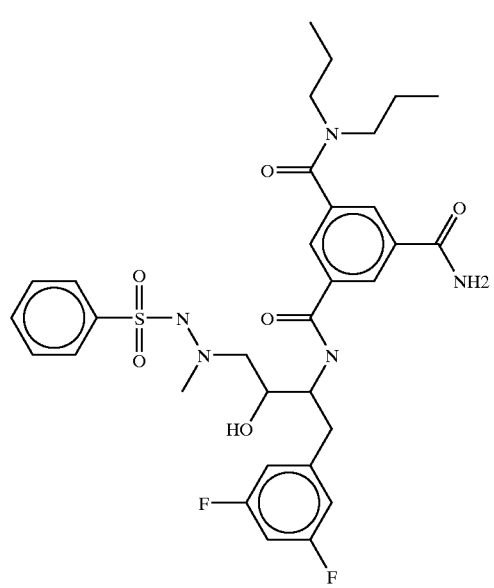
1:A1 1, 1, 1, 1
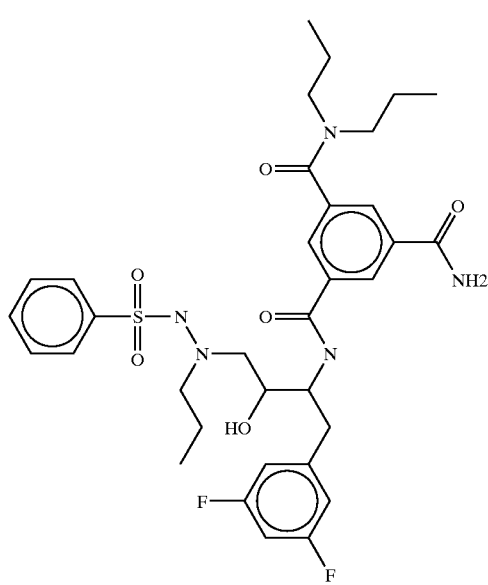
1:A3 1, 1, 1, 3

TABLE 1-continued
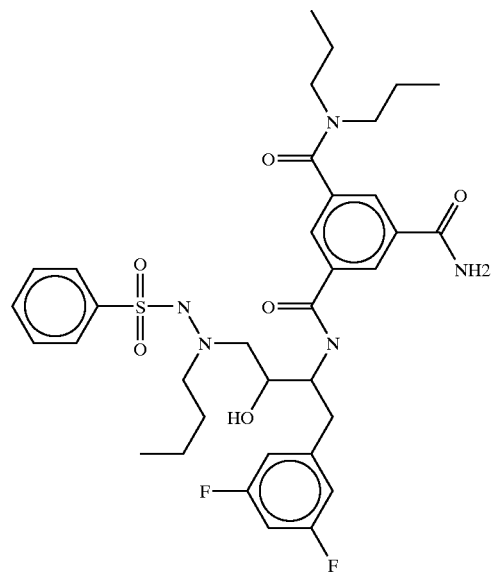
1:A4 1, 1, 1, 4
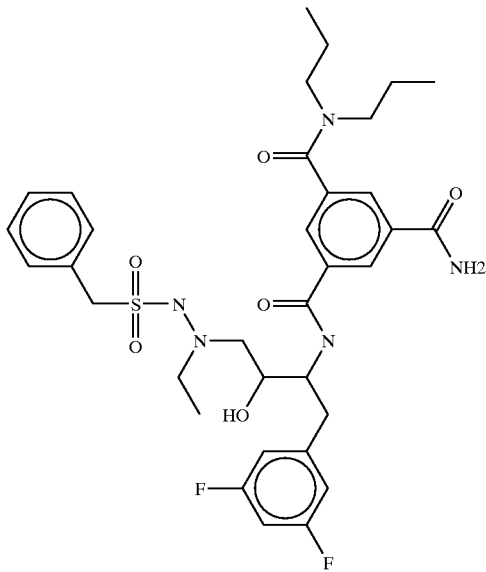
1:A6 1, 1, 2, 2
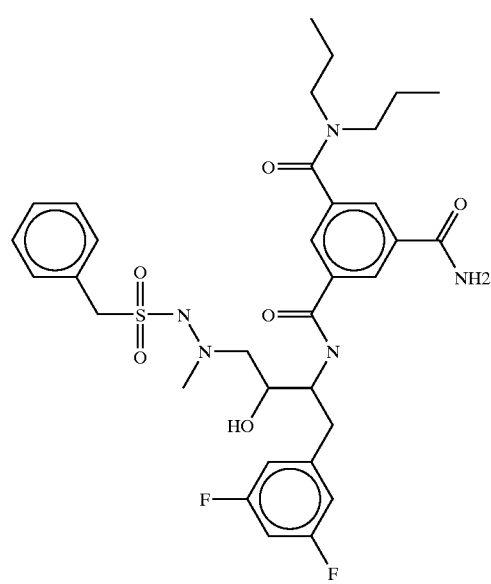
1:A5 1, 1, 2, 1
1:A7 1, 1, 2, 3

TABLE 1-continued
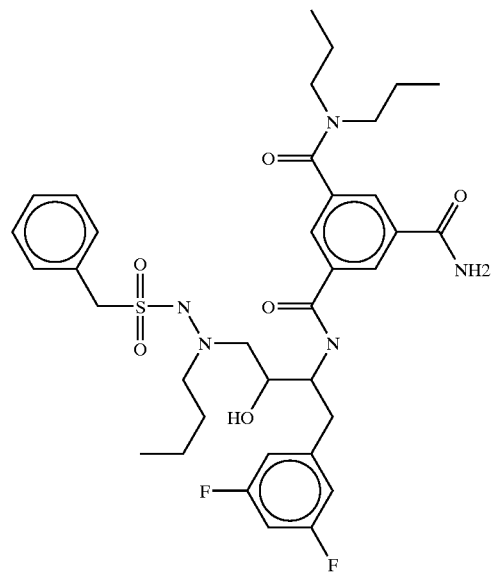
1:A8 1, 1, 2, 4
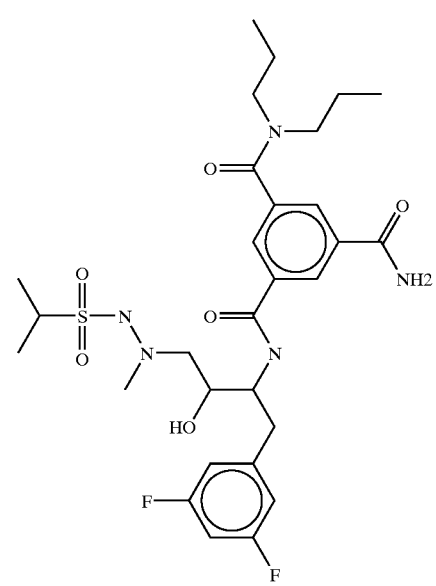
1:A9 1, 1, 3, 1
TABLE 1-continued
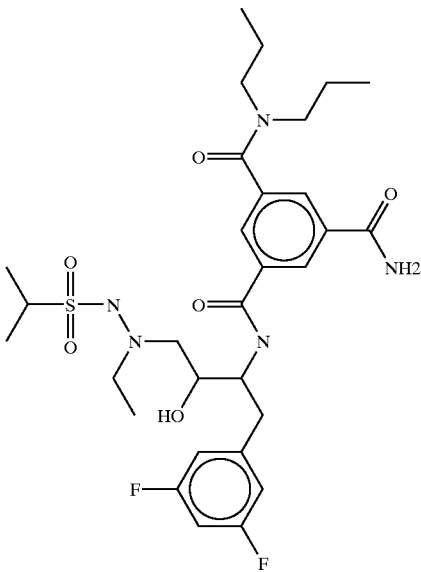
1:A10 1, 1, 3, 2
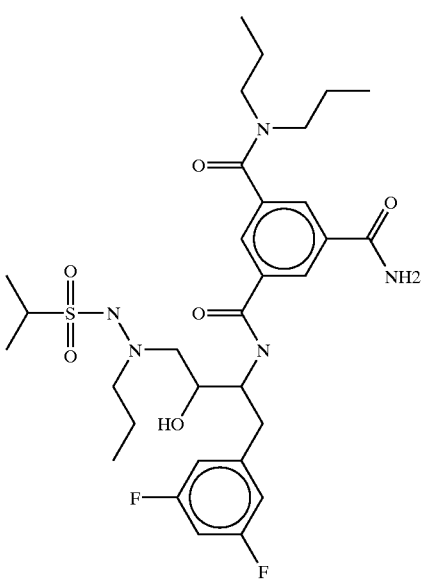
1:A11 1, 1, 3, 3

TABLE 1-continued
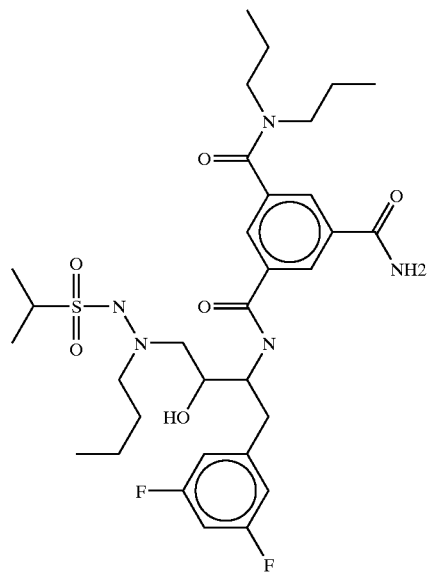
1:A12 1, 1, 3, 4
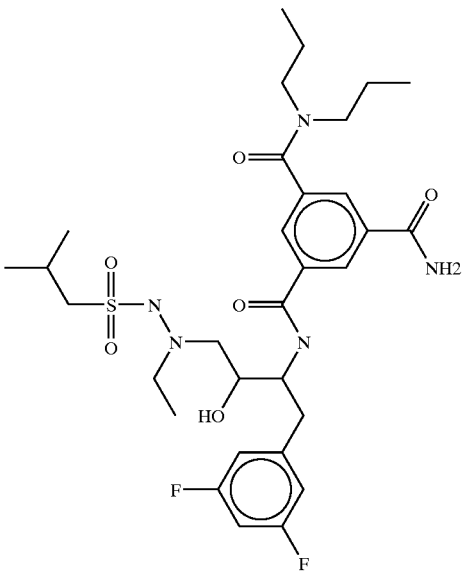
1:B2 1, 1, 4, 2
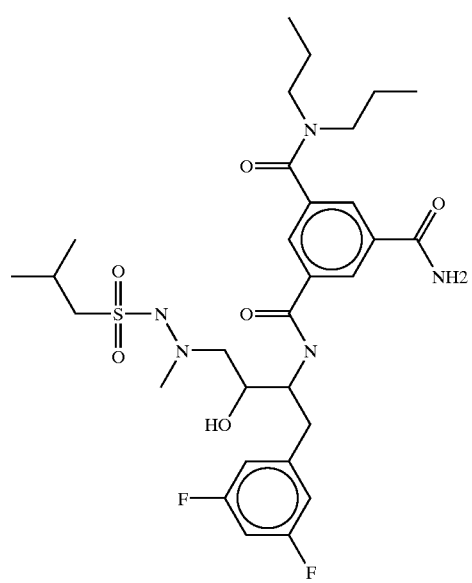
1:B1 1, 1, 4, 1
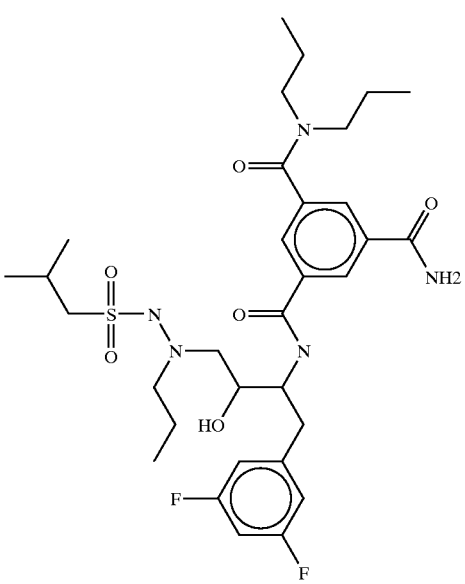
1:B3 1, 1, 4, 3

TABLE 1-continued
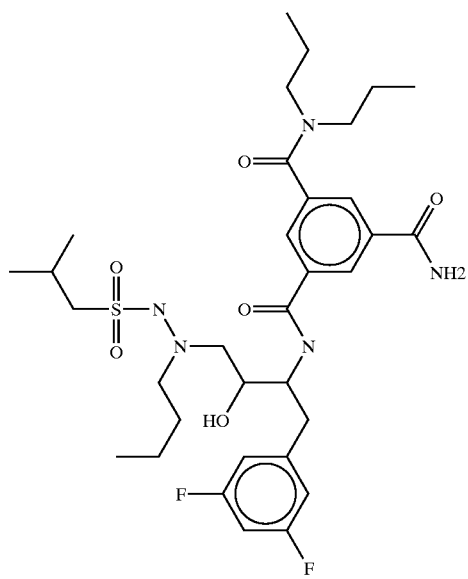
1:B4 1, 1, 4, 4
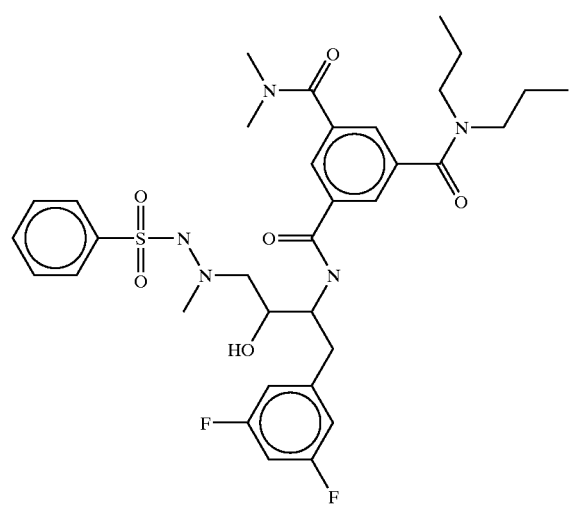
1:B5 1, 2, 1, 1
TABLE 1-continued
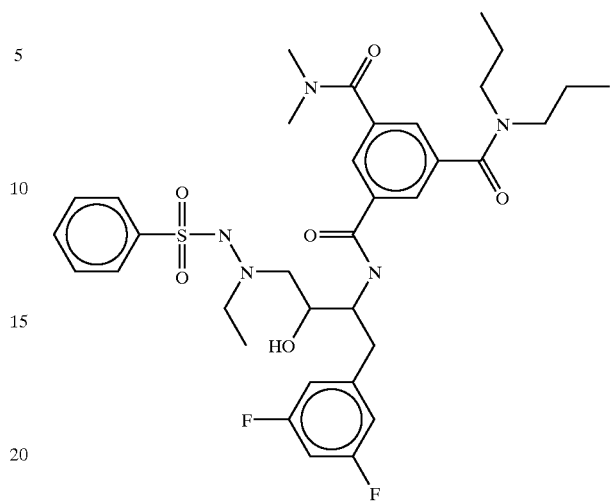
1:B6 1, 2, 1, 2
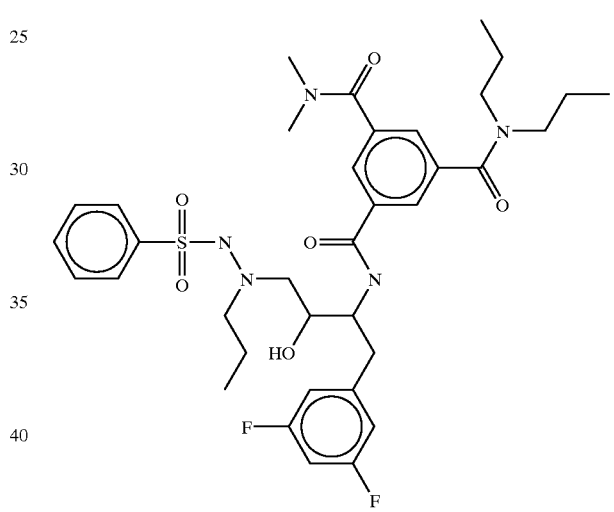
1:B7 1, 2, 1, 3
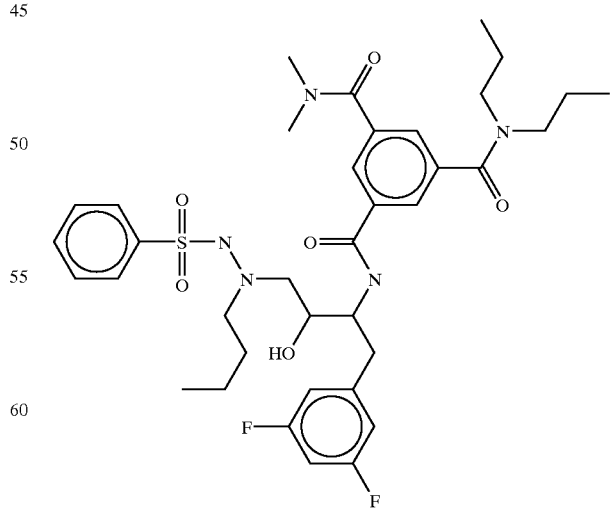
1:B8 1, 2, 1, 4

TABLE 1-continued
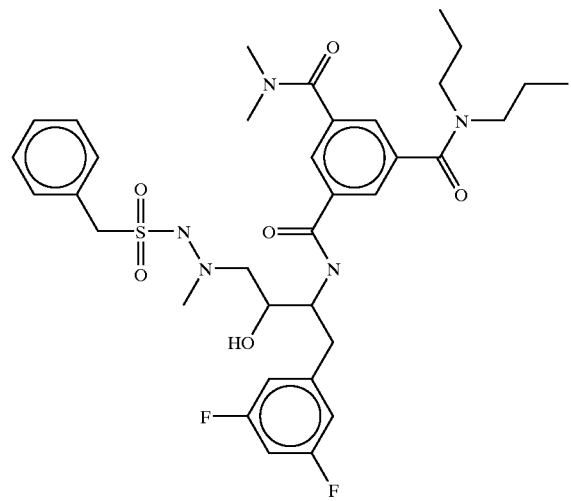
1:B9 1, 2, 2, 1
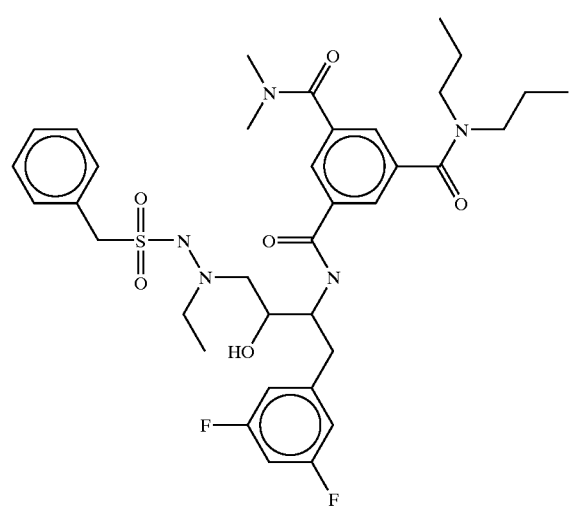
1:B10 1, 2, 2, 2
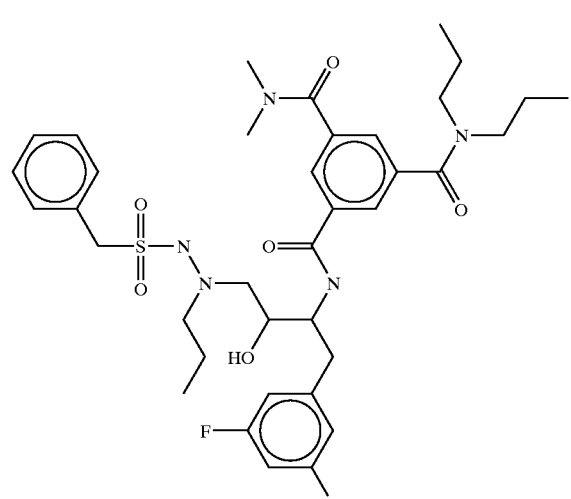
1:B11 1, 2, 2, 3
TABLE 1-continued
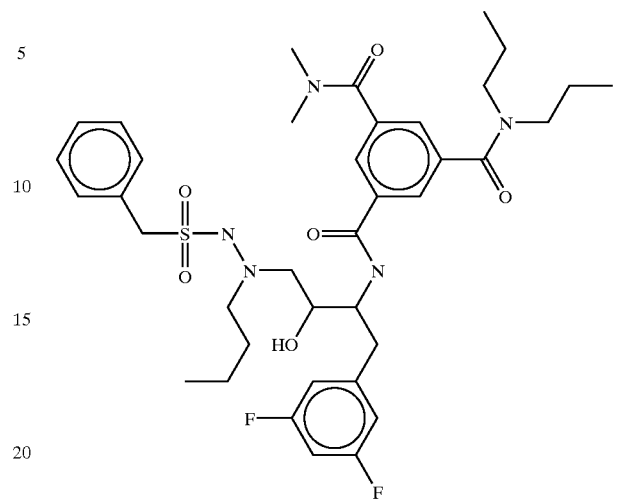
1:B12 1, 2, 2, 4
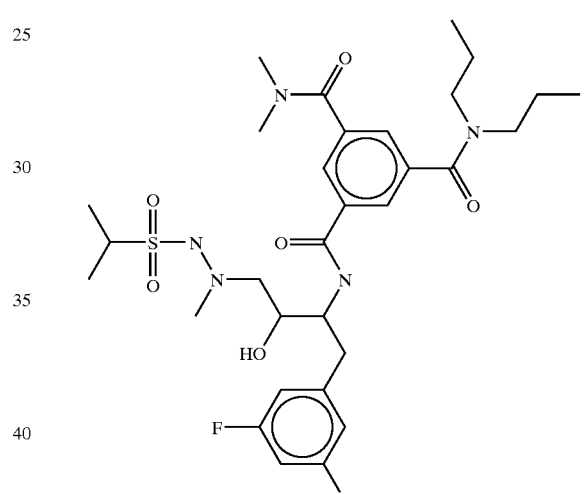
1:C1 1, 2, 3, 1
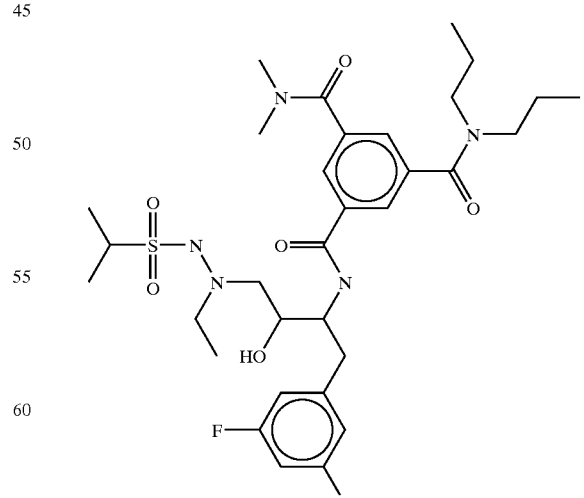
1:C2 1, 2, 3, 2

TABLE 1-continued
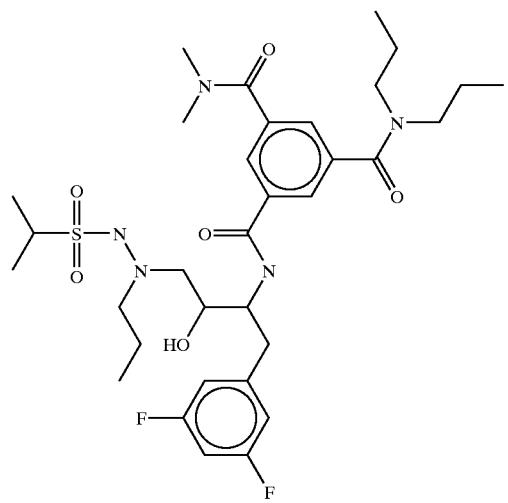
1:C3 1, 2, 3, 3
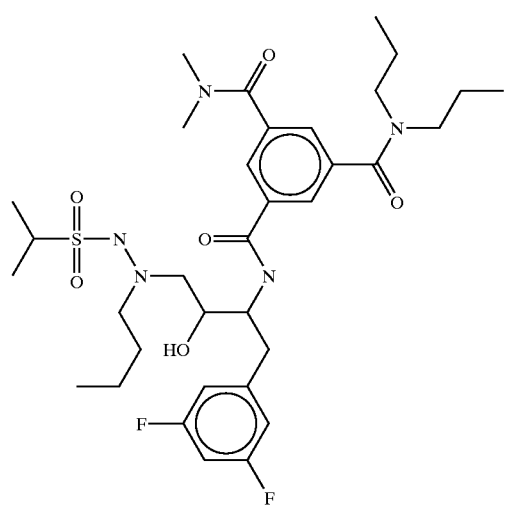
1:C4 1, 2, 3, 4
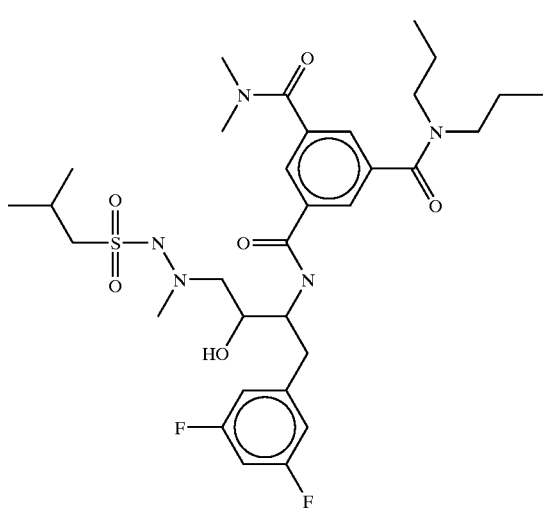
1:C5 1, 2, 4, 1
TABLE 1-continued
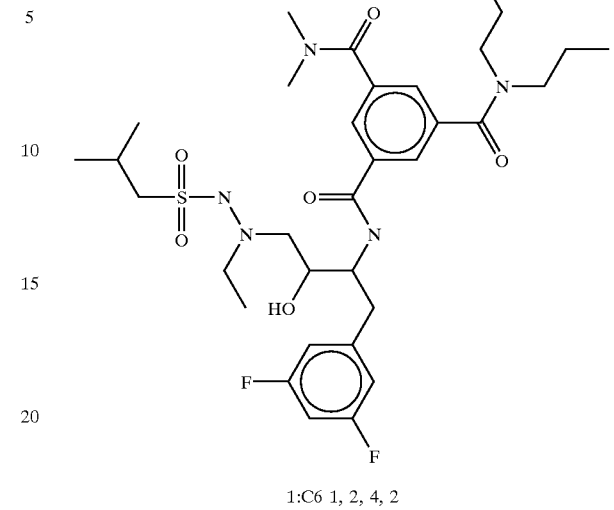
1:C6 1, 2, 4, 2
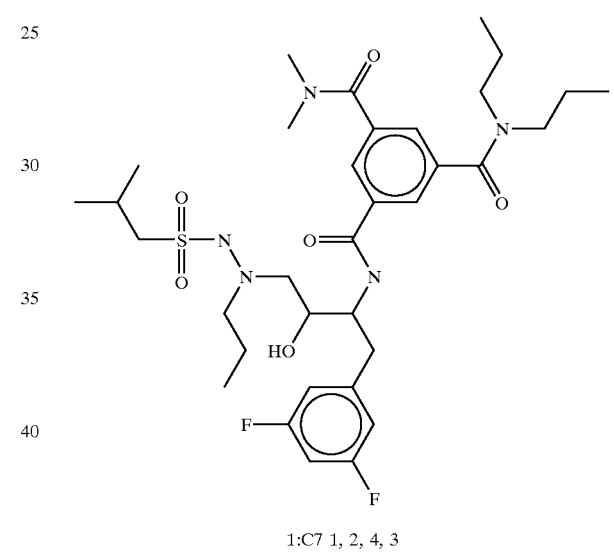
1:C7 1, 2, 4, 3
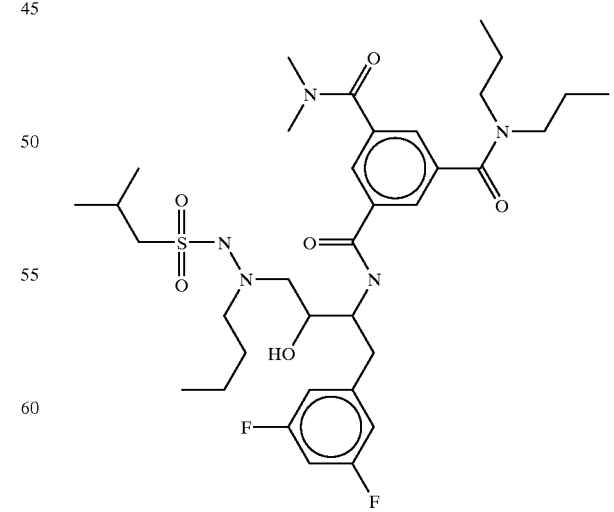
1:C8 1, 2, 4, 4

TABLE 1-continued
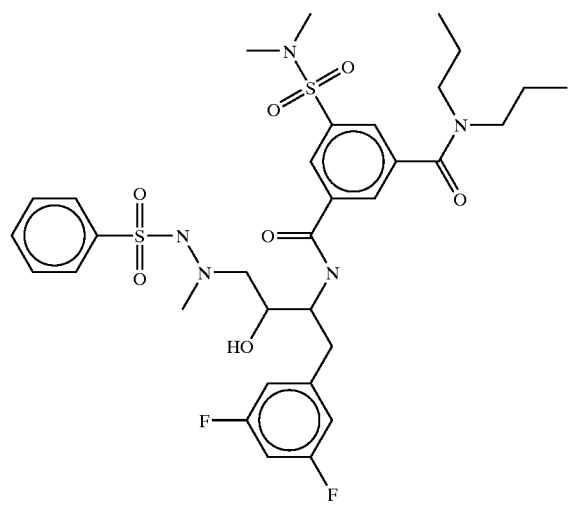
1:C9 1, 3, 1, 1
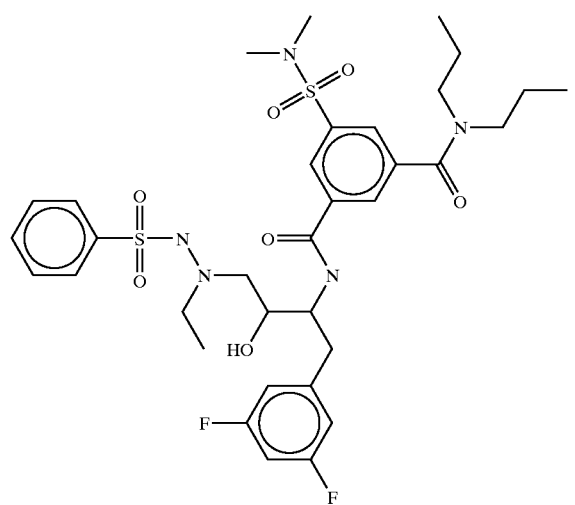
1:C10 1, 3, 1, 2
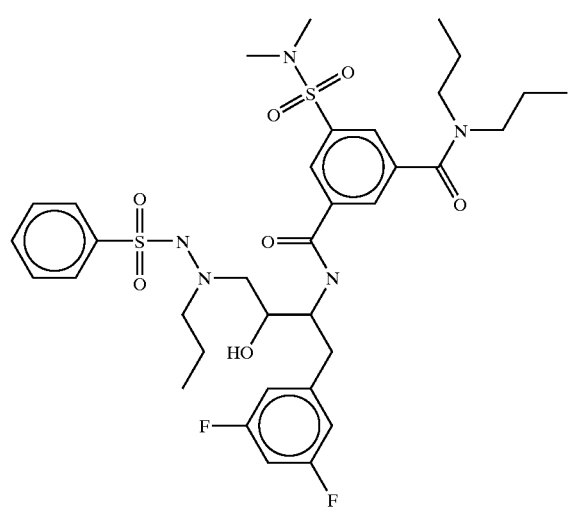
1:C11 1, 3, 1, 3
TABLE 1-continued
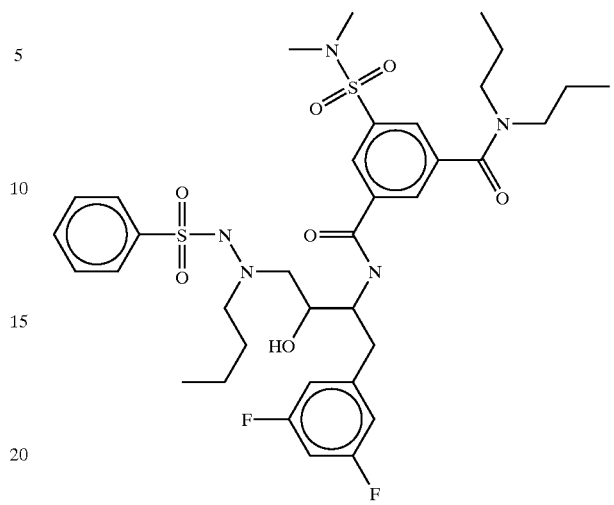
1:C12 1, 3, 1, 4
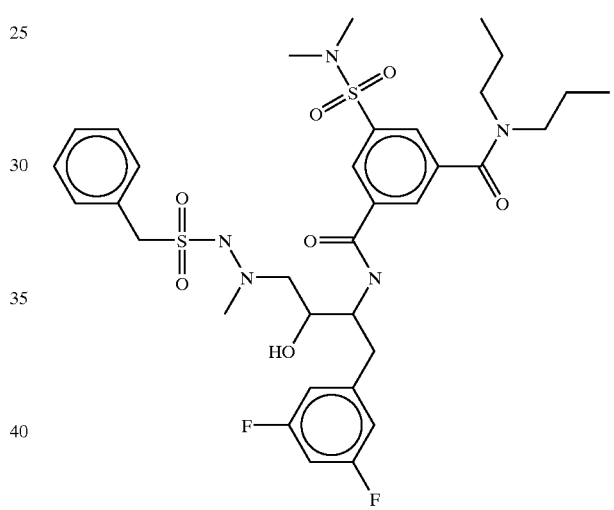
1:D1 1, 3, 2, 1
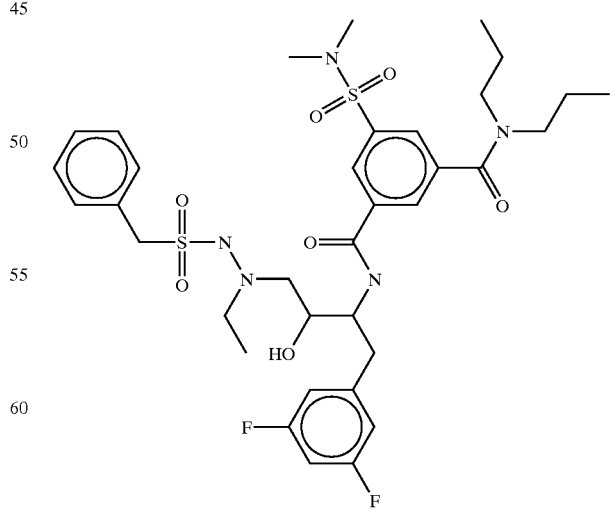
1:D2 1, 3, 2, 2

TABLE 1-continued
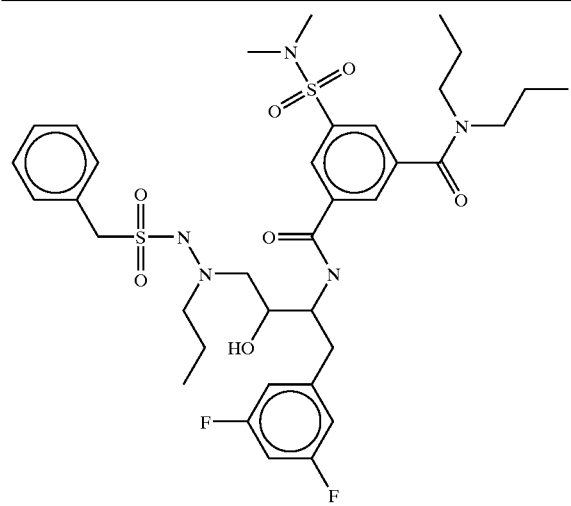
1:D3 1, 3, 2, 3
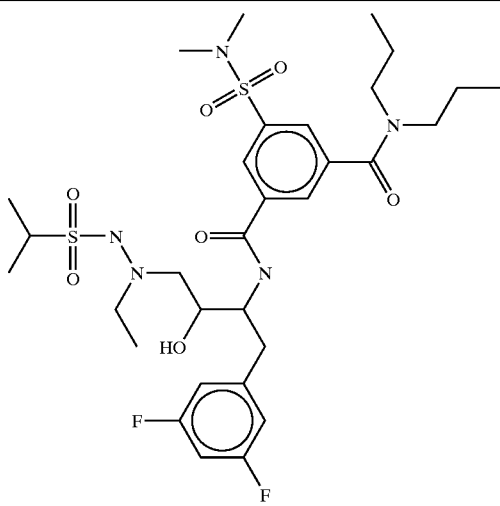
1:D6 1, 3, 3, 2
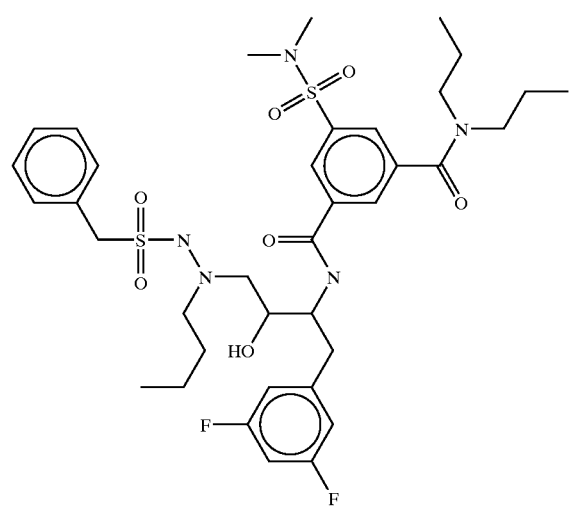
1:D4 1, 3, 2, 4
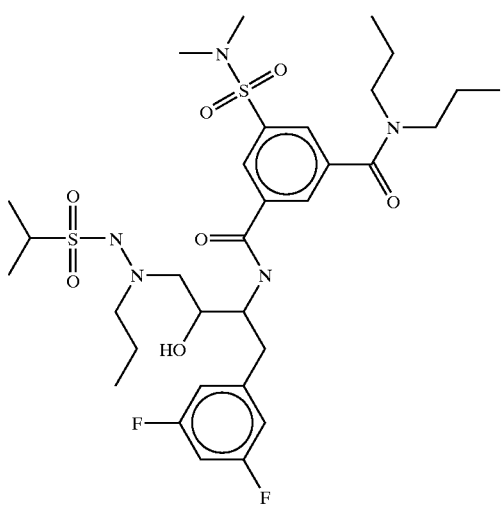
1:D7 1, 3, 3, 3
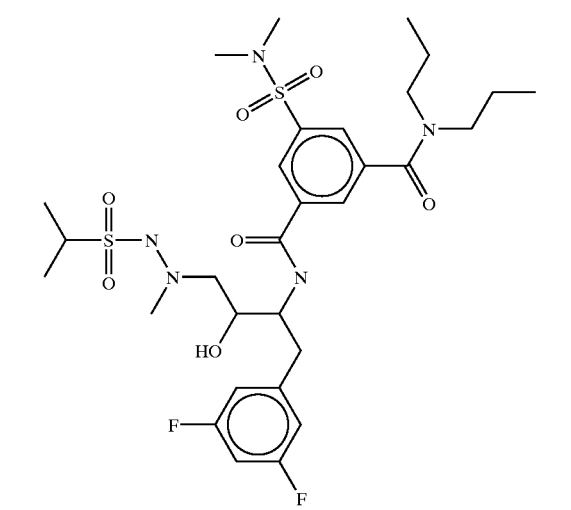
1:D5 1, 3, 3, 1
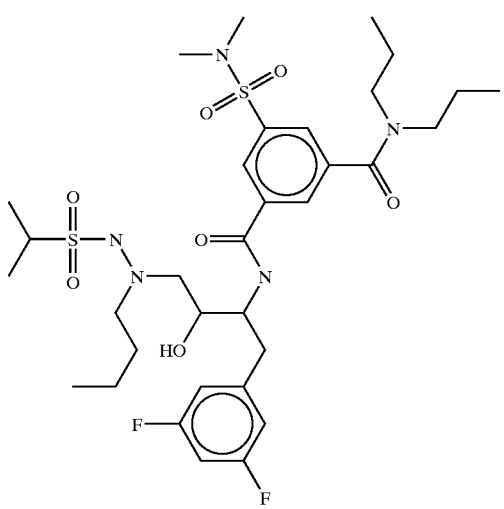
1:D8 1, 3, 3, 4

TABLE 1-continued
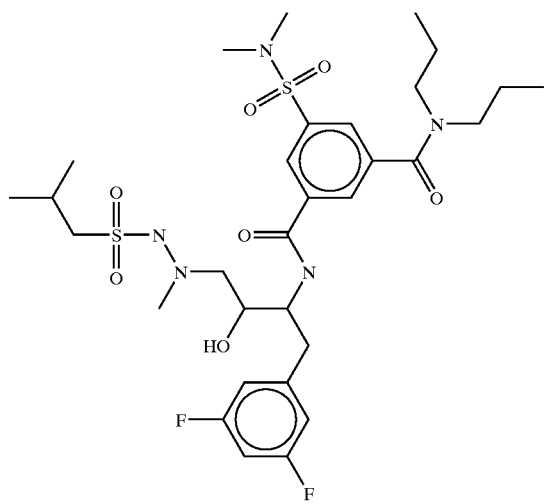
1:D9 1, 3, 4, 1
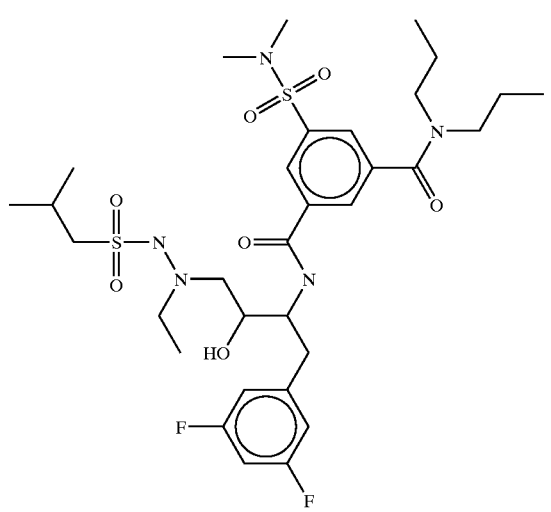
1:D10 1, 3, 4, 2
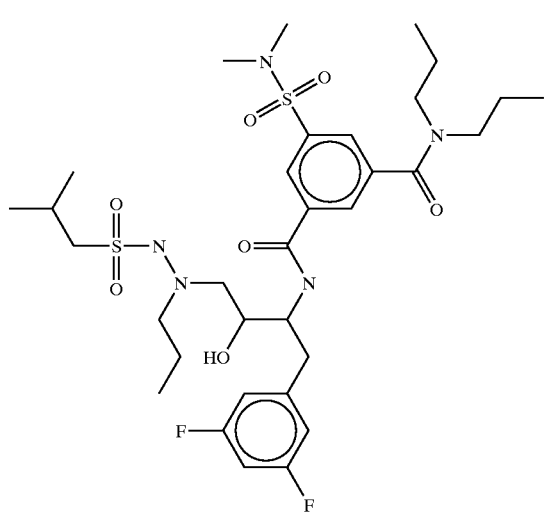
1:D11 1, 3, 4, 3
TABLE 1-continued
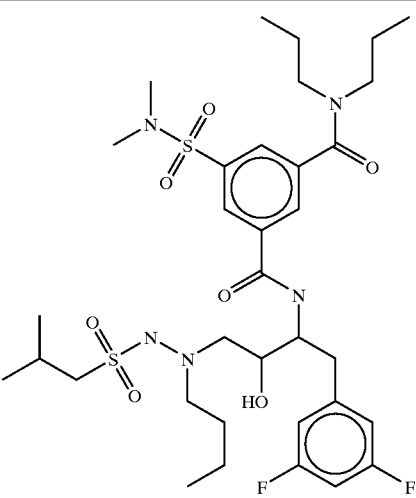
1:D12 1, 3, 4, 4
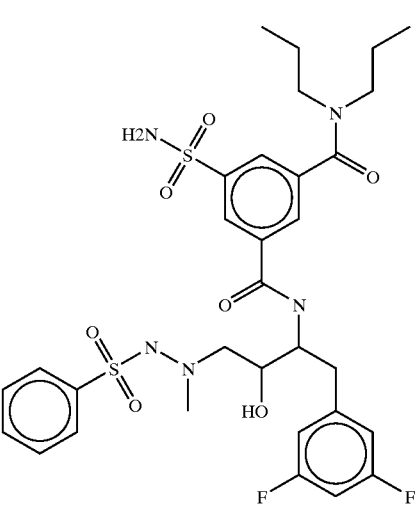
1:E1 1, 4, 1, 1
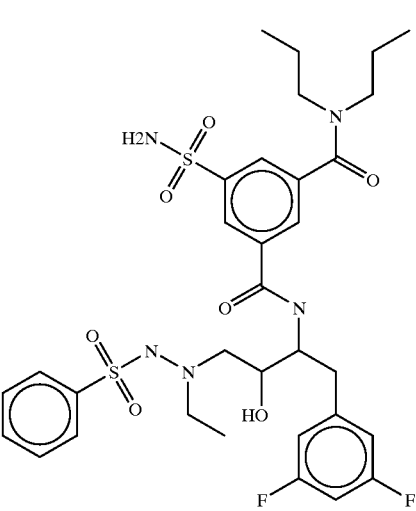
1:E2 1, 4, 1, 2

TABLE 1-continued
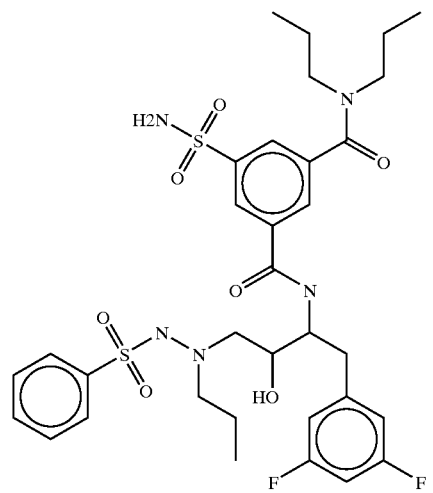
1:E3 1, 4, 1, 3
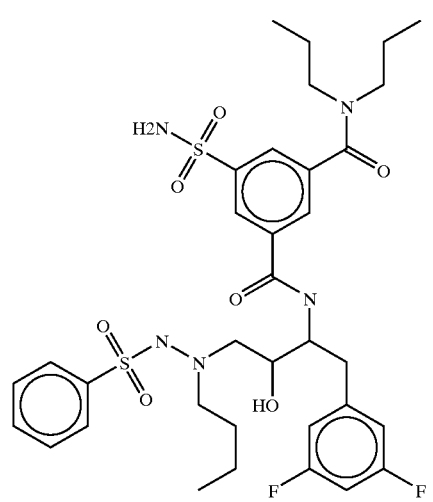
1:E4 1, 4, 1, 4
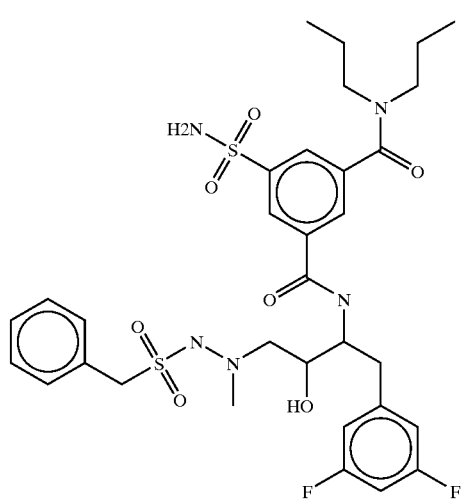
1:E5 1, 4, 2, 1
TABLE 1-continued
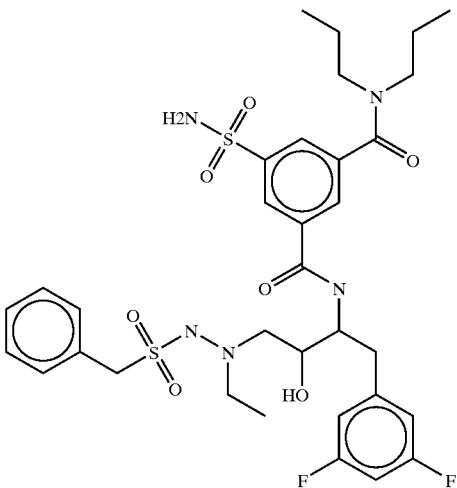
1:E6 1, 4, 2, 2
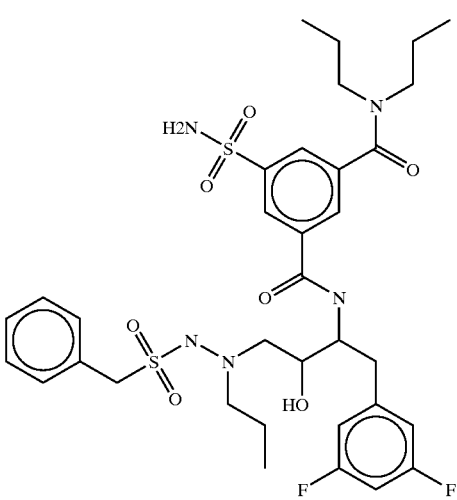
1:E7 1, 4, 2, 3
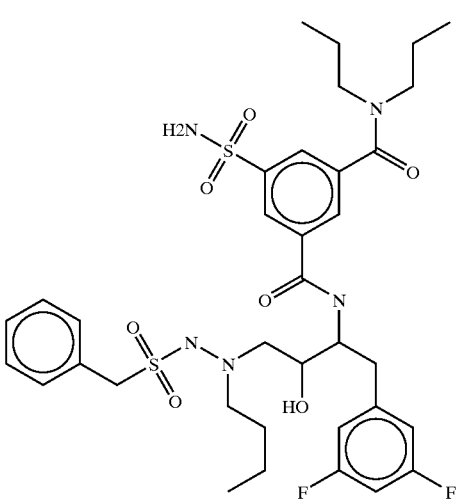
1:E8 1, 4, 2, 4

TABLE 1-continued
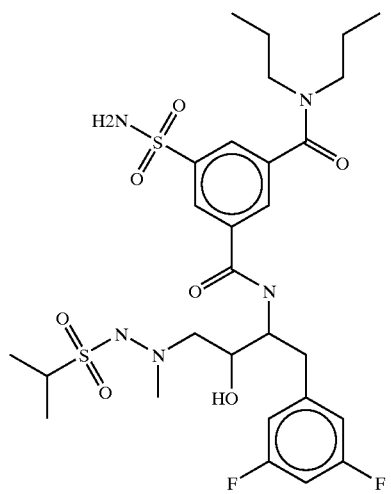
1:E9 1, 4, 3, 1
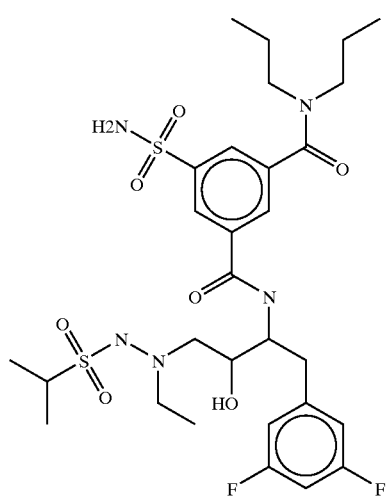
1:E10 1, 4, 3, 2
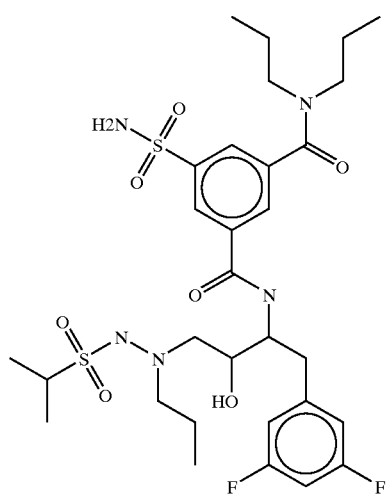
1:E11 1, 4, 3, 3
TABLE 1-continued
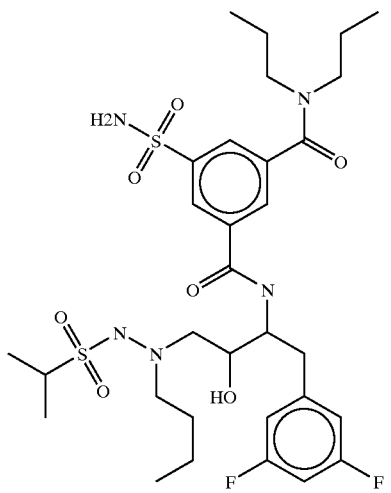
1:E12 1, 4, 3, 4
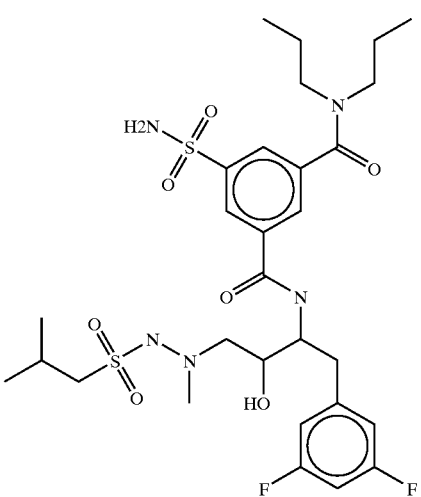
1:F1 1, 4, 4, 1
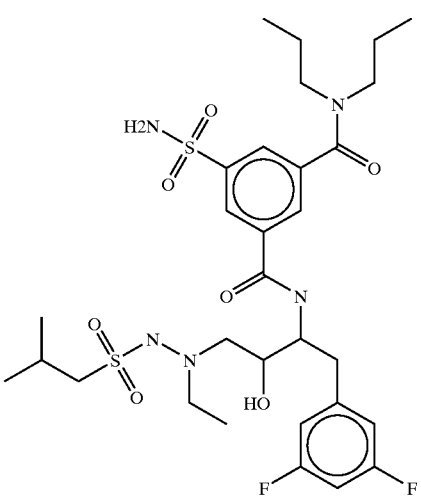
1:F2 1, 4, 4, 2

TABLE 1-continued
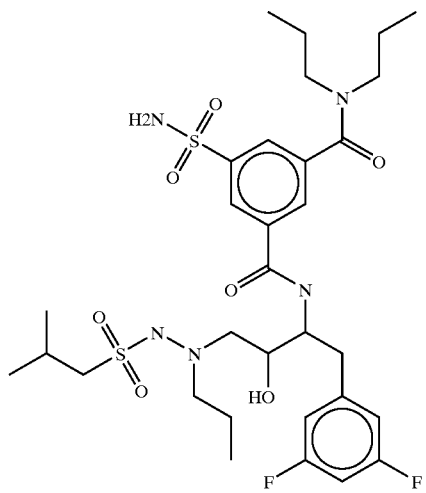
1:F3 1, 4, 4, 3
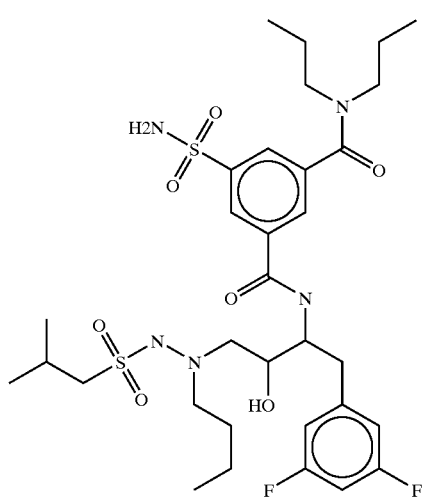
1:F4 1, 4, 4, 4
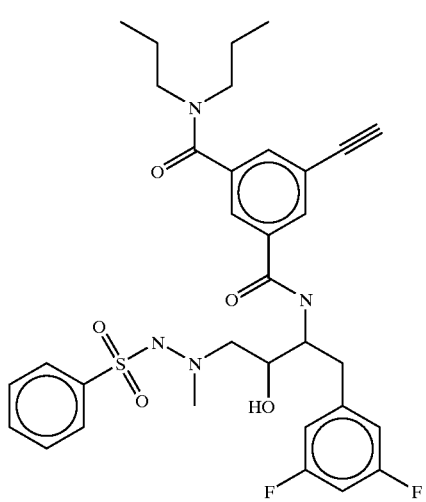
1:F5 1, 5, 1, 1
TABLE 1-continued
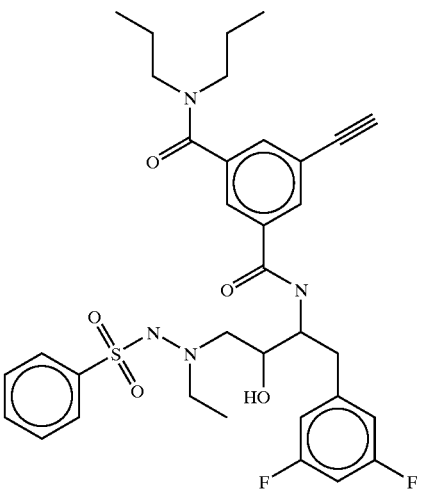
1:F6 1, 5, 1, 2
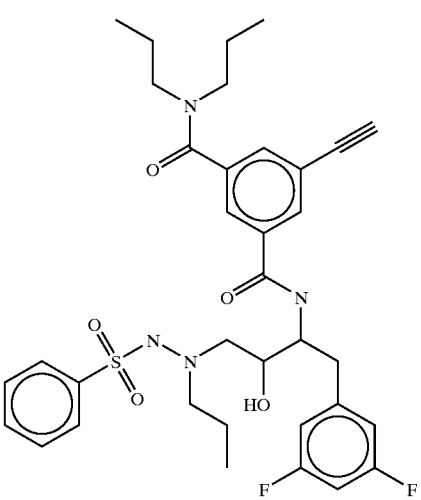
1:F7 1, 5, 1, 3
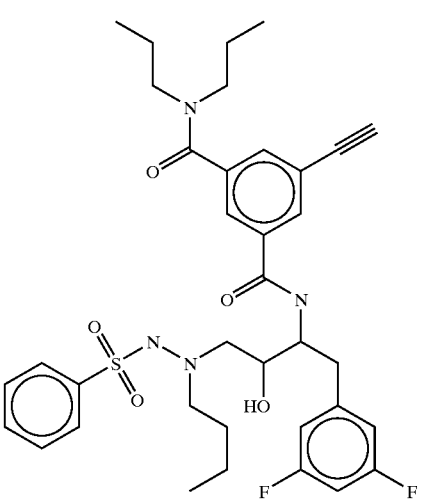
1:F8 1, 5, 1, 4

TABLE 1-continued
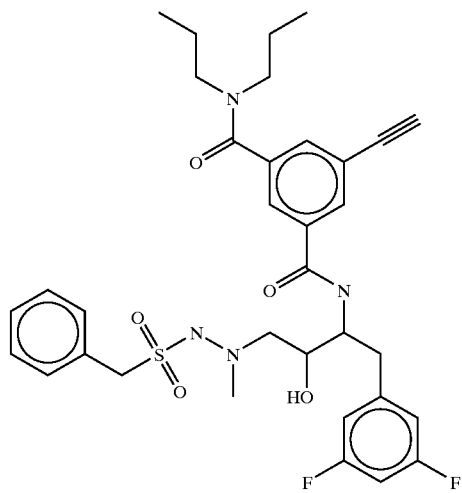
1:F9 1, 5, 2, 1
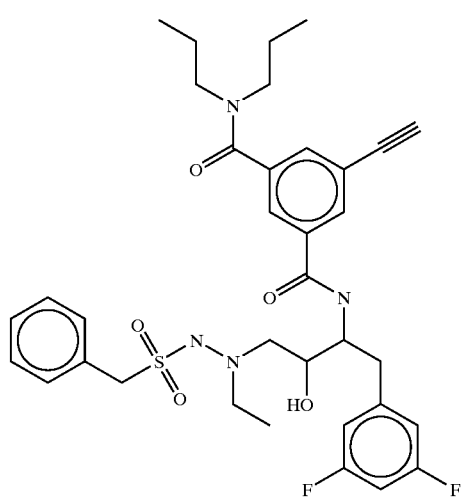
1:F10 1, 5, 2, 2
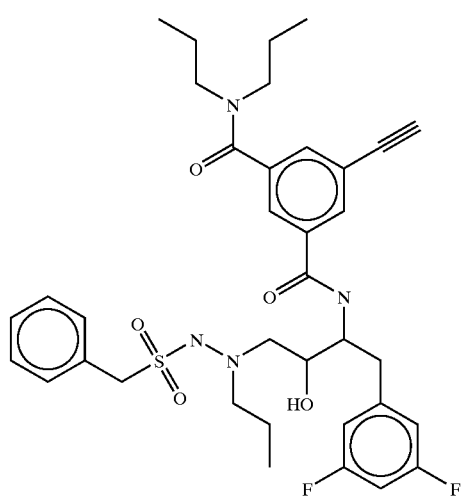
1:F11 1, 5, 2, 3
TABLE 1-continued
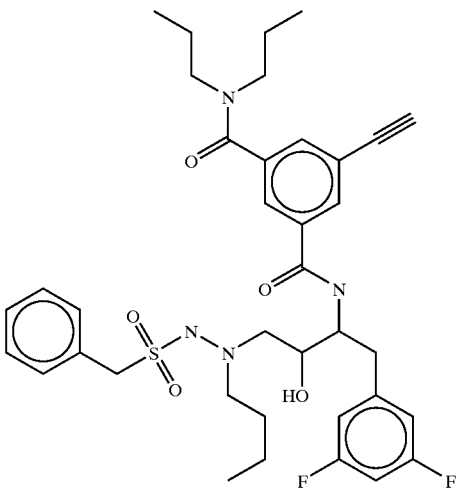
1:F12 1, 5, 2, 4
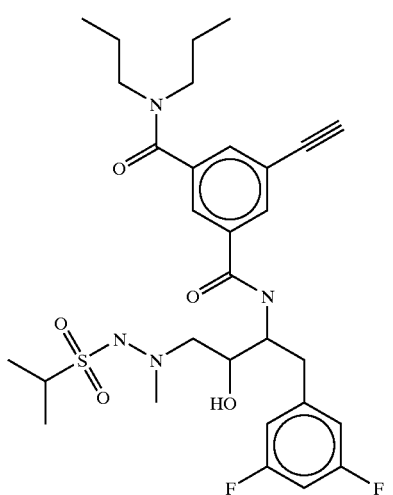
1:G1 1, 5, 3, 1
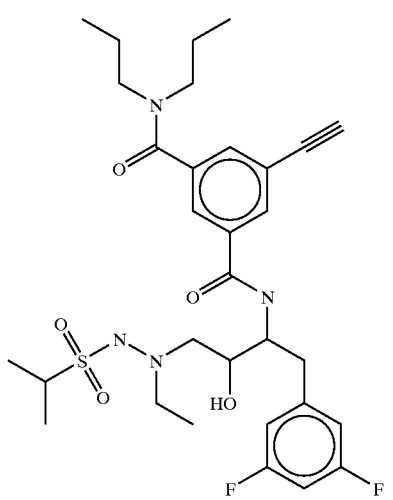
1:G2 1, 5, 3, 2

TABLE 1-continued
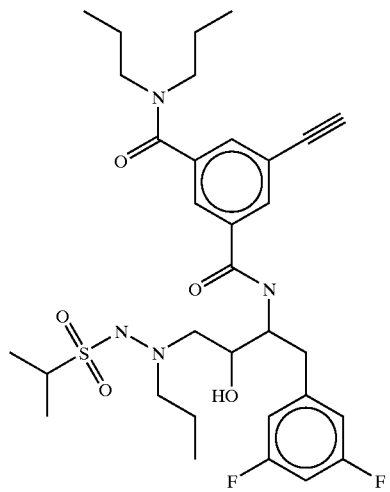
1:G3 1, 5, 3, 3
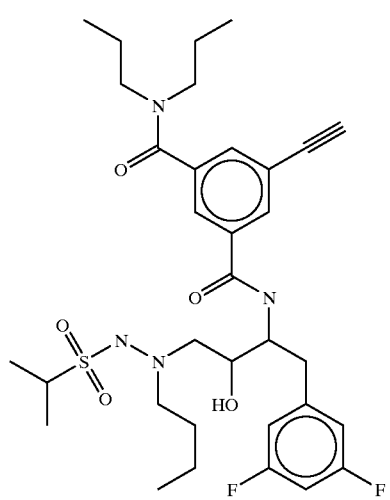
1:G4 1, 5, 3, 4
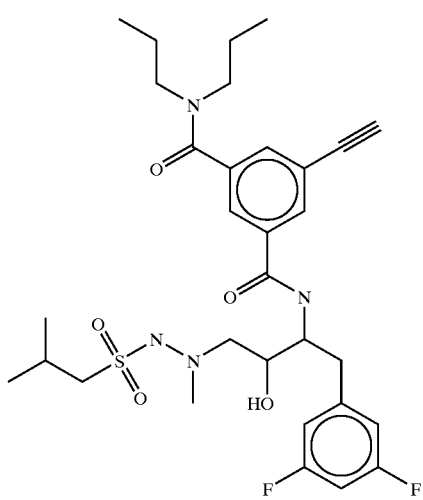
1:G5 1, 5, 4, 1
TABLE 1-continued
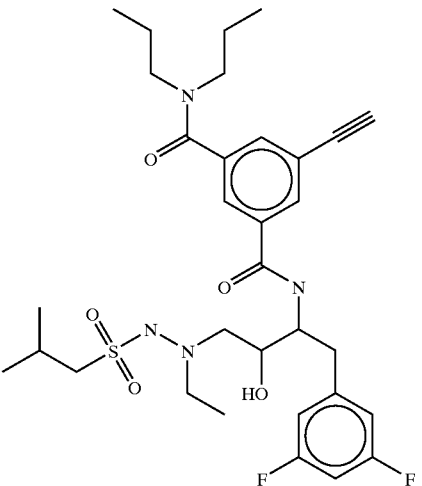
1:G6 1, 5, 4, 2
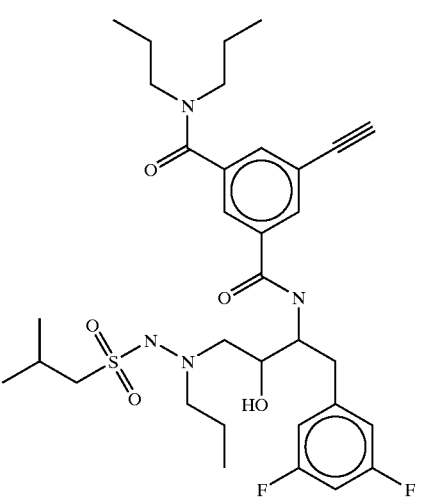
1:G7 1, 5, 4, 3
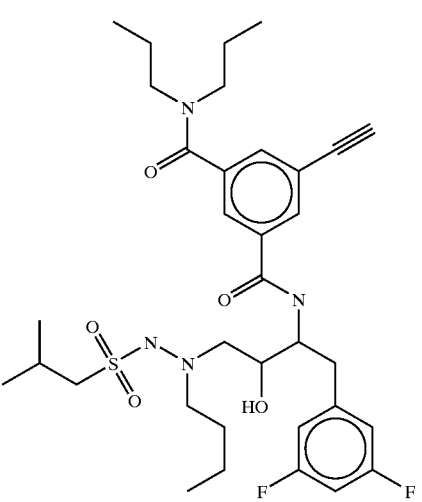
1:G8 1, 5, 4, 4

TABLE 1-continued
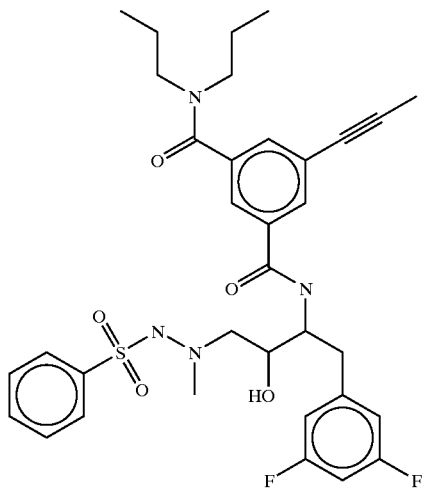
1:G9 1, 6, 1, 1
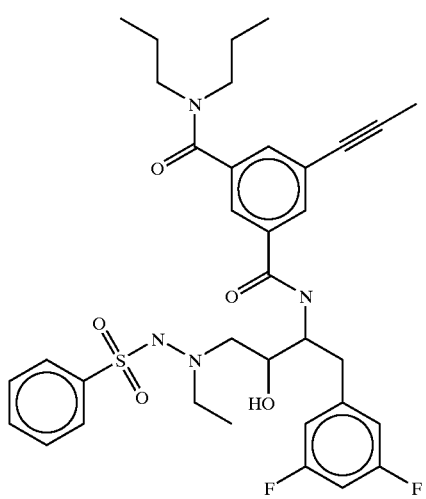
1:G10 1, 6, 1, 2
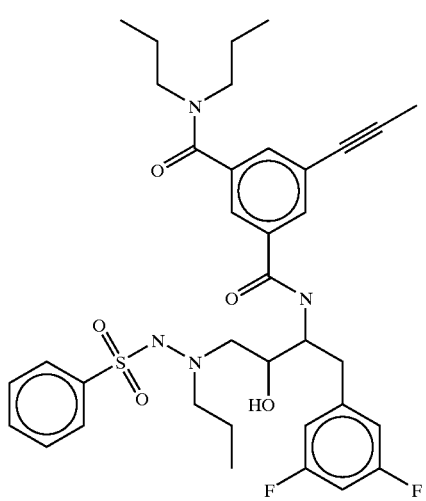
1:G11 1, 6, 1, 3
TABLE 1-continued
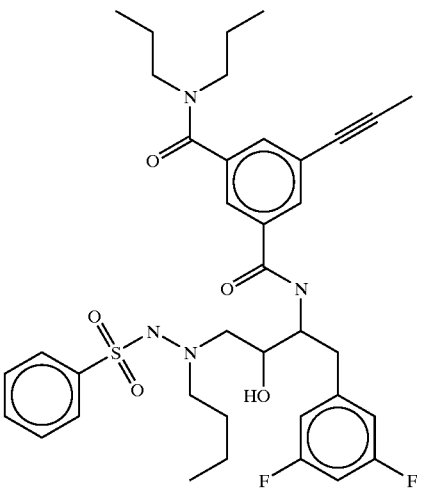
1:G12 1, 6, 1, 4
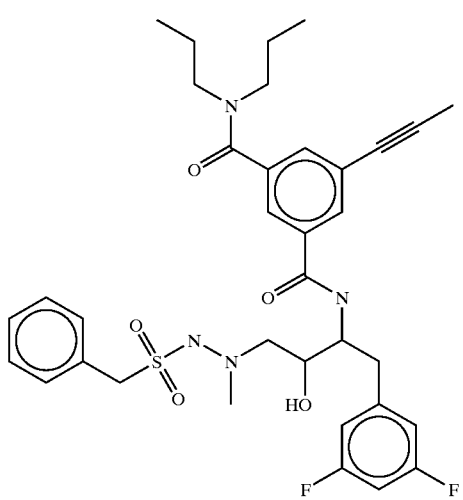
1:H1 1, 6, 2, 1
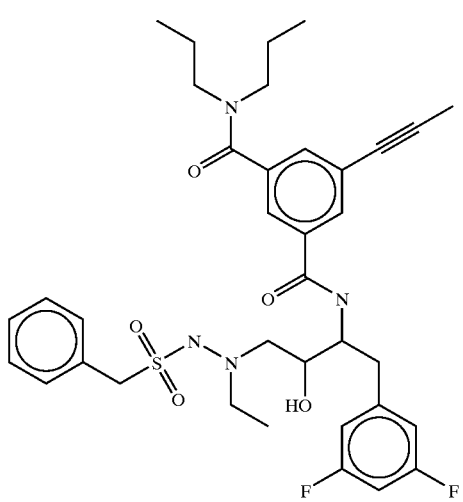
1:H2 1, 6, 2, 2

TABLE 1-continued
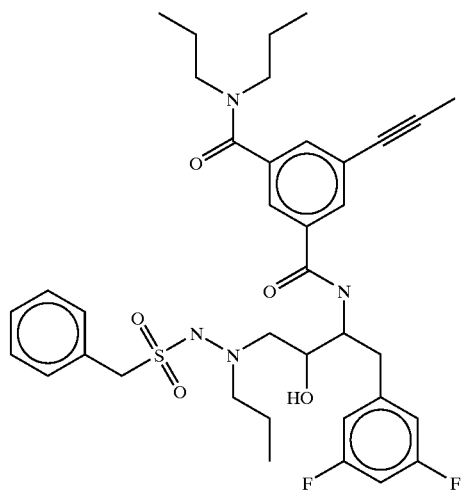
1:H3 1, 6, 2, 3
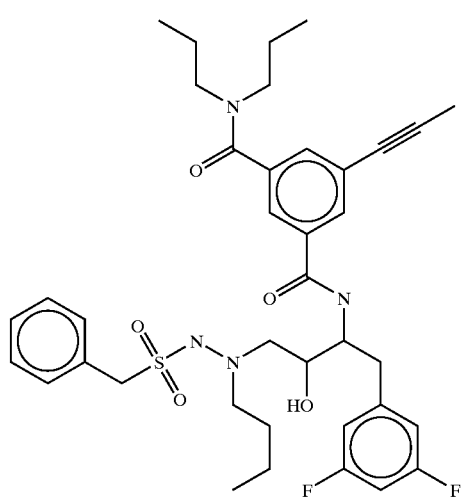
1:H4 1, 6, 2, 4
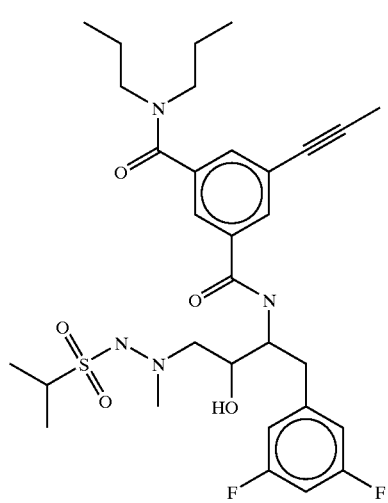
1:H5 1, 6, 3, 1
TABLE 1-continued
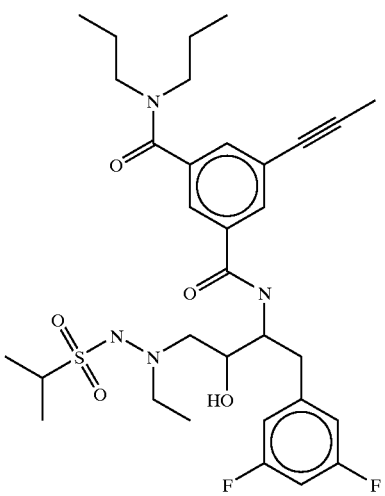
1:H6 1, 6, 3, 2
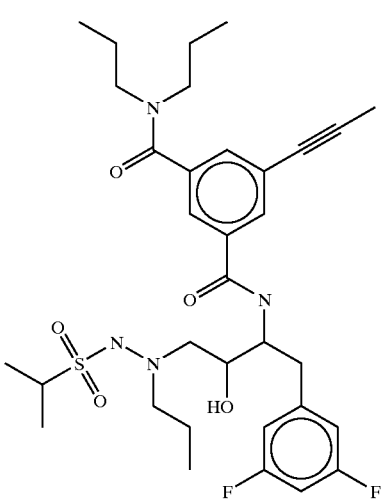
1:H7 1, 6, 3, 3
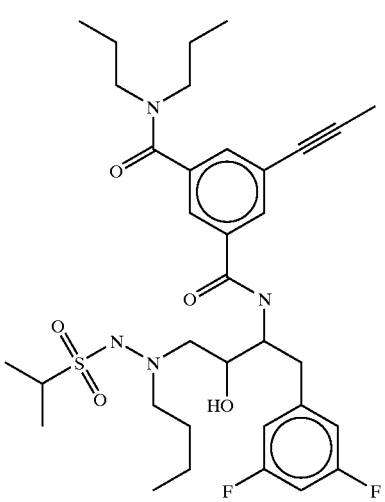
1:H8 1, 6, 3, 4

TABLE 1-continued
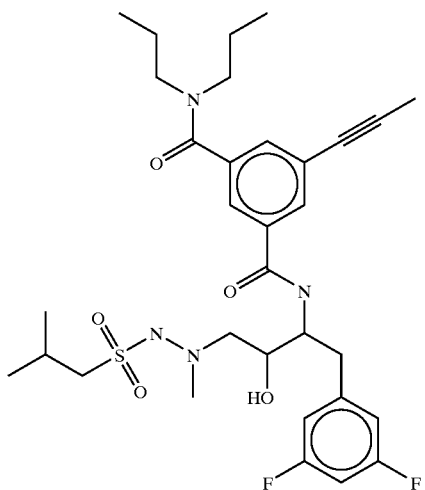
1:H9 1, 6, 4, 1
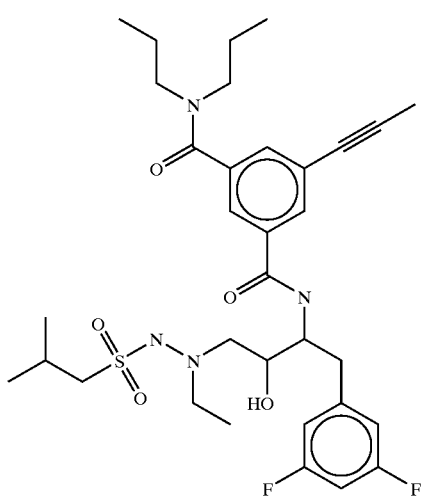
1:H10 1, 6, 4, 2
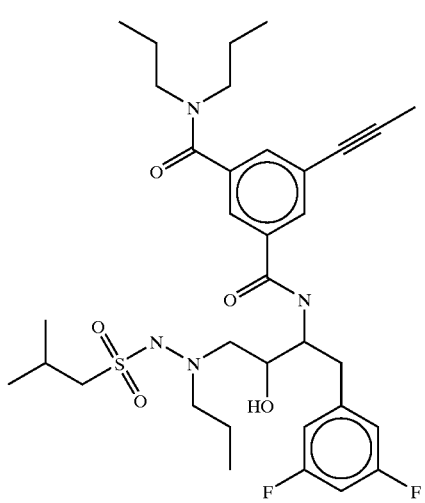
1:H11 1, 6, 4, 3
TABLE 1-continued
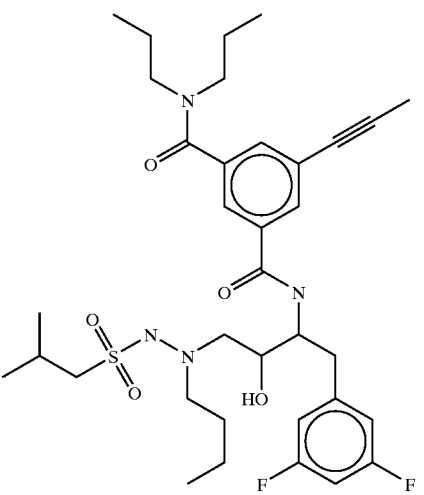
1:H12 1, 6, 4, 4
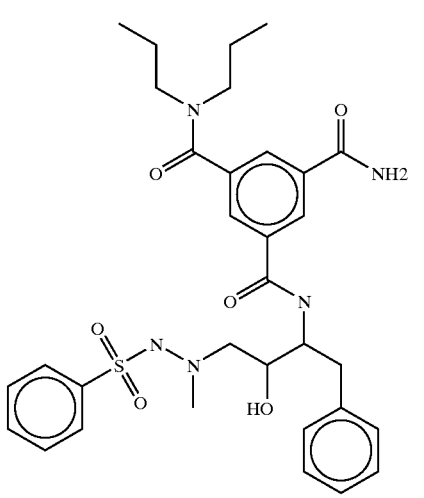
2:A1 2, 1, 1, 1
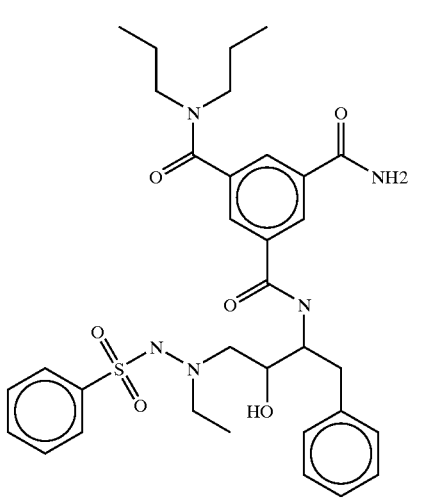
2:A2 2, 1, 1, 2

TABLE 1-continued
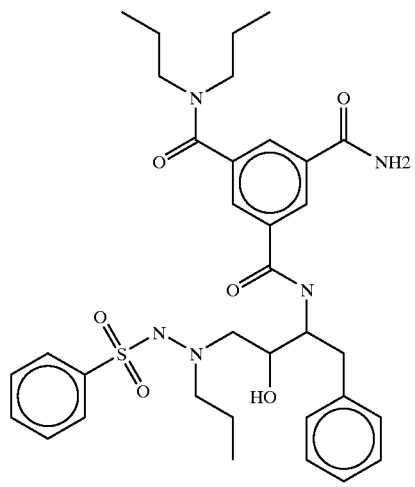
2:A3 2, 1, 1, 3
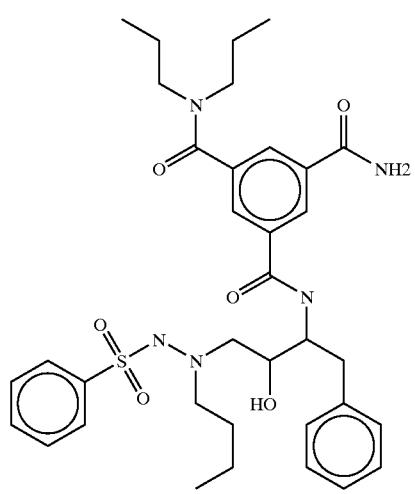
2:A4 2, 1, 1, 4
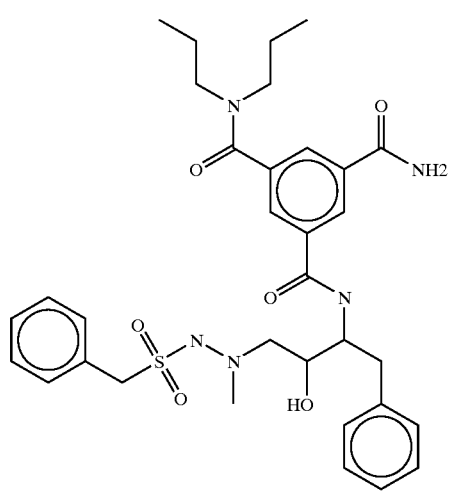
2:A5 2, 1, 2, 1
TABLE 1-continued
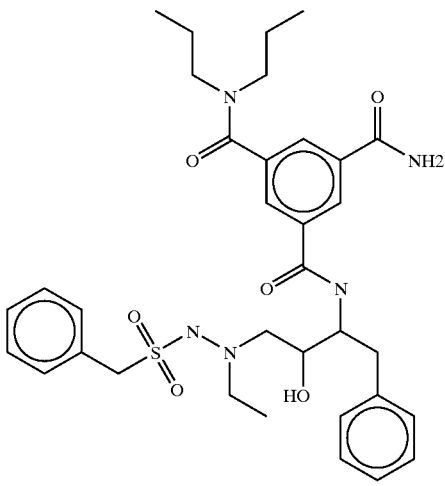
2:A6 2, 1, 2, 2
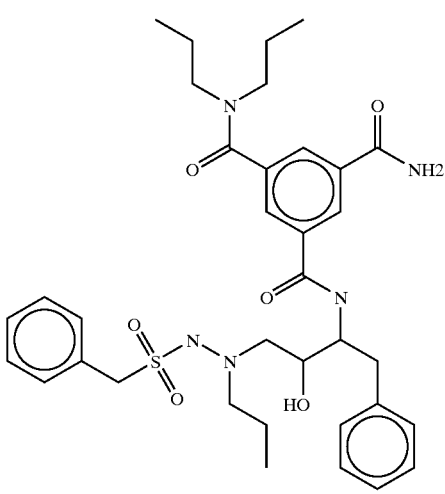
2:A7 2, 1, 2, 3
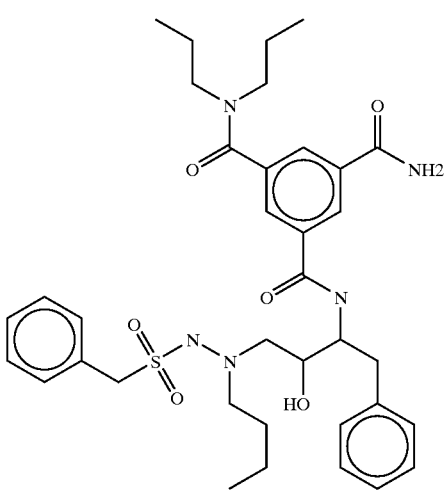
2:A8 2, 1, 2, 4

TABLE 1-continued
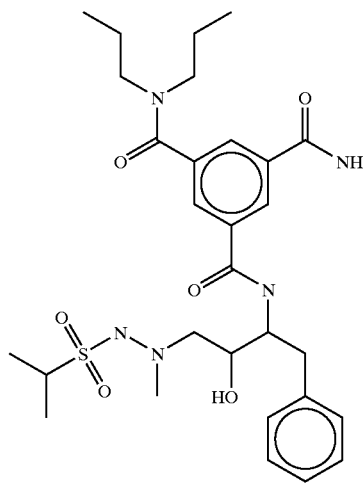
2:A9 2, 1, 3, 1
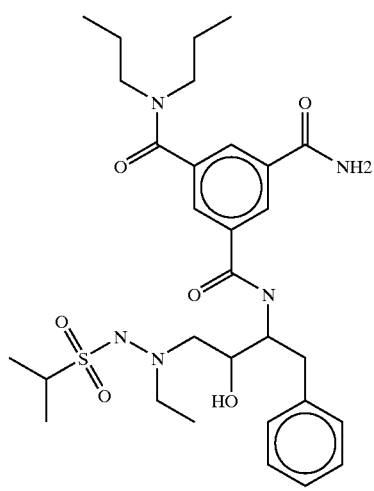
2:A10 2, 1, 3, 2
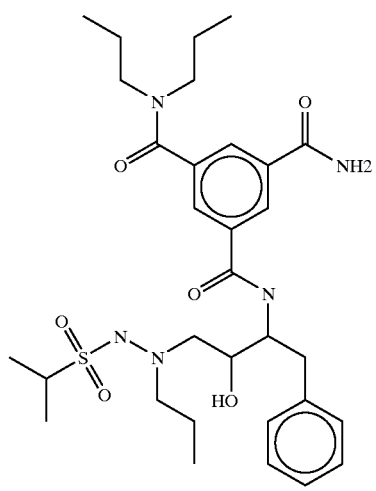
2:A11 2, 1, 3, 3
TABLE 1-continued
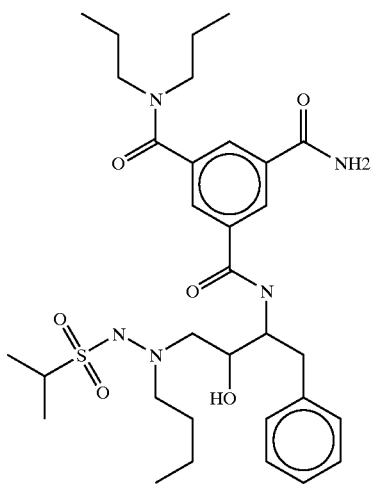
2:A12 2, 1, 3, 4
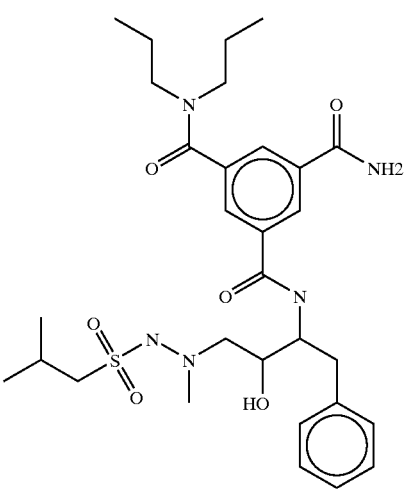
2:B1 2, 1, 4, 1
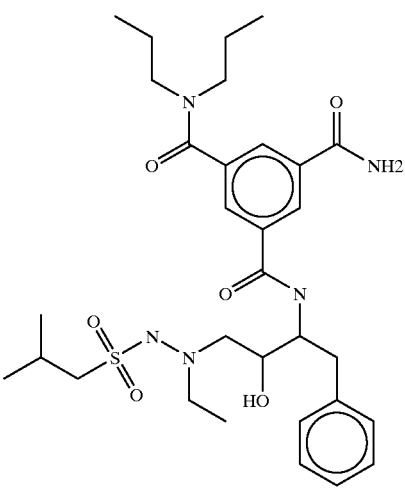
2:B2 2, 1, 4, 2

TABLE 1-continued
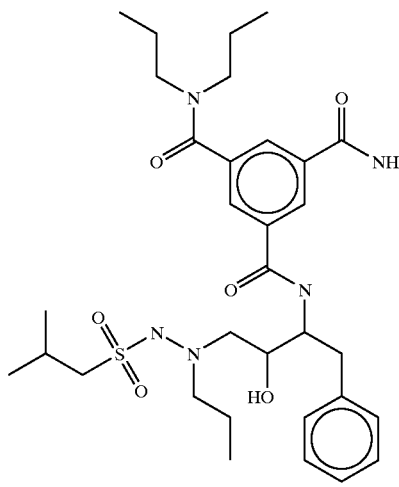
2:B3 2, 1, 4, 3
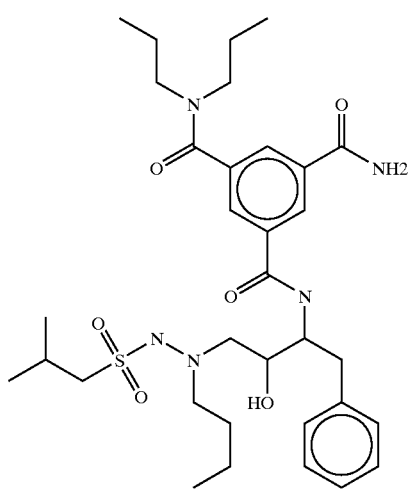
2:B4 2, 1, 4, 4
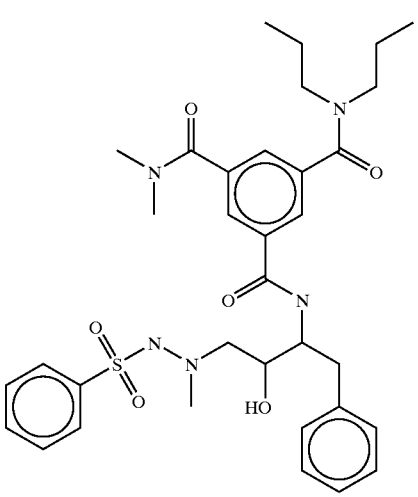
2:B5 2, 2, 1, 1
TABLE 1-continued
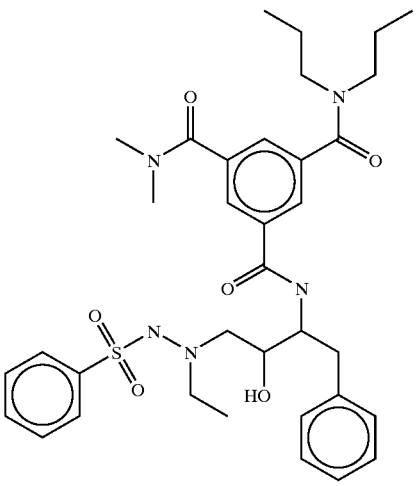
2:B6 2, 2, 1, 2
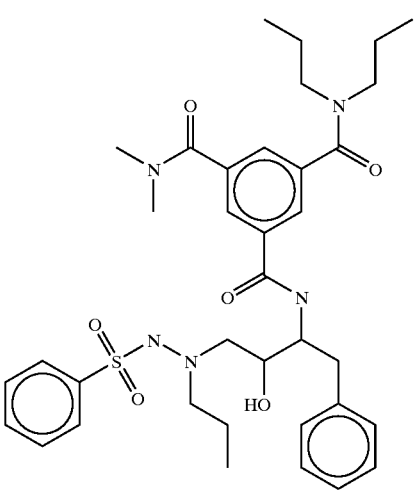
2:B7 2, 2, 1, 3
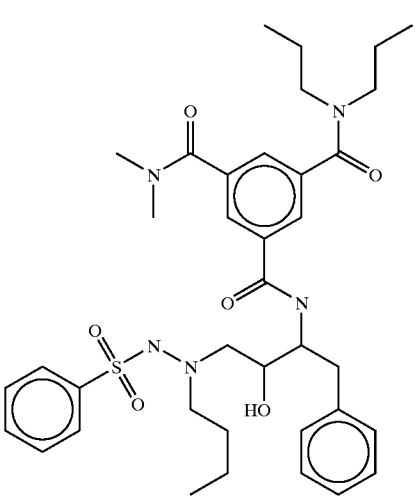
2:B8 2, 2, 1, 4

TABLE 1-continued
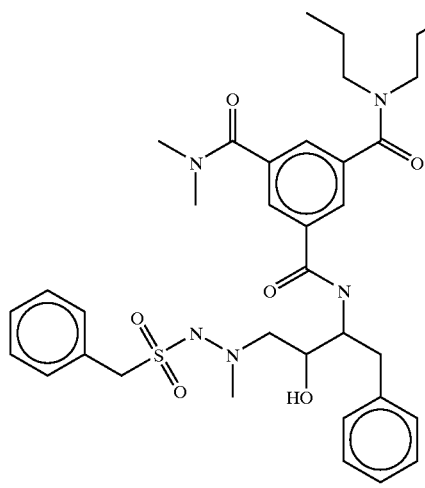
2:B9 2, 2, 2, 1
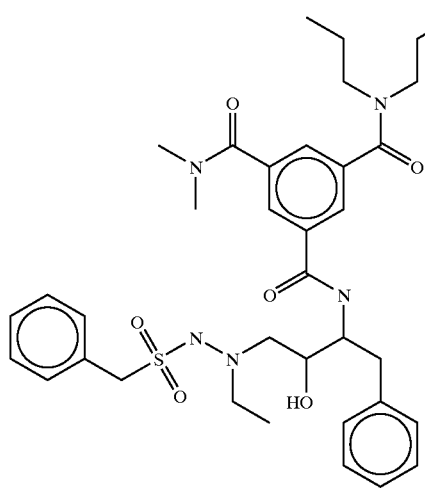
2:B10 2, 2, 2, 2
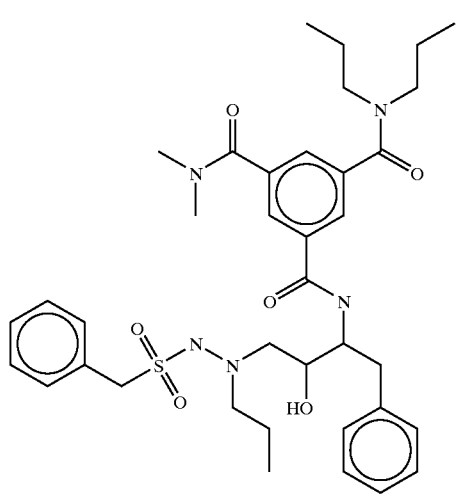
2:B11 2, 2, 2, 3
TABLE 1-continued
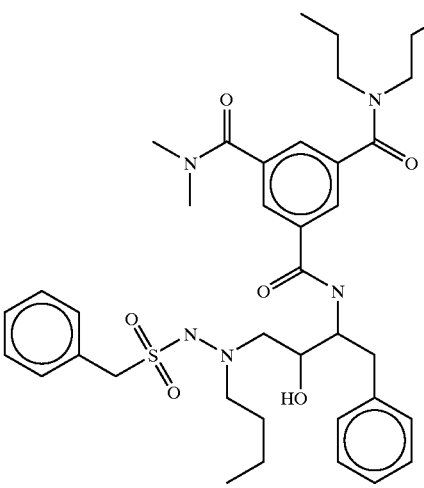
2:B12 2, 2, 2, 4
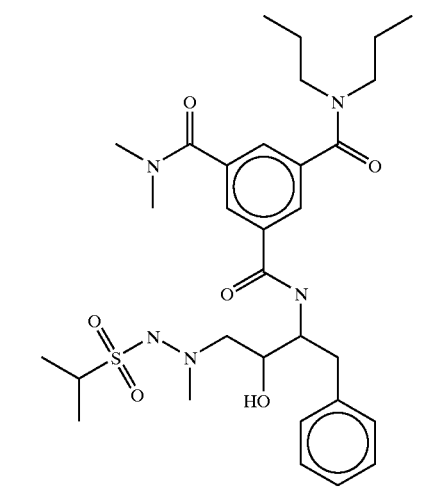
2:C1 2, 2, 3, 1
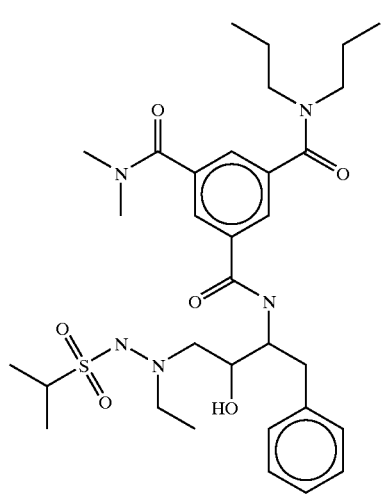
2:C2 2, 2, 3, 2

TABLE 1-continued
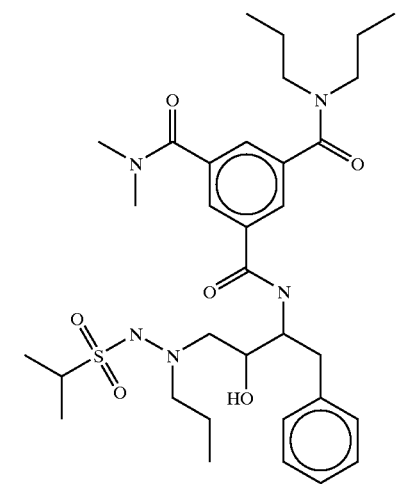
2:C3 2, 2, 3, 3
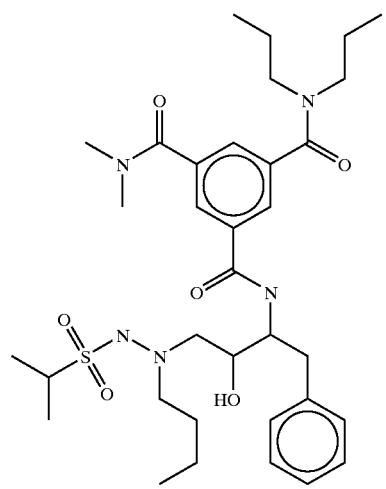
2:C4 2, 2, 3, 4
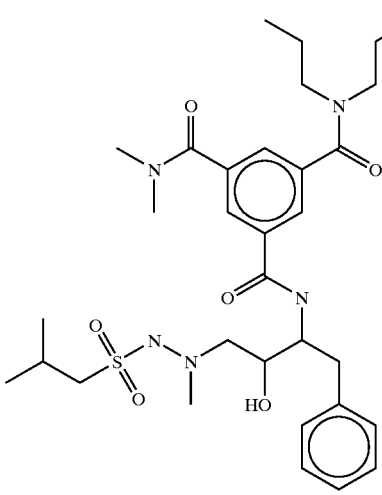
2:C5 2, 2, 4, 1
TABLE 1-continued
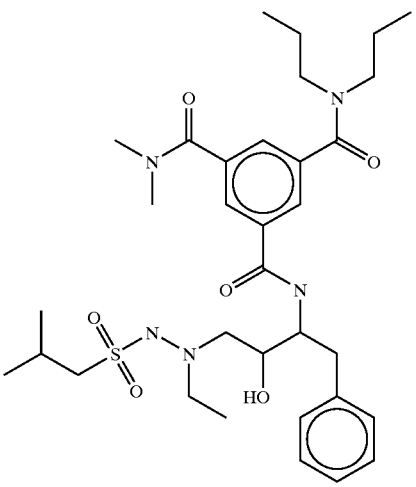
2:C6 2, 2, 4, 2
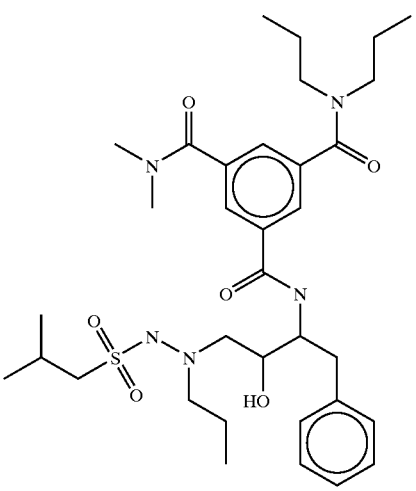
2:C7 2, 2, 4, 3
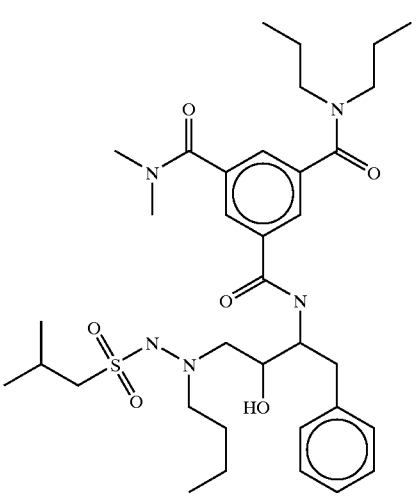
2:C8 2, 2, 4, 4

TABLE 1-continued
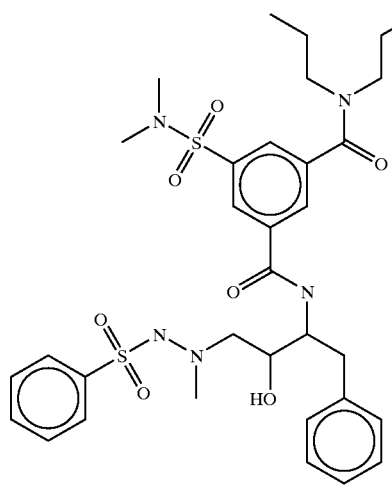
2:C9 2, 3, 1, 1
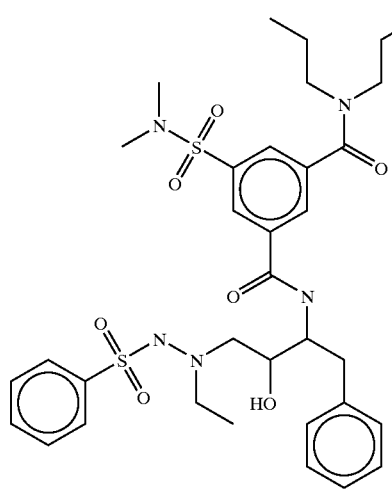
2:C10 2, 3, 1, 2
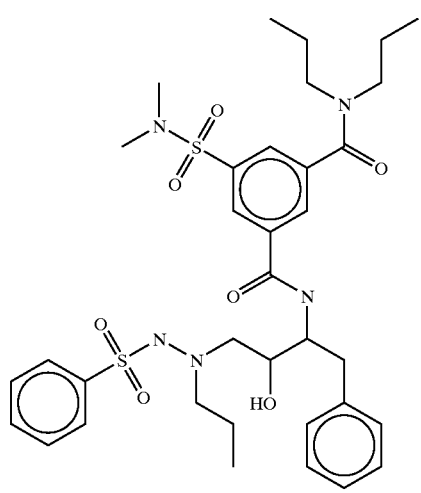
2:C11 2, 3, 1, 3
TABLE 1-continued
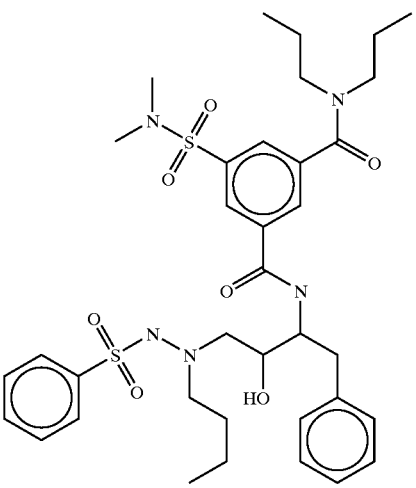
2:C12 2, 3, 1, 4
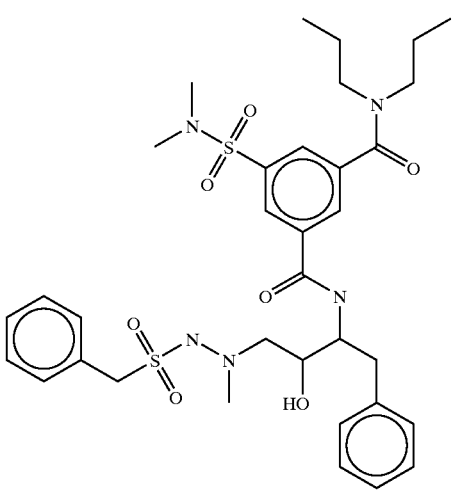
2:D1 2, 3, 2, 1
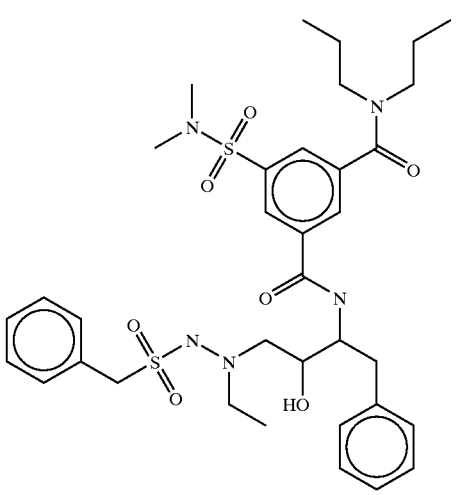
2:D2 2, 3, 2, 2

TABLE 1-continued
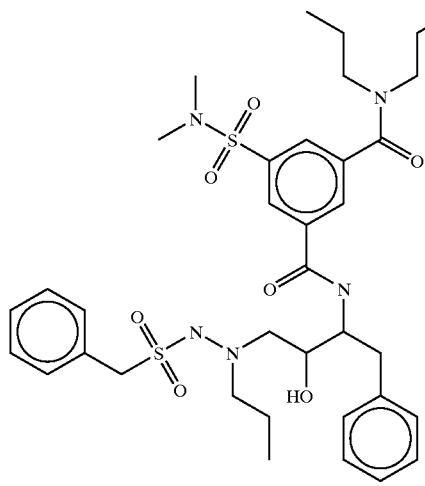
2:D3 2, 3, 2, 3
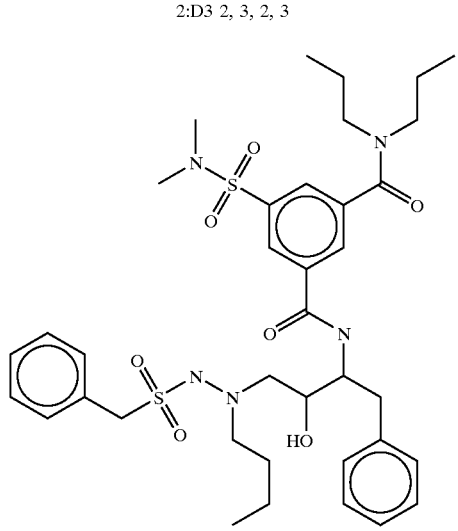
2:D4 2, 3, 2, 4
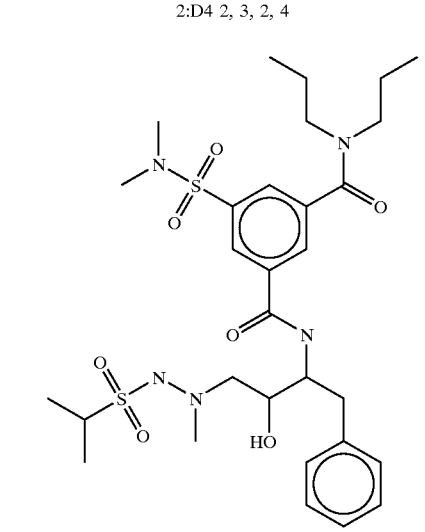
2:D5 2, 3, 3, 1
TABLE 1-continued
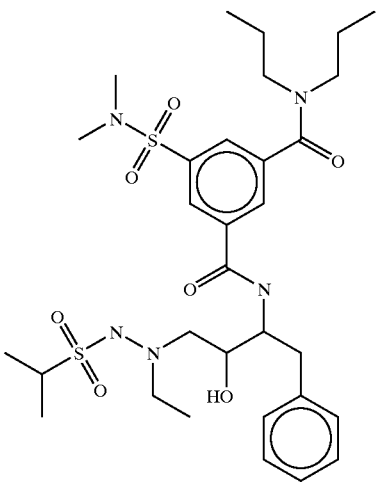
2:D6 2, 3, 3, 2
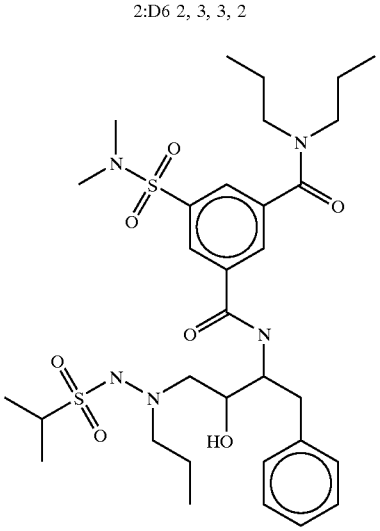
2:D7 2, 3, 3, 3
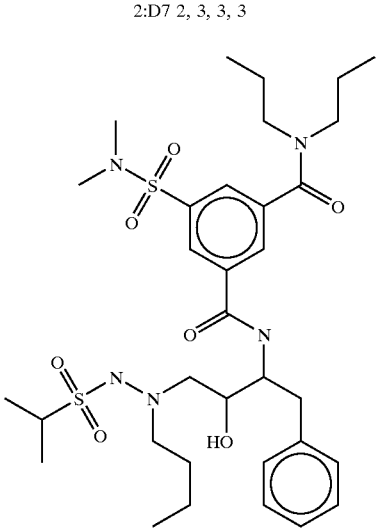
2:D8 2, 3, 3, 4

TABLE 1-continued
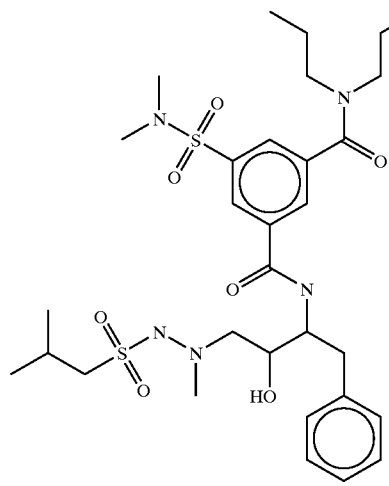
2:D9 2, 3, 4, 1
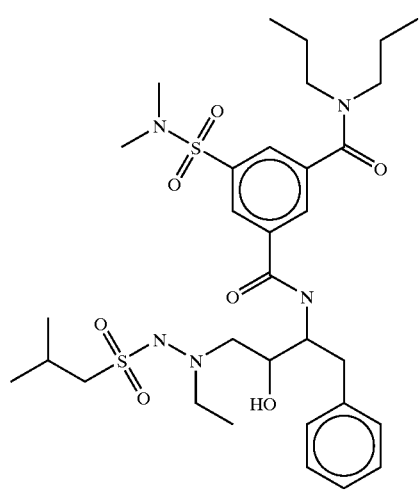
2:D10 2, 3, 4, 2
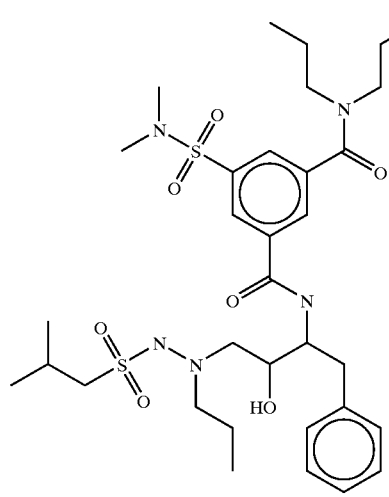
2:D11 2, 3, 4, 3
TABLE 1-continued
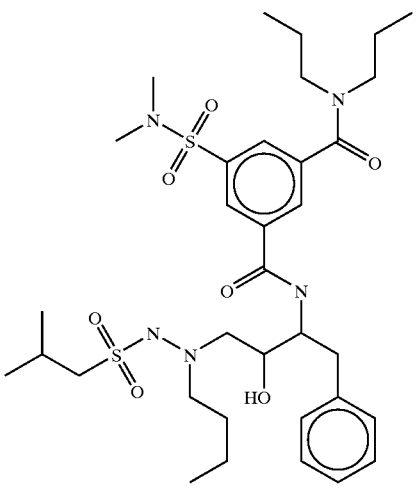
2:D12 2, 3, 4, 4
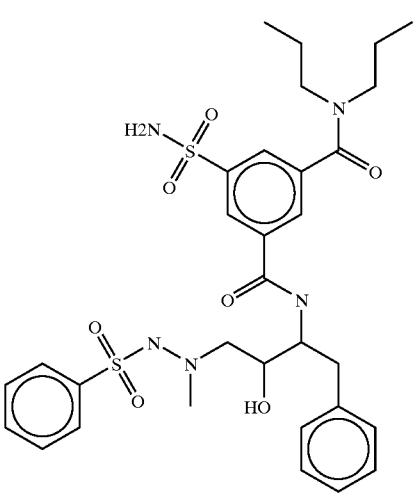
2:E1 2, 4, 1, 1
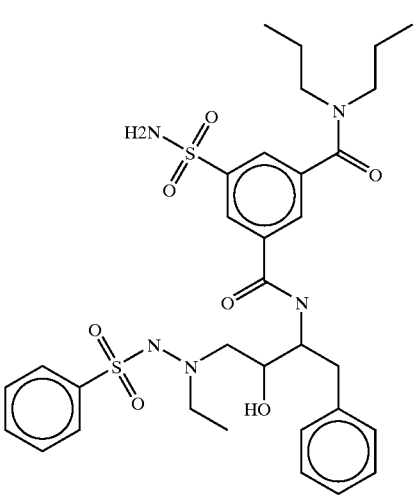
2:E2 2, 4, 1, 2

TABLE 1-continued
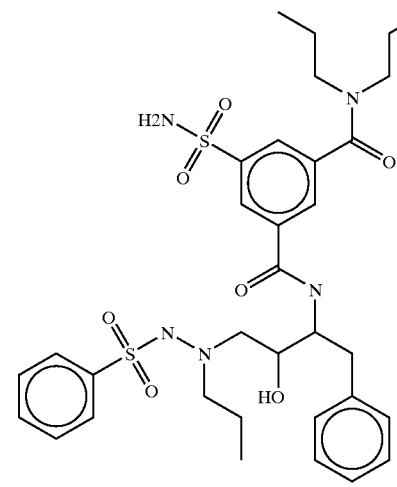
2:E3 2, 4, 1, 3
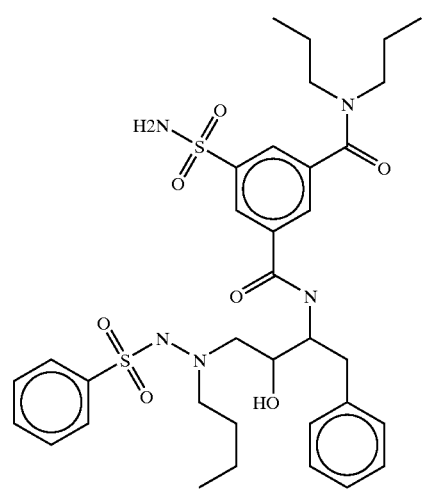
2:E4 2, 4, 1, 4
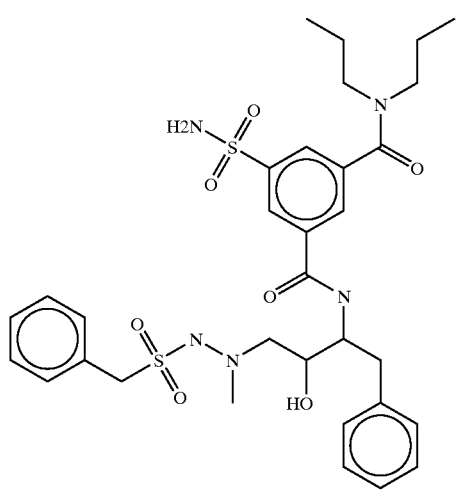
2:E5 2, 4, 2, 1
TABLE 1-continued
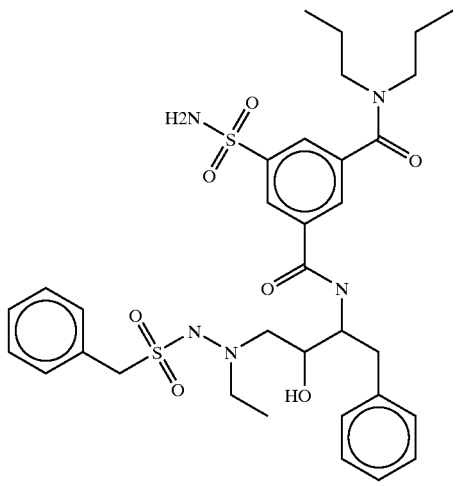
2:E6 2, 4, 2, 2
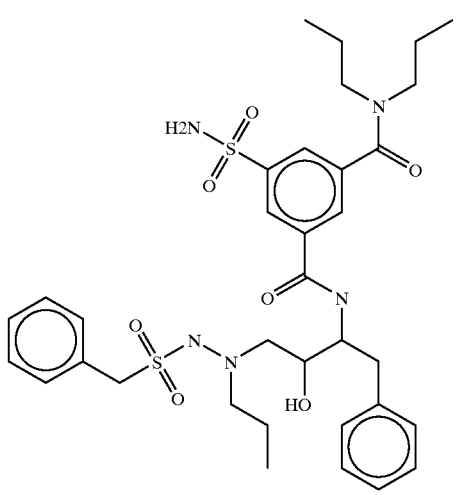
2:E7 2, 4, 2, 3
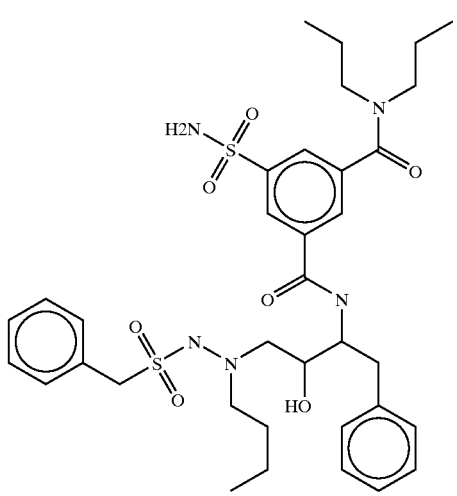
2:E8 2, 4, 2, 4

TABLE 1-continued
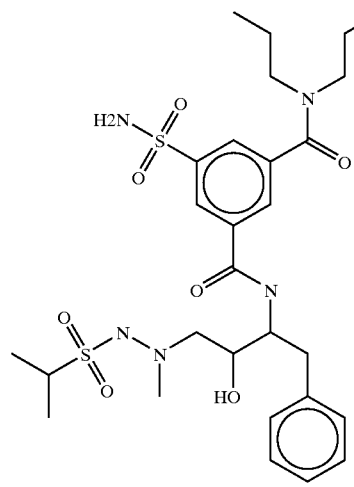
2:E9 2, 4, 3, 1
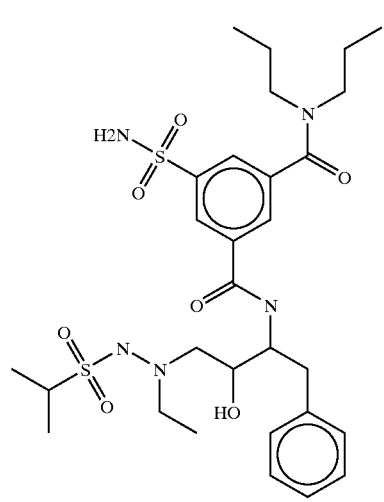
2:E10 2, 4, 3, 2
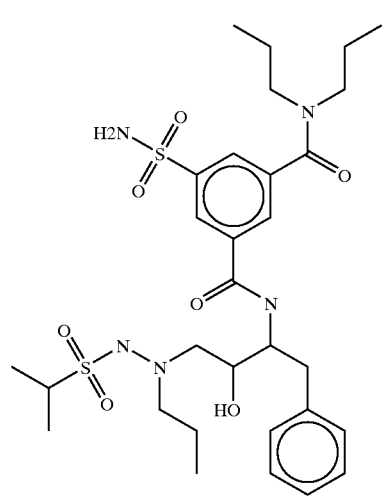
2:E11 2, 4, 3, 3
TABLE 1-continued
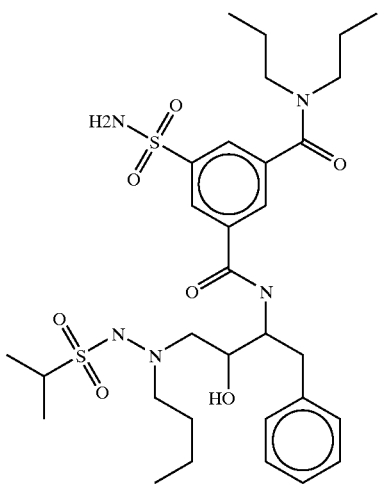
2:E12 2, 4, 3, 4
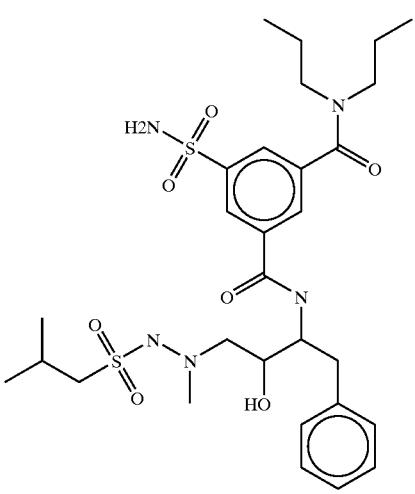
2:F1 2, 4, 4, 1
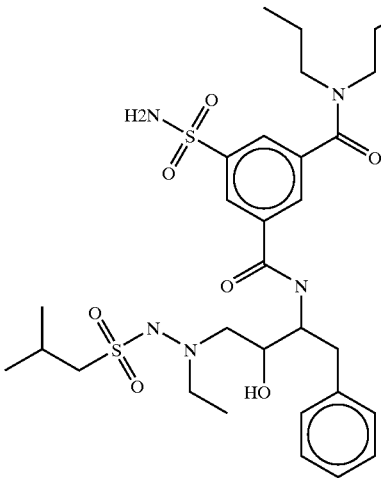
2:F2 2, 4, 4, 2

TABLE 1-continued
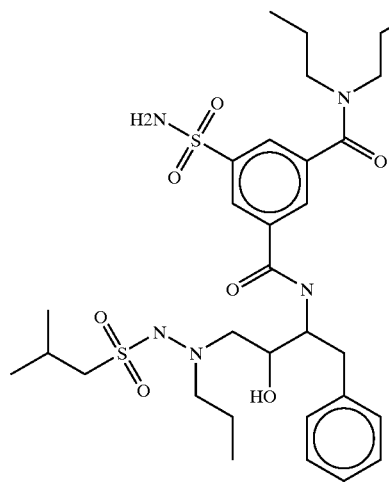
2:F3 2, 4, 4, 3
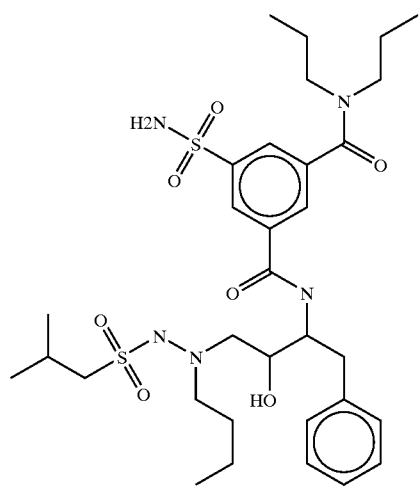
2:F4 2, 4, 4, 4
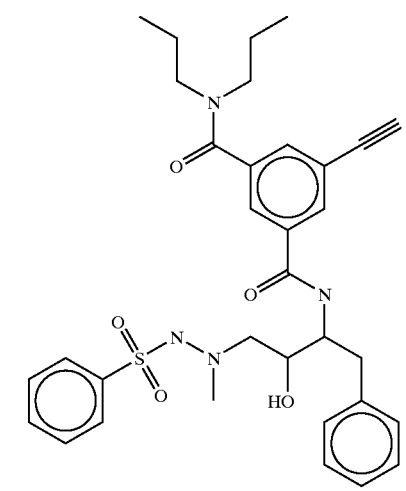
2:F5 2, 5, 1, 1
TABLE 1-continued
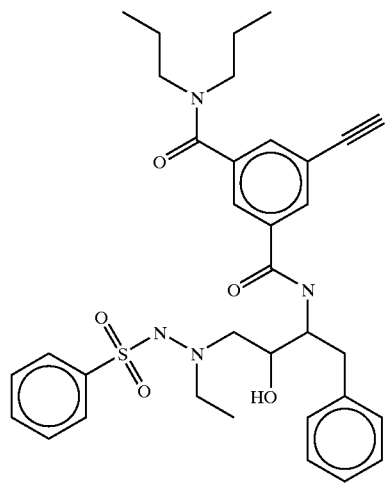
2:F6 2, 5, 1, 2
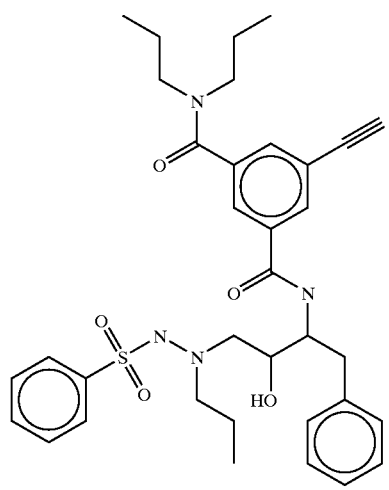
2:F7 2, 5, 1, 3
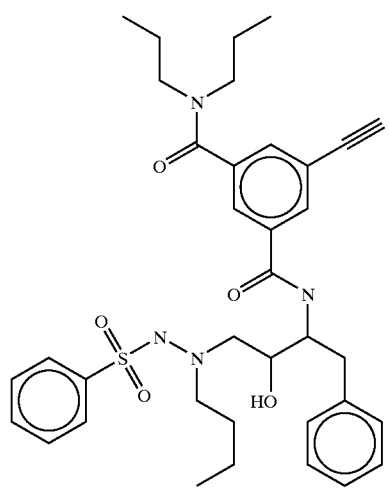
2:F8 2, 5, 1, 4

TABLE 1-continued
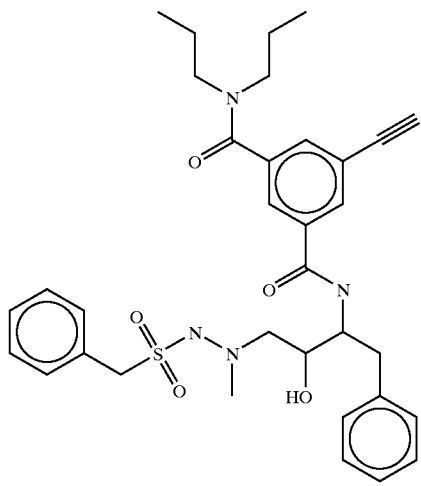
2:F9 2, 5, 2, 1
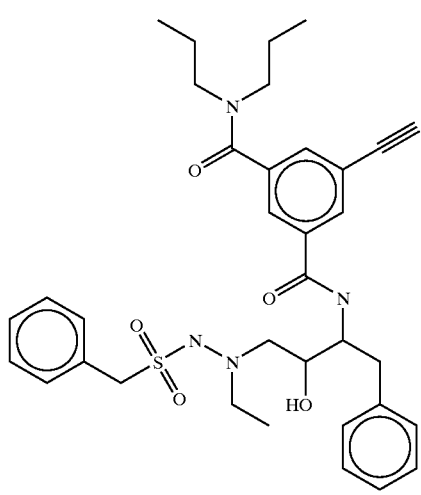
2:F10 2, 5, 2, 2
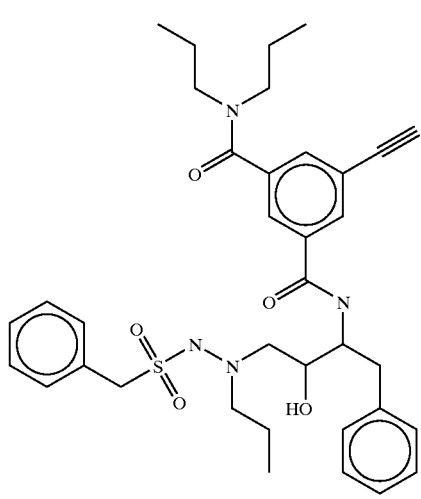
2:F11 2, 5, 2, 3
TABLE 1-continued
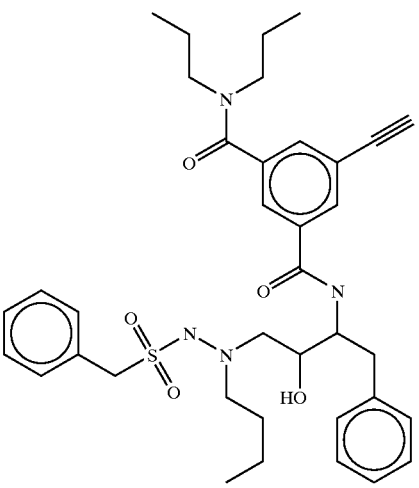
2:F12 2, 5, 2, 4
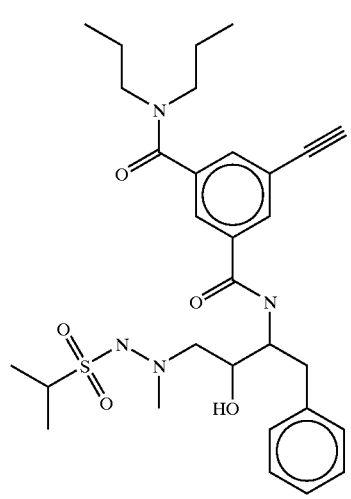
2:G1 2, 5, 3, 1
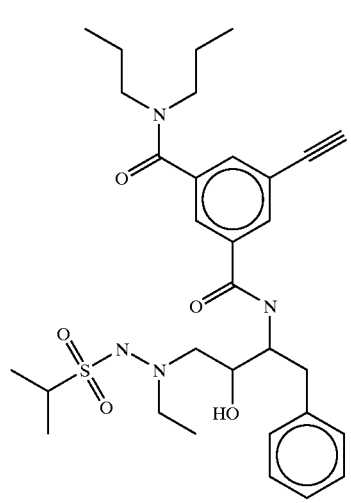
2:G2 2, 5, 3, 2

TABLE 1-continued
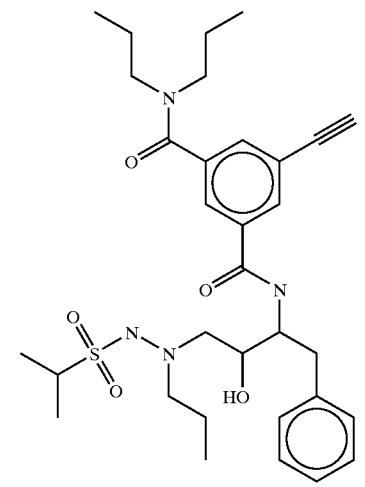
2:G3 2, 5, 3, 3
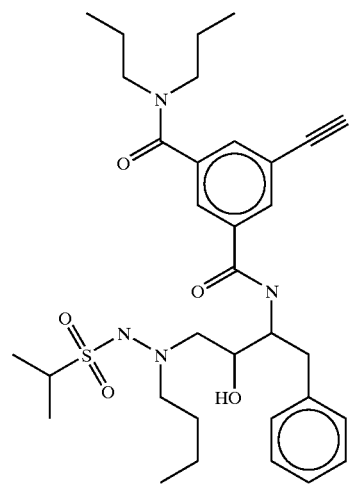
2:G4 2, 5, 3, 4
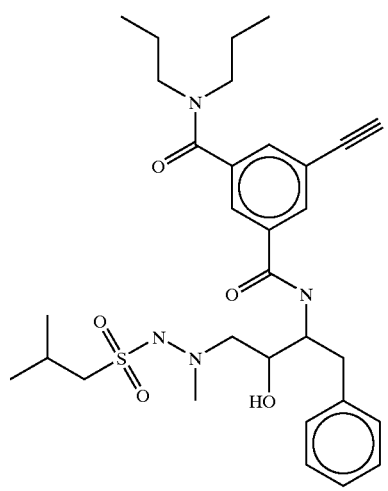
2:G5 2, 5, 4, 1
TABLE 1-continued
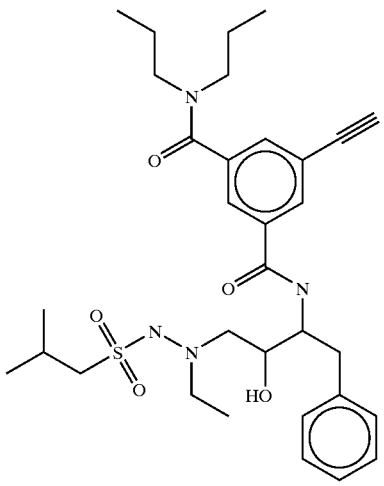
2:G6 2, 5, 4, 2
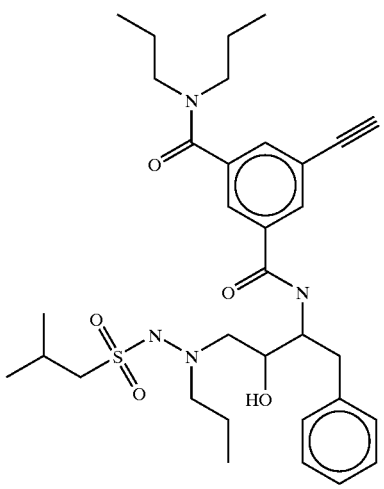
2:G7 2, 5, 4, 3
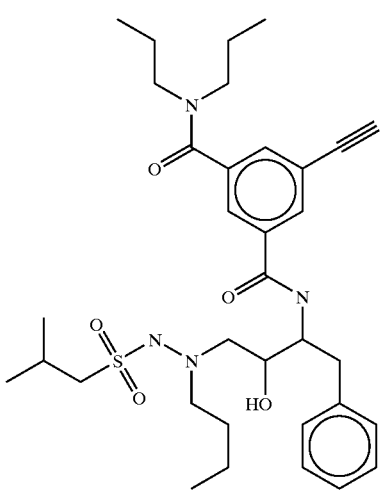
2:G8 2, 5, 4, 4

TABLE 1-continued
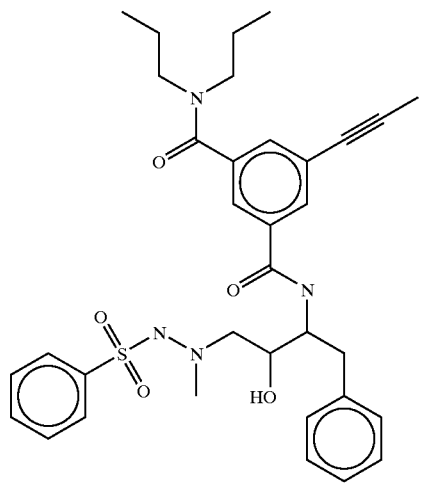
2:G9 2, 6, 1, 1
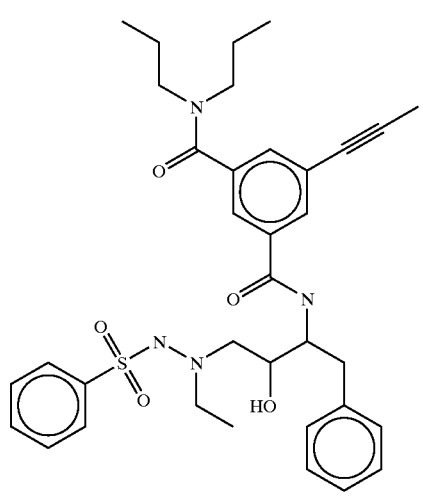
2:G10 2, 6, 1, 2
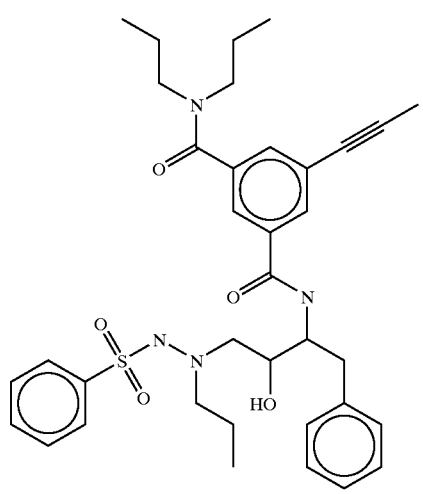
2:G11 2, 6, 1, 3
TABLE 1-continued
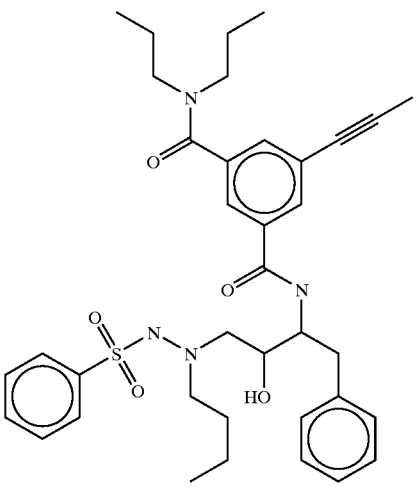
2:G12 2, 6, 1, 4
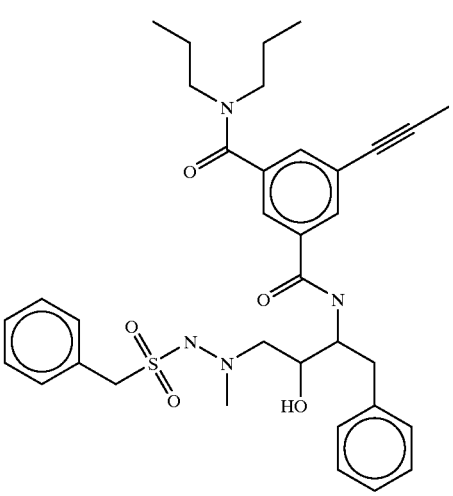
2:H1 2, 6, 2, 1
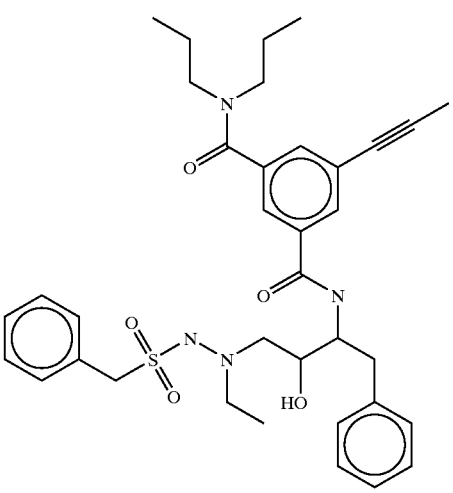
2:H2 2, 6, 2, 2

TABLE 1-continued
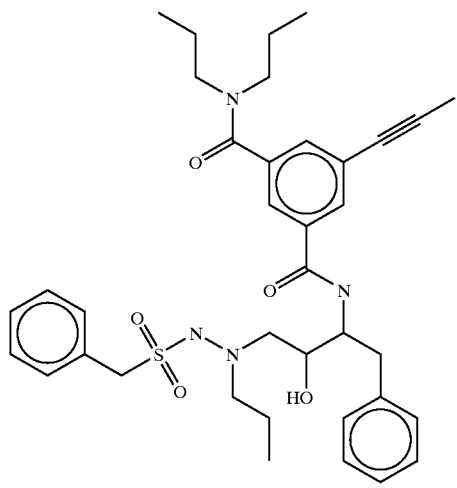
2:H3 2, 6, 2, 3
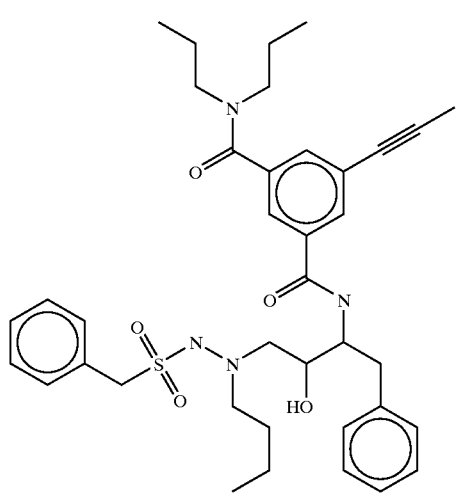
3:H4 2, 6, 2, 4
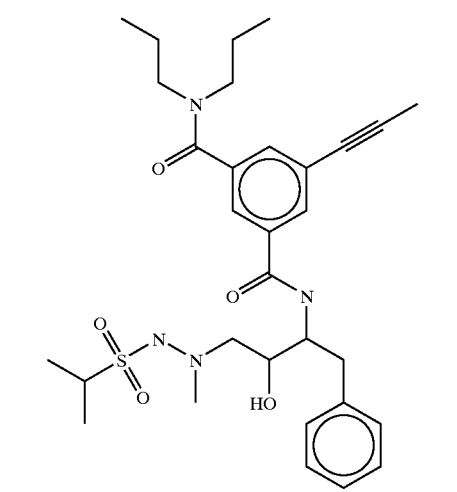
3:H5 2, 6, 3, 1
TABLE 1-continued
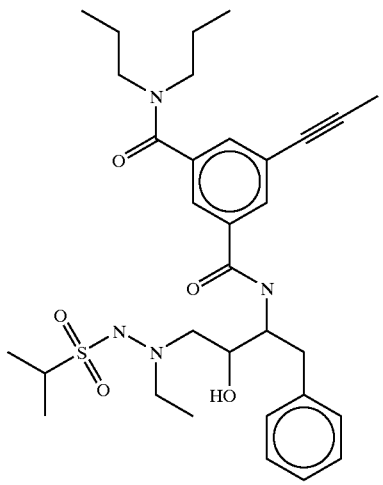
3:H6 2, 6, 3, 2
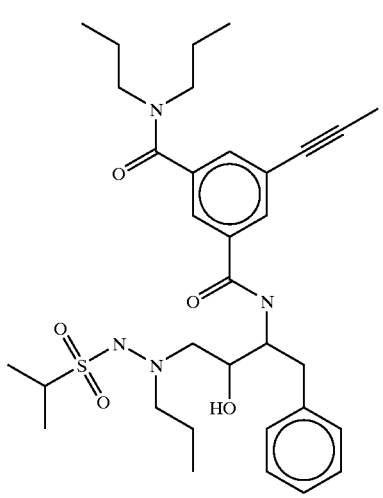
3:H7 2, 6, 3, 3
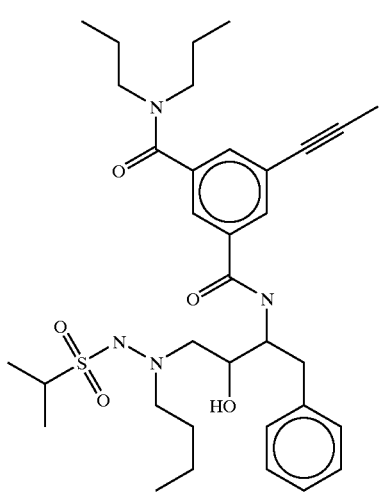
3:H8 2, 6, 3, 4

TABLE 1-continued
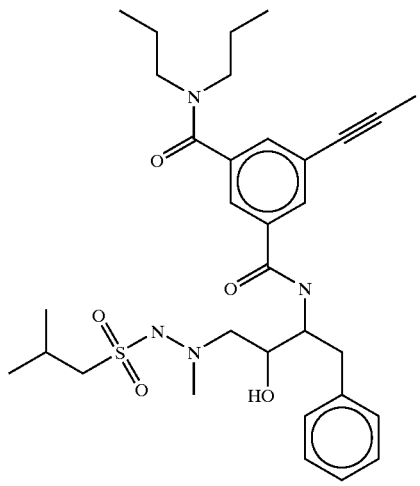
3:H9 2, 6, 4, 1
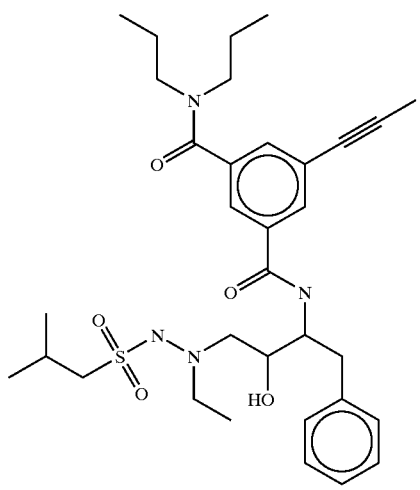
3:H10 2, 6, 4, 2
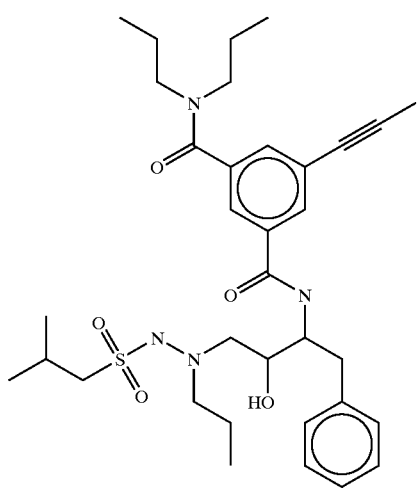
3:H11 2, 6, 4, 3
TABLE 1-continued
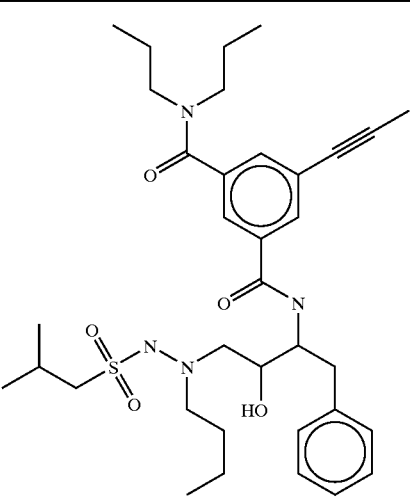
3:H12 2, 6, 4, 4
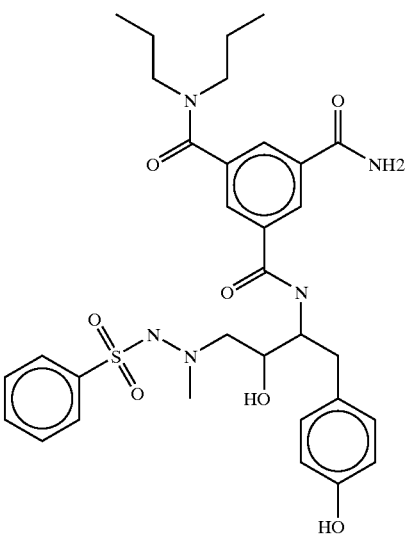
3:A1 3, 1, 1, 1

TABLE 1-continued
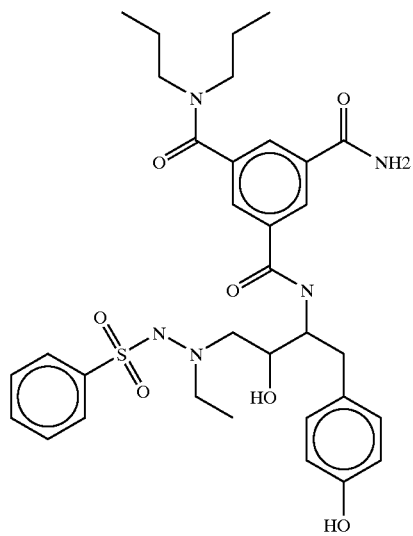
3:A2 3, 1, 1, 2
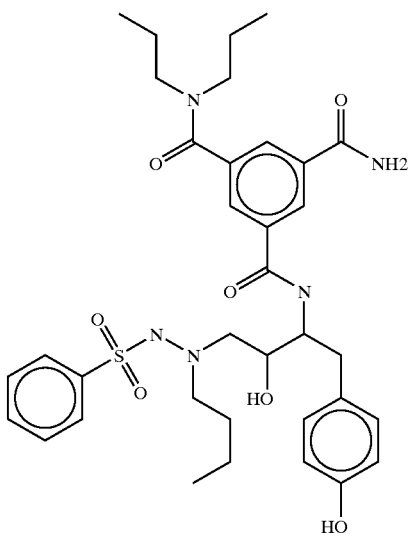
3:A4 3, 1, 1, 4
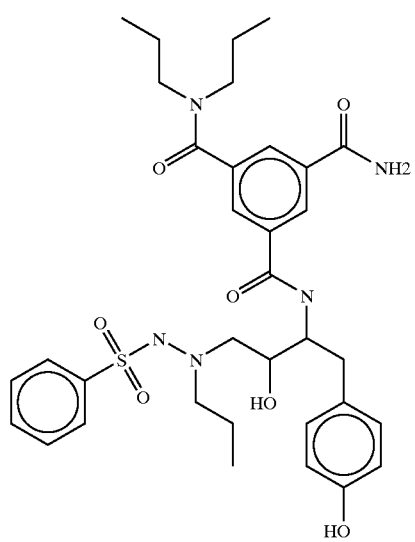
3:A3 3, 1, 1, 3
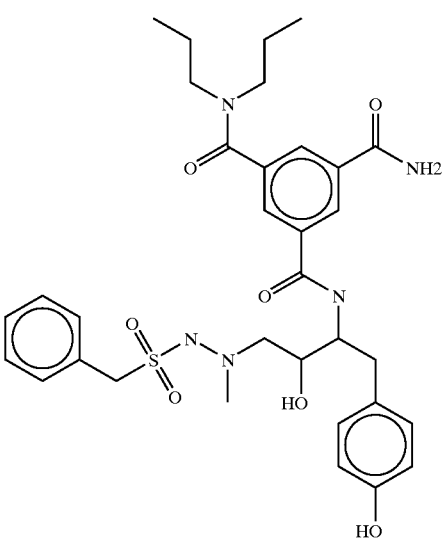
3:A5 3, 1, 2, 1

TABLE 1-continued
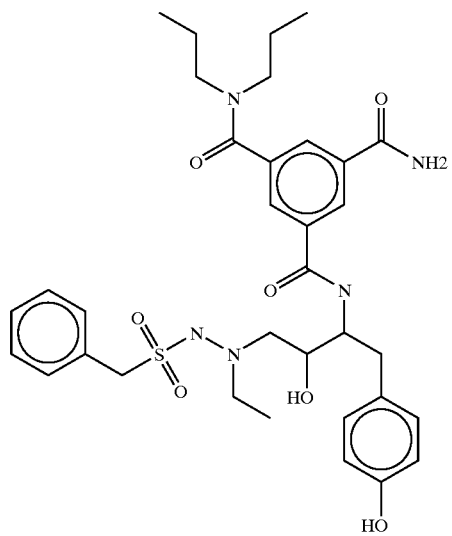
3:A6 3, 1, 2, 2
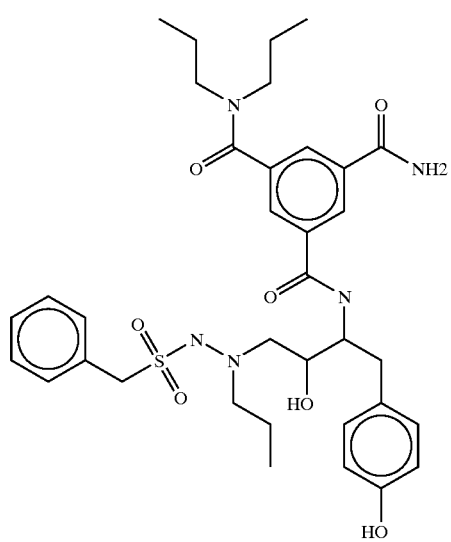
3:A7 3, 1, 2, 3
TABLE 1-continued
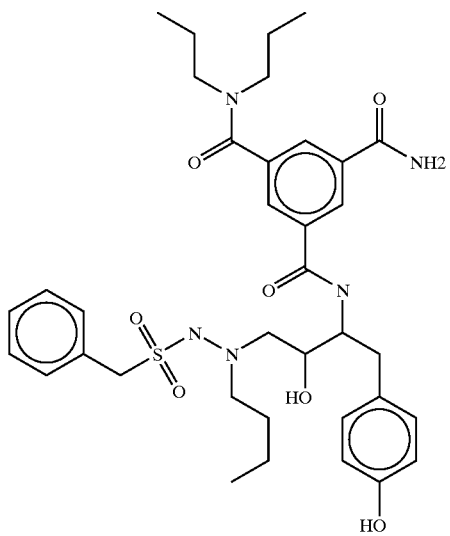
3:A8 3, 1, 2, 4
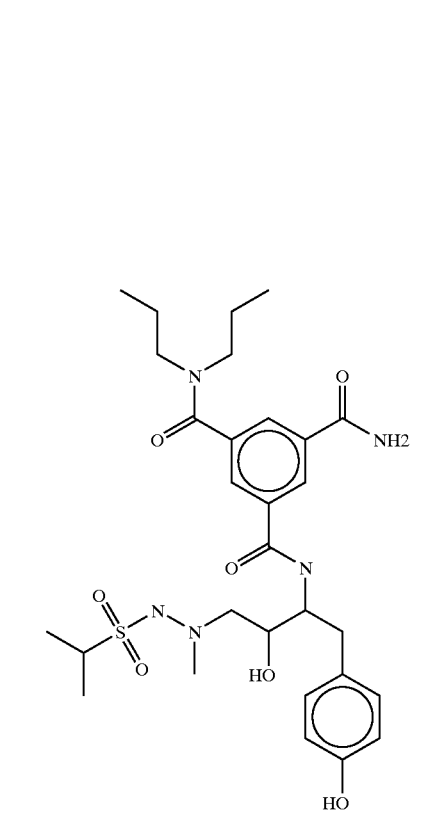
3:A9 3, 1, 3, 1

TABLE 1-continued
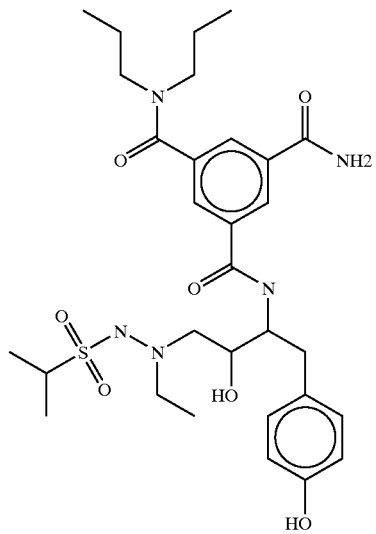
3:A10 3, 1, 3, 2
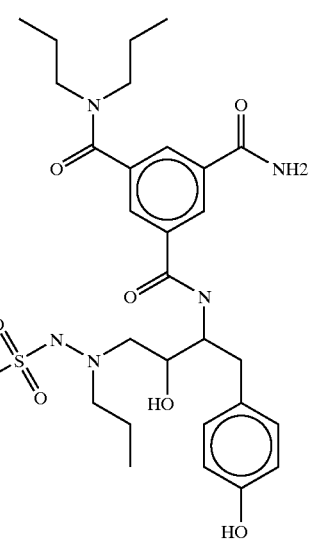
3:A11 3, 1, 3, 3
TABLE 1-continued
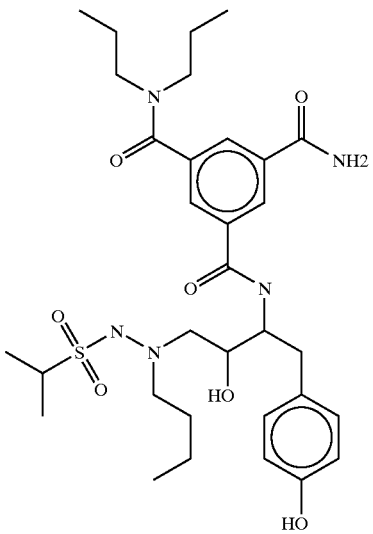
3:A12 3, 1, 3, 4
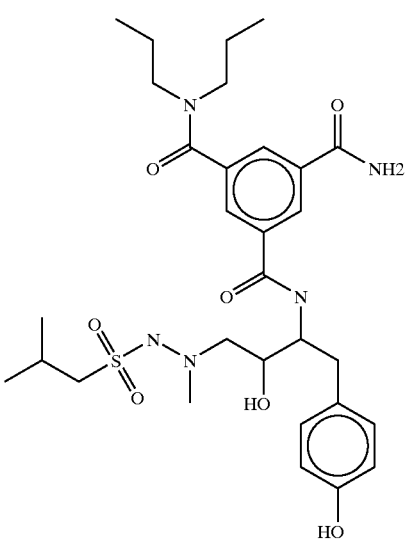
3:B1 3, 1, 4, 1

TABLE 1-continued
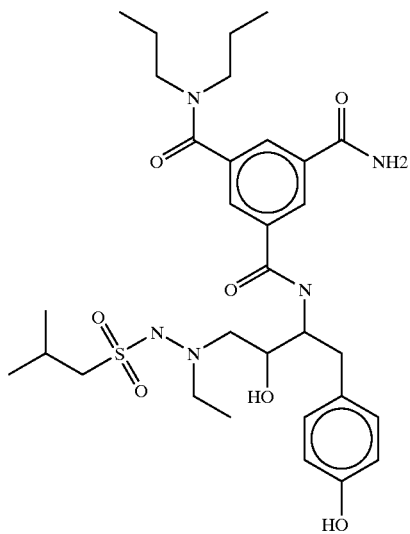
3:B2 3, 1, 4, 2
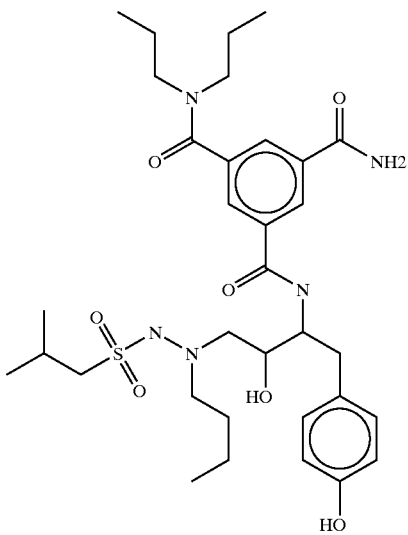
3:B4 3, 1, 4, 4
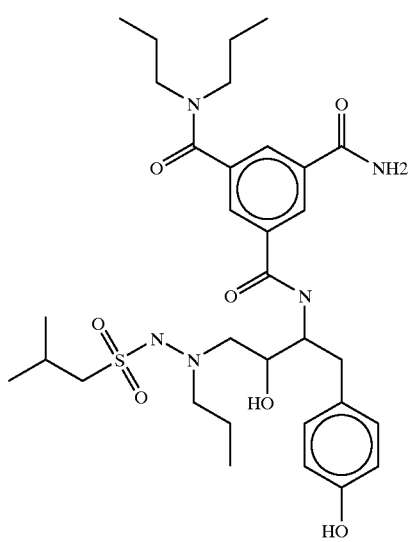
3:B3 3, 1, 4, 3
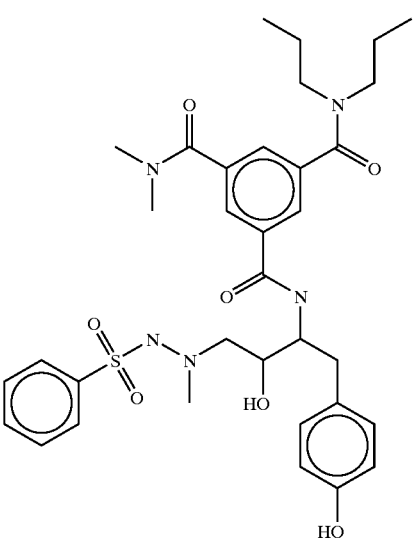
3:B5 3, 2, 1, 1

TABLE 1-continued
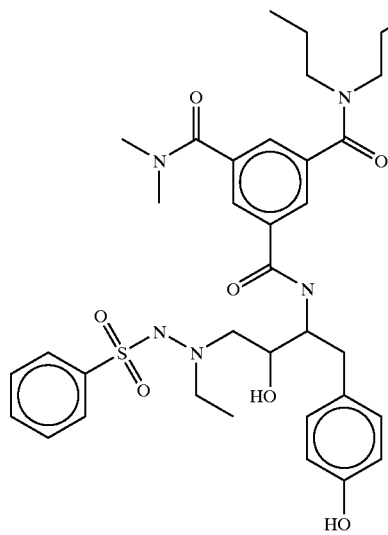
3:B6 3, 2, 1, 2
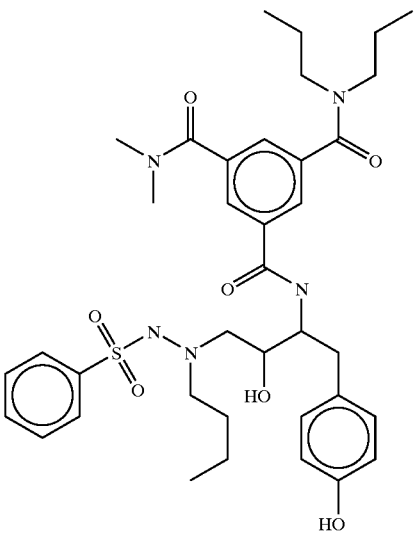
3:B8 3, 2, 1, 4
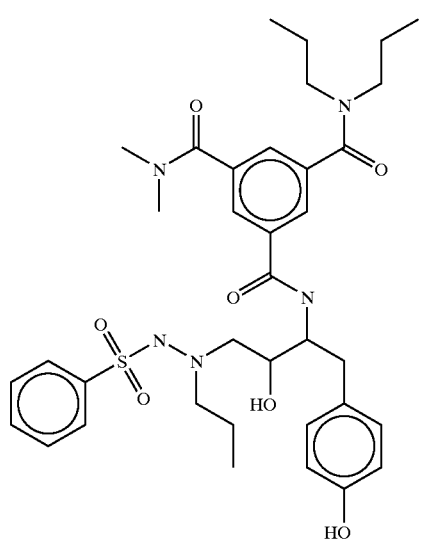
3:B7 3, 2, 1, 3
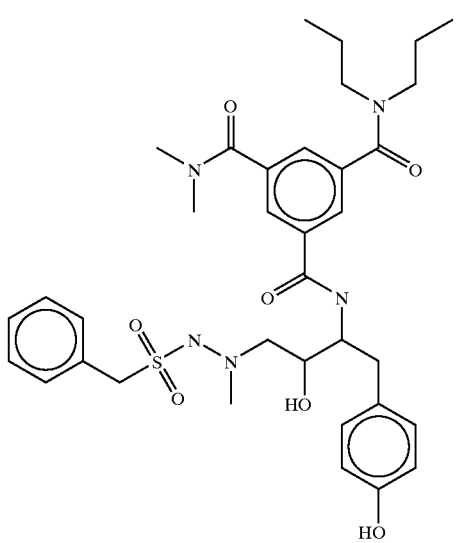
3:B9 3, 2, 2, 1

TABLE 1-continued
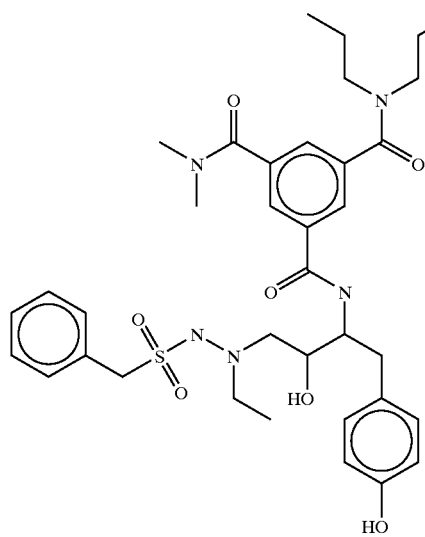
3:B10 3, 2, 2, 2
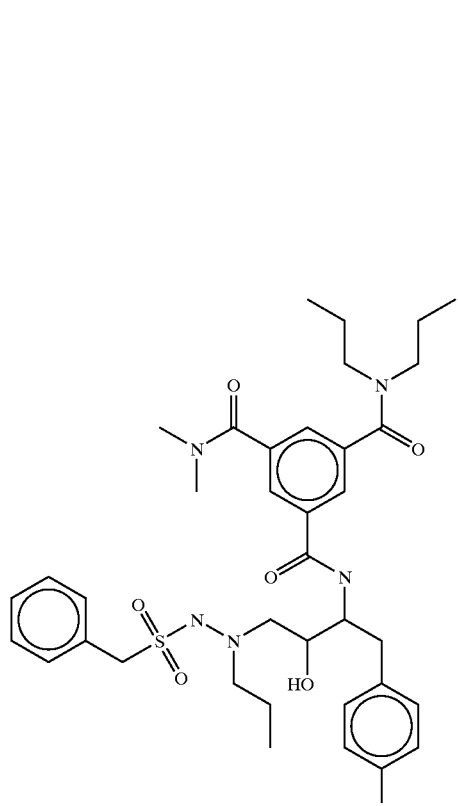
3:B11 3, 2, 2, 3
TABLE 1-continued
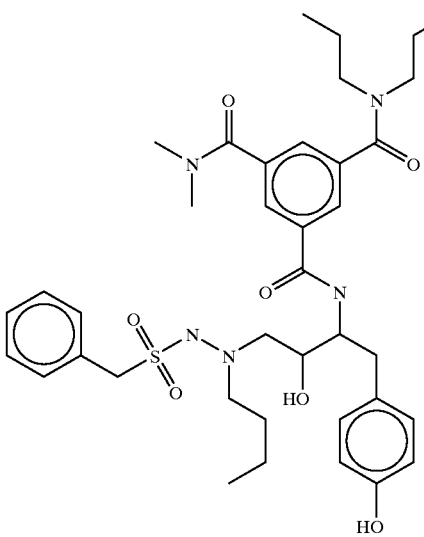
3:B12 3, 2, 2, 4
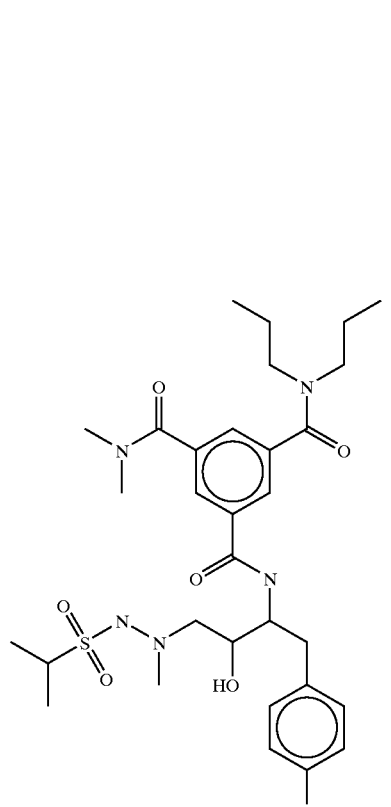
3:C1 3, 2, 3, 1

TABLE 1-continued
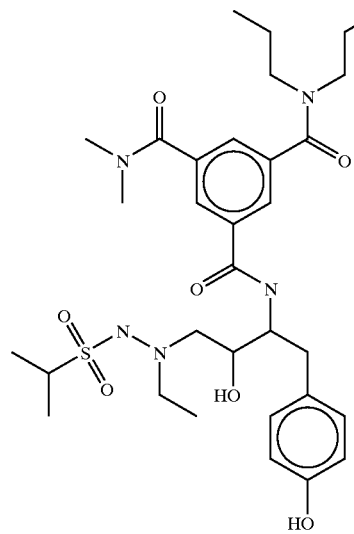
3:C2 3, 2, 3, 2
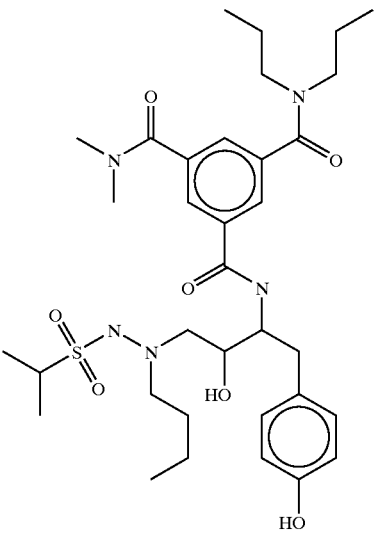
3:C4 3, 2, 3, 4
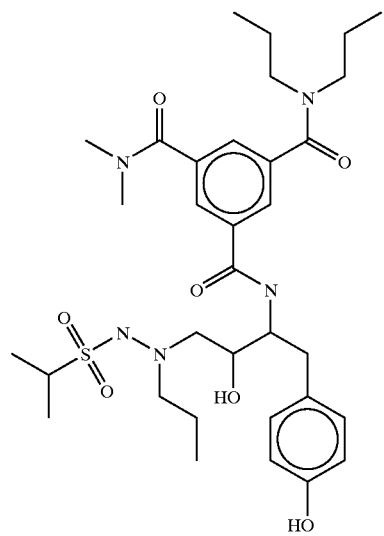
3:C3 3, 2, 3, 3
3:C5 3, 2, 4, 1

TABLE 1-continued
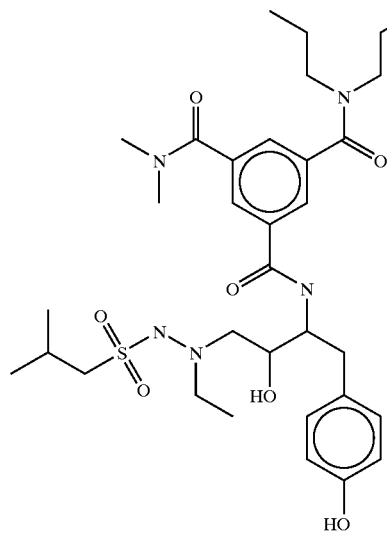
3:C6 3, 2, 4, 2
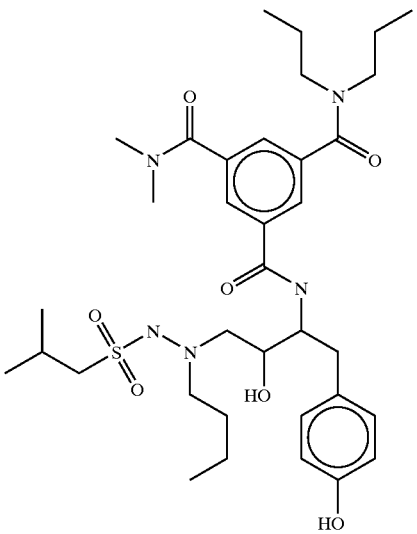
3:C8 3, 2, 4, 4
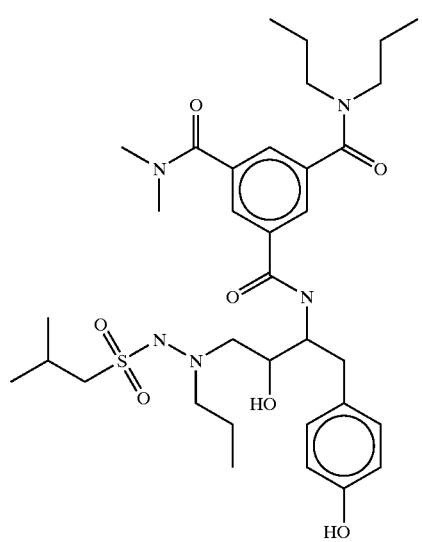
3:C7 3, 2, 4, 3
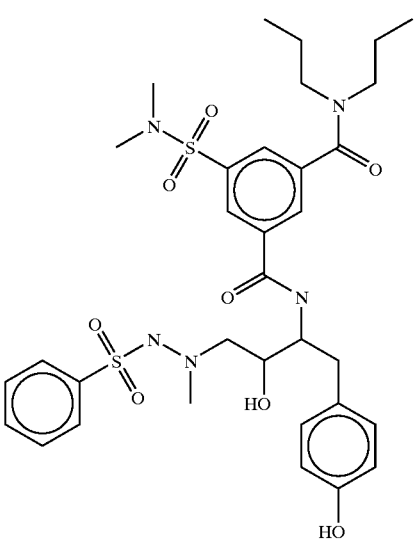
3:C9 3, 3, 1, 1

TABLE 1-continued
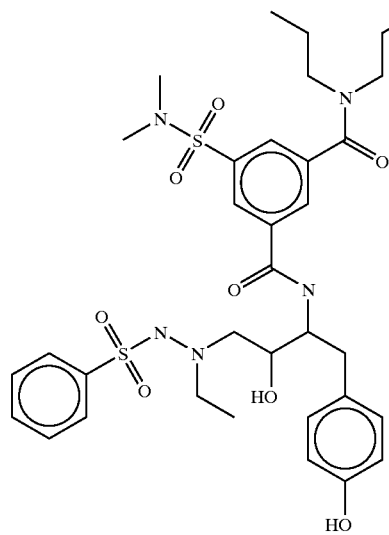
3:C10 3, 3, 1, 2
TABLE 1-continued
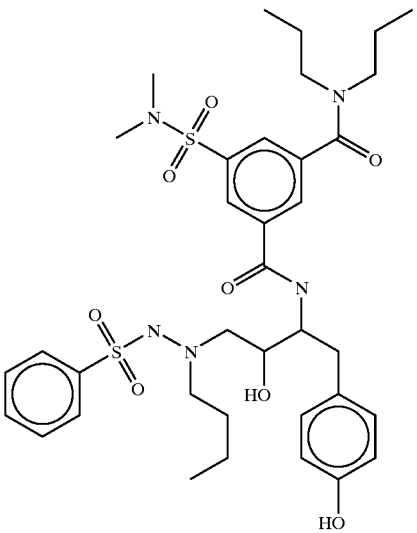
3:C12 3, 3, 1, 4
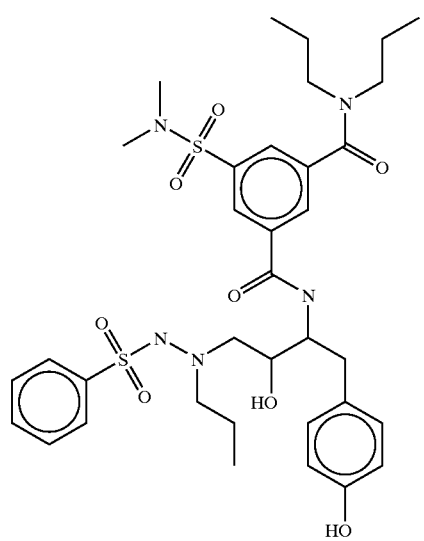
3:C11 3, 3, 1, 3
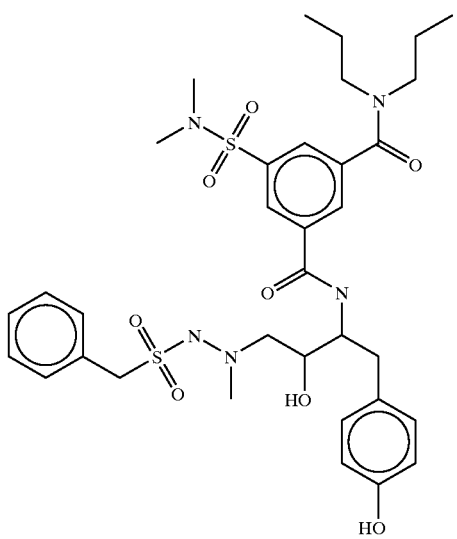
3:D1 3, 3, 2, 1

TABLE 1-continued
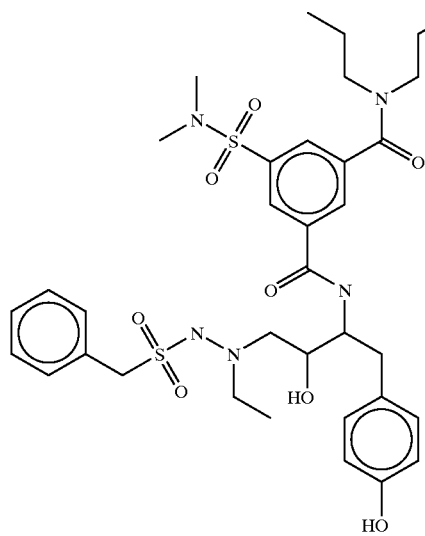
3:D2 3, 3, 2, 2
TABLE 1-continued
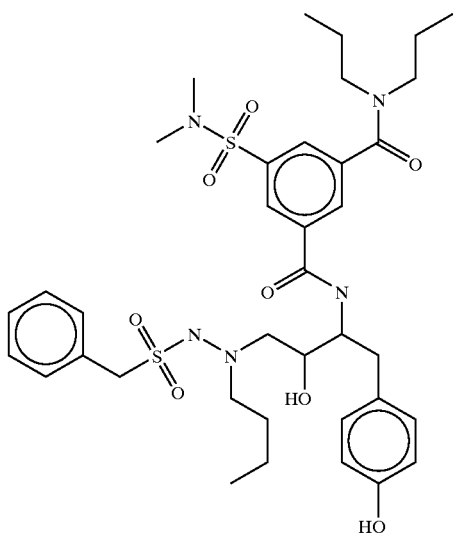
3:D4 3, 3, 2, 4
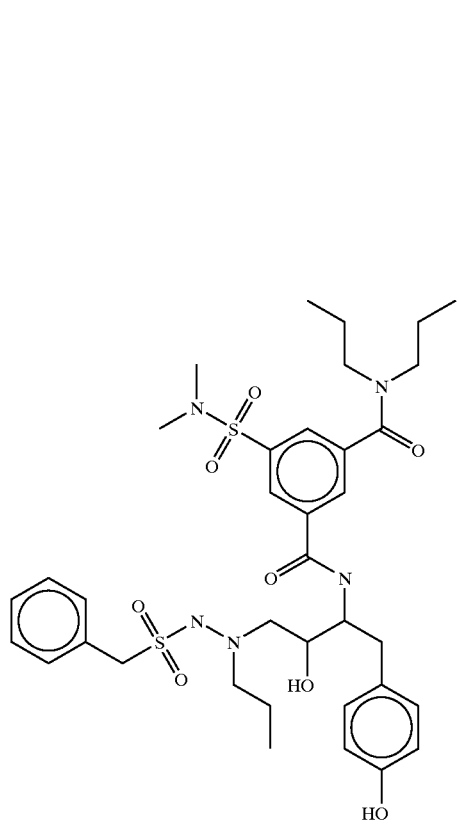
3:D3 3, 3, 2, 3
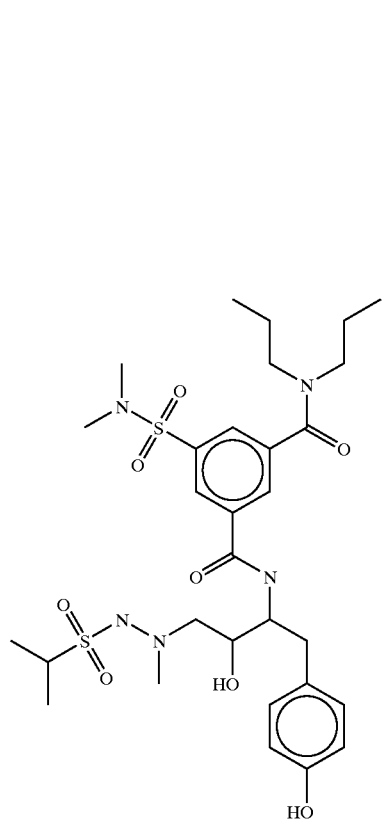
3:D5 3, 3, 3, 1

TABLE 1-continued
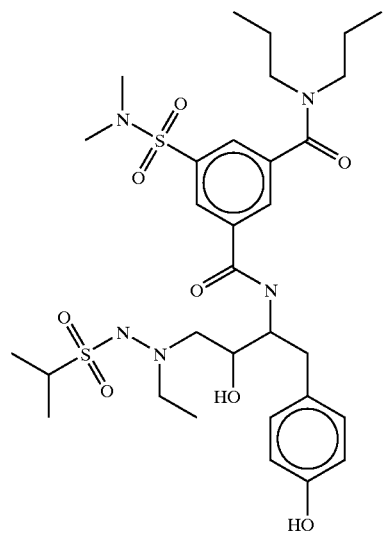
3:D6 3, 3, 3, 2
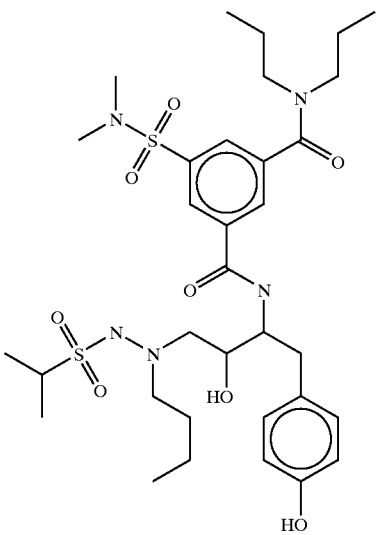
3:D8 3, 3, 3, 4
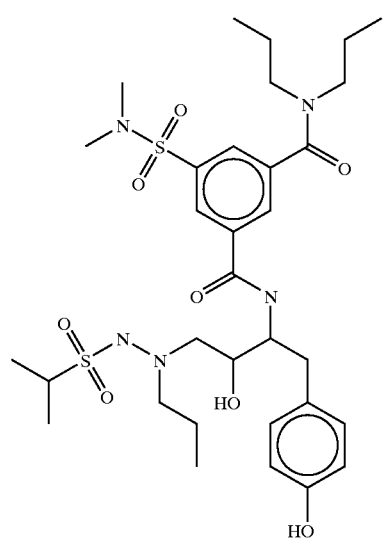
3:D7 3, 3, 3, 3
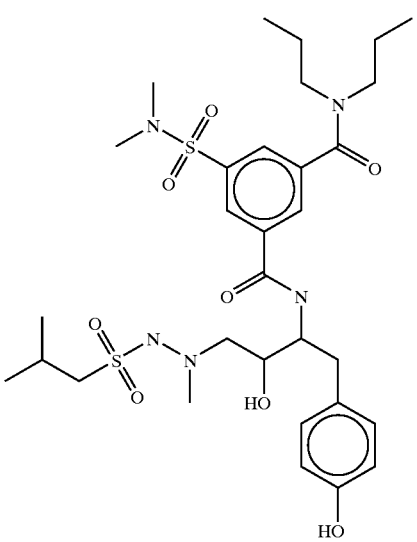
3:D9 3, 3, 4, 1

TABLE 1-continued
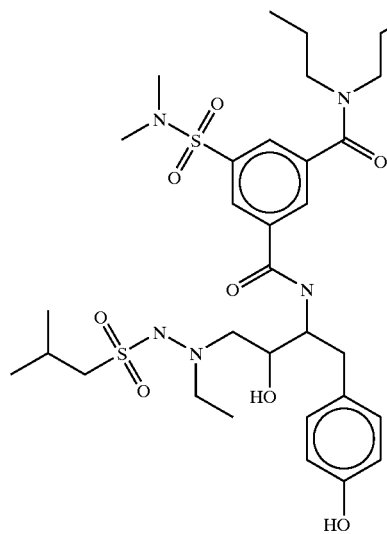
3:D10 3, 3, 4, 2
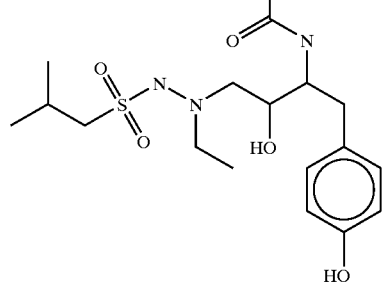
3:D11 3, 3, 4, 3
TABLE 1-continued
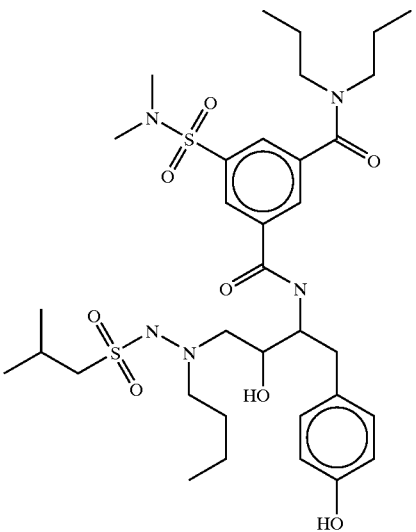
3:D12 3, 3, 4, 4
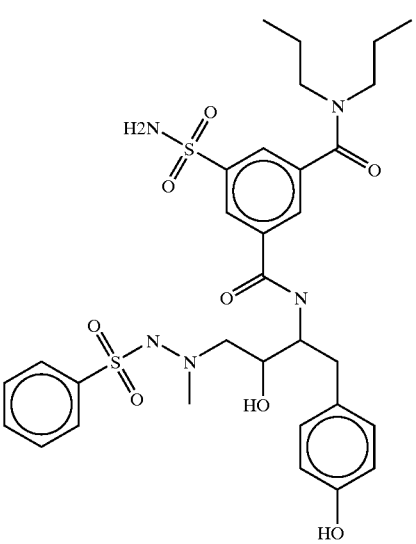
3:E1 3, 4, 1, 1

TABLE 1-continued
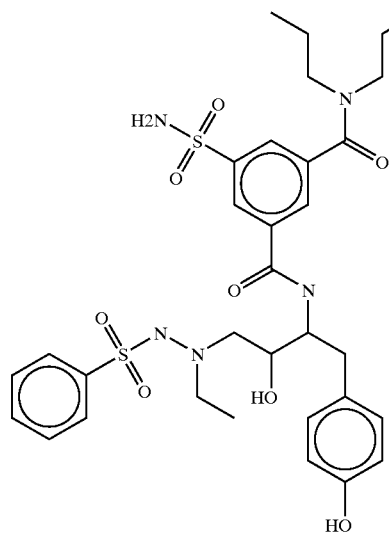
3:E2 3, 4, 1, 2
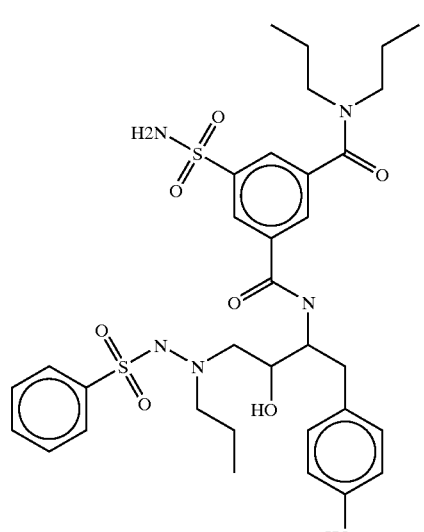
3:E3 3, 4, 1, 3
TABLE 1-continued
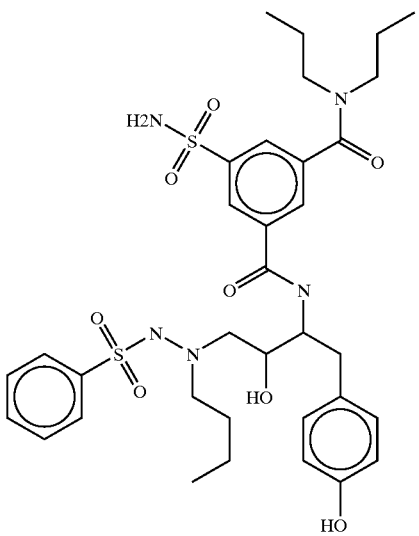
3:E4 3, 4, 1, 4
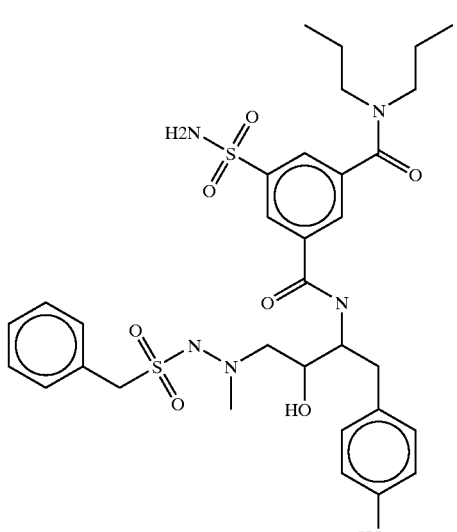
3:E5 3, 4, 2, 1

TABLE 1-continued
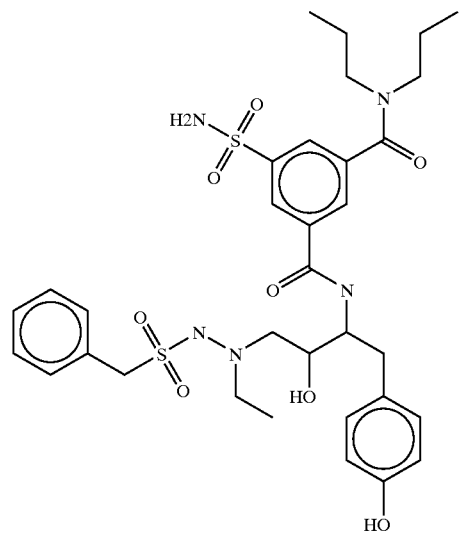
3:E6 3, 4, 2, 2
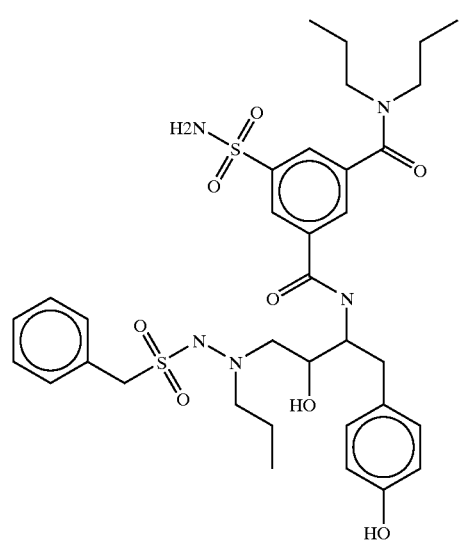
3:E7 3, 4, 2, 3
TABLE 1-continued
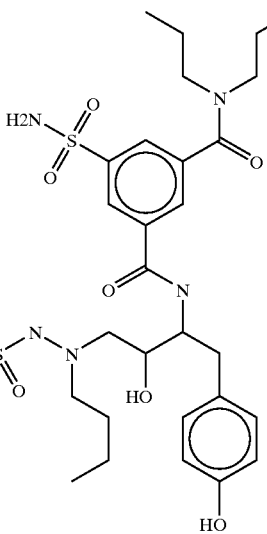
3:E8 3, 4, 2, 4
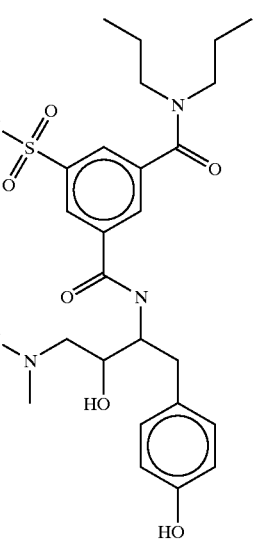
3:E9 3, 4, 3, 1

TABLE 1-continued
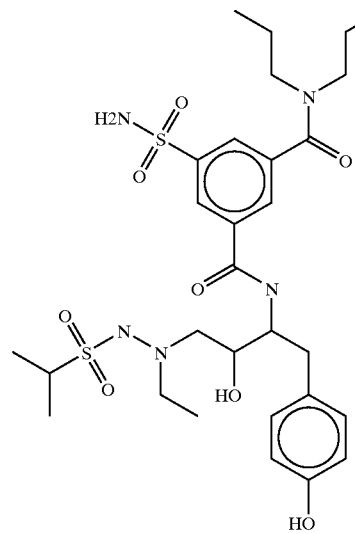
3:E10 3, 4, 3, 2
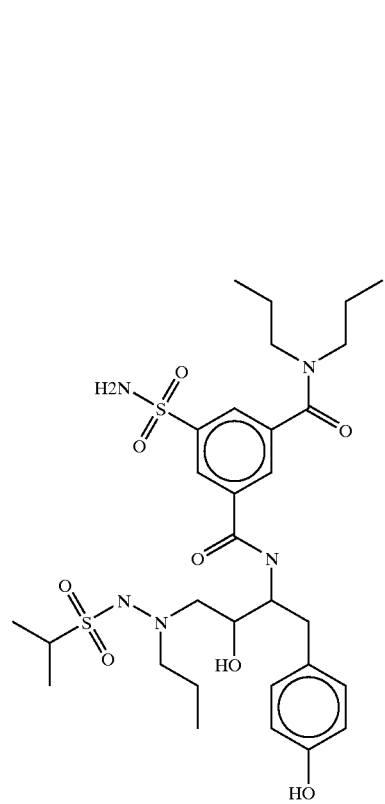
3:E11 3, 4, 3, 3
TABLE 1-continued
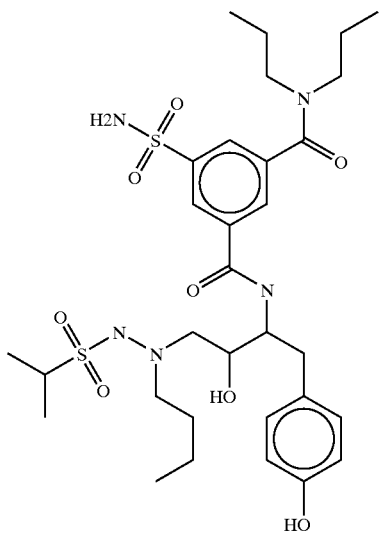
3:E12 3, 4, 3, 4
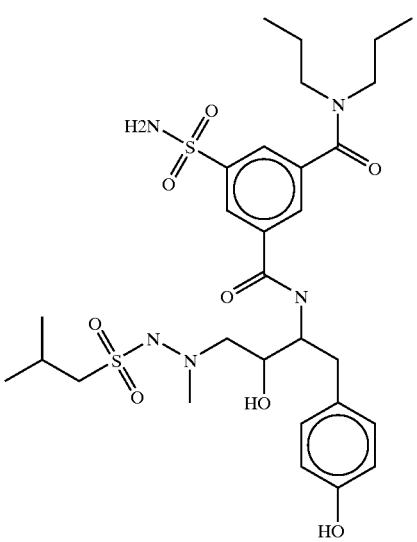
3:F1 3, 4, 4, 1

TABLE 1-continued
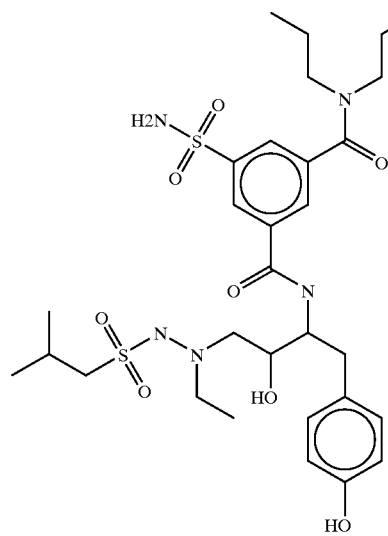
3:F2 3, 4, 4, 2
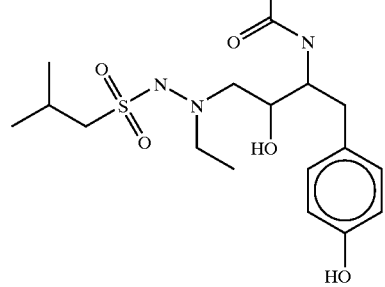
3:F3 3, 4, 4, 3
TABLE 1-continued
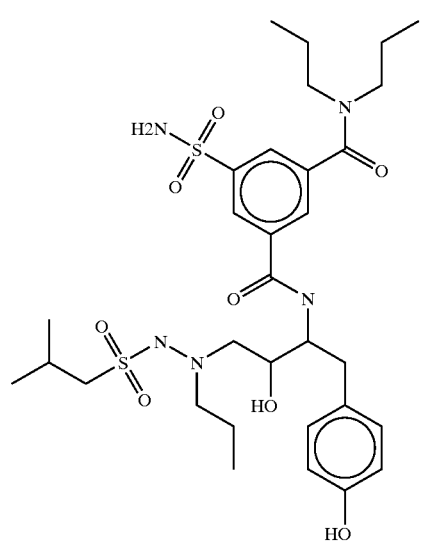
3:F4 3, 4, 4, 4
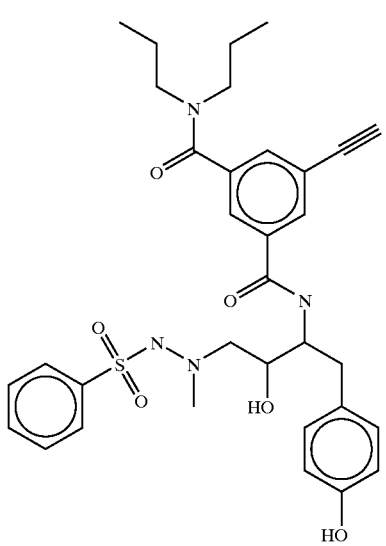
3:F5 3, 5, 1, 1

TABLE 1-continued
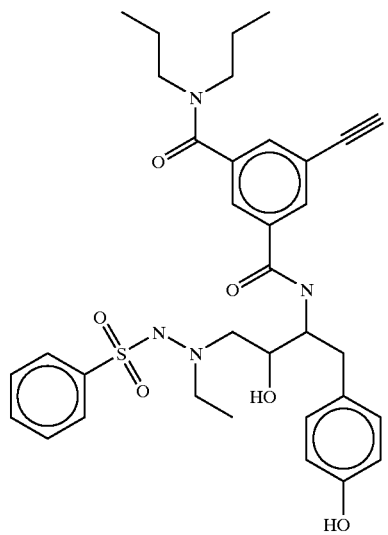
3:F6 3, 5, 1, 2
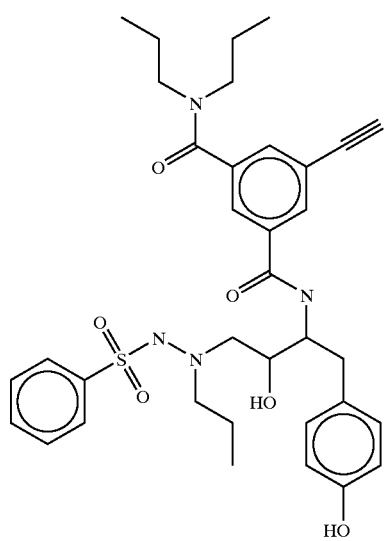
3:F7 3, 5, 1, 3
TABLE 1-continued
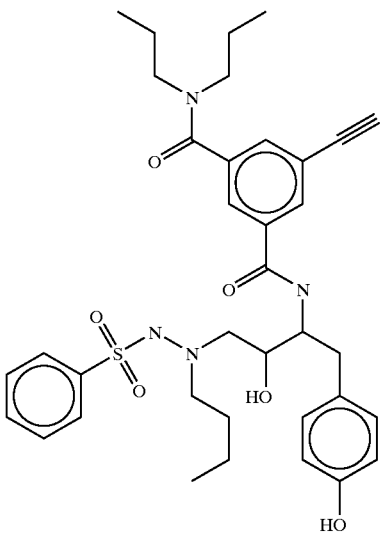
3:F8 3, 5, 1, 4
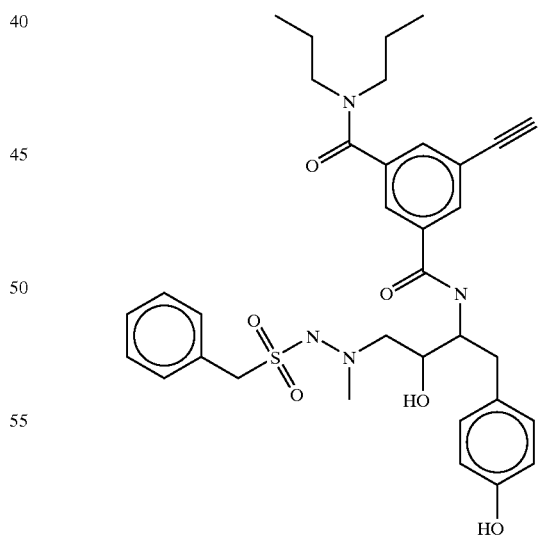
3:F9 3, 5, 2, 1

TABLE 1-continued
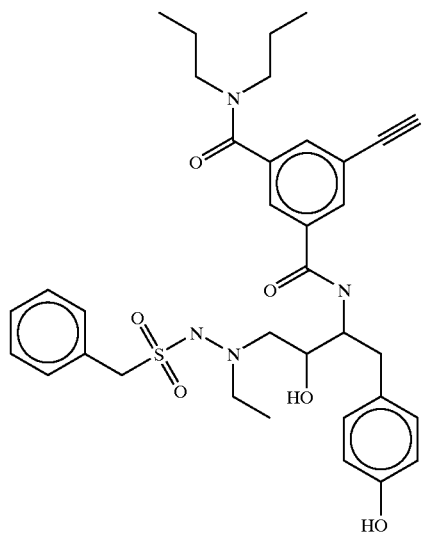
3:F10 3, 5, 2, 2
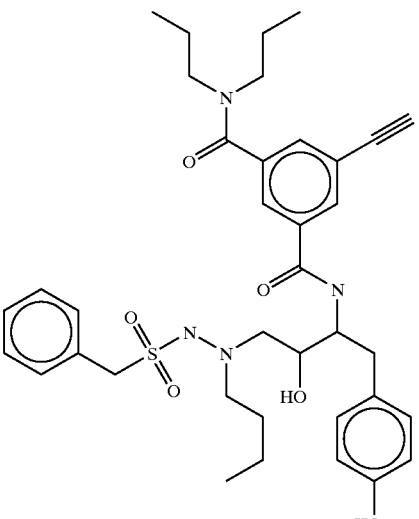
3:F12 3, 5, 2, 4
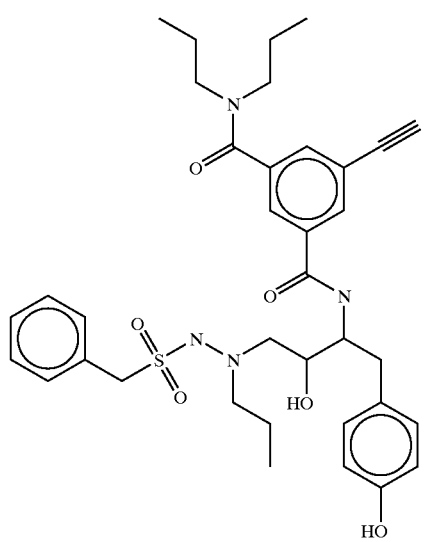
3:F11 3, 5, 2, 3
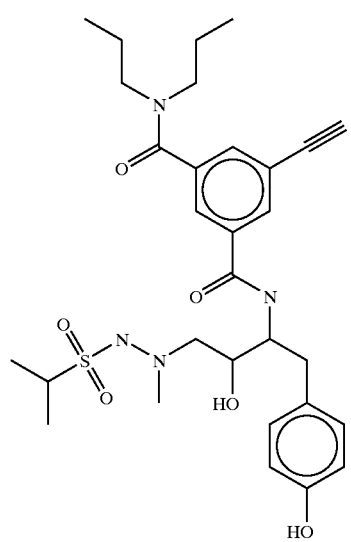
3:G1 3, 5, 3, 1

| 331 | 332 |
|---|---|
| TABLE 1-continued | TABLE 1-continued |
| 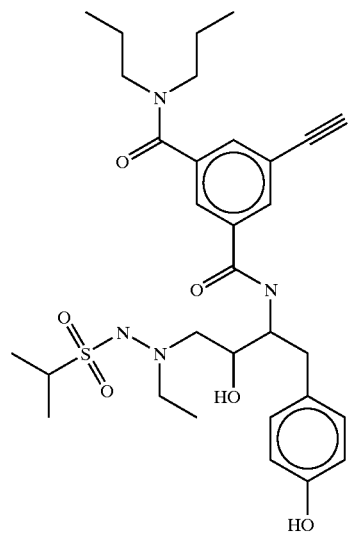 3:G2 3, 5, 3, 2 | 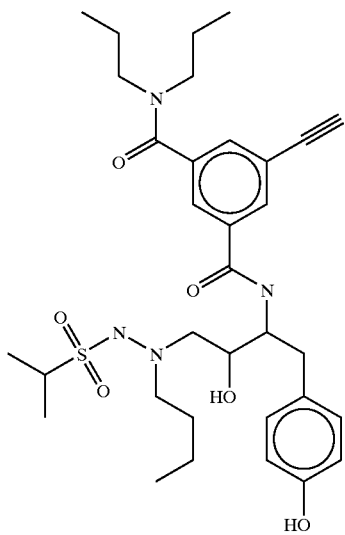 3:G4 3, 5, 3, 4 |
| 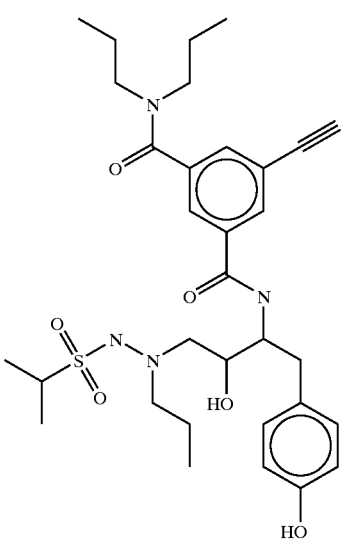 3:G3 3, 5, 3, 3 | 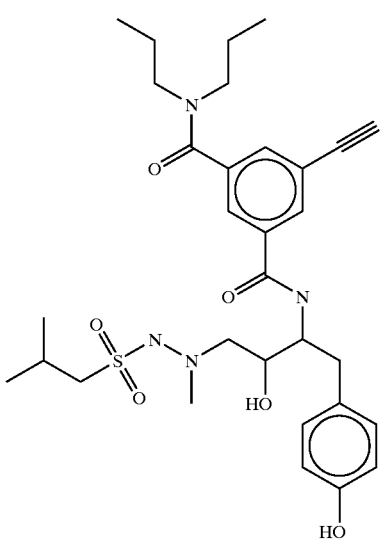 3:G5 3, 5, 4, 1 |

TABLE 1-continued
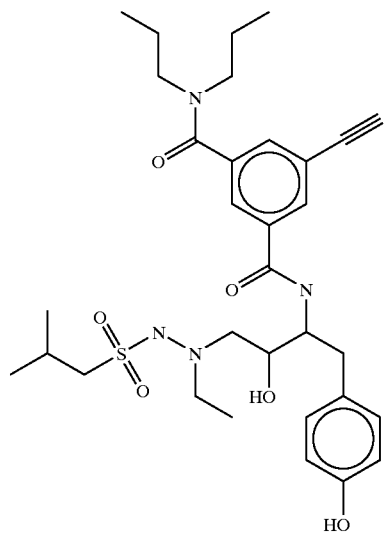
3:G6 3, 5, 4, 2
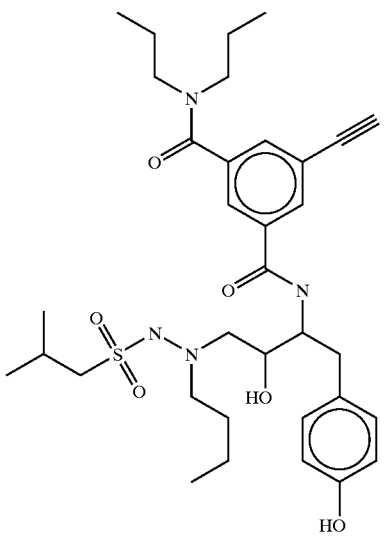
3:G8 3, 5, 4, 4
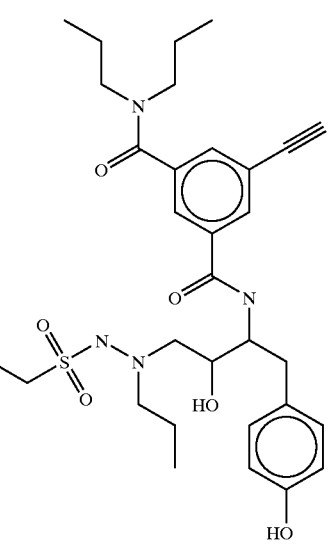
3:G7 3, 5, 4, 3
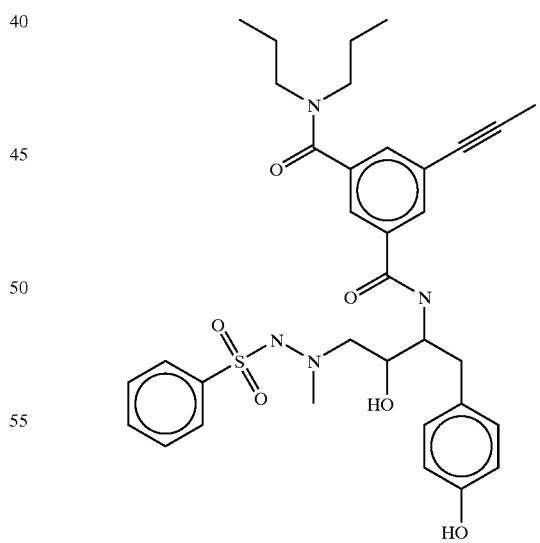
3:G9 3, 6, 1, 1

TABLE 1-continued
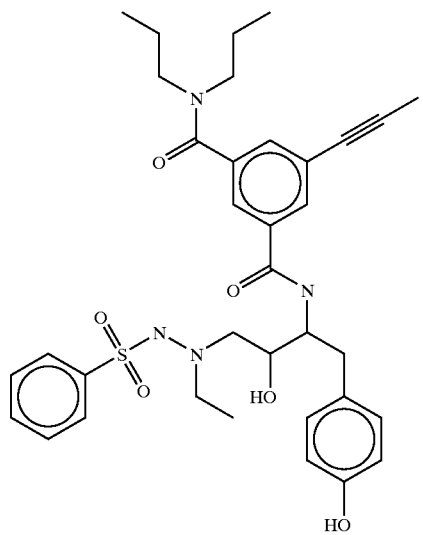
3:G10 3, 6, 1, 2
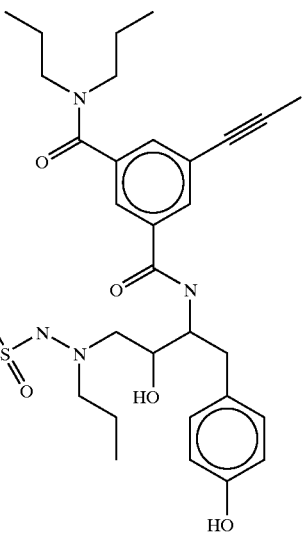
3:G11 3, 6, 1, 3
TABLE 1-continued
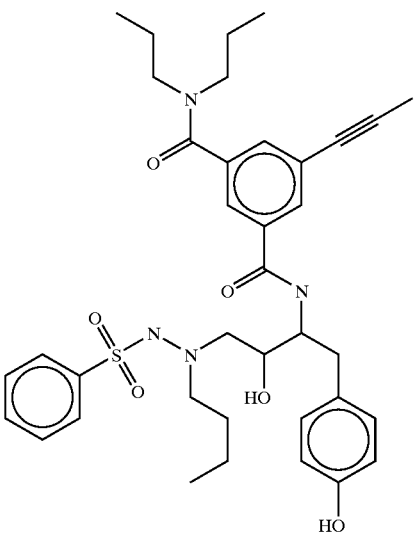
3:G12 3, 6, 1, 4
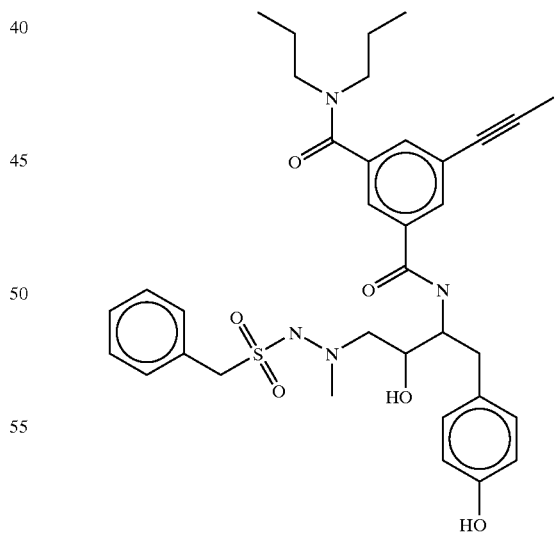
3:H1 3, 6, 2, 1

TABLE 1-continued
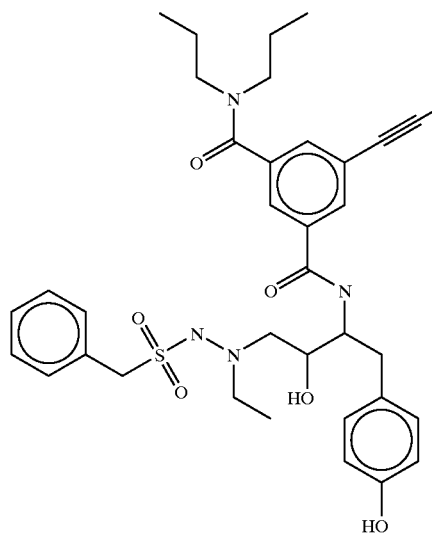
3:H2 3, 6, 2, 2
TABLE 1-continued
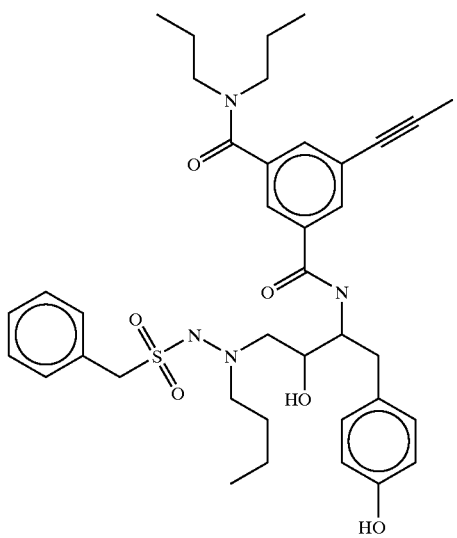
3:H4 3, 6, 2, 4
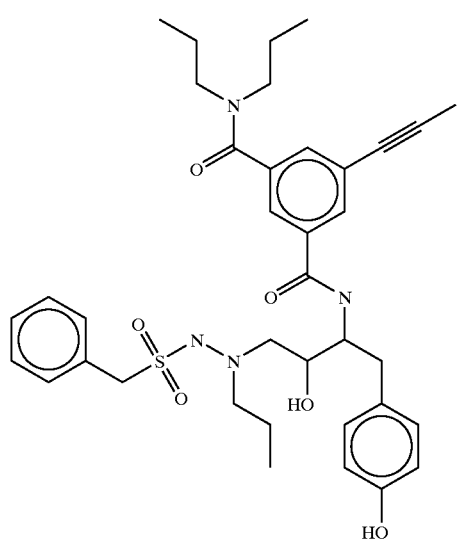
3:H3 3, 6, 2, 3
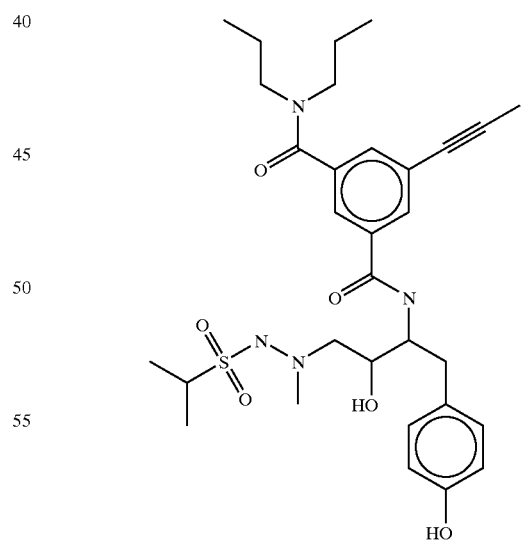
3:H5 3, 6, 3, 1

TABLE 1-continued
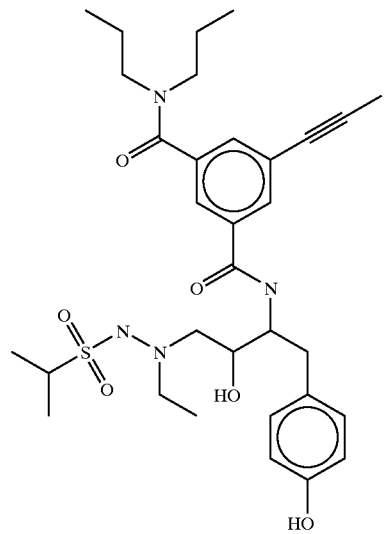
3:H6 3, 6, 3, 2
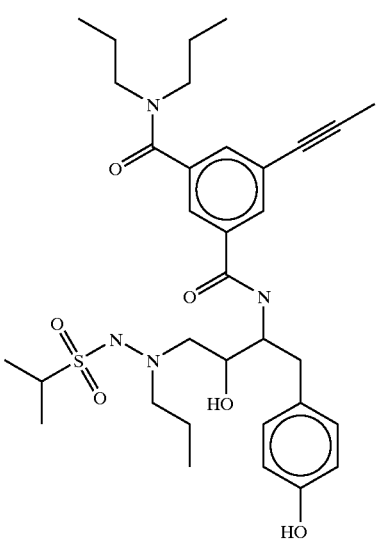
3:H7 3, 6, 3, 3
TABLE 1-continued
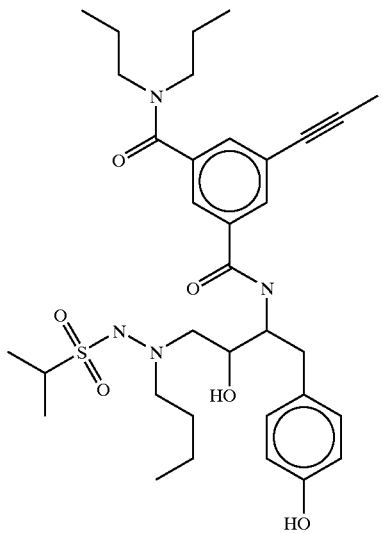
3:H8 3, 6, 3, 4
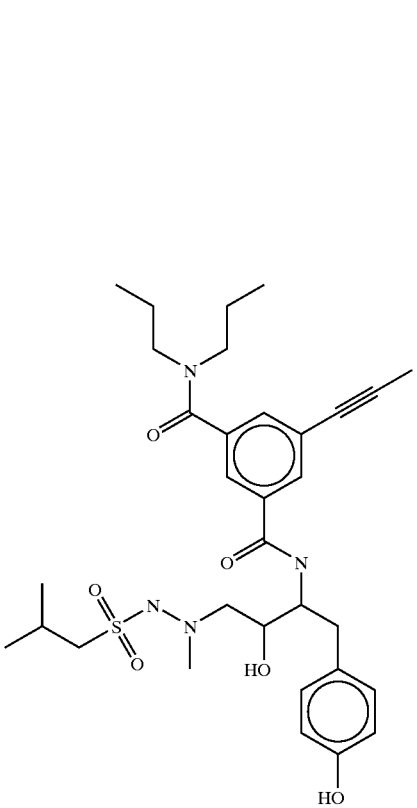
3:H9 3, 6, 4, 1

TABLE 1-continued

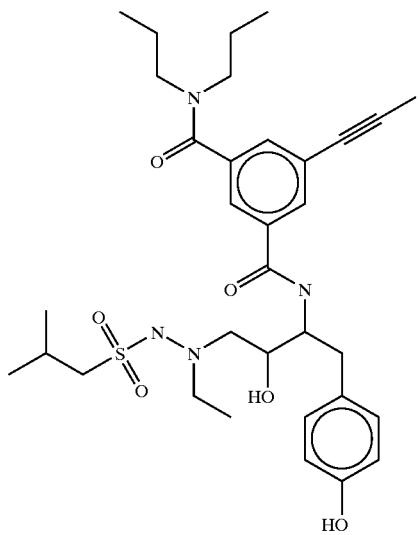

3:H10 3, 6, 4, 2

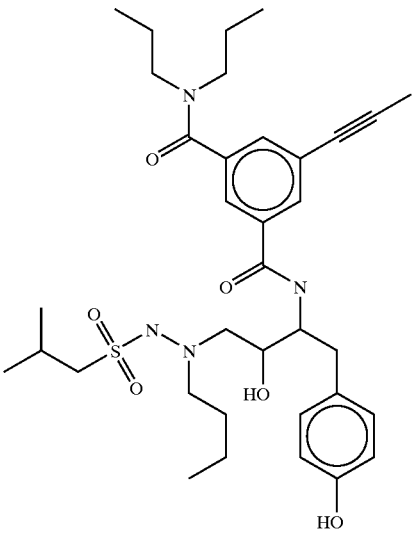

3:H12 3, 6, 4, 4

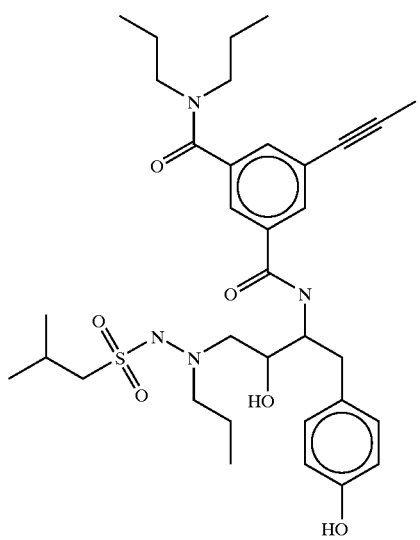

3:H11 3, 6, 4, 3

The compounds of the invention may exist as geometric or stereoisomers isomers as well as tautomers. Thus, the invention includes all tautomers and geometric isomers, such as the E and Z geometric isomers, as well as mixtures thereof. Furthermore, the invention includes pure enantiomers and diasteriomers as well as mixtures thereof, including racemic mixtures. The individual geometric isomers, enantiomers, or diasteriomers may be prepared or isolated by methods known in the art.

Compounds of the invention of designated stereochemistry may be included in mixtures, including racemic mixtures, with other enantiomers, diasteriomers, geometric isomers or tautomers. Compounds of the invention with designated stereochemistry are typically present in these mixtures in excess of 50 percent. Preferably, compounds of the invention with designated stereochemistry are present in these mixtures in excess of 80 percent. Most preferably, compounds of the invention with designated stereochemistry are present in these mixtures in excess of 90 percent.

Several of the compounds of formula (I) above are amines, and as such form salts when reacted with acids. Pharmaceutically acceptable salts are generally preferred over the corresponding amines of the invention since they typically produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.,* 33, 201–217 (1986) and *J. Pharm. Sci.,* 66(1), 1, (1977).

The invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

As previously mentioned, compounds of the invention, and pharmaceutically acceptable salts or esters thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, Arch. Neurol. 57:454), and other neurotropic agents of the future.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

The invention may be further understood with reference to the following biological examples. These examples are intended to be representative of specific embodiments of the invention, and are not intended as limiting the scope of the invention.

BIOLOGY EXAMPLES

Biology Example A
Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al, 1999, Nature 40:537–540) or recombinantly produced as the full-length enzyme (amino acids 1–501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C1225SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaOAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti-MBP antibody coated ELISA plate for capture, containing so microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Biology Example B
Cell Free Inhibition Assay Utilizing a Synthetic APP Substrate A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

Biotin-SEVNL-DAEFRC[Oregon green]KK [SEQ, ID NO:1]

Biotin-SEVKM-DAEFRC[Oregon green]KK [SEQ ID NO: 2]

Biotin-GLNIKTEEISEISY-EVEFRC[Oregon green]KK [SEQ ID NO: 3]

Biotin-ADRGLTTRPGSGLTNIKTEEISEVNL-DAEF C[Oregon green]KK [SEQ ID NO:4]

Biotin-FVNQHLCoxGSHLVEALY-LVCoxGERGFFYTPKAC[Oregon green]KK [SEQ ID NO: 5].

The enzyme (0.1 nanomolar) and test compounds (0.001–100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001–100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an $IC_{50}$ of less than 50 micromolar.

Biology Example C
Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:
(biotin)CGGADRGLTTRPGSGLTNIKTEEISEVNLDAEF [SEQ ID NO: 6].
The P26-P1 standard has the sequence:
(biotin)CGGADRGLTTRPGSGLTNIKTEEISEVNL [SEQ ID NO: 7].

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Biology Example D
Assays using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Biology Example E
Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, Nature 360:672–674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Biology Example F
Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, Nature 373:523–527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1–30 mg/ml; preferably 1–10 mg/ml). After time, e.g., 3–10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Biology Example G
Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Biology Example H
Prevention of A Beta Production in Patients at Risk for AD Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters; A beta present in CSF or plasma; brain or hippocampal volume; amyloid plaque in the brain; and scores for cognitive and memory function, as compared with control, non-treated patients.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs.

All patents and publications referred to herein are hereby incorporated by reference for all purposes.

The invention has been described with reference to various specific and preferred embodiments and techniques. However, it should be understood that many variations and modifications may be made while remaining within the spirit and scope of the invention.

What is claimed is:

1. A compound of the formula V:

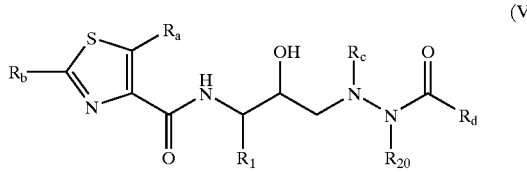

or a pharmaceutically acceptable salt thereof wherein $R_1$ represents phenyl ($C_1$–$C_6$)alkyl where the phenyl is optionally substituted with up to three groups independently selected from halogen, hydroxy, $C_1$–$C_2$ alkyl, $C_1$–$C_2$ alkoxy, amino, nitro, trifluoromethyl, cyano, mono($C_1$–$C_2$)alkylamino and di ($C_1$–$C_2$) alkylamino;

$R_a$ and $R_b$ independently represent hydrogen, hydroxy, $C_1$–$C_6$ alkyl, $C_1$–$C_6$ alkoxy, $C_3$–$C_7$ cycloalkyl, $C_3$–$C_7$ cycloalkyl($C_1$–$C_6$)alkyl, $C_3$–$C_7$ cycloalkyl($C_1$–$C_6$) alkoxy, halogen, cyano, amino, mono($C_1$–$C_6$) alkylamino, di($C_1$–$C_6$)alkylamino, mono- or di($C_1$–C6) alkylaminosulfonyl, $C_1$–$C_6$ alkyl sulfonylamino, $C_2$–$C_6$ alkenyl, $C_2$–$C_6$ alkynyl, trifluoromethyl, mono ($C_1$–$C_6$)alkylaminocarbonyl, or di($C_1$–$C_6$) alkylaminocarbonyl and provided that not both $R_a$ and $R_b$ are hydrogen simultaneously;

$R_c$ represents hydrogen, or $C_1$–$C_6$ alkyl, $C_2$–$C_6$ alkenyl, or $C_2$–$C_6$ alkynyl each of which is optionally substituted with halogen, hydroxy, amino, cyano, or trifluoromethyl;

$R_d$ represents phenyl optionally substituted with hydroxy, $C_1$–$C_6$ alkyl, $C_1$–$C_6$ alkoxy, $C_3$–$C_7$ cycloalkyl, $C_3$–$C_7$ cycloalkyl ($C_1$–$C_6$)alkyl, $C_3$–$C_7$ cycloalkyl($C_1$–$C_6$) alkoxy, halogen, cyano, amino, mono($C_1$–$C_6$) alkylamino, di($C_1$–$C_6$)alkylamino, mono- or di($C_1$–$C_6$)alkylaminosulfonyl, $C_1$–$C_6$ alkyl sulfonylamino, $C_2$–$C_6$ alkenyl, $C_2$–$C_6$ alkynyl; or $C_1$–$C_6$ alkyl optionally substituted with hydroxy, $C_1$–$C_6$ alkyl, $C_1$–$C_6$ alkoxy, halogen, cyano, amino, mono($C_1$–$C_6$)alkylamino, di($C_1$–$C_6$)alkylamino, $C_2$–$C_6$ alkenyl, $C_2$–$C_6$ alkynyl, or trifluoromethyl; and $R_{20}$ represents hydrogen, $C_1$–$C_6$ alkyl, $C_2$–$C_6$ alkenyl, $C_2$–$C_6$ alkynyl, or trifluoromethyl.

2. A compound according to claim 1, wherein $R_1$ is benzyl where the phenyl is optionally substituted.

3. A compound according to claim 2, wherein the phenyl is substituted with one or two groups independently selected from halogen, hydroxy, $C_1$–$C_3$ alkyl, amino, and trifluoromethyl.

4. A compound according to claim 3, wherein phenyl is substituted with two groups independently selected from halogen, hydroxy, and trifluoromethyl.

5. A compound according to claim 4, wherein phenyl is disubstituted with halogen.

6. A compound according to claim 5, wherein $R_1$ is 3,5-difluorobenzyl.

7. A compound according to claim 4, wherein $R_a$ and $R_b$ are different and $R_b$ represents $C_1$–$C_6$)alkylsulfonylamino.

8. A compound according to claim 4, wherein $R_d$ is phenyl optionally substituted with $C_1$–$C_3$ alkyl, $C_1$–$C_3$ alkoxy, amino, hydroxy, or halogen.

9. A compound according to claim 4, wherein $R_c$ is hydrogen or $C_1$–$C_4$ alkyl.

10. A compound according to claim 9, wherein $R_c$ is $C_1$–$C_3$ alkyl.

11. A compound according to claim 4, wherein $R_d$ is $C_1$–$C_6$ lower alkyl and $R_{20}$ is hydrogen.

12. A compound according to claim 4, which has the formula VI:

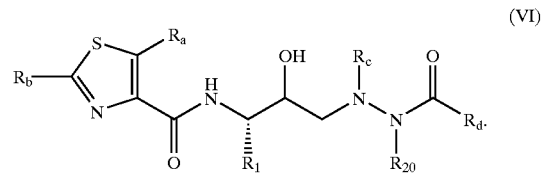

13. A compound according to claim 12, wherein $R_1$ is benzyl where the phenyl is disubstituted with chloro or fluoro;

$R_c$ is $C_1$–$C_3$ alkyl;

$R_d$ is $C_1$–$C_5$ lower alkyl;

$R_{20}$ is hydrogen or $C_1$–$C_6$ alkyl; and $R_b$ is alkylsulfonylamino attached to the 2-position of the thiazolyl group.

14. A compound according to claim 1, of the formula:

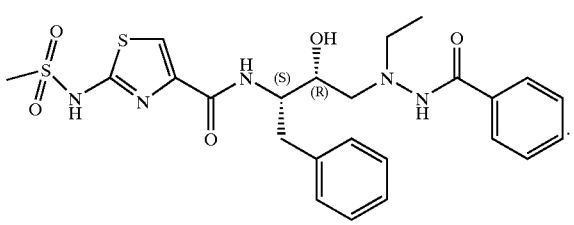

15. A compound according to claim 1, of the formula:

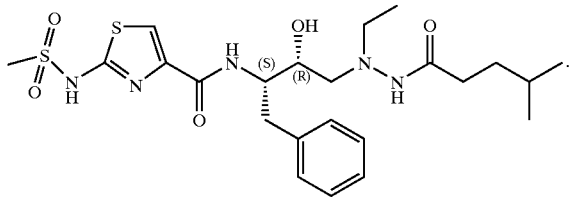

* * * * *